United States Patent
Blagg et al.

(10) Patent No.: US 6,936,619 B2
(45) Date of Patent: Aug. 30, 2005

(54) QUINAZOLINONE COMPOUNDS USEFUL IN THERAPY

(75) Inventors: Julian Blagg, Sandwich (GB); Michael Jonathan Fray, Sandwich (GB); Mark Llewellyn Lewis, Sandwich (GB); John Paul Mathias, Sandwich (GB); Mark Henryk Stefaniak, Sandwich (GB); Alan Stobie, Sandwich (GB)

(73) Assignee: Pfizer, Inc., New York, NY (US)

( * ) Notice: Subject to any disclaimer, the term of this patent is extended or adjusted under 35 U.S.C. 154(b) by 157 days.

(21) Appl. No.: 10/387,106

(22) Filed: Mar. 12, 2003

(65) Prior Publication Data
US 2004/0029859 A1 Feb. 12, 2004

Related U.S. Application Data
(60) Provisional application No. 60/374,894, filed on Apr. 23, 2002.

(30) Foreign Application Priority Data
Mar. 14, 2002 (GB) .............................. 0206033

(51) Int. Cl.⁷ ................ C07D 401/04; C07D 471/04; A61K 31/517
(52) U.S. Cl. ............... 514/266.2; 514/266.21; 544/284; 544/287
(58) Field of Search ................ 544/284, 287; 514/266.2, 266.21

(56) References Cited
U.S. PATENT DOCUMENTS
4,085,213 A * 4/1978 Bindra .................. 514/267

FOREIGN PATENT DOCUMENTS

| WO | WO 9723462 | 7/1997 | ......... C07D/215/42 |
|---|---|---|---|
| WO | WO 9830560 | 7/1998 | ......... C07D/409/04 |
| WO | WO 02053558 | 7/2002 | ......... C07D/401/04 |

* cited by examiner

Primary Examiner—Deepak Rao
(74) Attorney, Agent, or Firm—Peter C. Richardson; Gregg C. Benson; Carl J. Goddard

(57) ABSTRACT

Compounds of formula (I):

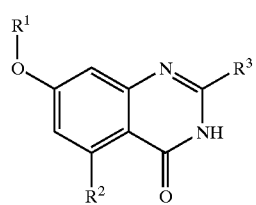

or pharmaceutically acceptable salts or solvates thereof, wherein $R^1$ represents $C_{1-4}$ alkyl;

$R^2$ represents halo, $C_{1-4}$ alkyl, $C_{3-6}$ cycloalkyl, $C_{3-6}$ cycloalkyloxy, —SO$_2$($C_{1-4}$ alkyl), optionally substituted $C_{1-4}$ alkyloxy, Het or —OHet;

$R^3$ represents a bicyclic group of the formula

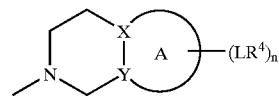

wherein X and Y are selected from C and N, provided that at least one is C;

Ring A together with X and Y represents a 5- or 6-membered aromatic ring containing 0, 1, 2 or 3 nitrogen atoms in the ring;

n is), 1 or 2

L represents a direct link, $C_{1-4}$ alkylene or $C_{1-4}$ alkoxyalkylene;

$R^4$ represents H, —NR$^5$R$^6$, $C_{3-6}$ cycloalkyl, —OR$^7$, Het$^1$ or Het$^4$;

$R^5$ and $R^6$ are independently selected from H, $C_{3-6}$ cycloalkyl, $C_{3-6}$ cycloalkyl-$C_{1-4}$ alkylene, —SO$_2$ ($C_{1-4}$ alkyl) and optionally substituted $C_{1-4}$ alkyl $R^7$ is selected from H, $C_{1-4}$ alkyl, $C_{1-4}$ alkoxyalkyl, $C_{3-6}$cycloalkyl, Het$^2$ and $C_{1-4}$alkyl-Het$^3$;

$R^8$ is H or $C_{1-4}$ alkyl;

Het, Het$^1$, Het$^2$ and Het$^3$ independently represent an optionally substituted 4 to 7 membered saturated heterocyclic group which may be mono- or bi-cyclic and which contains one or more heteroatoms selected from N, O or S;

Het$^4$ represents an optionally substituted 5 or 6 membered unsaturated heterocyclic group containing one or more heteroatoms selected from N, O or S;

$R^9$ is H or $C_{1-4}$ alkyl;

$R^{10}$ and $R^{11}$ are independently selected from H and $C_{1-4}$ alkyl;

are useful in the treatment of hypertension, myocardial infarction, male erectile dysfunction (MED), hyperlipidaemia, cardiac arrhythmia, glaucoma and benign prostatic hyperplasia (BPH). They also find utility in the treatment of female sexual arousal dysfunction (FSAD).

16 Claims, No Drawings

QUINAZOLINONE COMPOUNDS USEFUL IN THERAPY

This application is filed claiming priority to U.S. Provisional Application No. 60/374,894, filed Apr. 23, 2002, and GB Application No. 0206033.3, filed Mar. 14, 2002.

This invention relates to novel compounds useful in therapy. It also relates to compositions containing such derivatives and to their use. They have potential utility in the treatment of hypertension, myocardial infarction, male erectile dysfunction (MED), hyperlipidaemia, cardiac arrhythmia, glaucoma and benign prostatic hyperplasia (BPH). They also may be useful in the treatment of female sexual arousal dysfunction (FSAD).

International Patent Application WO 97/23462 discloses quinoline and quinazoline compounds having a 5-phenyl substituent. The compounds are indicated in the treatment of benign prostatic hyperplasia.

International Patent application WO 98/30560 discloses quinoline and quinazoline compounds indicated in the treatment of benign prostatic hyperplasia.

International Patent application WO02/053558 (published after the priority date of this application) discloses quinazoline derivatives indicated in the treatment of benign prostatic hyperplasia.

According to the present invention, there are provided compounds of the formula (I):

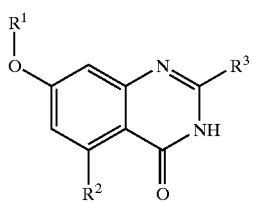

and pharmaceutically acceptable salts or solvates thereof, wherein $R^1$ represents $C_{1-4}$ alkyl;

$R^2$ represents halo, $C_{1-4}$ alkyl, $C_{3-6}$ cycloalkyl, $C_{3-6}$ cycloalkyloxy, —$SO_2(C_{1-4}$ alkyl), $C_{1-4}$ alkyloxy (optionally substituted by $C_3$–$C_6$ cycloalkyl or $C_1$–$C_4$ alkoxy), Het or -OHet;

$R^3$ represents a bicyclic group of the formula

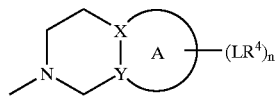

wherein X and Y are selected from C and N, provided that at least one is C;

Ring A together with X and Y represents a 5- or 6-membered aromatic ring containing 0, 1, 2 or 3 nitrogen atoms in the ring;

n is 0, 1 or 2

L independently represents a direct link, $C_{1-4}$ alkylene or $C_{1-4}$ alkoxyalkylene;

$R^4$ independently represents H, —$NR^5R^6$, $C_{3-6}$ cycloalkyl, —$OR^7$, $Het^1$ or $Het^4$;

$R^5$ and $R^6$ are independently selected from H, $C_{3-6}$ cycloalkyl, $C_{3-6}$ cycloalkyl-$C_{1-4}$ alkylene, —$SO_2(C_{1-4}$ alkyl) and $C_{1-4}$ alkyl (optionally substituted with —$OR^8$, —$NR^{10}R^{11}$, $Het^1$ or $Het^4$);

$R^7$ is selected from H, $C_{1-4}$ alkyl, $C_{1-4}$ alkoxyalkyl, $C_{3-6}$cycloalkyl, $Het^2$ and $C_{1-4}$alkyl-$Het^3$;

$R^8$ is H or $C_{1-4}$ alkyl;

Het, $Het^1$, $Het^2$ and $Het^3$ independently represent a 4 to 7 membered saturated heterocyclic group which may be mono- or bi-cyclic and which contains one or more heteroatoms selected from N, O or S, optionally substituted with $OR^9$ and/or $C_{1-4}$ alkyl optionally substituted by $OR^9$;

$Het^4$ represents a 5 or 6 membered unsaturated heterocyclic group containing one or more heteroatoms selected from N, O or S, optionally substituted with $C_{1-4}$ alkyl;

$R^9$ is H or $C_{1-4}$ alkyl;

$R^{10}$ and $R^{11}$ are independently selected from H and $C_{1-4}$ alkyl.

In the above definitions alkyl, alkoxy and cycloalkyl groups containing the requisite number of carbon atoms, except where indicated, can be unbranched- or branched-chain. Examples of alkyl groups include methyl, ethyl, n-propyl, i-propyl, n-butyl, i-butyl, sec-butyl and t-butyl. Examples of alkoxy groups include methoxy, ethoxy, n-propoxy, i-propoxy, n-butoxy, i-butoxy, sec-butoxy and t-butoxy. Examples of cycloalkyl groups include cyclopropyl, cyclobutyl, cyclopentyl and cyclohexyl.

Unless otherwise provided herein:

WSCDI means 1-(3-dimethylaminopropyl)-3-ethylcarbodiimide hydrochloride;

DCC means N,N'-dicyclohexylcarbodiimide;

HOAT means 1-hydroxy-7-azabenzotriazole;

HOBT means 1-hydroxybenzotriazole hydrate;

PyBOP® means Benzotriazol-1-yloxytris(pyrrolidino)phosphonium hexafluorophosphate;

PyBrOP® means bromo-tris-pyrrolidino-phosphonium hexafluorophosphate;

Mukaiyama's reagent means 2-chloro-1-methylpyridinium iodide;

KHMDS means potassium bis(trimethylsilyl)amide;

Hünig's base means N-ethyldiisopropylamine;

$Et_3N$ means triethylamine;

NMM means N-methylmorpholine;

DEAD means diethyl azodicarboxylate;

DIAD means diisopropyl azodicarboxylate;

DIBAL-H means diisobutylaluminium hydride;

BINAP means 2,2'-bis(diphenylphosphino)-1,1'-binaphthyl;

Dba means dibenzylideneacetone;

Boc means tert-butoxycarbonyl;

CBz means benzyloxycarbonyl;

$(Boc)_2O$ means di-tert-butyl dicarbonate;

MeOH means methanol, EtOH means ethanol, and EtOAc means ethyl acetate;

THF means tetrahydrofuran, DMSO means dimethyl sulphoxide, and DCM means dichloromethane;

AcOH means acetic acid, TFA means trifluoroacetic acid;

TFAA means trifluoroacetic anhydride and NMMO means 4-methylmorpholine N-oxide monohydrate.

The pharmaceutically acceptable salts of the compounds of the formula (I) include the acid addition and base salts thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and palmoate salts.

Suitable base salts are formed from bases which form non-toxic salts and examples are the sodium, potassium, aluminium, calcium, magnesium, zinc and diethanolamine salts. For a review on suitable salts see Berge et al, J. Pharm. Sci, 66, 1–19, 1977.

The pharmaceutically acceptable solvates of the compounds of the formula (I) or salts thereof include the hydrates thereof.

Also included within the present scope of the compounds of the formula (I) are polymorphs thereof.

A compound of the formula (I) may contain one or more asymmetric carbon atoms and therefore exist in two or more stereoisomeric forms. The present invention includes the individual stereoisomers of the compounds of formula (I) along with the individual tautomeric forms (1a, 1b and 1c) thereof, together with mixtures thereof.

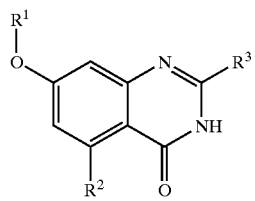

1a

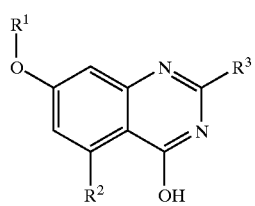

1b

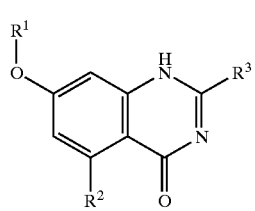

1c

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of a compound of the formula (I) or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts there of include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^{3}H$ or $^{14}C$ is incorporated, are useful in drug and/or substrate tissue distribution studies. Tritiated, i.e. $^{3}H$, and carbon-14, i.e. $^{14}C$, isotopes are particularly preferred for their ease of preparation and detectability. Further, substitution with isotopes such as deuterium, i.e. $^{2}H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof of this invention can generally be prepared by conventional procedures such as by the illustrative methods or by the preparations described in the Examples and Preparations hereafter using appropriate isotopic variations of suitable reagents.

Preferred groups of compounds that may be mentioned include those in which:

$Het^{1}$, $Het^{2}$ and $Het^{3}$ contain at least one N atom and are linked to L through an N atom.

More preferred groups of compounds include those in which:

$Het^{1}$, $Het^{2}$ and $Het^{3}$ include azetidine, pyrrolidine, piperidine, piperazine, azepane, morpholine, homomorpholine, or one of the following ring systems:

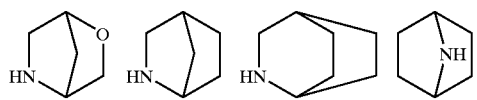

optionally substituted by $OR^{9}$ and/or $C_{1-4}$ alkyl optionally substituted by $OR^{9}$.

Still more preferred groups of compounds that may be mentioned include those in which:

(a) $R^{1}$ is $CH_{3}$;
(b) $R^{2}$ is cyclopropyl;
(c) L is methylene;
(d) $R^{3}$ represents a group chosen from a or b (bonded to the quinazolinone through the N-atom as indicated)

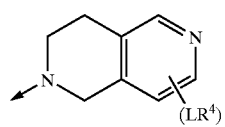

a

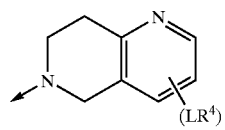

b where $LR^{4}$ is $CH_{2}Het^{1}$ or $CH_{2}NR^{5}R^{6}$ and $Het^{1}$, $R^{5}$ and $R^{6}$ are as hereinbefore defined;

(e) $Het^{1}$ represents an N-linked morpholinyl
(f) $R^{5}$ and $R^{6}$ are independently selected from H or $C_{1-3}$ alkyl optionally substituted by $OCH_{3}$;
(g) $Het^{1}$, $Het^{2}$ and $Het^{3}$ are selected from the group comprising pyrrolidine, piperidine, morpholine or

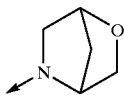

Compounds that may be prepared according to the invention, amongst others, are:

5-cyclopropyl-7-methoxy-2-(2-(4-methoxypiperidin-1-ylmethyl)-7,8-dihydro[1,6]naphthyridin-6(5H)-yl)-4(3H)-quinazolinone;
5-cyclopropyl-7-methoxy-2-(2-([dimethylamino]methyl)-7,8-dihydro[1,6]naphthyridin-6(5H)-yl)-4(3H)-quinazolinone;
5-cyclopropyl-7-methoxy-2-(2-(1-pyrrolidinylmethyl)-7,8-dihydro[1,6]naphthyridin-6(5H)-yl)-4(3H)-quinazolinone;
5-cyclopropyl-7-methoxy-2-(2-(4-morpholinylmethyl)-7,8-dihydro[1,6]naphthyridin-6(5H)-yl)-4(3H)-quinazolinone;
5-cyclopropyl-7-methoxy-2-(5-([dimethylamino]methyl)-3,4-dihydro[2,6]naphthyridin-2(1H)-yl)-4(3H)-quinazolinone;
5-cyclopropyl-7-methoxy-2-(5-(1-pyrrolidinylmethyl)-3,4-dihydro[2,6]naphthyridin-2(1H)-yl)-4(3H)-quinazolinone;
5-cyclopropyl-7-methoxy-2-(5-(1-piperidinylmethyl)-3,4-dihydro[2,6]naphthyridin-2(1H)-yl)-4(3H)-quinazolinone;
5-cyclopropyl-7-methoxy-2-(5-(4-morpholinylmethyl)-3,4-dihydro[2,6]naphthyridin-2(1H)-yl)-4(3H)-quinazolinone;
5-cyclopropyl-7-methoxy-2-(5-[(1S,4S)-2-oxa-5-azabicyclo[2.2.1]hept-5-ylmethyl]-3,4-dihydro[2,6]naphthyridin-2(1H)-yl)-4(3H)-quinazolinone;
5-cyclopropyl-7-methoxy-2-(2-[(1S,4S)-2-oxa-5-azabicyclo[2.2.1]hept-5-ylmethyl]-7,8-dihydro[1,6]naphthyridin-6(5H)-yl)-4(3H)-quinazolinone;
5-cyclopropyl-7-methoxy-2-[3-(morpholin-4-ylmethyl)-5,6-dihydroimidazo[1,5-a]pyrazin-7(8H)-yl]-4(3H)-4(3H)-quinazolinone;
5-cyclopropyl-2-[3-(hydroxymethyl)-5,6-dihydroimidazo[1,5-a]pyrazin-7(8H)-yl]-7-methoxy-4(3H)-quinazolinone;
5-cyclopropyl-7-methoxy-2-[3-(4-methoxypiperidin-1-yl)-5,6-dihydroimidazo[1,5-a]pyrazin-7(8H)-yl]-4(3H)-quinazolinone;
5-cyclobutyl-7-methoxy-2-[2-(morpholin-4-ylmethyl)-7,8-dihydro-1,6-naphthyridin-6(5H)-yl]-4(3H)-quinazolinone;
2-(7,8-dihydro-1,6-naphthyridin-6(5H)-yl)-5-isopropyl-7-methoxy-4(3H)-quinazolinone;
5-isopropyl-7-methoxy-2-[5-(morpholin-4-ylmethyl)-3,4-dihydroiso-4(3H)-quinolin-2(1H)-yl]-4(3H)-quinazolinone;
5-isopropyl-7-methoxy-2-[2-[(pyridin-2-ylmethyl)amino]-7,8-dihydro-1,6-naphthyridin-6(5H)-yl]-4(3H)-quinazolinone;
N-{2-[5-(cyclobutyloxy)-7-methoxy-4-oxo-3,4-dihydro-2-quinazolinyl]-1,2,3,4-tetrahydro-5-iso-4(3H)-quinolinyl}methanesulfonamide;
2-(7,8-dihydro-1,6-naphthyridin-6(5H)-yl)-5-isopropoxy-7-methoxy-4(3H)-quinazolinone;
5-isopropoxy-7-methoxy-2-[2-[(2-methoxyethyl)amino]-7,8-dihydro-1,6-naphthyridin-6(5H)-yl]-4(3H)-quinazolinone;
5-(cyclobutyloxy)-2-[5-[(diethylamino)methyl]-3,4-dihydroiso-4(3H)-quinolin-2(1H)-yl]-7-methoxy-4(3H)-quinazolinone;
2-(7,8-dihydro-1,6-naphthyridin-6(5H)-yl)-7-methoxy-5-(tetrahydrofuran-3-yloxy)-4(3H)-quinazolinone;
7-methoxy-2-[2-[(2-methoxyethyl)amino]-7,8-dihydro-1,6-naphthyridin-6(5H)-yl]-5-(tetrahydrofuran-3-yloxy)-4(3H)-quinazolinone;
7-methoxy-2-[2-[(pyridin-2-ylmethyl)amino]-7,8-dihydro-1,6-naphthyridin-6(5H)-yl]-5-(tetrahydrofuran-3-yloxy)-4(3H)-quinazolinone;
2-(7,8-dihydro-1,6-naphthyridin-6(5H)-yl)-7-methoxy-5-(2-methoxyethoxy)-4(3H)-quinazolinone;
7-methoxy-5-(2-methoxyethoxy)-2-[5-[(pyridin-2-ylmethyl)amino]-3,4-dihydro-2,6-naphthyridin-2(1H)-yl]-4(3H)-quinazolinone;
7-methoxy-5-(2-methoxyethoxy)-2-[2-[(2-methoxyethyl)amino]-7,8-dihydro-1,6-naphthyridin-6(5H)-yl]-4(3H)-quinazolinone;
7-methoxy-5-(2-methoxyethoxy)-2-[2-[(pyridin-2-ylmethyl)amino]-7,8-dihydro-1,6-naphthyridin-6(5H)-yl]-4(3H)-quinazolinone;
5-(cyclopropylmethoxy)-2-(7,8-dihydro-1,6-naphthyridin-6(5H)-yl)-7-methoxy-4(3H)-quinazolinone;
5-(cyclopropylmethoxy)-7-methoxy-2-[5-[(pyridin-2-ylmethyl)amino]-3,4-dihydro-2,6-naphthyridin-2(1H)-yl]-4(3H)-quinazolinone;
5-(cyclopropylmethoxy)-7-methoxy-2-[2-[(pyridin-2-ylmethyl)amino]-7,8-dihydro-1,6-naphthyridin-6(5H)-yl]-4(3H)-quinazolinone;
5-isopropoxy-7-methoxy-2-[2-[(pyridin-2-ylmethyl)amino]-7,8-dihydro-1,6-naphthyridin-6(5H)-yl]-4(3H)-quinazolinone;
5-cyclopropyl-7-methoxy-2-[5-{[(3R)-1-methylpyrrolidin-3-yl]oxy}-3,4-dihydroiso-4(3H)-quinolin-2(1H)-yl]-4(3H)-quinazolinone;
5-cyclopropyl-7-methoxy-2-[5-{[(3S)-1-methylpyrrolidin-3-yl]oxy}-3,4-dihydroiso-4(3H)-quinolin-2(1H)-yl]-4(3H)-quinazolinone;
5-cyclopropyl-7-methoxy-2-[5-{[(2S)-1-methylpyrrolidin-2-yl]methoxy}-3,4-dihydroiso-4(3H)-quinolin-2(1H)-yl]-4(3H)-quinazolinone;
5-cyclopropyl-7-methoxy-2-[5-{[(2R)-1-methylpyrrolidin-2-yl]methoxy}-3,4-dihydroiso-4(3H)-quinolin-2(1H)-yl]-4(3H)-quinazolinone;
5-cyclopropyl-7-methoxy-2-(2-methyl-7,8-dihydro-1,6-naphthyridin-6(5H)-yl)-4(3H)-quinazolinone;
5-cyclopropyl-7-methoxy-2-[2-(1-methylpiperidin-4-yl)-7,8-dihydro-1,6-naphthyridin-6(5H)-yl]-4(3H)-quinazolinone;
5-cyclopropyl-2-[2-{[(2-hydroxyethyl)amino]methyl}-7,8-dihydro-1,6-naphthyridin-6(5H)-yl]-7-methoxy-4(3H)-quinazolinone;
5-cyclopropyl-7-methoxy-2-[2-{[(2-methoxyethyl)(methyl)amino]methyl}-7,8-dihydro-1,6-naphthyridin-6(5H)-yl]-4(3H)-quinazolinone;
5-cyclopropyl-7-methoxy-2-[5-[(3-methoxyazetidin-1-yl)methyl]-3,4-dihydro-2,6-naphthyridin-2(1H)-yl]-4(3H)-quinazolinone;
5-cyclopropyl-7-methoxy-2-[5-{[(3S)-3-methoxypyrrolidin-1-yl]methyl}-3,4-dihydro-2,6-naphthyridin-2(1H)-yl]-4(3H)-quinazolinone;
5-cyclopropyl-7-methoxy-2-[5-[(1R,4R)-2-oxa-5-azabicyclo[2.2.1]hept-5-ylmethyl]-3,4-dihydro-2,6-naphthyridin-2(1H)-yl]-4(3H)-quinazolinone;
5-cyclopropyl-7-methoxy-2-[2-{[[(1S)-2-methoxy-1-methylethyl](methyl)amino]methyl}-7,8-dihydropyrido[4,3-d]pyrimidin-6(5H)-yl]-4(3H)-quinazolinone;
5-cyclopropyl-7-methoxy-2-[2-[(4-methoxypiperidin-1-yl)methyl]-7,8-dihydropyrido[4,3-d]pyrimidin-6(5H)-yl]-4(3H)-quinazolinone;

5-cyclopropyl-2-[3-(cyclopropylmethyl)-5,6-dihydroimidazo[1,5-a]pyrazin-7(8H)-yl]-7-methoxy-4(3H)-quinazolinone;

5-cyclopropyl-7-methoxy-2-(3-morpholin-4-yl-5,6-dihydroimidazo[1,5-a]pyrazin-7(8H)-yl)-4(3H)-quinazolinone;

5-cyclopropyl-7-methoxy-2-[2-[(1S,4S)-2-oxa-5-azabicyclo[2.2.1]hept-5-ylmethyl]-7,8-dihydro-1,6-naphthyridin-6(5H)-yl]-4(3H)-quinazolinone;

5-cyclohexyl-7-methoxy-2-[2-(morpholin-4-ylmethyl)-7,8-dihydro-1,6-naphthyridin-6(5H)-yl]-4(3H)-quinazolinone;

5-isopropyl-7-methoxy-2-[2-[(2-methoxyethyl)amino]-7,8-dihydro-1,6-naphthyridin-6(5H)-yl]-4(3H)-quinazolinone;

5-isopropyl-7-methoxy-2-[5-(morpholin-4-ylmethyl)-3,4-dihydro-2,6-naphthyridin-2(1H)-yl]-4(3H)-quinazolinone dihydrochloride;

5-isopropyl-7-methoxy-2-[5-{[(2-methoxyethyl)(methyl)amino]methyl}-3,4-dihydro-2,6-naphthyridin-2(1H)-yl]-4(3H)-quinazolinone dihydrochloride;

5-isopropyl-7-methoxy-2-[2-(pyrrolidin-1-ylmethyl)-7,8-dihydropyrido[4,3-d]pyrimidin-6(5H)-yl]-4(3H)-quinazolinone dihydrochloride;

2-(5-amino-3,4-dihydro-2,6-naphthyridin-2(1H)-yl)-5-isopropyl-7-methoxy-4(3H)-quinazolinone dihydrochloride;

2-[4-amino-2-[(2-methoxyethyl)amino]-7,8-dihydropyrido[4,3-d]pyrimidin-6(5H)-yl]-5-isopropyl-7-methoxy-4(3H)-quinazolinone dihydrochloride;

5-isopropyl-7-methoxy-2-[2-(methylamino)-7,8-dihydro-1,6-naphthyridin-6(5H)-yl]-4(3H)-quinazolinone dihydrochloride;

2-[4-[ethyl(methyl)amino]-5,8-dihydropyrido[3,4-d]pyrimidin-7(6H)-yl]-5-isopropyl-7-methoxy-4(3H)-quinazolinone dihydrochloride;

5-isopropyl-7-methoxy-2-[5-[(3-methoxyazetidin-1-yl)methyl]-3,4-dihydroiso-4(3H)-quinolin-2(1H)-yl]-4(3H)-quinazolinone dihydrochloride;

5-isopropyl-7-methoxy-2-[5-[(pyridin-2-ylmethyl)amino]-3,4-dihydro-2,6-naphthyridin-2(1H)-yl]-4(3H)-quinazolinone dihydrochloride;

5-isopropyl-7-methoxy-2-[5-{[(2-methoxyethyl)amino]methyl}-3,4-dihydroiso-4(3H)-quinolin-2(1H)-yl]-4(3H)-quinazolinone dihydrochloride;

2-[5-{[2-(dimethylamino)ethyl]amino}-3,4-dihydro-2,6-naphthyridin-2(1H)-yl]-5-isopropyl-7-methoxy-4(3H)-quinazolinone trihydrochloride;

2-[5-[(dimethylamino)methyl]-3,4-dihydroiso-4(3H)-quinolin-2(1H)-yl]-5-isopropyl-7-methoxy-4(3H)-quinazolinone dihydrochloride;

2-[4-amino-2-(dimethylamino)-5,8-dihydropyrido[3,4-d]pyrimidin-7(6H)-yl]-5-isopropyl-7-methoxy-4(3H)-quinazolinone dihydrochloride;

2-[2-(dimethylamino)-4-[(2-methoxyethyl)amino]-5,8-dihydropyrido[3,4-d]pyrimidin-7(6H)-yl]-5-isopropyl-7-methoxy-4(3H)-quinazolinone trihydrochloride;

5-isopropyl-7-methoxy-2-[5-[(4-methoxypiperidin-1-yl)methyl]-3,4-dihydro-2,6-naphthyridin-2(1H)-yl]-4(3H)-quinazolinone dihydrochloride;

5isopropyl-7-methoxy-2-[5-[(3-methoxyazetidin-1-yl)methyl]-3,4-dihydro-2,6-naphthyridin-2(1H)-yl]-4(3H)-quinazolinone dihydrochloride;

5-isopropyl-7-methoxy-2-[2-(morpholin-4-ylmethyl)-7,8-dihydropyrido[4,3-d]pyrimidin-6(5H)-yl]-4(3H)-quinazolinone dihydrochloride;

2-[5-[(dimethylamino)methyl]-3,4-dihydro-2,6-naphthyridin-2(1H)-yl]-5-isopropyl-7-methoxy-4(3H)-quinazolinone dihydrochloride;

2-[2-{[2-(dimethylamino)ethyl]amino}-7,8-dihydro-1,6-naphthyridin-6(5H)-yl]-5-isopropyl-7-methoxy-4(3H)-quinazolinone trihydrochloride;

5-isopropyl-7-methoxy-2-[5-[(2-methyl-1H-imidazol-1-yl)methyl]-3,4-dihydroiso-4(3H)-quinolin-2(1H)-yl]-4(3H)-quinazolinone dihydrochloride;

7-methoxy-2-[2-{[(2-methoxyethyl)(methyl)amino]methyl}-7,8-dihydropyrido[4,3-d]pyrimidin-6(5H)-yl]-5-tetrahydro-2H-pyran-4-yl-4(3H)-quinazolinone dihydrochloride;

7-methoxy-2-[2-(pyrrolidin-1-ylmethyl)-7,8-dihydropyrido[4,3-d]pyrimidin-6(5H)-yl]-5-tetrahydro-2H-pyran-4-yl-4(3H)-quinazolinone dihydrochloride;

2-(2-[(dimethylamino)methyl]-7,8-dihydropyrido[4,3d]pyrimidin-6(5H)-yl)-7-methoxy-5-tetrahydro-2H-pyran-4-yl-4(3H)-quinazolinone dihydrochloride;

7-methoxy-2-[5-(pyrrolidin-1-ylmethyl)-3,4-dihydro-2,6-naphthyridin-2(1H)-yl]-5-tetrahydro-2H-pyran-4-yl-4(3H)-quinazolinone dihydrochloride;

2-(5,6-dihydroimidazo[1,5-a]pyrazin-7(8H)-yl)-7-methoxy-5-tetrahydro-2H-pyran-4-yl-4(3H)-quinazolinone hydrochloride;

7-methoxy-2-[5-(morpholin-4-ylmethyl)-3,4-dihydro-2,6-naphthyridin-2(1H)-yl]-5-tetrahydro-2H-pyran-4-yl-4(3H)-quinazolinone dihydrochloride;

2-[5-[(dimethylamino)methyl]-3,4-dihydro-2,6-naphthyridin-2(1H)-yl]-7-methoxy-5-tetrahydro-2H-pyran-4-yl-4(3H)-quinazolinone dihydrochloride;

7-methoxy-2-[5-(morpholin-4-ylmethyl)-3,4-dihydroiso-4(3H)-quinolin-2(1H)-yl]-5-tetrahydro-2H-pyran-4-yl-4(3H)-quinazolinone dihydrochloride;

7-methoxy-2-[5-[(3-methoxyazetidin-1-yl)methyl]-3,4-dihydroiso-4(3H)-quinolin-2(1H)-yl]-5-tetrahydro-2H-pyran-4-yl-4(3H)-quinazolinone dihydrochloride;

7-methoxy-2-[2-[(2-pyrrolidin-1-ylethyl)amino]-7,8-dihydro-1,6-naphthyridin-6(5H)-yl]-5-tetrahydrofuran-2-yl-4(3H)-quinazolinone trihydrochloride;

7-methoxy-2-[2-[(2-methoxyethyl)amino]-7,8-dihydro-1,6-naphthyridin-6(5H)-yl]-5-tetrahydrofuran-2-yl-4(3H)-quinazolinone dihydrochloride;

2-[2-{[2-(dimethylamino)ethyl]amino}-7,8-dihydro-1,6-naphthyridin-6(5H)-yl]-7-methoxy-5-tetrahydrofuran-2-yl-4(3H)-quinazolinone trihydrochloride;

2-(5-amino-3,4-dihydro-2,6-naphthyridin-2(1H)-yl)-7-methoxy-5-tetrahydrofuran-2-yl-4(3H)-quinazolinone trihydrochloride;

5-chloro-7-methoxy-2-[2-(pyrrolidin-1-ylmethyl)-7,8-dihydropyrido[4,3-d]pyrimidin-6(5H)-yl]-4(3H)-quinazolinone dihydrochloride;

5-chloro-7-methoxy-2-(5-[(1S,4S)-2-oxa-5-azabicyclo[2.2.1]hept-5-ylmethy]-3,4-dihydro[2,6]naphthyridin-2(1H)-yl)-4(3H)-quinazolinone dihydrochloride;

5-cyclopropyl-2-[2-{[ethyl(2-methoxyethyl)amino]methyl}-7,8-dihydropyrido[4,3-d]pyrimidin-6(5H)-yl]-7-methoxy-4(3H)-quinazolinone dihydrochloride;

2-[2-(aminomethyl)-7,8-dihydro-1,6-naphthyridin-6(5H)-yl]-5-isopropyl-7-methoxy-4(3H)-quinazolinone dihydrochloride;

2-(7,8-dihydro-1,6-naphthyridin-6(5H)-yl)-7-methoxy-5-(1-methylpiperidin-2-yl)-4(3H)-quinazolinone trihydrochloride;

2-(6,7-dimethoxy-3,4-dihydroiso-4(3H)-quinolin-2(1H)-yl)-7-methoxy-5-(1-methylpiperidin-2-yl)-4(3H)-quinazolinone dihydrochloride;

7-methoxy-2-[2-[(2-methoxyethyl)amino]-7,8-dihydro-1,6-naphthyridin-6(5H)-yl]-5-(1-methylpiperidin-2-yl)-4(3H)-quinazolinone trihydrochloride;

5-(butylsulfonyl)-7-methoxy-2-[5-[(2-methoxyethyl)
amino]-3,4-dihydro-2,6-naphthyridin-2(1H)-yl]-4(3H)-
quinazolinone;

5-(butylsulfonyl)-7-methoxy-2-[5-[(pyridin-2-ylmethyl)
amino]-3,4-dihydro-2,6-naphthyridin-2(1H)-yl]-4(3H)-
quinazolinone;

5-isopropyl-7-methoxy-2-[1-(2-pyrrolidin-1-ylethyl)-1,4,6,
7-tetrahydro-5H-pyrazolo[4,3-c]pyridin-5-yl]-4(3H)-
quinazolinone;

5-isopropyl-7-methoxy-2-[2-(2-pyrrolidin-1-ylethyl)-2,4,6,
7-tetrahydro-5H-pyrazolo[4,3-c]pyridin-5-yl]-4(3H)-
quinazolinone;

5-chloro-7-methoxy-2-[5-(pyrrolidin-1-ylmethyl)-3,4-
dihydro-2,6-naphthyridin-2(1H)-yl]-4(3H)-
quinazolinone;

5-isopropyl-7-methoxy-2-[2-(4-methylpiperazin-1-yl)-7,8-
dihydro-1,6-naphthyridin-6(5H)-yl]-4(3H)-
quinazolinone trihydrochloride;

5-Isopropyl-7-methoxy-2-(5-methylaminomethyl-3,4-
dihydro-1H-[2,6]naphthyridin-2-yl)-3H-quinazolin-4-
one dihydrochloride;

and pharmaceutically acceptable salts or solvates thereof.

The compounds of the invention are useful because they possess pharmacological activity in animals. In particular, the compounds are useful in the treatment of a number of conditions including hypertension, myocardial infarction, male erectile dysfunction, hyperlipidaemia, cardiac arrhythmia, glaucoma and benign prostatic hyperplasia. They may also be useful in the treatment of female sexual arousal dysfunction. Benign prostatic hyperplasia is of greatest interest.

Thus, according to another aspect of the invention, there is provided a pharmaceutical composition including a compound of the formula (I), a tautomer, or a pharmaceutically acceptable salt or solvate thereof, together with a pharmaceutically acceptable excipient, diluent or carrier. Also provided is a method of treatment of benign prostatic hyperplasia, which comprises administering a therapeutically effective amount of a compound of the invention to a patient suffering from such a disorder. The use of the compounds of the invention as pharmaceuticals, and the use of the compounds of the invention in the manufacture of a medicament for the treatment of benign prostatic hyperplasia, are also provided.

The compounds of the invention may be administered by any convenient route, for example orally, parenterally (e.g. intravenously, transdermally) or rectally. The daily dose required will of course vary with the particular compound used, the particular condition being treated and with the severity of that condition. However, in general a total daily dose of from about 0.01 to 10.0 mg/kg of body weight, and preferably about 0.01 to 2.5 mg/kg, is suitable, administered from 1 to 2 times a day. Oral administration is of particular interest.

The compounds of the invention will generally be administered in the form of a suitable pharmaceutical formulation. Thus, according to another aspect of the invention, there is provided a pharmaceutical formulation including preferably less than 50% by weight of a compound of the invention in admixture with a pharmaceutically acceptable adjuvant, diluent or carrier. The pharmaceutical formulation is preferably in unit dose form. Such forms include solid dosage forms, for example tablets, pills, capsules, powders, granules, and suppositories for oral, parenteral or rectal administration; and liquid dosage forms, for example sterile parenteral solutions or suspensions, suitably flavoured syrups, flavoured emulsions with edible oils such as cotton- seed oil, sesame oil, coconut oil and peanut oil, and elixirs and similar pharmaceutical vehicles. Oral formulations are preferably controlled-release formulations.

Solid formulations may be prepared by mixing the active ingredient with pharmaceutical carriers, for example conventional tabletting ingredients such as corn starch, lactose, sucrose, sorbitol, talc, stearic acid, magnesium stearate, dicalcium phosphate, gums and other diluents, for example water, to form a homogeneous preformulation formulation in which the active ingredient is uniformly dispersed so that it may be readily subdivided into equally effective unit dosage forms containing typically from 1.0 to about 70.0 mg of the active ingredient. The solid dosage forms may be coated or otherwise compounded to prolong the action of the formulation.

Formulations intended for the treatment of benign prostatic hyperplasia may contain a compound of the invention in combination with a compound that attenuates the growth of the prostate gland. For example, a formulation is envisaged that combines a compound of the invention with human 5-α reductase inhibitory compound [see International Patent Application WO 95/28397]. Alternatively, a compound of the invention could be presented in a pharmaceutical pack also containing a human 5-α reductase inhibitory compound as a combined preparation for simultaneous, separate or sequential use.

The compounds of the invention may be tested in the screen set out below:

Contractile Responses of Rabbit Aorta ($\alpha_{1L}$ Receptor)

A single rabbit aorta was cleaned of connective tissue, cut into rings ~3 mm in length, then denuded of epithelium by rubbing very gently with a probe. The lengths of tissue are then mounted in the 5 mL organ baths, which contain the modified Krebs of the following composition (mM): NaCl (119), KCl (4.7), $CaCl_2$ (2.5), $KH_2PO_4$ (1.2), $MgSO_4$ (1.2), $NaHCO_3$ (25), glucose (11), and gassed with 95% $O_2$/5% $CO_2$. The tissues are placed under ~1.5 g tension, and are left to equilibrate for ~60 minutes on a pump speed of ~5 mL\minute, adjusting the tension to 1–1.5 g if necessary after 15 and 45 minutes. A 1M stock solution ($1\times10^{-3}$M bath conc.) of methoxamine in water was made and 1:10 dilutions made using the same diluent. A sensitising dose of 120 mM KCl (bath concentration) was added to each bath. After the maximum response had been reached (usually about 6–8 minutes), the tissues are washed with Krebs solution for 60 minutes, pump speed at ~2.97 mL/min.

A cumulative dose response curve was constructed, bath concentrations of methoxamine being $1\times10^{-7}$M to a maximum of $3\times10^{-4}$M. Each dose was allowed to exert its maximum effect before the next dose was added (6–8 mins). On completion of this curve, the tissues were washed, (pump speed ~10 mL/min for 10 minutes, 2.97 mL/min for 50 minutes) until the tissues were stable at baseline tension.

The compound under investigation was made up to a stock concentration of 1 mM in 100% DMSO. Three chosen concentrations for a $pA_2$ estimation were then made up in DMSO, and 5 μl of each concentration added in duplicate to the tissues, with a vehicle control (DMSO). The tissues were left in the presence of compound or vehicle for 60 minutes before a second CDRC to methoxamine was constructed up to a maximum of $3\times10^{-3}$M The data was captured on ADA analysis in-vitro software, which expresses the readings as a % of the maximum response of the control curve, draws control and test compound dose response curves, and calculates a $EC_{50}$ and then dose ratio (DR), the ratio between control and treatment curve $EC_{50}$, for each treatment. The results are reported as $pK_b$, or where possible $pA_2$.

$$pKb = -\log\frac{[\text{Antagonist concentration}]}{(DR^* - 1)}$$

$$\text{where } DR^* = \frac{\text{dose ratio compound}}{\text{dose ratio control}}$$

NB. If the value of (DR*−1) was less than or equal to 2, the result could not be used for a pA$_2$ estimation. The control curves must not have shifted by more than 2.5. The pA$_2$ was plotted on a Schild analysis. i.e. y axis=log (DR*−1); x axis=−log antagonist concentration The compounds of the invention may have the advantage that they are more potent, have a longer duration of action, have a broader range of activity, are more stable, have fewer side effects or are more selective (in particular they may have beneficial effects in benign prostatic hyperplasia without causing undesirable cardiovascular effects, for example because they are able to selectively antagonise prostatic receptor subtypes of the α$_1$-adrenoceptor), or have other more useful properties than the compounds of the prior art. It will be apparent to those skilled in the art that sensitive functional groups may need to be protected and deprotected during synthesis of a compound of the invention. This may be achieved by conventional techniques, for example as described in 'Protective Groups in Organic Synthesis' by T W Greene and P G M Wuts, John Wiley and Sons Inc, 1991.

The compounds of the invention may be obtained by the reaction of an amine (III) with alkylating agent (II) as shown in the scheme below, where R$^1$, R$^2$, X, Y etc. are as previously defined:

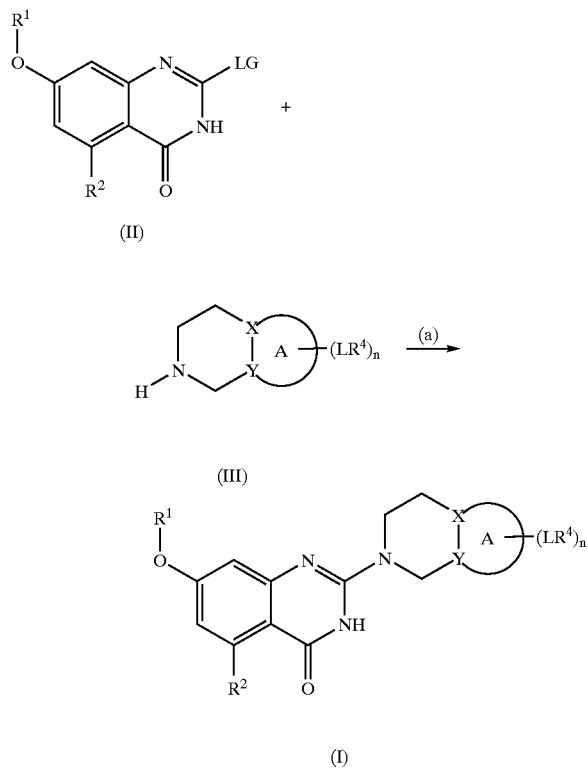

Step (a): Amine (III) is reacted with quinazolinone (II), where LG is a suitable leaving group (for example halo, tosylate or mesylate), in the presence of an excess of 3° amine base (as H$^+$ acceptor) (for example Et$_3$N, Hünig's base or NMM) in a suitable high boiling solvent at elevated temperature for 1–6 hrs. For example, preferred conditions for a) are 1–2 eq. amine (III), 1.5–8 eq. of 3° amine base (for example Et$_3$N or Hünig's base), in n-BuOH at reflux for 1–6 hours. Preferably leaving group LG is Halo. More preferably LG is Cl.

Quinazolinone (II) may be prepared according to scheme 2, where R$^1$ and R$^2$ are as previously defined:

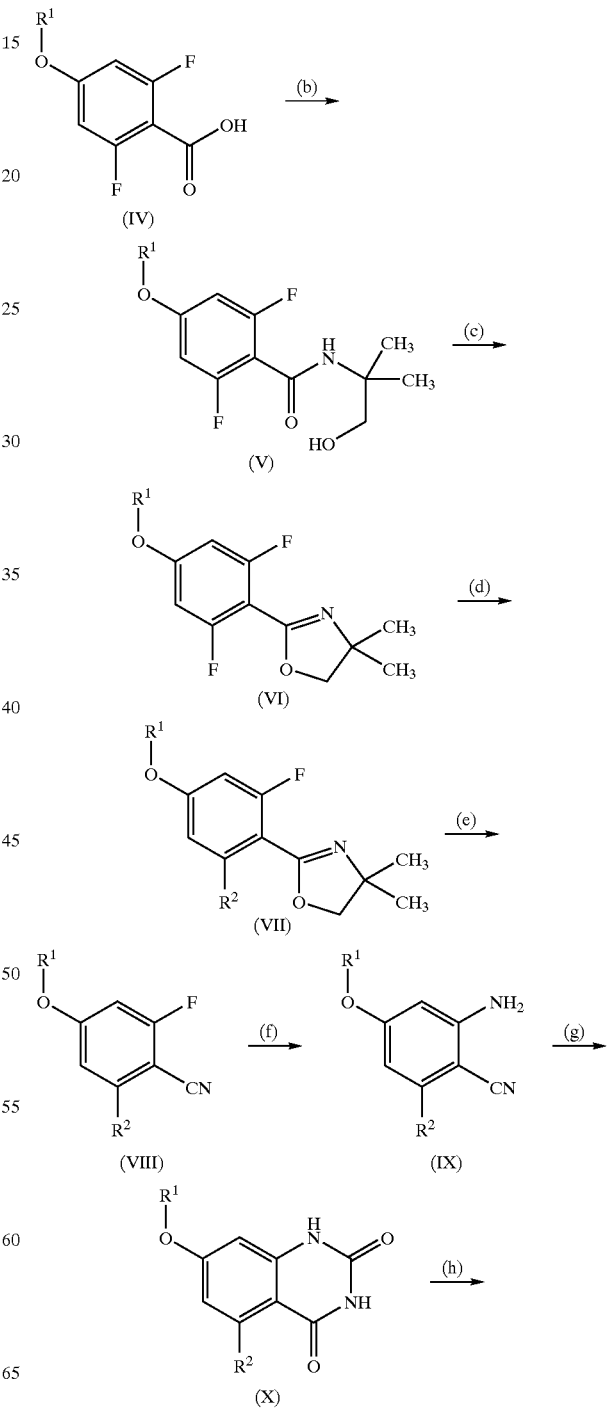

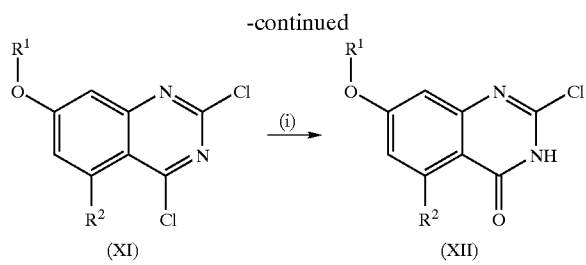

Step (b): This acid/amine coupling may be undertaken by using either (i) an acyl chloride derivative of acid (IV)+amine, with an excess of acid acceptor in a suitable solvent, or (ii) the acid (IV) with a conventional coupling agent+ amine, optionally in the presence of a catalyst, with an excess of acid acceptor in a suitable solvent.

Typically the conditions are as follows:

acid chloride of acid (IV) (generated in-situ), an excess of amine, optionally with an excess of 3° amine such as $Et_3N$, Hünig's base or NMM, in DCM or THF, without heating for 1 to 24 hrs, or (ii) acid (IV), WSCDI/DCC and HOBT/HOAT, an excess of amine, with an excess of NMM, $Et_3N$, Hünig's base in THF, DCM or EtOAc, at rt. for 4 to 48 hrs; or, acid (IV), PYBOP®/PyBrOP®/Mukaiyama's reagent, an excess of amine, with an excess of NMM, $Et_3N$, Hünig's base in THF, DCM or EtOAc, at rt. for 4 to 24 hrs.

The preferred conditions are: acid chloride of acid (IV) (generated in-situ), 3.6 eq. amine, in DCM at r.t. for 1 hr.

Step (c): The hydroxy group of compound (V) is converted into a suitable leaving group (LG, where LG is halo, mesylate, or tosylate), followed by an in-situ alkylation/ring formation.

Typically LG is halo. It is preferred that LG is Cl. Chlorination is carried out under standard conditions, using a chlorinating agent ($SOCl_2$, $POCl_3$) optionally in the presence of a 3° amine base (e.g. Hünig's base, $Et_3N$), optionally in a suitable solvent (DCM) at room temperature to reflux temperature for 1–16 hours. Preferred conditions are: 1.1 eq. $SOCl_2$, in DCM for 1.5 hrs at rt.

Step (d): An organometallic addition/elimination is undertaken by reacting fluoro compound (VI) with "activated" $R^2$ (such as $R^2MgBr$, $R^2MgCl$, $R^2Li$), in a suitable solvent (tetrahydrofuran, ether, cyclohexane, 1,4-dioxane) at 0° C. to room temperature for 1–24 hrs. Preferred conditions are: 1–2 eq. of $R^2MgBr$ or $R^2MgCl$ (generated in-situ, using standard Grignard methodology), 1 eq. of fluoro compound (VI), in tetrahydrofuran, at between 0° C. and room temperature, for 3 hours.

Step (e): The nitrile (VIII) is preferably formed from compound (VII) under the following conditions: 2 eq. $POCl_3$, 10 eq. pyridine, EtOAc, reflux for 5 hours.

Step (f): Amination of compound (VIII) is achieved by reaction with $R^aNH_2$ ($R^a$ is H) at an elevated temperature and pressure, in a suitable solvent (DMSO, MeOH) for about 18–72 hrs. It is preferred to carry out the reaction under the following conditions: $R^aNH_2$ in DMSO at elevated temperature (about 140° C.) and pressure (sealed vessel) for 18–72 hrs.

Step (g): Quinazolinedione (X) is formed by $CO_2$ insertion, derived from the method of Mizuno et. al. Tet. Lett. 41 (2000) 1051. The following conditions are preferred: 2 eq. of DBU (1,8-diazabicyclo[5.4.0]undec-7-ene), $CO_2$ (solid), in N,N-dimethylformamide, at 140° C. and elevated pressure (sealed vessel) for 18 hrs.

Step (h): This chlorination step can be done under standard conditions, using an excess of chlorinating agent ($SOCl_2$, $POCl_3$) optionally in the presence of a 3° amine base (e.g. Hünig's base, $Et_3N$), optionally in a suitable solvent (DCM) at room temperature to reflux temperature for 1–16 hours. It is preferred to use the following conditions: 30 eq. $POCl_3$ (as solvent), optionally in the presence of a base, e.g. 2.4 eq. Hünig's base, at reflux for 1–7 hours Step (i): Selective hydrolysis of compound (XI) is achieved by reaction with an $OH^-$ source (typically an alkali metal hydroxide) in a suitable solvent, at room temperature for 2 hours. Preferred conditions are: 3 eq. NaOH(aq.) in dioxane at room temperature for 2 hours.

Suitable amines for use as compound (III) may be prepared as described below in schemes 3 to 13:

Scheme 3

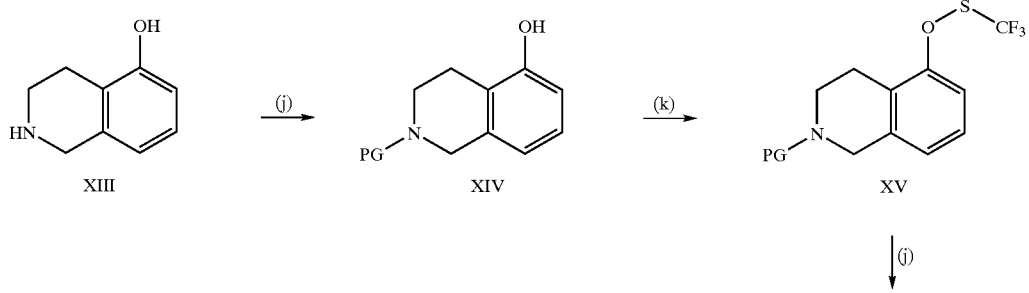

-continued

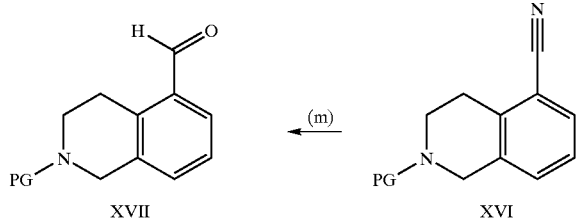

PG = N protecting group

Compounds XVII and XIV can then be further elaborated according to schemes 4 and 5 respectively:

when $R^4$ represents $NR^5R^6$ or an N-linked Het,

Scheme 4.

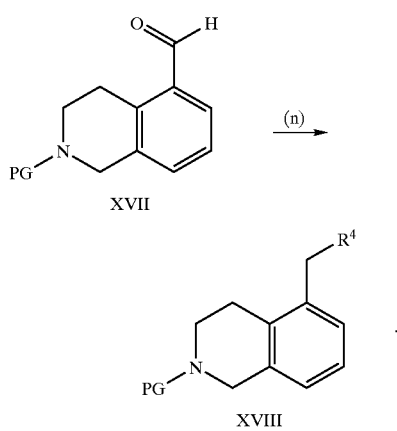

PG = N protecting group

Scheme 5.

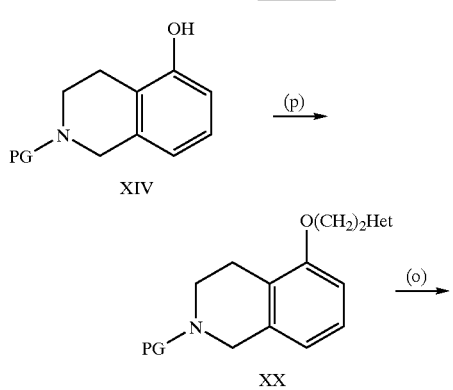

-continued

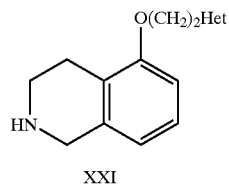

PG = N protecting group

When $R^4$ represents $NR^5R^6$ or N-linked Het, compounds of formula (XIX) may also be prepared according to scheme 6:

Scheme 6

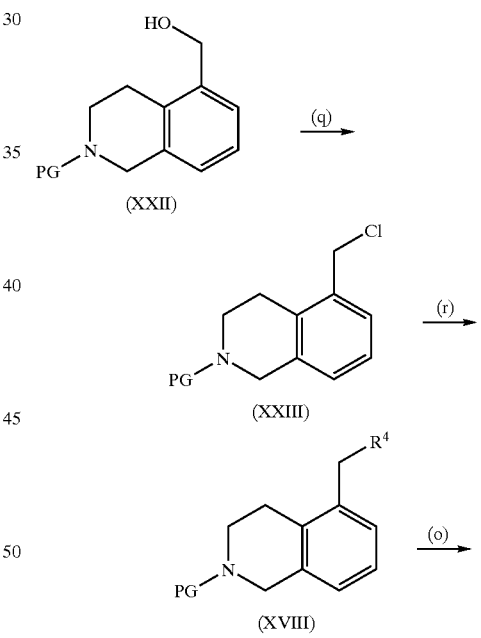

PG = N protecting group

Step (j): The amine (XIII) is protected using standard methodology for introducing nitrogen protecting groups, such as that found in textbooks, (e.g. "Protecting Groups in Organic Synthesis" by T. W. Greene and P. Wutz). It is preferred to use the tert-butoxycarbonyl (Boc) protecting group which is introduced under the following conditions: 2.3 eq. (Boc)$_2$O, in dioxane/1N NaOH solution (1:2 by volume) at room temperature for 16 hrs.

Step (k): Triflate (XV) is formed by reaction of alcohol (XIV) with a slight excess of a suitable triflating reagent, in the presence of an excess of a 3° amine base (e.g. Et$_3$N, NMM, Hünig's base) in a suitable solvent (DCM) at between −30° C. and room temperature for up to 24 hours. Preferred conditions are as follows: 1.1 eq. N-phenylbis (trifluoromethanesulphonimide) or triflic anhydride, 1.1 eq. Et$_3$N, in DCM at 0° C. and room temperature for 2 to 16 hours.

Step (l): Nitrile (XVI) is obtained via metal catalysed (preferably palladium, nickel) cross-coupling with a suitable nitrile source (e.g. Zn(CN)$_2$), in the presence of a suitable additive (preferably LiCl) in a suitable solvent at elevated temperature for up to 24 hrs. It is preferred to use the following conditions: 1 eq. Zn(CN)$_2$, 1 eq. LiCl, cat Pd(PPh$_3$)$_4$, in N,N-dimethylformamide at 110–125° C. for 8 to 24 hrs.

Step (m): Nitrile (XVI) is reduced with a suitable metal hydride reducing agent (LiAlH$_4$, NaAlH$_4$, DIBAL-H) in a suitable solvent (toluene, tetrahydrofuran) at low temp (−78° C.), followed by acid or base catalysed hydrolysis of the intermediate imine compound to give aldehyde (XVII). Preferred conditions are: 2 eq. DIBAL-H, in toluene at −78° C. for 2 hrs, then MeOH, HCl at −78° C. to 0° C.

When PG is benzyl, then the preferred conditions are: 10% Pd/C (1:1 w/w), 2–25 eq. ammonium formate or formic acid, in MeOH at reflux for between 3 mins and 1.5 hrs, or 10% Pd/C (about 10% w/w), in methanol, optionally in the presence of HCl, at about 30° C. and 30 psi for about 17 hrs.

Step (p): A Mitsunobu reaction between alcohol (XIV) and HO(CH$_2$)$_2$Het is carried out using standard methodology, as discussed in Synthesis 1 (1981) or Org. React. 42; 335 (1992). Preferred conditions are: 2.1 eq. DEAD (Diethylazodicarboxylate), 2.25 eq. PPh$_3$, 2.65 eq. of HO(CH$_2$)$_2$Het, in DCM for 34 hrs at rt.

Step q: The alcohol (XXII) (when Prot is Boc, the alcohol may be obtained as described in WO 02/053558) may be chlorinated to provide the chloride (XXIII) using standard methodology, but preferably under non-acidic conditions. Preferred conditions are: 1.2 eq. MeSO$_2$Cl, and 1.5 eq. Et$_3$N, in tetrahydrofuran for 30 mins, followed by 1.5 eq. Bu$_4$NCl, at r.t. for about 2 hours.

Step (r): The chloride (XXIII) is reacted with an amine (R$^5$R$^6$NH) or N-linked Het, in the presence of a suitable base (e.g. alkali metal hydride, such as NaH or LiH) in a suitable solvent (e.g. ether, tetrahydrofuran) at between room temperature and reflux for up to 18 hours to provide compounds of formula (XVIII). Preferred conditions are: 1.05 eq. NaH, 1.1 eq. amine/N-linked Het, in tetrahydrofuran at between r.t. and reflux for 18 hrs.

Scheme 7.

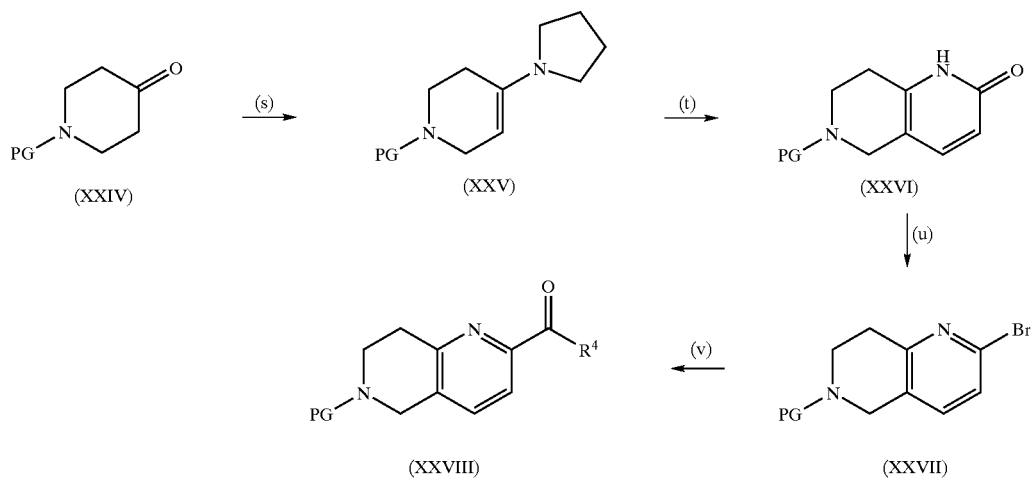

Step (n): Aldehyde (XVII) is reacted with an amine (NR$^5$R$^6$ or N-linked Het) to form an intermediate compound, which is reduced by a suitable reducing agent, such as NaCN(BH)$_3$ or Na(OAc)$_3$BH, optionally in the presence of NaOAc or AcOH, optionally in the presence of a drying agent (molecular sieves, MgSO$_4$) in a suitable solvent (tetrahydrofuran, DCM) at room temperature for 3–72 hrs. Preferred conditions are: 1–2 eq. amine, 2–5 eq. of Na(OAc)$_3$BH, optionally with 1–4 eq. of AcOH or NaOAc, optionally in the presence of 3 Å sieves, in tetrahydrofuran at room temperature for 3–72 hrs.

Step (o): Deprotection is undertaken using standard methodology, as described in "Protecting Groups in Organic Synthesis" by T. W. Greene and P. Wutz".

When PG is Boc, then preferred conditions are: HCl(g) in DCM or MeOH at rt. for 30 min to 2 hrs, or DCM:TFA (1:1 by volume) at room temperature for 3 hrs.

Step (s): Compound (XXIV) is reacted with pyrrolidine, with the concomitant removal of water, in a suitable high boiling solvent, at an elevated temperature for up to 48 hours, to give compound (XXV). The following conditions are preferred: 1.5 eq. pyrrolidine and ketone (XXII) in toluene at reflux under Dean and Stark conditions, for 4.5 hrs.

Step (t): 2 equivalents of propiolamide to 1 equivalent of compound (XXV) in a high boiling solvent (e.g. Toluene) at reflux for 16 hours.

Step (u): Compound (XXVI) is brominated using standard methodology, with a suitable brominating agent (POBr$_3$), optionally in the presence of anisole, in a suitable solvent (MeCN), at elevated temp for about 1 hr. The following conditions are preferred: 5 eq. of POBr$_3$, in MeCN/anisole (1:1 by volume) at 120° C. for 1 hr.

Step (v): Metalation of compound (XXVII) is undertaken with a suitable base (nBuLi) at low temp (−78° C.), followed by quench of the intermediate anion by an excess of carbonyl or formyl source (N,N-dimethylformamide) for about 1 hr, to give the desired compound. Preferred conditions are: 1.1–1.5 eq. n-BuLi, tetrahydrofuran, −78° C., for 5–15 min, then 3 eq N,N-dimethylformamide or R⁴COH for 1 hour.

Compound (XXVIII), when $R^4$ in scheme 7 represents H, can then be further elaborated by reductive amination followed by deprotection in a manner similar to that depicted in scheme 4.

Compounds (XXIX) and (XXVII) can be further elaborated according to schemes 8, 9, 10, and 11 respectively. PG represents a N-protecting group, preferably Bn:

Scheme 8.

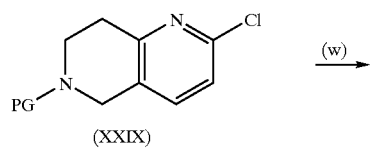

(XXIX)

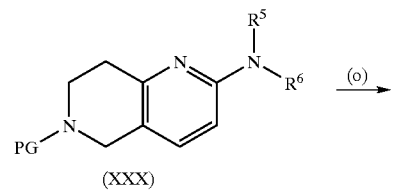

(XXX)

Scheme 10.

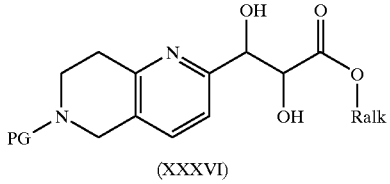

(XXIX)

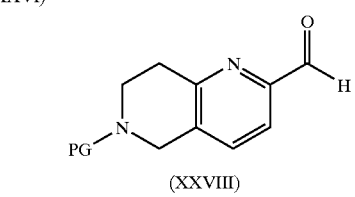

(XXXV)

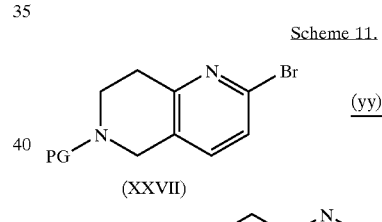

(XXXVI)

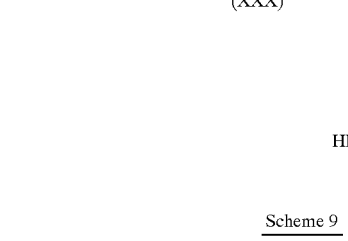

(XXVIII)

PG = N-protecting group
Ralk = $C_1$–$C_4$ alkyl

When Het is linked through N,

Scheme 11.

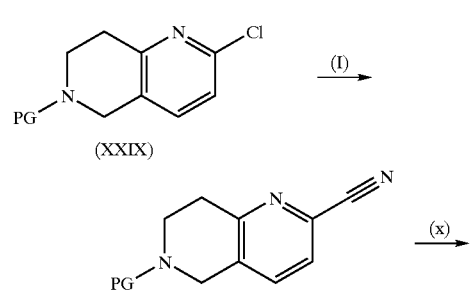

(XXVII)

(XXXVII)

(XXXVIII)

Scheme 9.

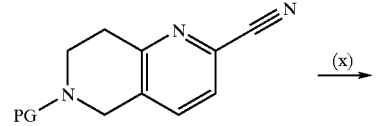

(XXIX)

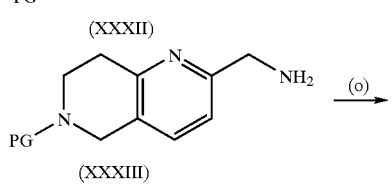

(XXXII)

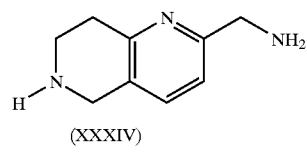

(XXXIII)

(XXXIV)

Compound (XXVI) may be further reacted to provide compounds where Het is linked through C, according to scheme 12:

Scheme 12.

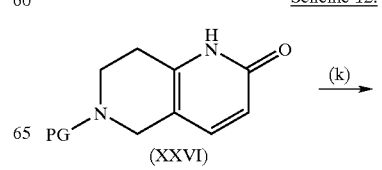

(XXVI)

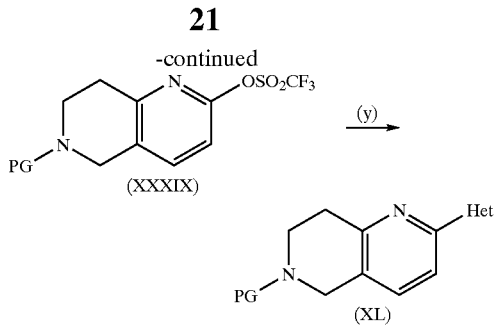

Step (w): Amination of compound (XXIX) (when PG is Bn, obtained as described in WO 9830560) is achieved by reaction with $R^5R^6NH$ at elevated temperature and pressure, optionally in a suitable solvent (DMSO, MeOH) and optionally in the presence of a suitable catalyst, for about 18–72 hrs. It is preferred to carry out the reaction under the following conditions: $R^5R^6NH$ optionally in DMSO at the reflux temperature of the reaction, at elevated pressure (sealed vessel) for 18–72 hrs, optionally in the presence of $CuSO_4$.

Step (x): Reduction of the nitrile (XXXII) to provide the amine (XXXIII) may be achieved using a suitable reducing agent ($LiAlH_4$, $BH_3Me_2S$) or by hydrogenation in the presence of a suitable metal (e.g. Raney® Nickel). Typically the reaction is carried out according to the method of Satoh and Suzuki (Tet. Lett. 4555; 1969). The preferred conditions are: 2 eq. $CoCl_2$, 10 eq. $NaBH_4$ in MeOH at r.t. for up to 2 hrs.

Step (y): A metal (e.g. palladium, nickel or zinc) catalysed cross-coupling reaction is undertaken, optionally using a suitable base (Nat-BuO, $K_2CO_3$ or $Et_3N$), a catalytic amount of suitable additive and metal catalyst in a suitable solvent such as toluene, dioxan or N,N-dimethylformamide at elevated temp for up to 18 hrs, to give the desired compound. The preferred conditions are: 3 eq. vinyl ester, 0.1 eq. $Pd(dba)_3$, 0.3 eq. $P(t-Bu)_3$, excess $Et_3N$ in dioxan at reflux for 17 hrs.

Step (yy): A metal (e.g. palladium, nickel or zinc) catalysed cross-coupling reaction is undertaken, optionally using a suitable base (Nat-BuO, $K_2CO_3$ or $Et_3N$), a catalytic amount of suitable additive and metal catalyst in a suitable solvent such as toluene, dioxan or N,N-dimethylformamide at elevated temp for up to 18 hrs, to give the desired compound. The preferred conditions are: 1.5 eq. Het, (e.g. morpholine), 1.5 eq. Nat-BuO, 0.08 eq BINAP, 0.04 eq. $Pd(dba)_3$, in toluene at 100° C. for 18 hrs.

Step (z): Hydroxylation of compound (XXXV) using a suitable agent, such as $OsO_4$ or $KMnO_4$ optionally in the presence of a suitable oxidant (e.g. NMMO) provides the diol (XXXVI). The preferred conditions are: cat $OsO_4$, 1.1 eq. NMMO in $H_2O$:acetone (1:2 by volume) at r.t. for 72hrs.

Step (aa): The aldehyde (XXVIII) may be obtained from the diol (XXXVI) by oxidation, according to the methods described in Synthesis, 229 (1974).

The preferred conditions are: 1.1 eq. $NaIO_4$, in MeCN at r.t. for 2 hrs.

Scheme 13.

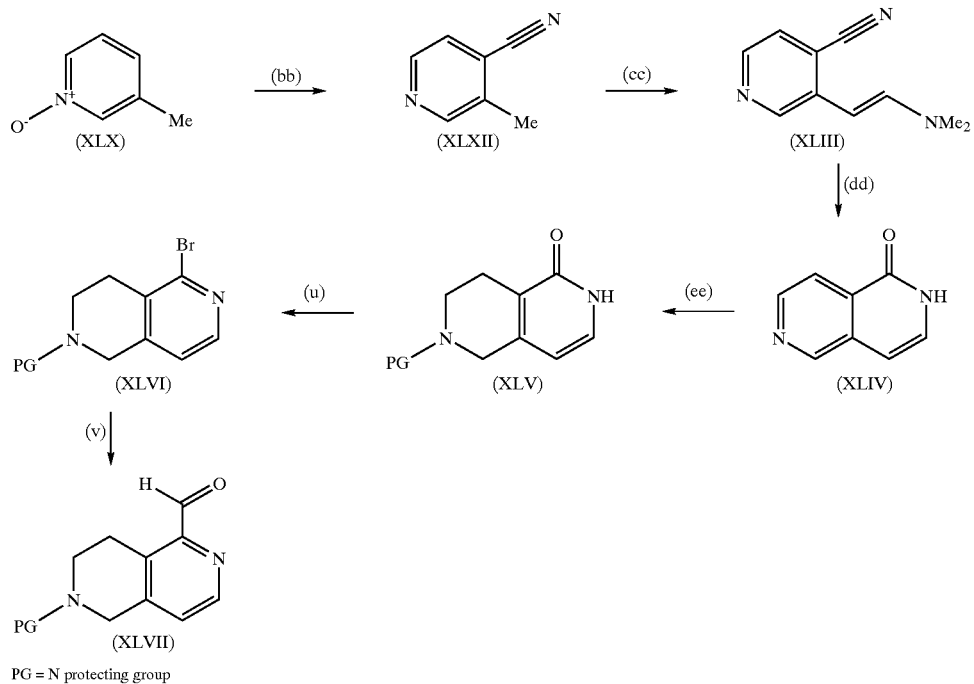

PG = N protecting group

Step (bb): O-alkylation and addition by cyanide is undertaken using the preferred conditions of 3 eq. EtI, in DCM at rt. for 16 hrs, followed by 2 eq. NaCN in $H_2O$ at 60° C. for 1 hr.

Step (cc): Condensation with N,N-dimethylformamide dimethylacetal is undertaken using the preferred conditions: Substrate (XLII) in N,N-dimethylformamide/N,N-dimethylformamide dimethylacetal (1:1 to 1:10 by volume) as solvent, at reflux for 8–16 hrs.

Step (dd): Cyclisation is undertaken using the preferred conditions: substrate (XLIII) in EtOH/48% HBr (about 1:1 by volume) for 18 hour.

Step (ee): Protection of the N atom of (XLIV) followed by reduction is achieved using standard methodology, e.g. PG is Benzyl, followed by reduction of the ring using a suitable reducing agent (e.g. NaBH$_4$). Preferred conditions are 1.5 eq benzyl bromide, in MeCN at reflux for 2 hours, followed by an excess of NaBH$_4$ in EtOH at 0° C. to rt. for 16 hrs.

Compound (XLVII) may be further elaborated in a manner analogous to that shown in scheme 4.

Scheme 14.

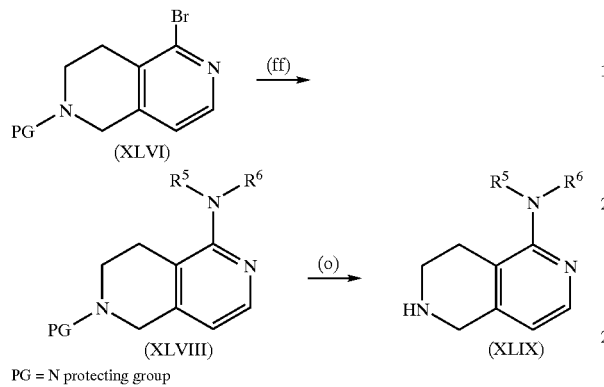

PG = N protecting group

Step (ff): Excess amine (R$^5$R$^6$NH) is reacted with the bromide (XLVI), optionally in the presence of a 3° amine base (e.g. Hünig's base), at elevated temperature and optionally at elevated pressure, for up to 24 hrs leading to formation of compound (XLVIII). Preferably an excess of amine R$^5$R$^6$NH (as solvent) is used, at between 140 and 170° C. for up to 20 hrs and optionally at elevated pressure.

Scheme 15.

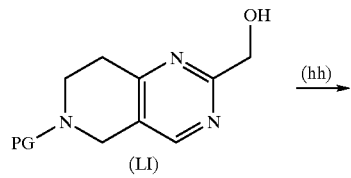

Compound (LI) can then be elaborated according to scheme 16 and 17 below. When R$^4$ represents NR$^5$R$^6$ or an N-linked Het:

Scheme 16.

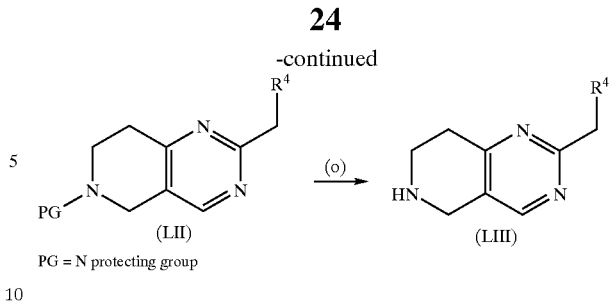

PG = N protecting group

Scheme 17.

(image continues)

PG = N protecting group

Step (gg): Condensation of compound (L) is achieved with a suitable formamidine in the presence of a suitable base (alkali metal alkoxide, or hydride, such as NaOEt, NaH) in a suitable solvent (e.g. EtOH) at elevated temperature. Preferred conditions are: NaOEt, (generated in-situ), carbonyl compound (L), slight excess of (NH$_2$CH(N)CH$_2$OH), in EtOH at reflux for 3 hours.

Step (hh): Alcohol (LI) is reacted, in-situ, to form a suitable alkylating agent (halo, mesylate, tosylate), followed by reaction with an excess of NR$^5$R$^6$ or an N-linked Het, in the presence of a 3° amine base (Et$_3$N, Hünig's base) in a suitable solvent. The preferred conditions are: 1.2 eq. MsCl, 2.5 eq-5 eq. NR$^5$R$^6$ or an N-linked Het, 1.5–2.2 eq. base (Et$_3$N, Hünig's base) in DCM or tetrahydrofuran for 1–18 hrs between r.t. and reflux.

Step (ii): The aldehyde (LIV) may be obtained by the oxidation of the alcohol (LI) according to the method of Swern, (J. Org. Chem. 41, 957, 1976). The preferred conditions are: 2 eq. DMSO, 1.1 eq. TFAA, in DCM at −60° C. for 30 mins, followed by 5 eq. Et$_3$N.

Compounds of formula (LIV) may be further elaborated using methods analogous to those shown in scheme 4, to provide compounds of formula (LIII).

Scheme 18.

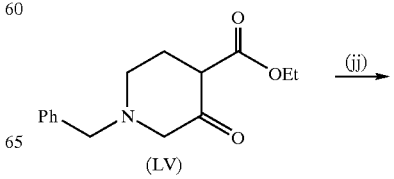

-continued

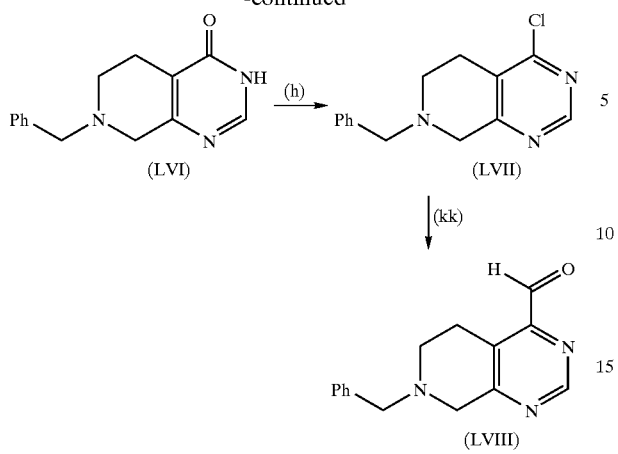

PG = N protecting group

Step (jj): Condensation of the compound (LV) is undertaken with a suitable formamidine in the presence of a suitable base (alkali metal alkoxide, or hydride, such as NaOEt, NaH) in a suitable solvent (e.g. alcohol, EtOH) at elevated temperature. The preferred conditions are: 2.3 eq. NaOEt (generated in-situ), dicarbonyl compound (LV), 1.1 eq. formamidine acetate in EtOH at reflux for 40 hrs.

Step (kk)-Metalation of compound (LVII) is undertaken following the method of Kondo et. al (J. Chem. Soc., Perkin Trans. 1, 1996), followed by quench of the intermediate anion by an excess of formyl source (e.g. N,N-dimethylformamide), to provide compound (LVIII). Preferred conditions are: 1.1 eq Te, 1.12 eq. n-BuLi, tetrahydrofuran at r.t. for 30 mins, then 1.12 eq n-BuLi, excess N,N-dimethylformamide at −78° C. for 45 mins.

Compounds (LVIII) may then be elaborated further in an analogous manner to scheme 4.

Compounds of formula:

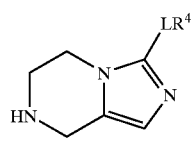

(LIX)

may be prepared by analogy to the methods described in WO 02\053558, from readily available starting materials using appropriate reagents and conditions.

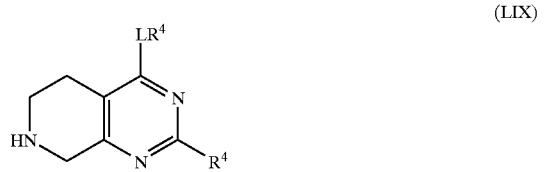

(LX)

Compounds of formula (LX) may be prepared by analogy to the methods described in JP 07101959, and to those described herein, from readily available starting materials using appropriate reagents and reaction conditions.

Alternatively, they may be prepared according to scheme 19 below, when Het is N-linked:

Scheme 19.

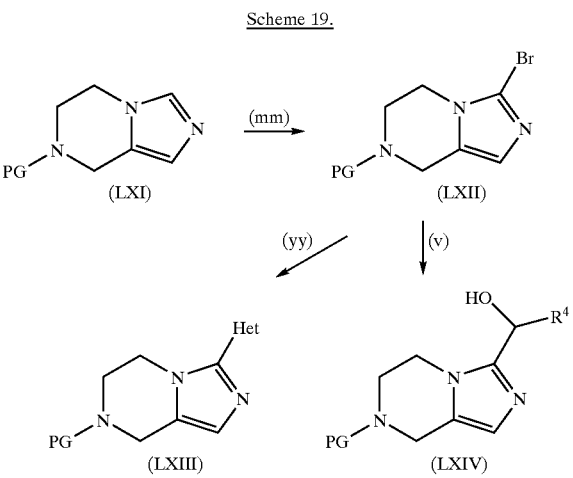

Step (mm): Metalation of compound (LXI) is undertaken with a suitable base (e.g. nBuLi) at low temp. (−78° C.), followed by quench with bromine, to give compound (LXII). Preferred conditions are: 1.1 eq. nBuLi, in tetrahydrofuran at −78° C. for 15 mins, then 1.1 eq. Bromine.

Compound (LXIII) may be obtained by reaction with Het, according to the methods described previously in step yy.

Compound (LXIV) may be obtained by reaction of bromide (LXII) with $R^4COH$, according to the conditions described previously for step v.

(LXV)

Compounds of formula (LXV) may be prepared by analogy to the method described in WO 97/30053, and to those described herein, from appropriate aminomethylketones, prepared in accordance with the method of Yinglin and Hongwen, Synthesis 1990; 615, and other readily available starting materials.

Scheme 20.

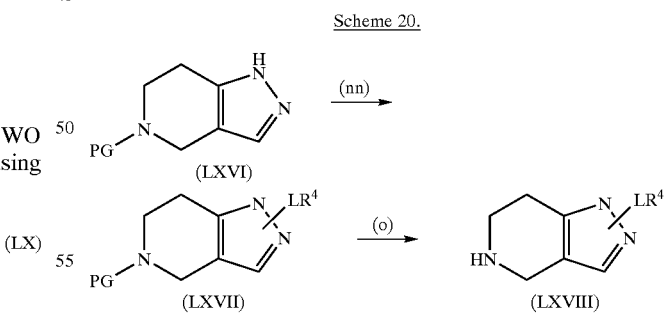

Step (nn): Alkylation of compound (LXVI), where PG is a suitable N-protecting group, (preferably Boc or benzyl) is achieved, using a suitable alkylating agent, $LR^4$-LG, (where $LR^4$ is as previously defined, and LG is a suitable leaving group, preferably halo) in the presence of a suitable alkali metal base (e.g. NaOH, $K_2CO_3$) in a solvent such as N,N-dimethylformamide or MeCN, at elevated temperature. The preferred conditions are: 1.2 eq. ZLG, 3 eq. $K_2CO_3$ in N,N-dimethylformamide at 65° C. for 26 hrs.

Compounds of formula (I) may also be prepared by the method shown in Scheme 21.

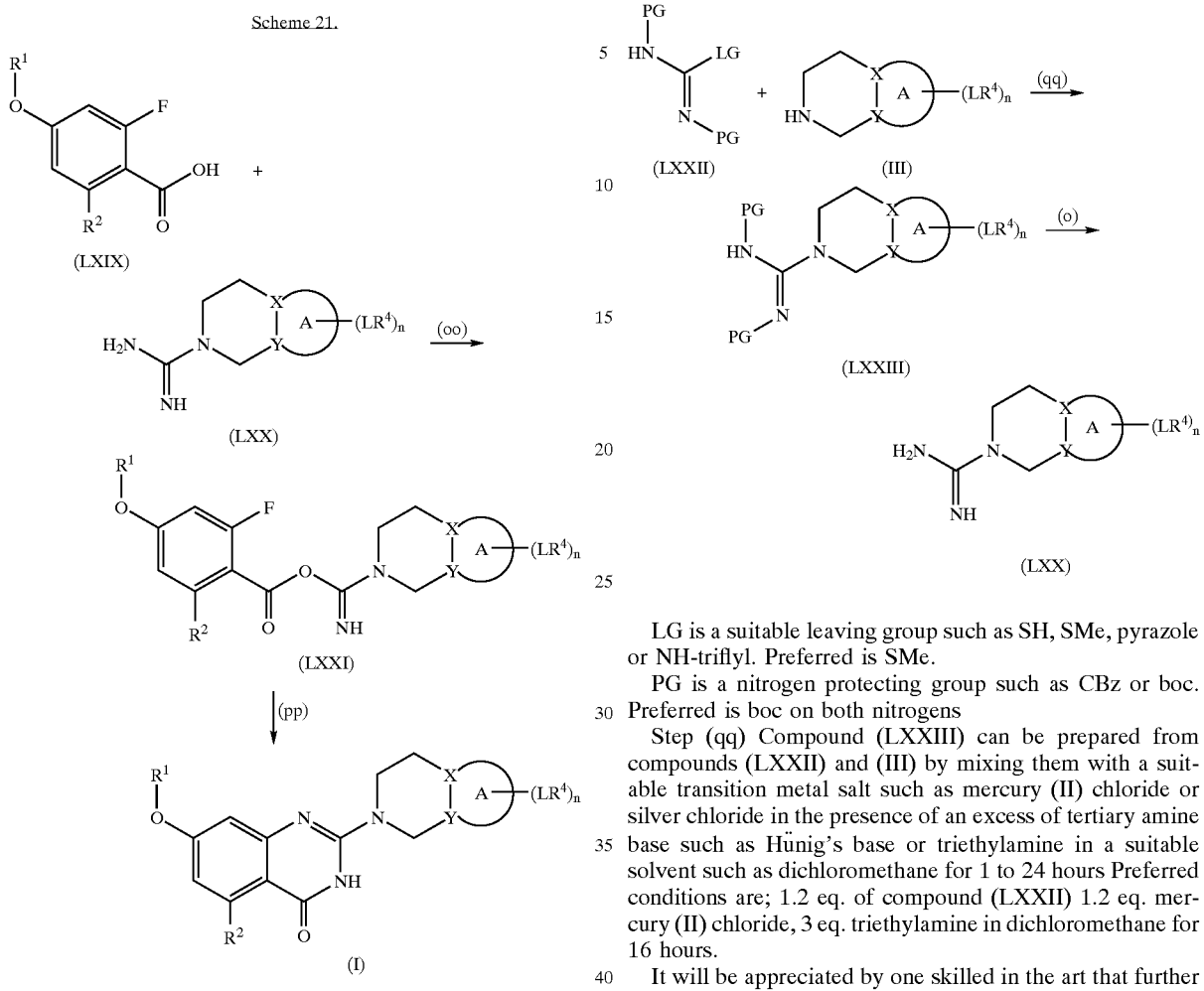

Step (oo) The acyl guanidine (LXXI) may be prepared by using either
(i) the acid chloride of acid (LXIX) and the anion of the guanidine (LXX) prepared in situ, in the presence of a base such as K$^t$BuO, NaOH, K$_2$CO$_3$ or Cs$_2$CO$_3$ in a suitable solvent e.g. DMF, or
(ii) the acid (LXIX) with a conventional coupling agent such as CDI or DCC and the guanidine (LXX), in the presence of base such as caesium carbonate in a suitable solvent e.g. DMF.

Typically the conditions are as follows:
(i) acid chloride of acid (LXIX) (generated in-situ), an excess of guanidine (LXX), with an excess of base such as K$^t$BuO or NaH, in DMF, without heating for 1 to 24 hrs, or
(ii) acid (LXIX), CDI, an excess of guanidine (LXX), with an excess Cs$_2$CO$_3$ in DMF, at room temperature for 12 to 48 hrs.

Step (pp) Cyclisation of the acyl guanidine (LXXI) to give compound (I) is accomplished by reaction in the presence of a suitable base such as NaOH or K$^t$BuO in a suitable high boiling solvent such as 3-methyl-pentan-3-ol or ethylene glycol Typically the conditions are as follows
The guanidine (LXXI) with excess potassium t-butoxide in 3-methyl-pentan-3-ol under reflux for 1 to 24 hours Compounds suitable for use as compound (LXX) may be prepared from appropriate compounds of formula (III) by the methods shown in Scheme 22.

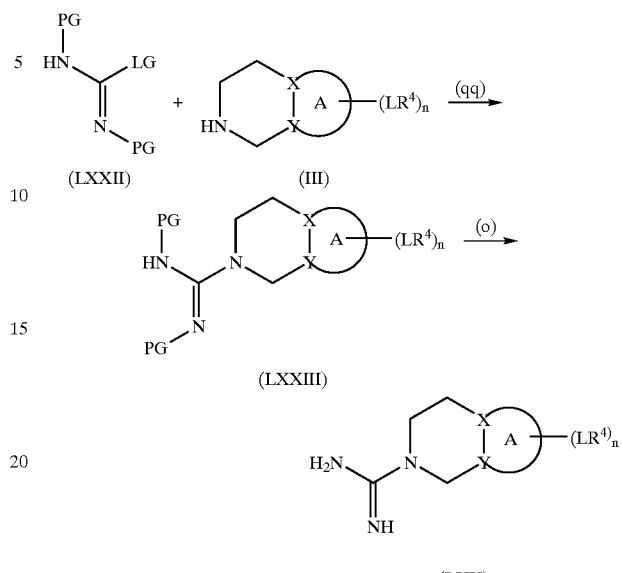

LG is a suitable leaving group such as SH, SMe, pyrazole or NH-triflyl. Preferred is SMe.

PG is a nitrogen protecting group such as CBz or boc. Preferred is boc on both nitrogens Step (qq) Compound (LXXIII) can be prepared from compounds (LXXII) and (III) by mixing them with a suitable transition metal salt such as mercury (II) chloride or silver chloride in the presence of an excess of tertiary amine base such as Hünig's base or triethylamine in a suitable solvent such as dichloromethane for 1 to 24 hours Preferred conditions are; 1.2 eq. of compound (LXXII) 1.2 eq. mercury (II) chloride, 3 eq. triethylamine in dichloromethane for 16 hours.

It will be appreciated by one skilled in the art that further elaboration of suitable R$^2$ groups (for example those containing a "reactive" N atom, which optionally may be part of a ring) may be achieved using standard chemical transformations (for example alkylation, reduction or reductive amination). Furthermore, it will be appreciated that standard protecting and deprotecting group strategies may be employed.

The following preparations describe the preparation of certain intermediate compounds used for the synthesis of compounds of the formula (I):

Spectroscopic data were recorded on a Finnigan Mat. Navigator (LRMS, either positive (ES$^+$) or negative (ES$^-$) electrospray mode), and Varian Unity Inova-400 (NMR, 400 MHz) instruments and are consistent with the assigned structures. Optical rotations were obtained using a Perkin Elmer 341 polarimeter.

Combustion analyses were performed by Exeter Analytical (UK) Limited, Uxbridge, Middlesex. Reactions were performed under an atmosphere of dry nitrogen unless otherwise noted. Flash chromatography refers to column chromatography on silica gel (Kieselgel 60, 230–400 mesh, from E. Merck, Darmstadt). Kieselgel 60 F$_{254}$ plates from E. Merck were used for TLC, and compounds were visualised using UV light, 5% aqueous potassium permanganate or chloroplatinic acid/potassium iodide solution.

In cases where compounds were analysed as hydrates, the presence of water was evident in the enhanced peak due to water in the NMR spectra. The purity of compounds was carefully assessed using analytical TLC and proton NMR (400 MHz), and the latter was used to calculate the amount of solvent in solvated samples. In multistep sequences, the purity and structure of intermediates were verified spectroscopically by NMR and LRMS.

Preparation 1

2,6-Difluoro-N-(2-hydroxy-1,1-dimethylethyl)-4-methoxybenzamide

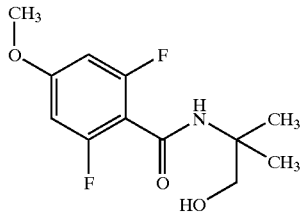

The 2,6-difluoro-4-methoxybenzoic acid (Mol. Cryst. Liq. Cryst. 1989; 172; 165) (2.09 g, 11.1 mmol) was suspended in dichloromethane (110 mL) and a few drops of N,N-dimethylformamide was added followed by oxalyl chloride (2.79 g, 22.2 mmol). The reaction mixture was stirred for 45 minutes at room temperature, after which time a clear homogeneous solution had formed. The reaction mixture was concentrated under reduced pressure and redissolved in dichloromethane (100 mL). The reaction mixture was then added slowly to an ice-cold solution of amino-2-methylpropanol (3.56 g, 40 mmol), in dichloromethane (50 mL). After stirring at room temperature for 1 hour, the reaction mixture was washed with water (75 mL), 0.2N hydrochloric acid (50 mL), dried ($MgSO_4$) and concentrated under reduced pressure to give the title compound as a white solid (2.77 g, 96%).

$^1$H-nmr ($CDCl_3$, 400 MHz) δ: 1.38 (s, 6H), 3.70 (m, 2H), 3.80 (s, 3H), 5.90 (bs, 1H), 6.42 (2xs, 2H). LRMS: m/z ($ES^+$) 260 [$MH^+$]

Preparation 2

2-(2,6-Difluoro-4-methoxyphenyl)-4,4-dimethyl-4,5-dihydro-1,3-oxazole

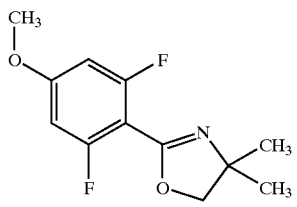

To a solution of the alcohol from preparation 1 (2.75 g, 10.6 mmol) in anhydrous dichloromethane (50 mL) was added thionyl chloride (1.43 g, 12 mmol) and the reaction stirred for 1.5 hours at room temperature. The reaction mixture was poured into 1M sodium hydroxide solution (50 mL) and extracted with dichloromethane (2×50 mL). The combined organic solutions were dried ($MgSO_4$) and concentrated under reduced pressure. The residue was purified by column chromatography on silica gel (eluting with dichloromethane:methanol 96:4) to give the title compound as a clear oil (2.40 g, 94%).

$^1$H-nmr ($CDCl_3$, 400 MHz) δ: 1.40 (s, 6H), 3.80 (s, 3H), 4.04 (s, 2H), 6.42 (m, 2H). LRMS: m/z ($ES^+$) 242 [$MH^+$]

Preparation 3

2-(2-Cyclopropyl-6-fluoro-4-methoxyphenyl)-4,4-dimethyl-4,5-dihydro-1,3-oxazole

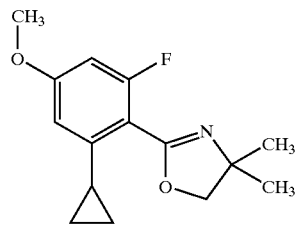

To a solution of cyclopropyl bromide (12.1 g, 100 mmol) in anhydrous tetrahydrofuran (100 mL) was added magnesium turnings (2.4 g, 100 mmol) followed by a crystal of iodine, at room temperature. After a few minutes the reaction initiated and came to reflux without any additional heating. When the reflux was complete the reaction was cooled to room temperature and stirred for 2 hours. A solution of the fluoro compound from preparation 2 (9.64 g, 40 mmol) in tetrahydrofuran (50 mL) was cooled in an ice-bath to 0° C., and the grignard solution (50 mL) was added dropwise over 15 minutes, the cooling bath was removed and reaction warmed to room temperature and stirred for 1 hour. Further grignard solution (20 mL) was added and stirred for 1 hour. Further grignard solution (10 mL) was added and stirred for 1 hour. The reaction mixture was then quenched with 1M citric acid (30 mL), as some solid remained undissolved 2M hydrochloric acid (30 mL) was added. The resultant mixture was partitioned between ethyl acetate (400 mL) and water (200 mL), basified with concentrated ammonia solution and the organic layer separated, washed with water (150 mL), brine (150 mL), dried ($MgSO_4$) and concentrated under reduced pressure. The residue was purified by flash chromatography on silica gel (eluting with hexane:isopropyl alcohol 85:15) to give the title compound as a clear oil (10.32 g, 98%).

$^1$H-nmr ($CDCl_3$, 40 MHz) δ: 0.66 (m, 2H), 0.94 (m, 2H), 1.40 (s, 6H), 2.18 (m, 1H), 3.78 (s, 3H), 4.07 (s, 2H), 6.25 (s, 1H), 6.42 (m, 1H). LRMS: m/z ($ES^+$) 286 [$MNa^+$]

Preparation 4

2-(2-Cyclobutyl-6-fluoro-4-methoxyphenyl)-4,4-dimethyl-4,5-dihydro-1,3-oxazole

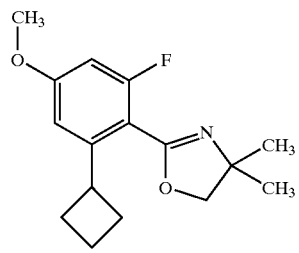

To a solution of cyclobutyl chloride (5.64 g, 62 mmol) in anhydrous tetrahydrofuran (60 mL) was added magnesium turnings (1.56 g, 65 mmol) followed by a crystal of iodine, at room temperature. The mixture was stirred at room temperature for 1 hour, followed by a further hour under reflux. A solution of the fluoro compound from preparation 2 (7.23 g, 30 mmol) in tetrahydrofuran (80 mL) was cooled in an ice-bath to 0° C., and the grignard solution (40 mL) was added dropwise over 15 minutes, the cooling bath was removed and reaction warmed to room temperature and stirred for 2 hours. Further grignard solution (10 mL) was added and the reaction stirred for a further 30 minutes. The reaction was poured into a solution of ethylenediaminetetraacetic acid disodium salt (12 g) in 1N sodium hydroxide (100 mL), and the mixture extracted with ethyl acetate (1×200 mL, 2×100 mL). The combined organic extracts were dried (MgSO$_4$) and evaporated under reduced pressure, to afford the title compound as a pale yellow oil, 8.31 g.

$^1$H-nmr (CDCl$_3$, 40 MHz) δ: 1.43 (s, 6H), 1.77–1.88 (m, 1H), 1.91–2.07 (m, 1H), 2.07–2.20 (m, 2H), 2.24–2.36 (m, 2H), 3.82 (s, 3H), 3.83 (m, 1H), 4.10 (s, 2H), 6.48 (dd, 1H), 6.66 (d, 1H). LRMS: m/z (APCl$^+$) 278 [MNH$_4^+$]

Preparation 5

2-(2-Cyclohexyl-6-fluoro-4-methoxyphenyl)-4,4-dimethyl-4,5-dihydro-1,3-oxazole

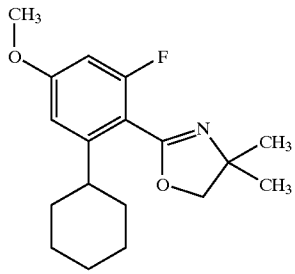

Cyclohexylmagnesium chloride (22 mL, 2M in diethyl ether, 44 mmol) was added slowly to an ice-cooled solution of the compound from preparation 2 (9.64 g, 40 mmol) in tetrahydrofuran (100 mL), and the solution then stirred at room temperature for 2 hours. Water (10 mL) was added, the mixture poured into ethyl acetate, and washed with a solution of ethylenediaminetetracetic acid disodium salt (24 g) in water (200 mL), then 1N sodium hydroxide solution (100 mL) and brine. The organic solution was dried (MgSO$_4$) and evaporated under reduced pressure to afford the title compound as a colourless oil, 12.4 g.

$^1$H-nmr (CDCl$_3$, 400 MHz) δ: 1.15–1.50 (m, 10H), 1.76 (d, 2H), 1.84 (m, 2H), 1.90 (m, 2H), 2.86 (m, 1H), 3.80 (s, 3H), 4.13 (s, 2H), 6.47 (dd, 1H), 6.63 (d, 1H). LRMS: m/z (APCl$^+$) 306 [MH$^+$]

Preparation 6

2-Cyclopropyl-6-fluoro-4-methoxybenzonitrile

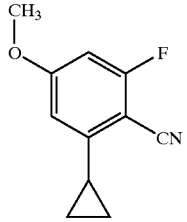

Pyridine (31.6 g, 400 mmol) was added to a solution of the compound from preparation 3 (10.32 g, 39.2 mmol) in ethyl acetate (150 mL), followed by phosphorous oxychloride (12.27 g, 80 mmol). The reaction was stirred at reflux for 5 hours, cooled and poured onto ice. This aqueous mixture was extracted with ethyl acetate, the organic solution washed with 2M hydrochloric acid, and brine then dried (MgSO$_4$) and evaporated under reduced pressure. The residue was purified by column chromatography on silica gel using dichloromethane to afford the title compound as a white solid, 6.41 g.

$^1$H-nmr (CDCl$_3$, 400 MHz) δ: 0.88 (m, 2H), 1.16 (m, 2H), 2.20 (m, 1H), 3.80 (s, 6H), 6.21 (s, 1H), 6.49 (m, 1H). LRMS: m/z (ES$^+$) 214 [MNa$^+$]

Preparation 7

2-Cyclobutyl-6-fluoro-4-methoxybenzonitrile

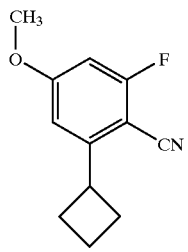

The title compound was obtained as a pale yellow oil in 99% yield from the compound from preparation 4, following a similar procedure to that described in preparation 6, except the compound was isolated without column chromatography.

$^1$H-nmr (CDCl$_3$, 400 MHz) δ: 1.78–1.94 (m, 1H), 1.99–2.24 (m, 3H), 2.41–2.55 (m, 2H), 3.81 (m, 1H), 3.87 (s, 3H), 6.53 (dd, 1H), 6.69 (d, 1H). LRMS: m/z (APCl$^+$) 223 [MNH$_4^+$]

Preparation 8

2-Cyclohexyl-6-fluoro-4-methoxybenzonitrile

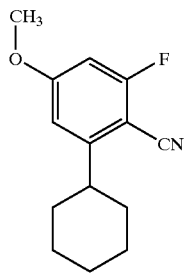

The title compound was obtained as a colourless oil in 93% yield from the compound from preparation 5, following a similar procedure to that described in preparation 6.

$^1$H-nmr (CDCl$_3$, 400 MHz) δ: 1.18–1.57 (m, 4H), 1.73–1.96 (m, 6H), 2.85–2.96 (m, 1H), 3.85 (s, 3H), 6.54 (dd, 1H), 6.65 (d, 1H). LRMS: m/z (APCl$^+$) 251 [MNH$_4^+$]

Preparation 9

2-Amino-6-cyclopropyl-4-methoxybenzonitrile

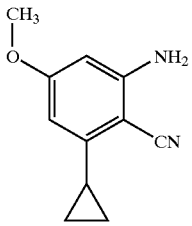

The fluoro compound from preparation 6 (3.0 g, 15.7 mmol) was added to a saturated solution of 0.88 ammonia in dimethylsulphoxide (20 mL), and the solution stirred in a sealed vessel for 18 hours at 150° C. The cooled mixture was partitioned between ethyl acetate and water and the layers separated. The organic phase was dried (MgSO$_4$) and evaporated under reduced pressure. The residue was purified by column chromatography on silica gel using dichloromethane as eluant to afford the title compound as a white crystalline solid, 1.28 g.

$^1$H-nmr (CDCl$_3$, 400 MHz) δ: 0.74 (m, 2H), 1.02 (m, 2H), 2.10 (m, 1H), 3.76 (s, 6H), 4.38 (bs, 2H), 5.82 (s, 1H), 6.00 (s, 1H). LRMS: m/z (ES$^+$) 211 [MNa$^+$]

Preparation 10

2-Amino-6-cyclobutyl-4-methoxybenzonitrile

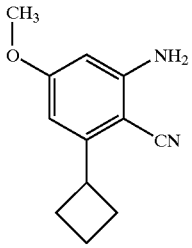

The title compound was obtained as a white solid in 54% yield from the fluoro compound from preparation 7, following a similar procedure to that described in preparation 9, except dichloromethane:ethyl acetate (100:0 to 80:20) was used as the column eluant.

$^1$H-nmr (CDCl$_3$, 400 MHz) δ: 1.76–1.90 (m, 1H), 1.94–2.21 (m, 3H), 2.37–2.49 (m, 2H), 3.66–3.77 (m, 1H), 3.80 (s, 3H), 4.06–4.43 (bs, 2H), 6.05 (s, 1H), 6.27 (s, 1H). LRMS: m/z (ES$^+$) 225 [MNa$^+$]

Preparation 11

2-Amino-6-cyclohexyl-4-methoxybenzonitrile

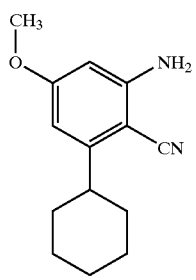

The title compound was obtained as a yellow solid in 44% yield from the fluoro compound from preparation 8, following the procedure described in preparation 9.

$^1$H-nmr (CDCl$_3$, 400 MHz) δ: 1.17–1.53 (m, 5H), 1.72–1.96 (m, 5H), 2.80 (m, 1H), 3.78 (s, 3H), 6.05 (d, 1H), 6.22 (d, 1H). LRMS: m/z (APCl$^+$) 231 [MH$^+$]

Preparation 12

5-Cyclopropyl-7-methoxy-2,4(1H,3H)-quinazolinedione

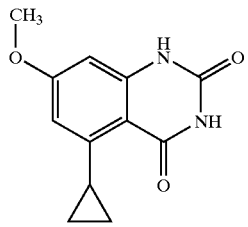

A solution of the compound from preparation 9 (1.25 g, 6.65 mmol) in N,N-dimethylformamide (10 mL) and 1,8-diazabicyclo[5.4.0]undec-7-ene (2 mL) was cooled to −78° C., and solid carbon dioxide added. The reaction vessel was sealed and heated to 140° C. for 18 hours. The cooled mixture was poured into water (150 mL), then acidified using 2N hydrochloric acid, and the mixture stirred for 10 minutes. The resulting precipitate was filtered off, washed with water and acetone, to afford the title compound as a white solid, 1.44 g.

$^1$H-nmr (DMSOd$_6$, 400 MHz) δ: 0.68 (m, 2H), 0.95 (m, 2H), 3.40 (m, 1H), 3.76 (s, 3H), 6.18 (s, 1H), 6.42 (s, 1H). LRMS: m/z (ES$^-$) 231 [M−H$^-$]

Preparation 13

5-Cyclobutyl-7-methoxy-2,4(1H,3H)-quinazolinedione

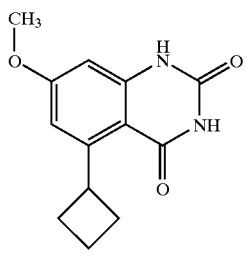

The title compound was obtained as an off-white solid in 75% yield, from the compound from preparation 10, following the procedure described in preparation 12.

$^1$H-nmr (DMSOd$_6$, 400 MHz) δ: 1.72 (m, 1H), 1.81–2.05 (m, 3H), 2.29 (m, 2H), 3.81 (s, 3H), 4.45 (m, 1H), 6.50 (d, 1H), 6.62 (d, 1H), 10.79 (s, 1H), 10.85 (s, 1H). LRMS: m/z (APCl$^-$) 245 [M−H$^-$]

Preparation 14

5-Cyclohexyl-7-methoxy-2,4(1H,3H)-quinazolinedione

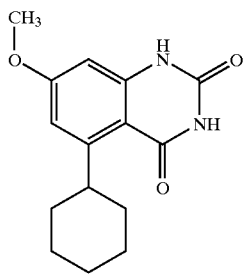

The title compound was obtained as a white solid in 77% yield, from the compound from preparation 11, following the procedure described in preparation 12.

$^1$H-nmr (DMSOd$_6$, 400 MHz) δ: 1.14–1.45 (m, 5H), 1.63–1.82 (m, 5H), 3.78 (s, 3H), 4.08 (t, 1H), 6.50 (d, 1H), 6.58 (d, 1H), 10.80 (s, 1H), 10.85 (s, 1H). LRMS: m/z (APCl$^-$) 273 [M−H$^-$]

Preparation 15

2,4-Dichloro-5-cyclopropyl-7-quinazolinyl methyl ether

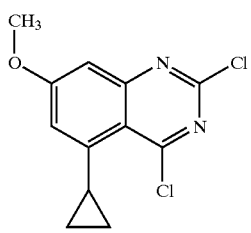

To a solution of the compound from preparation 12 (3.87 g, 16.7 mmol) in phosphorous oxychloride (50 mL) was added N,N-diisopropylethylamine (5.17 g, 40 mmol). The reaction mixture was heated at 100° C. for 1 hour, at reflux for 6 hours then cooled to room temperature. The phosphorous oxychloride was removed under reduced pressure. The resultant oil was partitioned between ethyl acetate (500 mL) and ice-water (300 mL), the layers were separated, the organic phase washed with 1M hydrochloric acid (100 mL), brine (100 mL), dried (MgSO$_4$) and concentrated under reduced pressure. The residue was purified by column chromatography on silica gel eluting with a solvent gradient of dichloromethane:ethyl acetate (100:0 to 94:6) to give the title compound as a white solid (3.97 g, 88%).

$^1$H-nmr (CDCl$_3$, 400 MHz) δ: 0.84 (m, 2H), 1.17 (m, 2H), 2.70 (m, 1H), 2.94 (s, 3H), 7,10 (s, 1H), 7.14 (s, 1H). LRMS: m/z (ES$^+$) 291 [MNa$^+$]

Preparation 16

2,4-Dichloro-5-cyclobutyl-7-quinazolinyl methyl ether

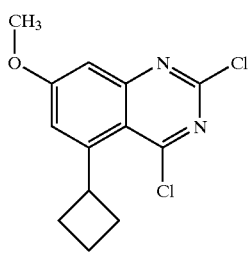

To a solution of the compound from preparation 13 (2.46 g, 10 mmol) in phosphorous oxychloride (25 mL) was added N,N-diisopropylethylamine (3.1 g, 24 mmol) and the reaction mixture was heated at reflux for 7 hours then cooled to room temperature. The solution was poured cautiously onto ice, diluted with water, and the mixture extracted with dichloromethane (3×100 mL). The combined organic solutions were dried (MgSO$_4$) and concentrated under reduced pressure. The residue was purified by column chromatography on silica gel eluting with a solvent gradient of dichloromethane:ethyl acetate (100:0 to 94:6) to give the title compound as a white solid, 1.74 g.

$^1$H-nmr (CDCl$_3$, 400 MHz) δ: 1.84–1.94 (m, 1H), 2.00–2.23 (m, 3H), 2.49–2.60 (m, 2H), 3.97 (s, 3H), 4.60 (m, 1H), 7.14 (d, 1H), 7.27 (d, 1H). LRMS: m/z (ES$^+$) 305 [MNa$^+$]

Preparation 17

2,4-Dichloro-5-cyclohexyl-7-quinazolinyl methyl ether

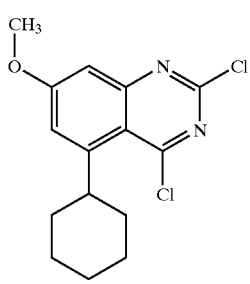

The title compound was obtained as a white solid in 64% yield, from the compound from preparation 14, following the procedure described in preparation 16.

$^1$H-nmr (CDCl$_3$, 400 MHz) δ: 1.21–1.60 (m, 5H), 1.73–2.07 (m, 5H), 3.96 (s, 3H), 4.05 (m, 1H), 7.16 (d, 1H), 7.23 (d, 1H). LRMS: m/z (APCl$^+$) 311 [MH$^+$]

Preparation 18

2-Chloro-5-cyclopropyl-7-methoxy-4(3H)-quinazolinone

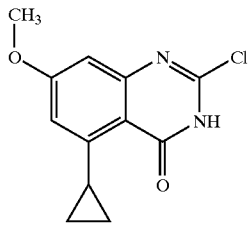

1N Sodium hydroxide solution (30 mL) was added to a solution of the chloro compound from preparation 15 (2.2 g, 8.18 mmol) in dioxane (50 mL) and the reaction stirred at room temperature for 2 hours. The reaction was acidified using 2M hydrochloric acid and extracted with dichloromethane:methanol (95:5) (3×150 mL). The combined organic solutions were dried (MgSO$_4$) and evaporated under reduced pressure to give the title compound as a white solid, 1.85 g.

$^1$H-nmr (CDCl$_3$, 400 MHz) δ: 0.73 (m, 2H), 1.09 (m, 2H), 3.31 (m, 1H), 3.86 (s, 3H), 6.60 (d, 1H), 6.89 (d, 1H). LRMS: m/z (ES$^+$) 273 [MNa$^+$]

Preparation 19

2-Chloro-5-cyclobutyl-7-methoxy-4(3H)-quinazolinone

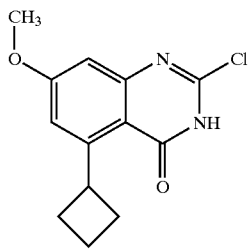

2M Sodium hydroxide solution (12.5 mL, 25 mmol) was added to a solution of the dichloride from preparation 16 (1.71 g, 6.04 mmol) in dioxane (50 mL), and the solution stirred at room temperature for 8 hours. The mixture was acidified using 2M hydrochloric acid (20 mL), the resulting precipitate filtered off, washed with water, acetone and diethyl ether, and dried in vacuo, to afford the title compound, 1.26 g.

$^1$H-nmr (DMSOd$_6$, 400 MHz) δ: 1.69–1.79 (m, 1H), 1.86–2.10 (m, 3H), 2.27–2.38 (m, 2H), 3.87 (s, 3H), 4.51 (m, 1H), 6.90 (d, 1H), 6.94 (d, 1H), 12.83 (bs, 1H). LRMS: m/z (ES$^+$) 287 [MNa$^+$]

Preparation 20

2-Chloro-5-cyclohexyl-7-methoxy-4(3H)-quinazolinone

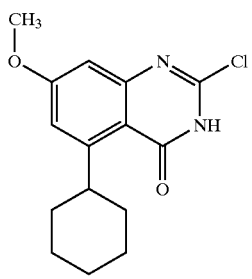

The title compound was obtained as a white solid in 96% yield, after trituration with diethyl ether, from the dichloride from preparation 17, following a similar procedure to that described in preparation 18.

$^1$H-nmr (DMSOd$_6$, 400 MHz) δ: 1.14–1.47 (m, 5H), 1.66–1.84 (m, 5H), 3.85 (s, 3H), 4.13 (m, 1H), 6.88 (d, 1H), 6.90 (d, 1H), 12.84 (bs, 1H). LRMS: m/z (ES$^+$) 293 [MH$^+$]

Preparation 21

3-Methoxyazetidine hydrochloride

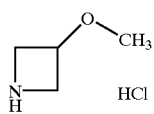

1N Ethereal hydrochloric acid was added to a solution of 1-(diphenylmethyl)-3-methoxyazetidine (WO 9613502) (1.3 g, 5.14 mmol) in dichloromethane (10 mL), until a precipitate formed, and the mixture evaporated under reduced pressure. The residual foam was re-dissolved in methanol (75 mL), 10% palladium on charcoal (900 mg) and ammonium formate (6.5 g) added, and the mixture heated under reflux for 30 minutes. The cooled mixture was filtered through Arbocel®, the filtrate evaporated under reduced pressure, and the residue partitioned between dichloromethane and water. The layers were separated, the aqueous phase acidified using 1N hydrochloric acid, and the solution evaporated under reduced pressure. The residual solid was triturated with ethanol and then dichloromethane, and the solid filtered off. The filtrate was evaporated under reduced pressure to give the title compound as a yellow oil, 130 mg.

$^1$H-nmr (CDCl$_3$, 400 MHz) δ: 3.22 (bs, 3H), 3.88 (m, 2H), 4.10 (m, 2H), 4.26 (m, 1H).

Preparation 22 tert-Butyl 5-hydroxy-3,4-dihydro-2(1H)-isoquinolinecarboxylate

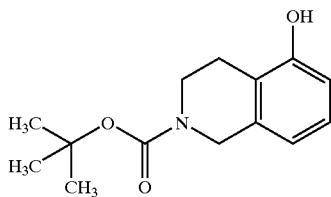

A solution of di-tert-butyl dicarbonate (66.75 g, 0.31 mol) was suspended in 1M sodium hydroxide solution (200 mL) and 1,4-dioxane (300 mL) under nitrogen gas. A solution of 1,2,3,4-tetrahydro-5-isoquinolinol (20.0 g, 134 mmol) in 1,4-dioxane (100 mL) was added and the resulting suspension stirred at room temperature for 16 hours. The reaction mixture was concentrated under reduced pressure, and the residue partitioned between IM hydrochloric acid (300 mL) and dichloromethane (500 mL). The aqueous phase was re-extracted with dichloromethane (200 mL). The combined organic extracts were dried (MgSO$_4$) and concentrated under reduced pressure to give an orange oil. The crude product was dissolved in 1,4-dioxane (200 mL) and methanol (100 mL) under nitrogen gas followed by the addition of 2N sodium hydroxide solution (150 mL) and the resulting cloudy mixture was stirred at room temperature for 3 hours. The reaction mixture was concentrated under reduced pressure, and the residue partitioned between ethyl acetate (600 mL) and water (200 mL). The organic phase was separated, washed with 2N hydrochloric acid (200 mL), brine (250 mL) then dried (MgSO$_4$) and concentrated under reduced pressure to give a tan solid. The solid was suspended in dichloromethane (150 mL) then pentane added (800 mL) and filtered to give the title compound as a white solid (32.04 g, 84%).

$^1$H-nmr (CDCl$_3$, 300 MHz) δ: 1.49 (s, 9H), 2.76 (t, 2H), 3.66 (t, 2H), 4.56 (s, 2H), 5.29 (bs, 1H), 6.67 (dd, 2H), 7.05 (dd, 1H). LRMS: m/z (ES$^+$) 272 [MNa$^+$]. Microanalysis: Found: C, 67.30; H, 7.68; N, 5.61. C$_{14}$H$_{19}$NO$_3$ requires C, 67.45; H, 7.68; N, 5.62%

Preparation 23 tert-Butyl 5-{[(trifluoromethyl)sulfonyl]oxy}-3,4-dihydro-2(1H)-isoquinolinecarboxylate

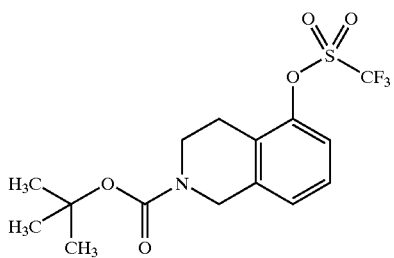

Triethylamine (20.1 mL, 144 mmol) was added to a suspension of the compound from preparation 22 (32.65 g, 131 mmol) in dichloromethane (400 mL) under nitrogen gas. The mixture was cooled to 0° C. and N-phenylbistrifluoromethanesulfonamide (51.46 g, 144 mmol) was added portionwise. The resulting brown solution was allowed to warm to room temperature and stirred for 16 hours. The reaction mixture was washed consecutively with water (200 mL), 0.5M hydrochloric acid (200 mL), brine (250 mL) and then dried (MgSO$_4$) and concentrated under reduced pressure to give a brown oil. The crude product was purified by column chromatography on silica gel eluting with a solvent gradient of n-pentane:diethyl ether (100:0 to 70:30). The product was co-evaporated with dichloromethane (2×100 mL) to give the title compound as a colourless gum (40.1 g, 80%).

$^1$H-nmr (CDCl$_3$, 300 MHz) δ: 1.49 (s, 9H), 2.89 (t, 2H), 3.65 (t, 2H), 4.59 (s, 2H), 7.13 (m, 2H), 7.24 (dd, 1H). LRMS: m/z (ES$^+$) 404 [MNa$^+$].

Preparation 24 tert-Butyl 5-cyano-3,4-dihydro-2(1H)-isoquinolinecarboxylate

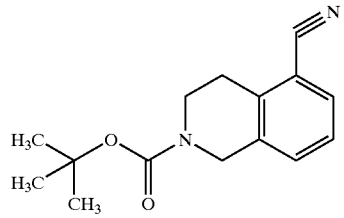

The compound from preparation 23 (20.0 g, 52 mmol) was dissolved in N,N-dimethylformamide (120 mL) under nitrogen gas. Zinc cyanide (6.15 g, 52 mmol), lithium chloride (2.22 g, 52 mmol) and tetrakis(triphenylphosphine) palladium (0) (2.42 g, 2.1 mmol) were added and the mixture heated at 110° C. for 8 hours. The reaction mixture was concentrated under reduced pressure, and the residue partitioned between dichloromethane (500 mL) and saturated sodium bicarbonate solution (250 mL). The aqueous phase was re-extracted with dichloromethane (300 mL). The combined organic solutions were dried (MgSO$_4$) and concentrated under reduced pressure to give a golden oil. The crude product was purified by column chromatography on silica gel using n-pentane:ethyl acetate (90:10) as eluant. The product was co-evaporated with dichloromethane (2×100 mL) to give the title compound as a colourless oil (13.32 g, 49%).

$^1$H-nmr (CDCl$_3$, 300 MHz) δ: 1.48 (s, 9H), 3.02 (t, 2H), 3.70 (t, 2H), 4.58 (s, 2H), 7.20–7.35 (m, 2H), 7.50 (d, 1H). LRMS: m/z (ES$^+$) 281 [MNa$^+$].

Preparation 25 tert-Butyl 5-formyl-3,4-dihydro-2(1H)-isoquinolinecarboxylate

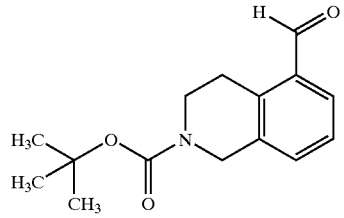

A solution of the compound from preparation 24 (9.1 g, 35 mmol) in toluene (100 mL) was cooled to −78° C. under nitrogen gas. Over 1 hour, diisobutylaluminium hydride (80 mL of a 1M solution in toluene, 80 mmol) was added dropwise keeping the internal temperature below −60° C. and the resulting mixture stirred for 2 hours at −78° C. Methanol (20 mL) was pre-cooled to −78° C. and the added dropwise to the reaction mixture keeping the internal temperature below −60° C. Over 20 mins the reaction mixture was poured into 1N hydrochloric acid (200 mL) that had been pre-cooled to 0° C. The reaction mixture was extracted with ethyl acetate (3×400 mL) and the combined organic extracts were washed with brine (200 mL), dried (MgSO$_4$) and concentrated under reduced pressure. The product was co-evaporated with dichloromethane (2×50 mL) to give the title compound as a yellow oil (8.14 g, 88%).

$^1$H-nmr (DMSOd$_6$, 400 MHz) δ: 1.40 (s, 9H), 3.19 (t, 2H), 3.55 (t, 2H), 4.55 (s, 2H), 7.40 (dd, 2H), 7.47 (d, 1H), 7.70 (d, 1H). LRMS: m/z (ES$^+$) 284 [MNa$^+$].

Preparation 26

1-Benzyl-4-(1-pyrrolidinyl)-1,2,3,6-tetrahydropyridine

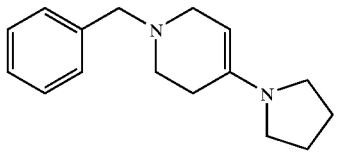

Pyrrolidine (31.8 mL, 0.38 mol) was added to a solution of 1-benzyl-4-piperidinone (48.0 g, 0.25 mol) in toluene (180 mL) and the mixture refluxed under Dean-Stark conditions for 4.5 hours. The reaction mixture was allowed to cool to room temperature and concentrated under reduced pressure to give the title compound as an orange oil (61.8 g, 100%).

$^1$H-nmr (400 MHz, CDCl$_3$) δ: 1.80–1.84 (m, 4H), 2.32 (m, 2H), 2.59 (t, 2H), 3.02 (4Hm,), 3.07 (s, 2H), 3.57 (s, 2H), 4.18 (s, 1H), 7.22–7.30 (m, 3H), 7.35–7.36 (d, 2H).

Preparation 27

6-Benzyl-5,6,7,8-tetrahydro[1,6]naphthyridin-2(1H)-one

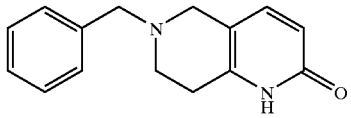

A mixture of the compound from preparation 26 (61.50 g, 0.25 mol) and propiolamide (J. Am. Chem. Soc. 1988; 110; 3968) (35.05 g, 0.51 mol) were heated under reflux in toluene (500 mL) under nitrogen gas for 16 hours. The reaction mixture was allowed to cool to room temperature and concentrated under reduced pressure. The residue was partitioned between dichloromethane (800 mL) and saturated sodium bicarbonate solution (400 mL). The aqueous phase was further extracted with dichloromethane (3×500 mL). The combined organic solutions were dried (MgSO$_4$) and concentrated under reduced pressure. The residue was purified by column chromatography on silica gel eluting with a solvent gradient of dichloromethane:methanol (100:0 to 95:05) to give the title compound as an orange solid (27.71 g, 45%).

$^1$H-nmr (DMSOd$_6$, 400 MHz) δ: 2.53 (t, 2H), 2.63 (t, 2H), 3.24 (s, 2H), 3.60 (s, 2H), 6.06 (d, 1H), 7.08 (d, 1H), 7.24 (m, 1H), 7.30 (m, 4H). LRMS: m/z (ES$^+$) 263 [MNa$^+$].

Preparation 28

6-Benzyl-2-bromo-5,6,7,8-tetrahydro[1,6]naphthyridine

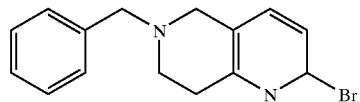

The compound from preparation 27 (9.51 g, 31 mmol) was suspended in acetonitrile (45 mL) and anisole (45 mL). Phosphorous oxybromide (44.8 g, 156 mmol) was added portionwise and the mixture heated for 1 hour at 120° C. The reaction was allowed to cool to room temperature and then poured onto ice (400 g). Dichloromethane (400 mL) was added and the mixture was then neutralised with saturated sodium carbonate solution (450 mL). The organic layer was collected and the aqueous layer extracted with dichloromethane (500 mL). The combined organic solutions were dried (MgSO$_4$) and concentrated under reduced pressure. The residue was purified by column chromatography on silica gel eluting with a solvent gradient of dichloromethane:methanol (100:0 to 97:03) to give the title compound as a brown oil (5.79 g, 61%).

$^1$H-nmr (CDCl$_3$, 400 MHz) δ: 2.83 (t, 2H), 3.03 (t, 2H), 3.56 (s, 2H), 3.70 (s, 2H), 7.12 (d, 1H), 7.21 (d, 1H), 7.26–7.36 (m, 5H). LRMS: m/z (ES$^+$) 303 [MH$^+$].

Preparation 29a

6-Benzyl-5,6,7,8-tetrahydro[1,6]naphthyridine-2-carbaldehyde

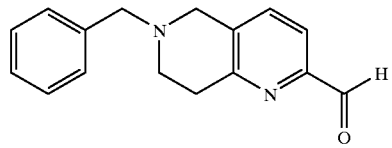

The bromide from preparation 28 (3.00 g, 9.90 mmol) was dissolved in tetrahydofuran (70 mL) and cooled to −78° C. n-Butyl lithium (5.5 mL as a 2.5M solution in hexanes, 13.8 mmol) was added and the reaction stirred for a 5 minutes. N,N-Dimethylformamide (2.3 mL, 29.7 mmol) was then added and the reaction stirred for 1 hour, the cooling bath removed and the reaction quenched by the addition of saturated potassium dihydrogenphosphate solution (100 mL). The residue was purified by flash chromatography on silica gel eluting with dichloromethane: methanol (98:2) to give the title compound as a tan solid (2.10 g, 85%).

$^1$H-nmr (DMSOd$_6$, 400 MHz) δ: 2.92 (m, 2H), 3.15 (m, 2H), 3.71 (s, 2H), 3.75 (s, 2H), 7.26–7.38 (m, 5H), 7.45 (d, 1H), 7.73 (d, 1H), 10.02 (s, 1H). LRMS: m/z (ES$^+$) 275 [MNa$^+$].

Preparation 29b

6-Benzyl-5,6,7,8-tetrahydro[1,6]naphthyridine-2-carbaldehyde

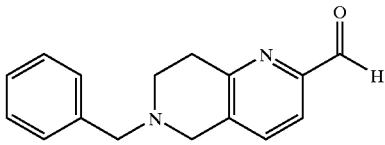

A solution of sodium periodate (4.38 g, 20.5 mmol) in water (38 ml) was added dropwise to a solution of the diol from preparation 154 (7.2 g, 18.7 mmol) in acetonitrile (200 ml), and the reaction was stirred at room temperature for 2 hours. The mixture was partitioned between ethyl acetate (300 ml) and water (300 ml), containing a small volume of brine, and the layers separated. The aqueous phase was further extracted with ethyl acetate (2×100 ml), and the combined organic solutions dried over magnesium sulphate and concentrated under reduced pressure, co-evaporating with tetrahydrofuran. The residual oil was purified by column chromatography on silica gel using an elution gradient of dichloromethane: ethyl acetate (80:20 to 50:50) to afford the title compound, as an oil that crystallised on standing (1.3 g).

$^1$H-nmr (CDCl$_3$, 400 MHz) δ: 2.90 (t, 2H), 3.16 (t, 2H), 3.69 (s, 2H), 3.74 (s, 2H), 7.23–7.39 (m, 5H), 7.42 (d, 1H), 7.72 (d, 1H), 10.00 (s, 1H). LRMS: m/z (ES$^+$) 275 [MNa$^+$]

Preparation 30

3-Methylisonicotinonitrile

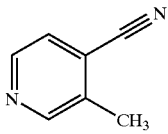

To a solution of 3-picoline N-oxide (60 g, 0.55 mol) in dichloromethane (1000 mL) was added ethyl iodide (132 mL, 1.65 mol) and the mixture stirred at room temperature for 16 hours. The precipitate was collected by filtration and washed with diethyl ether (200 mL) to give a white solid. The solid was dissolved in water (600 mL) and warmed to 50° C. Sodium cyanide (50 g, 1.02 mol) was added as a solution in water (180 mL) over 1 hour, keeping the internal temperature below 60° C. and the resulting dark brown solution was stirred at 55° C. for a further 1 hour. The reaction mixture was extracted with diethyl ether (3×600 mL). The combined organic extracts were dried (MgSO$_4$) and concentrated under reduced pressure to give a brown oil. The crude product was purified by column chromatography on silica gel eluting with a solvent gradient of n-pentane:dichloromethane (40:60 to 0:100). The product was co-evaporated with dichloromethane (2×300 mL) to give the title compound as a colourless oil (30.5 g, 47%).

$^1$H-nmr (CDCl$_3$, 400 MHz) δ: 2.55 (s, 3H), 7.47 (d, 1H), 8.60 (d, 1H), 8.67 (s, 1H).

Preparation 31

3-[(E)-2-(Dimethylamino)ethenyl]isonicotinonitrile

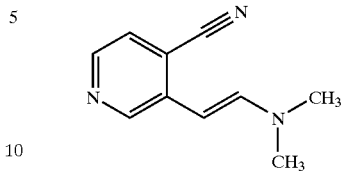

A mixture of the nitrile from preparation 30 (30.49 g, 0.26 mol) in N,N-dimethylformamide dimethyl acetal (200 mL) and N,N-dimethylformamide (200 mL) under nitrogen gas was heated under reflux for 16 hours. The reaction mixture was concentrated under reduced pressure to give a brown solid. The crude product was dissolved in dichloromethane (100 mL) and n-pentane added until a precipitate formed. The solid was collected by filtration, washed with n-pentane and dried under reduced pressure to give the title compound as a green solid (25.1 g, 56%).

$^1$H-nmr (CDCl$_3$, 400 MHz) δ: 2.95 (s, 6H), 5.23 (d, 1H), 7.24 (d, 1H), 8.15 (d, 1H), 8.70 (s, 1H). LRMS: m/z (ES$^+$) 174 [MH$^+$]

Preparation 32

[2,6]Naphthyridin-1(2H)-one

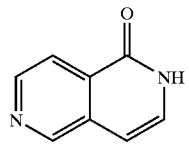

48% Hydrobromic acid (97 mL, 578 mmol) was added over 20 minutes, to a solution of the compound from preparation 31 (10.0 g, 57.8 mmol) in ethanol (100 mL), and the reaction heated under reflux for 18 hours. The cooled mixture was filtered, and the collected solid was washed with ethanol (25 mL), and dried in vacuo, to afford the title compound as fine yellow crystals, 8.54 g.

$^1$H-nmr (DMSOd6, 400 MHz) δ: 6.65 (d, 1H), 7.30 (d, 1H), 7.98 (d, 1H), 8.60 (d, 1H), 9.06 (s, 1H), 11.60 (bs, 1H). LRMS: m/z (ES$^+$) 147.5 [MH$^+$]

Preparation 33

6-Benzyl-5,6,7,8-tetrahydro[2,6]naphthyridin-1(2H)-one

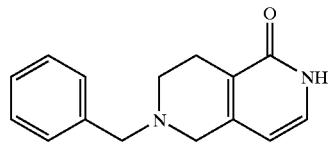

To a suspension of the compound from preparation 32 (20.0 g, 0.14 mol) in acetonitrile (350 mL) under nitrogen gas was added benzyl bromide (24.4 mL, 0.21 mol) and the reaction heated under reflux for 2 hours. After the reaction mixture had cooled to room temperature it was concentrated under reduced pressure to give a brown oil which was re-dissolved in ethanol (500 mL). This solution was cooled to 0° C. and sodium borohydride (25.9 g, 0.69 mol) added portionwise over 30 min and then stirred at 0° C. for 1 hour, followed by stirring at room temperature for a further 16 hours. The reaction mixture was cooled to 0° C. and 6M hydrochloric acid (200 mL) was added dropwise over 30 minutes and then stirred at room temperature for 90 minutes. The resulting precipitate was filtered off, and the aqueous filtrate was basified with 2M sodium hydroxide (1000 mL). With stirring, ethyl acetate (250 mL) and then cyclohexane (250 mL) were added and the resulting precipitate collected by filtration to give the title compound as a light yellow solid (15.50 g, 53%).

$^1$H-nmr (DMSOd$_6$, 400 MHz) δ: 2.27 (t, 2H), 2.60 (t, 2H), 3.28 (s, 2H), 3.62 (s, 2H), 5.87 (d, 1H), 7.10 (d, 1H), 7.21–7.25 (m, 5H), 11.23 (bs, 1H). LRMS: m/z (ES$^+$) 241 [MH$^+$].

Preparation 34

2-Benzyl-5-bromo-1,2,3,4-tetrahydro[2,6]naphthyridine

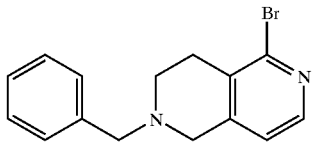

Phosphorous oxybromide (74.57 g, 260 mmol) was added portionwise to a suspension of the compound from preparation 33 (15.5 g, 64.6 mmol) anisole (200 mL) and acetonitrile (100 mL), and the solution stirred under reflux for 4 hours. The cooled mixture was poured onto ice (500 g) and diluted with dichloromethane (500 mL). The mixture was slowly neutralised using saturated sodium bicarbonate solution, the phase separated, and the aqueous layer extracted with further dichloromethane (500 mL). The combined organic solutions were dried (MgSO$_4$) and evaporated under reduced pressure to give a green oil. The crude product as purified by column chromatography on silica gel using an elution gradient of ethyl acetate:pentane (50:50 to 60:40), and repeated using diethyl ether:pentane (50:50) to afford the title compound as a white solid, 17.4 g.

$^1$H-nmr (CDCl$_3$, 400 MHz) δ: 2.79 (m, 4H), 3.55 (s, 2H), 3.67 (s, 2H), 6.85 (d, 1H), 7.23–7.33 (m, 5H), 8.06 (d, 1H). LRMS: m/z (ES$^+$) 326 [MNa$^+$]

Preparation 35

6-Benzyl-5,6,7,8-tetrahydro[2,6]naphthyridine-1-carbaldehyde

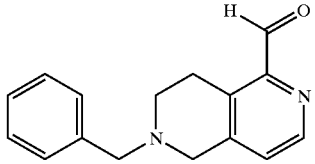

The compound from preparation 34 (3.2 g, 10.6 mmol) was dissolved in dry tetrahydrofuran (80 mL) under nitrogen gas and cooled to –78° C. n-Butyl lithium (7.3 mL as a 1.6M solution in hexanes, 11.6 mmol) was added dropwise over 3 minute s and the reaction stirred for a further 3minutes. N,N-Dimethylformamide (2.5 mL, 31.8 mmol) was then added, the reaction stirred for 15 minutes and the cooling bath removed and the reaction stirred for a further 15 minutes before being quenched by water (20 mL). The reaction mixture was partitioned between ethyl acetate (250 mL) and water (100 mL). The organic phase was separated, washed with water (100 mL), brine (100 mL) then dried (MgSO$_4$) and concentrated under reduced pressure. The residue was purified by column chromatography on silica gel eluting with a solvent gradient of dichloromethane:methanol (100:0 to 80:20) to give the title compound as an orange semi-solid (1.27 g, 48%).

$^1$H-nmr (CDCl$_3$, 400 MHz) δ: 2.77 (t, 2H), 3.30 (t, 2H), 3.62 (s, 2H), 3.67 (s, 2H), 7.08 (d, 1H), 7.23–7.35 (m, 5H), 8.50 (d, 1H), 10.15 (s, 1H). LRMS: m/z (ES$^+$) 275 [MNa$^+$]

Preparation 36 tert-Butyl-3-[(dimethylamino)methylene]-4-oxo-1-piperidinecarboxylate

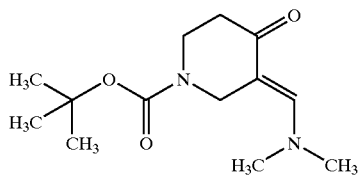

Tert-butyl-4-oxo-1-piperidinecarboxylate (10 g, 50 mmol) and N,N-dimethylformamide dimethyl acetal (7.3 mL, 55 mmol) were added to N,N-dimethylformamide (75 mL) under nitrogen gas and the mixture heated at 90° C. for 8 hours and then stirred for a further 16 hours at room temperature. The reaction mixture was concentrated under reduced pressure, and the residue partitioned between ethyl acetate (200 mL) and brine (200 mL). The aqueous phase was re-extracted with ethyl acetate (200 mL). The combined organic extracts were dried (Na$_2$SO$_4$) and concentrated under reduced pressure to give a brown oil that solidified on standing. Trituration with cyclohexane (20 mL) gave the title compound as a light brown solid (8.5 g, 67%).

$^1$H-NMR (400 MHz, CDCl$_3$) δ: 1.45 (s, 9H), 2.42 (t, 2H), 3.06 (s, 6H), 3.59 (t, 2H), 4.54 (s, 2H), 7.43 (s, 1H). LRMS: m/z (ES$^+$) 277 [MNa$^+$].

Preparation 37 tert-Butyl 2-(hydroxymethyl)-7,8-dihydropyrido[4,3-d]pyrimidine-6(5H)-carboxylate

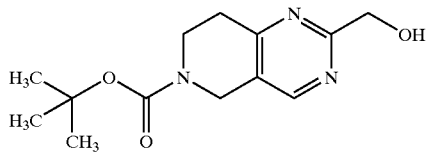

Sodium metal (414 mg, 16.5 mmol) was added to ethanol (42 mL) and stirred at room temperature under nitrogen gas until a clear solution had formed. The compound from preparation 24 (4.2 g, 16.5 mmol) and 2-hydroxyethanimidamide (J. Am. Chem. Soc.; 68; 1946; 2394) (2 g, 18 mmol) were added and the reaction mixture heated under reflux for 3 hours and then allowed to cool to room temperature and partitioned between ethyl acetate (100 mL) and saturated sodium bicarbonate solution (100 mL). The aqueous phase was re-extracted with ethyl acetate (50 mL). The combined organic extracts were dried (Na$_2$SO$_4$) and concentrated under reduced pressure to give a brown oil which was purified by column chromatography on silica gel eluting with a solvent gradient of ethyl acetate : methanol (100:0 to 97:03) to give the title compound as a brown oil (3.00 g, 73%).

$^1$H-NMR (400 MHz, CDCl$_3$) δ: 1.49 (s, 9H), 2.95 (t, 2H), 3.46 (bs, 1H), 3.75 (t, 2H), 4.59 (s, 2H), 4.77 (d, 2H), 8.44 (s, 1H).

Preparation 38

7-Benzyl-5,6,7,8-tetrahydropyrido[3,4-d]pyrimidin-4(3H)-one

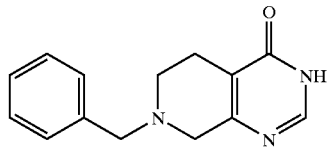

Sodium metal (10.1 g, 0.44 mol) was added to ethanol (520 mL) and stirred at room temperature under nitrogen gas until a clear solution had formed. Ethyl-3-oxo-N-benzylpiperidine-4-carboxylate hydrochloride (56.5 g, 0.19 mol) and formamidine acetate (22.9 g, 0.22 mol) were then added and the reaction mixture heated under reflux for 40 hours. The reaction mixture was concentrated under reduced pressure, and the residue partitioned between water (400 mL) and dichloromethane (400 mL). The aqueous phase was re-extracted with dichloromethane (2×100 mL). The combined organic extracts were dried (MgSO$_4$) and concentrated under reduced pressure. The resulting solid was triturated with diethyl ether (100 mL) and the product collected by filtration to give the title compound as a light brown solid (32.0 g, 70%).

$^1$H-nmr (400 MHz, CDCl$_3$) δ: 2.64 (m, 2H), 2.73 (m, 2H), 3.48 (s, 2H), 3.70 (s, 2H), 7.25–7.34 (m, 5H), 7.97 (s, 1H), 12.37 (bs, 1H). LRMS (ES$^+$): m/z 264 [MNa$^+$]

Preparation 39

7-Benzyl-4-chloro-5,6,7,8-tetrahydropyrido[3,4-d]pyrimidine

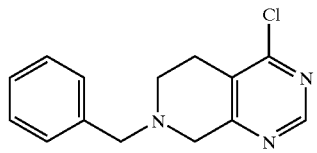

The compound from preparation 38 (11.0 g, 42 mmol) was mixed with phosphorous oxychloride (80 mL) and heated to 90° C. under nitrogen gas for 1 hour. The reaction mixture was concentrated under reduced pressure, re-dissolved in dichloromethane (100 mL) and poured onto ice (100 g). The mixture was stirred for 10 minutes, and then basified with saturated sodium bicarbonate solution. The aqueous phase was extracted with dichloromethane (3×150 mL) and the combined organic extracts were dried (MgSO$_4$) and concentrated under reduced pressure. The residue was purified by column chromatography on silica gel eluting with a solvent gradient of dichloromethane:methanol (100:0 to 90:10) to give the title compound as a brown oil (9.75 g, 90%).

$^1$H-nmr (400 MHz, CDCl$_3$) δ: 2.81 (t, 2H), 2.85 (t, 2H), 3.68 (s, 2H), 3.72 (s, 2H), 7.29–7.34 (m, 5H), 8.70 (s, 1H).

Preparation 40

7-Benzyl-5,6,7,8-tetrahydropyrido[3,4-d]pyrimidine-4-carbaldehyde

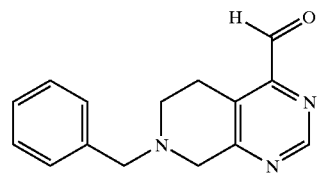

Tellurium metal (5.72 g, 45 mmol) was suspended in tetrahydrofuran (100 mL) at room temperature under nitrogen gas and n-butyl lithium (20 mL of a 2.5M solution in hexanes, 50 mmol) added over 1 minute. This mixture was stirred for a further 15 minutes and then added to a solution of the compound from preparation 39 (9.75 g, 37.5 mmol) in tetrahydrofuran (100 mL) and the mixture stirred for 15 minutes before being cooled to –78° C. n-Butyl lithium (20 mL of a 2.5M solution in hexanes, 50 mmol) was added over 1 minute and the mixture stirred for 5 minutes before N,N-dimethylformamide (20 mL) was added. The reaction was stirred for a further 30 minutes at –78° C., quenched with water (10 mL) then allowed to warm to room temperature. Ethyl acetate (200 mL) and water (100 mL) were added, the organic layer separated and washed with brine (100 mL), dried (MgSO$_4$) and concentrated under reduced pressure. The residue was purified by column chromatography on silica gel eluting with a solvent gradient of dichloromethane:ethyl acetate (100:0 to 50:50) to give the title compound as a brown oil, 3.10 g.

$^1$H-nmr (400 MHz, CDCl$_3$) δ: 2.79 (t, 2H), 3.27 (t, 2H), 3.73 (s, 2H), 3.76 (s, 2H), 7.33 (m, 5H), 9.16 (s, 1H), 10.11 (s, 1H). LRMS (ES$^+$): m/z 276 [MNa$^+$]

Preparation 41 tert-Butyl 5-[(cyclopropylamino)methyl]-3,4-dihydro-2(1H)-isoquinolinecarboxylate

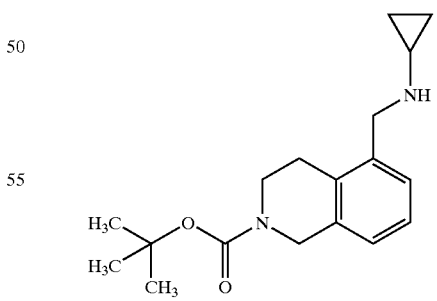

Cyclopropylamine (0.81 mL, 11.4 mmol) and acetic acid (0.49 μl, 0.85 mmol) were added to a solution of the aldehyde from preparation 25 (2.0 g, 7.65 mmol) in tetrahydrofuran (50 mL), and the solution stirred at room temperature for 2 hours. Sodium triacetoxyborohydride (4.0-g, 19.1 mmol) was added, and the reaction stirred at room temperature for 72 hours. The mixture was partitioned between 0.88 ammonia (20 mL), water (25 mL) and ethyl acetate (75 mL). The layers were separated, the organic phase washed with brine, dried (MgSO$_4$) and evaporated under reduced pressure to give the title compound as a clear oil, 2.34 g.

$^1$Hnmr (CDCl$_3$, 400 MHz) δ: 0.38 (m, 2H), 0.42 (m, 2H), 1.46 (s, 9H), 2.16 (m, 1H), 2.84 (t, 2H), 3.65 (t, 2H), 3.80 (s, 2H), 4.58 (s, 2H), 7.01 (m, 1H), 7.18 (m, 2H). LRMS: m/z (ES$^+$) 303 [MH$^+$], 325 [MNa$^+$]

Preparation 42 tert-Butyl 5-(3-azabicyclo[3.1.0]hex-3-ylmethyl)-3,4-dihydro-2(1H)-isoquinolinecarboxylate

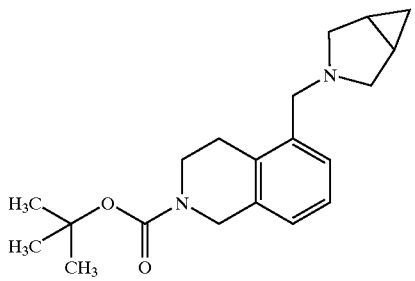

3-Azabicyclo[3.1.0]hexane hydrochloride (WO 9522547) (203 mg, 1.7 mmol) sodium acetate (140 mg, 1.7 mmol), powdered 4 Å molecular sieves (500 mg) and acetic acid (0.49 μl, 0.85 mmol) were added to a solution of the aldehyde from preparation 25 (403 mg, 1.55 mmol) in tetrahydrofuran (10 mL), and the solution stirred at room temperature for 1 hour. Sodium triacetoxyborohydride (720 mg, 3.4 mmol) was added, and the reaction stirred at room temperature for 18 hours. The mixture was partitioned between sodium hydroxide solution (60 mL, 1N) and ethyl acetate (60 mL) and the layers separated. The organic phase was washed with brine (60 mL), dried (MgSO$_4$) and evaporated under reduced pressure. The crude product was purified by column chromatography on silica gel using ethyl acetate: methanol (95:5) as eluant, to give a colourless oil. This was dissolved in diethyl ether (20 mL) and the solution extracted with 1N hydrochloric acid (2×20 mL). The combined aqueous solutions were then basified to pH 11 using 1N sodium hydroxide solution (50 mL), and this aqueous solution extracted with ethyl acetate. These combined organic extracts were dried (MgSO$_4$) and evaporated under reduced pressure to afford the title compound as a white solid, 224 mg.

$^1$H-nmr (CDCl$_3$, 400 MHz) δ: 0.30 (m, 1H), 0.66 (m, 1H), 1.31 (m, 2H), 1.48 (s, 9H), 2.33 (d, 2H), 2.82 (m, 4H), 3.56 (s, 2H), 3.60 (t, 2H), 4.57 (s, 2H), 6.99 (m, 1H), 7.09 (m, 2H). LRMS: m/z (ES$^+$) 351 [MNa$^+$]

Preparation 43 tert-Butyl 5-[(3-methoxy-1-azetidinyl)methyl]-3,4-dihydro-2(1H)-isoquinolinecarboxylate

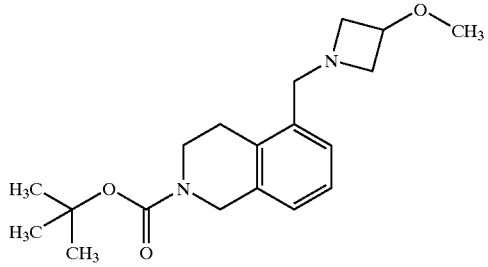

Sodium acetate (82 mg, 1.0 mmol) the aldehyde from preparation 25 (264 mg, 1.05 mmol) and acetic acid (0.07 mL, 1.2 mmol) were added to a solution of the amine hydrochloride from preparation 21 (130 mg, 1.05 mmol) in tetrahydrofuran (10 mL), and the solution stirred at room temperature for 0.5 hour. Sodium triacetoxyborohydride (530 mg, 2.5 mmol) was added, and the reaction stirred at room temperature for 18 hours. The mixture was diluted with ethyl acetate and basified to pH 11 using 0.88 ammonia. The layers were separated, the aqueous phase extracted with ethyl acetate and the combined organic solutions dried (MgSO$_4$) and evaporated under reduced pressure. The residual yellow oil was purified by column chromatography on silica gel using dichloromethane:methanol (97:3) as eluant to afford the title compound as an oil, 226 mg.

$^1$H-nmr (CDCl$_3$, 400 MHz) δ: 1.45 (s, 9H), 2.81 (t, 2H), 2.95 (t, 2H), 3.22 (s, 3H), 3.60 (m, 6H), 4.01 (m, 1H), 4.58 (s, 2H), 7.00 (m, 1H), 7.13 (m, 2H). LRMS: m/z (ES$^+$) 333.3 [MH$^+$]

Preparation 44 tert-Butyl 5-[(4-methyl-1-piperazinyl)methyl]-1-3,4-dihydro-2(1H)-isoquinolinecarboxylate Acetic acid (0.078 mL, 1.3 mmol) followed by sodium triacetoxyborohydride (572 mg, 2.7 mmol) were added to a solution of 1-methylpiperazine (0.139 mL, 1.25 mmol) and the aldehyde from preparation 25 (250 mg, 0.96 mmol) in tetrahydrofuran (10 mL), and the solution stirred at room temperature for 3 hours. The reaction was poured into 2N sodium hydroxide solution (50 mL), and the mixture extracted with ethyl acetate (3×). The combined organic extracts were washed with brine, dried (MgSO$_4$) and evaporated under reduced pressure. The crude product was purified by column chromatography on silica gel using dichloromethane:methanol:0.88 ammonia (95:5:0.5) as eluant to afford the title compound, 201 mg.

¹H-nmr (CDCl₃, 400 MHz) δ: 1.46 (s, 9H), 1.75 (m, 2H), 2.25 (s, 3H), 2.42 (m, 6H), 2.90 (t, 2H), 3.43 (s, 2H), 3.63 (t, 2H), 4.55 (s, 2H), 7.01 (m, 1H), 7.14 (m, 2H). LRMS: m/z (ES⁺) 346 [MH⁺]

Preparation 45 tert-Butyl 5-(4-morpholinylmethyl)-3,4-dihydro-2(1H)-isoquinolinecarboxylate

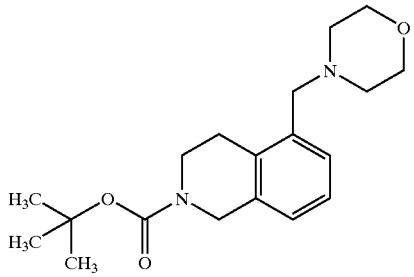

A solution of morpholine (1.34 mL, 15.3 mmol) and the aldehyde from preparation 25 (2.0 g, 7.65 mmol) in acetonitrile (40 mL) was stirred at room temperature for 1.5 hours, then cooled in an ice-bath. Sodium triacetoxyborohdride (1.95 g, 9.18 mmol) was added portionwise, the reaction allowed to warm to room temperature and stirred for 6 hours. The reaction was diluted with water (30 mL), extracted with ethyl acetate (3×50 mL) and the combined organic extracts dried (MgSO₄) and evaporated under reduced pressure to give a yellow oil, 2.60 g.

This was purified by column chromatography on silica gel using dichloromethane:diethyl ether (90:10 to 80:20) to afford the title compound as a colourless oil, 2.09 g.

¹H-nmr (CDCl₃, 400 MHz) δ: 1.47 (s, 9H), 2.39 (m, 4H), 2.90 (m, 2H), 3.40 (s, 2H), 3.62 (m, 6H), 4.57 (s, 2H), 7.00 (m, 1H), 7.10 (m, 2H). LRMS: m/z (ES⁺) 355 [MNa⁺]

Preparation 46 tert-Butyl 5-{[cyclopropyl(methyl)amino]methyl}-3,4-dihydro-2(1H)-isoquinolinecarboxylate

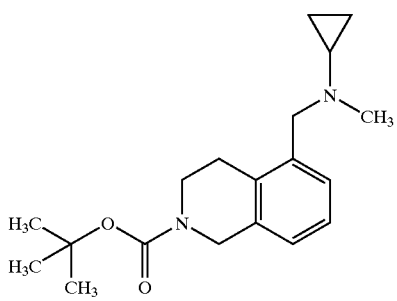

A mixture of the amine from preparation 41 (1.1 g, 3.43 mmol), 37% aqueous formaldehyde (1.05 mL, 10.9 mmol) and sodium triacetoxyborohydride (3.1 g, 14.64 mmol) in dichloromethane (50 mL) was stirred at room temperature for 18 hours. The reaction mixture was partitioned between 0.88 ammonia (15 mL), water (30 mL) and dichloromethane (40 mL), and the layers separated. The organic phase was washed with brine, dried (MgSO₄) and evaporated under reduced pressure to afford the title compound as a clear oil, 940 mg.

¹H-nmr (CDCl₃, 400 MHz) δ: 0.37 (m, 2H), 0.43 (m, 2H), 1.46 (s, 9H), 1.69 (m, 1H), 2.20 (s, 3H), 2.86 (m, 2H), 3.60 (m, 4H), 4.53 (s, 2H), 7.00 (m, 1H), 7.10 (m, 2H). LRMS: m/z (ES⁺) 317 [MH⁺], 339 [MNa⁺]

Preparation 47 tert-Butyl 5-[(1-methyl-4-piperidinyl)oxy]-3,4-dihydro-2(1H)-isoquinolinecarboxylate

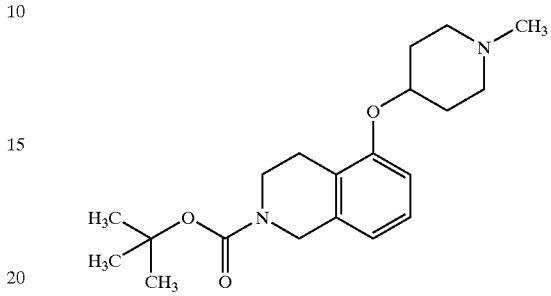

A solution of diethylazodicarboxylate (505 mg, 2.9 mmol) in dichloromethane (3 mL) was added dropwise to a cooled (4° C.) solution of the tetrahydroisoquinolinol from preparation 22 (498 mg, 2 mmol) and triphenylphosphine (787 mg, 3 mmol) in dichloromethane (25 mL) and the solution stirred at this temperature for 30 minutes. 1-Methyl-4-hydroxypiperidine (403 mg, 3.5 mmol) was added and the reaction stirred at room temperature for 17 hours. An additional solution of triphenylphosphine (393 mg, 1.5 mmol) and diethylazodicarboxylate (226 mg, 1.3 mmol) in dichloromethane (2 mL), followed by 1-methyl-4-hydroxypiperidine (207 mg, 1.8 mmol) were added and the reaction stirred for a further 17 hours at room temperature. The mixture was diluted with dichloromethane (50 mL), washed with water (2×75 mL), dried (MgSO₄) and concentrated under reduced pressure. The residual orange oil was purified by column chromatography on silica gel using an elution gradient of dichloromethane:methanol:0.88 ammonia (97:3:0.2 to 93:7:0.7) to give the title compound as a yellow oil, 466 mg.

¹Hnmr (CDCl₃, 400 MHz) δ: 1.48 (s, 9H), 1.86 (m, 2H), 1.97 (m, 2H), 2.29 (s, 3H), 2.32 (m, 2H), 2.61 (m, 2H), 2.77 (t, 2H), 3.63 (t, 2H), 4.34 (m, 1H), 4.54 (s, 2H), 6.69 (d, 2H), 7.09 (dd, 1H). LRMS: m/z (ES⁺) 347 [MH⁺]

Preparations 48 to 50

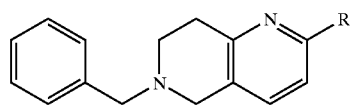

Acetic acid (2.5–3.5 eq) followed by the appropriate amine (1.1–1.7 eq) were added to a solution of the aldehyde from preparation 29 (1 eq) in tetrahydrofuran (5 mL per mmol) and the solution stirred for 15 minutes. Sodium triacetoxyborohydride (2–2.3 eq.) was added, and the reaction stirred at room temperature for 17 hours. 2N hydrochloric acid was added, to give a pH of 1, the mixture stirred for 15 minutes, then re-basified to pH 12 using 2N sodium hydroxide solution. The mixture was extracted with dichloromethane, the combined organic extracts dried (MgSO₄) and evaporated under reduced pressure. The crude product was purified by column chromatography on silica gel using an elution gradient of dichloromethane:methanol:0.88 ammonia (95:5:0.5 to 90:10:1) to afford the desired compound.

| Prep | R | Yield % | Data |
|---|---|---|---|
| 48 | ![CH3-N-CH3 structure] | 76 yellow gum | ¹H-nmr(CDCl₃, 400MHz) δ: 2.25(s, 6H), 2.83(t, 2H), 3.01(t, 2H), 3.54(s, 2H), 3.60(s, 2H), 3.70(s, 2H), 7.15(d, 1H), 7.23(m, 2H), 7.35(m, 4H). LRMS: m/z(ES⁺) 304[MNa⁺] |
| 49 | ![pyrrolidine structure] | 86 yellow oil | ¹H-nmr(CDCl₃, 400MHz) δ: 1.77(m, 4H), 2.55(m, 4H), 2.83(t, 2H), 3.03(t, 2H), 3.59(s, 2H), 3.69(s, 2H), 3.72(s, 2H), 7.14–7.38(m, 7H). LRMS: m/z (ES⁺) 308[MH⁺] |
| 50 | ![morpholine structure] | 73 yellow oil | ¹H-nmr(CDCl₃, 400MHz) δ: 2.49(m, 4H), 2.84(t, 2H), 3.03(t, 2H), 3.59(m, 4H), 3.70(m, 6H), 7.16–7.38(m, 7H). LRMS m/z(ES⁺) 346[MNa⁺] |

Preparation 51

2-(3-Azabicyclo[3.1.0]hex-3-ylmethyl)-6-benzyl-5,6,7,8-tetrahydro[1,6]naphthyridine

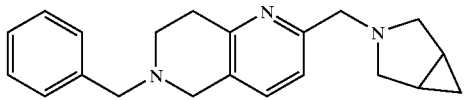

3-Azabicyclo[3.1.0]hexane hydrochloride (WO 9522547) (300 mg, 2.49 mmol), sodium acetate (223 mg, 2.71 mmol) and acetic acid (0.8 mL) were added to a solution of the aldehyde from preparation 29 (570 mg, 2.26 mmol) in tetrahydrofuran (15 mL) and dichloromethane (10 mL), and the solution stirred at room temperature for 0.5 hour. Sodium triacetoxyborohydride (960 mg, 4.52 mmol) was added, and the reaction stirred at room temperature for 18 hours. The mixture was partitioned between sodium hydroxide solution (60 mL, 1N) and ethyl acetate (60 mL) and the layers separated. The organic phase was washed with brine (60 mL), dried (MgSO₄) and evaporated under reduced pressure. The crude product was purified by column chromatography on silica gel using dichloromethane:methanol:0.88 ammonia (95:5:0.5) as eluant, to give the title compound as a yellow oil, 375 mg.

¹H-nmr (DMSOd₆, 400 MHz) δ: 0.30 (m, 1H), 0.62 (m, 1H), 1.35 (m, 2H), 2.35 (m, 2H), 2.76 (m, 2H), 2.88 (m, 4H), 3.52 (s, 2H), 3.57 (s, 2H), 3.64 (s, 2H), 7.03 (d, 1H), 7.30 (m, 6H). LRMS: m/z (ES⁺) 320 [MH⁺]

Preparation 52

(1S,4S)-5-[(6-Benzyl-5,6,7,8-tetrahydro[1,6] naphthyridin-2-yl)methyl]-2-oxa-5-azabicyclo[2.2.1] heptane

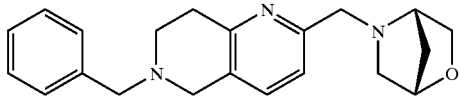

A mixture of the aldehyde from preparation 29 (866 mg, 3.44 mmol), 1S,4S-2-aza-5-oxabicyclo[2.2.1]heptane hydrochloride (700 mg, 5.16 mmol), sodium acetate (423 mg, 5.16 mmol) and acetic acid (310 mg, 5.16 mmol) in tetrahydrofuran (20 mL) was stirred at room temperature for 2 hours. 2M Hydrochloric acid (20 mL) was added cautiously, the mixture stirred for 10 minutes, then the mixture basified using 1N sodium hydroxide solution. The mixture was extracted with dichloromethane (3×60 mL), the combined organic solutions dried (MgSO₄) and evaporated under reduced pressure. The residue was purified by column chromatography on silica gel using an elution gradient of dichloromethane:methanol (100:0 to 90:10) to afford the title compound as a yellow oil, 783 mg.

¹H-nmr (CDCl₃, 400 MHz) δ: 1.79 (m, 1H), 1.99 (m, 1H), 2.69 (m, 1H), 2.86 (t, 2H), 2.93 (m, 1H), 3.03 (t, 2H), 3.52 (m, 1H), 3.62 (s, 2H), 3.66 (m, 1H), 3.72 (s, 2H), 3.89 (m, 2H), 4.16 (m, 1H), 4.44 (m, 1H), 7.21–7.83 (m, 7H). LRMS: m/z (APCl⁺) 336 [MH⁺]

Preparation 53

6-Benzyl-2-[(4-methoxy-1-piperidinyl)methyl]-5,6,7,8-tetrahydro[1,6]naphthyridine

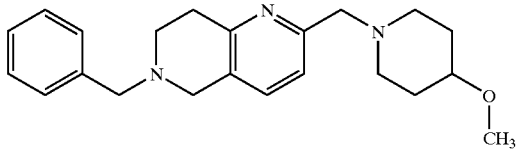

Triethylamine (0.43 mL, 3.2 mmol) followed by the aldehyde from preparation 29 (750 mg, 3.0 mmol) was added to a solution of the piperidine hydrochloride from preparation 94 (483 mg, 3.2 mmol) in tetrahydrofuran (20 mL), and the solution stirred for 1 hour. Sodium triacetoxyborohydride (745 mg, 3.5 mmol) was added portionwise, and the reaction stirred at room temperature for 18 hours. 2N Hydrochloric acid (4 mL) was added, the solution stirred for 5 minutes, then poured into water (80 mL), and the pH adjusted to 9 using 2N sodium hydroxide solution. The mixture was extracted with dichloromethane (3×100 mL), the combined organic extracts dried (MgSO₄) and evaporated under reduced pressure. The crude product was purified by column chromatography on silica gel using dichloromethane:methanol:0.88 ammonia (95:5:0.5) to afford the title compound as an oil, that crystallised on standing, 710 mg.

¹H-nmr (DMSOd₆, 400 MHz) δ: 1.40 (m, 2H), 1.80 (m, 2H), 2.10 (m, 2H), 2.62 (m, 2H), 2.76 (m, 2H), 2.82 (m, 2H), 3.16 (m, 1H), 3.20 (s, 3H), 3.46 (s, 2H), 3.54 (s, 2H), 3.64 (s, 2H), 7.16 (2xs, 2H), 7.20–7.40 (m, 5H). LRMS: m/z (ES⁺) 352 [MH⁺]

Preparation 54

N-(6-Benzyl-5,6,7,8-tetrahydro[1,6]naphthyridin-2-yl)-N-methylamine

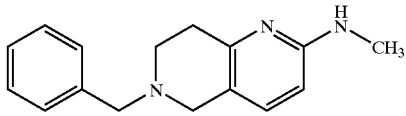

Liquid methylamine (20 mL) was added to a cooled (−70° C.) solution of 6-benzyl-2-chloro-5,6,7,8-tetrahydro[1,6]naphthyridine (WO 9830560) (5.5 g, 21.25 mmol) in methanol (30 mL). The mixture was heated to 140° C. in a sealed vessel for 72 hours, then cooled. The reaction mixture was evaporated under reduced pressure and the residual brown oil purified by column chromatography on silica gel using an elution gradient of dichloromethane:methanol:0.88 ammonia (97:3:0 to 96:4:0.5) to afford the title compound as a white solid, 2.97 g $^1$H-nmr (CDCl$_3$, 400 MHz) δ: 2.80 (m, 4H), 2.87 (s, 3H), 3.49 (s, 2H), 3.68 (s, 2H), 4.36 (bs, 1H), 6.19 (d, 1H), 7.05 (d, 1H), 7.24 (m, 1H), 7.31 (m, 2H), 7.36 (m, 2H). LRMS: m/z (ES$^+$) 254 [MH$^+$]

Preparation 55

6-Benzyl-2-(4-morpholinyl)-5,6,7,8-tetrahydro[1,6]naphthyridine

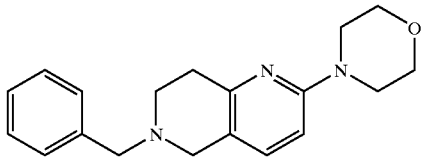

Morpholine (0.33 mL, 3.7 mmol), sodium tert-butoxide (337 mg, 3.7 mmol), racemic 2,2'-bis(diphenylphosphino)-1,1'-binaphthyl (124 mg, 0.2 mmol) and tris(dibenzylideneacetone)dipalladium (0) (92 mg, 0.1 mmol) were added sequentially to a solution of the bromide from preparation 28 (763 mg, 2.5 mmol) in toluene (10 mL), and the solution purged with nitrogen. The reaction was then stirred at 100° C. for 18 hours, cooled and filtered through silica gel, washing through with a solution of dichloromethane:methanol. The filtrate was concentrated under reduced pressure and the residue purified by column chromatography on silica gel using an elution gradient of dichloromethane:methanol (98:2 to 95:5) to afford the title compound.

$^1$H-nmr (CDCl$_3$, 400 MHz) δ: 2.79 (m, 2H), 2.81 (m, 2H), 3.41 (m, 4H), 3.46 (s, 2H), 3.67 (s, 2H), 3.78 (m, 4H), 6.41 (d, 1H), 7.12 (s, 1H), 7.30 (m, 5H). LRMS: m/z (ES$^+$) 310 [MH$^+$]

Preparation 56

6-Benzyl-2-(4-methyl-1-piperazinyl)-5,6,7,8-tetrahydro[1,6]naphthyridine

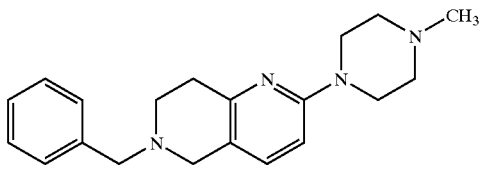

The title compound was obtained in 36% yield, from the bromide from preparation 28 and 1-methylpiperazine, following the procedure described in preparation 55.

$^1$H-nmr (CDCl$_3$, 400 MHz) δ: 2.30 (s, 3H), 2.49 (m, 4H), 2.79 (m, 2H), 2.82 (m, 2H), 3.49 (m, 6H), 3.08 (s, 2H), 6.42 (d, 1H), 7.09 (d, 1H), 7.35 (m, 5H). LRMS: m/z (ES$^+$) 345 [MNa$^+$]

Preparation 57

N-[(6-Benzyl-5,6,7,8-tetrahydro[2,6]naphthyridin-1-yl)methil]-N-methyl-2-propanamine

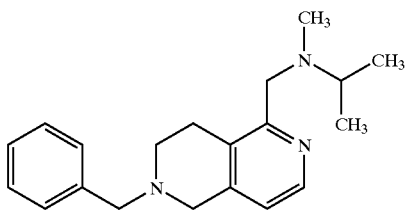

N-Isopropyl-N-methylamine (330 μl, 3.15 mmol) followed by acetic acid (132 μl, 2.31 mmol) were added to a solution of the aldehyde from preparation 35 (530 mg, 2.1 mmol) in tetrahydrofuran (15 mL), and the solution stirred at room temperature for 1 hour. Sodium triacetoxyborohydride (1.11 g, 5.26 mmol) was then added, and the reaction stirred for 18 hours. The reaction mixture was partitioned between 1N sodium hydroxide solution (30 mL), and ethyl acetate (30 mL) and the layers separated. The aqueous phase was extracted with ethyl acetate (30 mL) and the combined organic extracts were dried (MgSO$_4$), and evaporated under reduced pressure to give an oil. This was purified by column chromatography on silica gel using an elution gradient of dichloromethane:methanol:0.88 ammonia (100:0:0 to 90:10:1) to afford the title compound as a yellow oil, 272 mg.

$^1$H-nmr (CDCl$_3$, 400 MHz) δ: 1.06 (d, 6H), 2.13 (s, 3H), 2.77 (t, 2H), 2.85 (m, 1H), 2.99 (t, 2H), 3.58 (s, 2H), 3.62 (s, 2H), 3.66 (s, 2H), 6.78 (m, 1H), 7.35 (m, 5H), 8.23 (m, 1H). LRMS: m/z (ES$^+$) 310 [MH$^+$]

Preparation 58

2-Benzyl-5-(4-morpholinylmethyl)-1,2,3,4-tetrahydro[2,6]naphthyridine

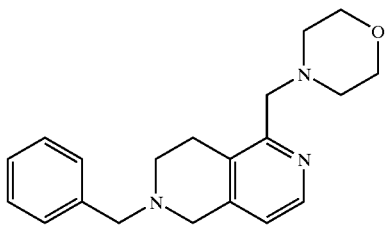

The title compound was obtained as a yellow oil, from the aldehyde from preparation 35 and morpholine, following a similar procedure to that described in preparation 57.

$^1$H-nmr (CDCl$_3$, 400 MHz) δ: 2.42 (m, 4H), 2.79 (m, 2H), 2.99 (m, 2H), 3.57–3.78 (m, 10H), 6.80 (d, 1H), 7.20–7.39 (m, 5H), 8.22 (d, 1H). LRMS m/z (ES$^+$) 346 [MNa$^+$]

Preparation 59

(6-Benzyl-5,6,7,8-tetrahydro[2,6]naphthyridin-1-yl)-N,N-dimethylmethanamine

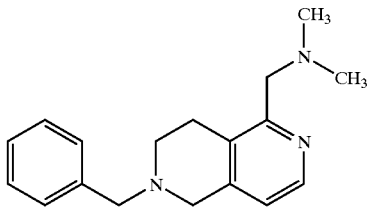

Dimethylamine (2 mL, 2M in tetrahydrofuran, 4 mmol) followed by acetic acid (480 mg, 8 mmol) were added to a solution of the aldehyde from preparation 35 (756 mg, 3 mmol) in tetrahydrofuran (15 mL), and the solution stirred at room temperature for 10 minutes. Sodium triacetoxyborohydride (1.27 g, 6 mmol) was then added, and the reaction stirred for 3 hours. The reaction was quenched by the addition of 2N hydrochloric acid, this solution stirred for 15 minutes, basified using 1N sodium hydroxide solution, then extracted with dichloromethane (3×50 mL). The combined organic extracts were dried (MgSO$_4$), and evaporated under reduced pressure to afford the title compound as an oil, 942 mg.

$^1$H-nmr (CDCl$_3$, 400 MHz) δ: 2.23 (s, 6H), 2.79 (m, 2H), 2.98 (m, 2H), 3.50 (s, 2H), 3.59 (s, 2H), 3.64 (s, 2H), 6.80 (d, 1H), 7.21–7.39 (m, 5H), 8.25 (d, 1H).

Preparation 60

2-Benzyl-5-(1-pyrrolidinylmethyl)-1,2,3,4-tetrahydro[2,6]naphthyridine

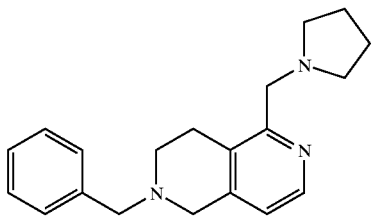

The title compound was obtained in 73% yield from the aldehyde from preparation 35 and pyrrolidine, following a similar procedure described in preparation 59, except the reaction was worked up using ethyl acetate and 0.88 ammonia.

1H-nmr (CDCl$_3$, 400 MHz) δ: 1.76 (m, 4H), 2.55 (m, 4H), 2.78 (m, 2H), 2.97 (m, 2H), 3.58 (s, 2H), 3.67 (s, 2H), 3.70 (s, 2H), 6.79 (d, 1H), 7.30 (m, 5H), 8.26 (d, 1H). LRMS: m/z (ES$^+$) 308 [MH$^+$]

Preparation 61

2-Benzyl-5-(1-piperidinylmethyl)-1,2,3,4-tetrahydro[2,6]naphthyridine

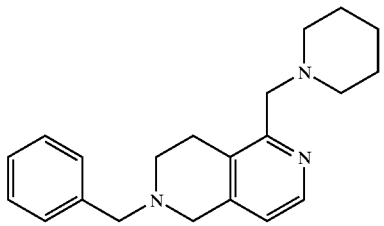

The title compound was obtained in 68% yield from the aldehyde from preparation 35 and piperidine, following a similar procedure to that described in preparation 60.

$^1$H-nmr (CDCl$_3$, 400 MHz) δ: 1.40 (m, 2H), 1.50 (m, 4H), 2.40 (m, 4H), 2.77 (m, 2H), 3.00 (m, 2H), 3.52 (s, 2H), 3.59 (s, 2H), 3.67 (s, 2H), 6.79 (d, 2H), 7.25–7.38 (m, 5H), 8.24 (d, 1H). HRMS: m/z (ES$^+$) 322.2283 [MH$^+$] C$_{21}$H$_{27}$N$_3$—322.2278 [MH$^+$]

Preparation 62

2-Benzyl-5-[(4-methoxy-1-piperidinyl)methyl]-1,2,3,4-tetrahydro[2,6]naphthyridine

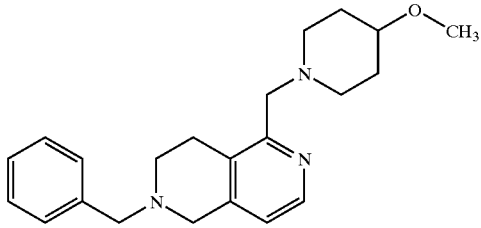

The title compound was obtained as an orange oil from the aldehyde from preparation 35 and 4-methoxypiperidine hydrochloride from preparation 94, following a similar procedure to that described in preparation 60.

¹H-nmr (CDCl₃, 400 MHz) δ: 1.58 (m, 2H), 1.85 (m, 2H), 2.22 (m, 2H), 2.77 (m, 4H), 2.99 (m, 2H), 3.19 (m, 1H), 3.32 (s, 3H), 3.60 (m, 4H), 3.69 (s, 2H), 6.80 (d, 1H), 7.20–7.40 (m, 5H), 8.22 (d, 1H). LRMS: m/z (ES⁺) 352 [MH⁺].

Preparation 63

(1S,4S)-5-[(6-benzyl-5,6,7,8-tetrahydro[2,6]naphthyridin-1-yl)methyl]-2-oxa-5-azabicyclo[2.2.1]heptane

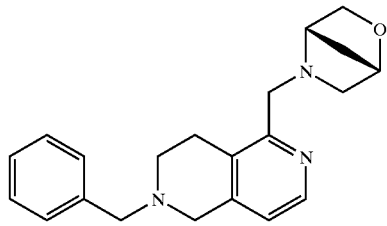

(1S,4S)-2-Oxa-5-azabicyclo[2.2.1]heptane hydrochloride (344 mg, 2.54 mmol), followed by sodium acetate (152 mg, 1.86 mmol) and acetic acid (0.1 mL, 1.86 mmol) were added to a solution of the aldehyde from preparation 35 (427 mg, 1.69 mmol) in tetrahydrofuran (15 mL), and the solution stirred at room temperature for 1 hour. Sodium triacetoxyborohydride (897 mg, 4.23 mmol) was added and the reaction stirred at room temperature for 18 hours. The mixture was concentrated under reduced pressure and the residue partitioned between ethyl acetate (50 mL) and 0.88 ammonia (50 mL), the layers separated, and the aqueous phase further extracted with ethyl acetate (50 mL). The combined organic extracts were dried (Na₂SO₄) and concentrated under reduced pressure. The crude product was purified by column chromatography on silica gel using an elution gradient of dichloromethane:methanol (98:2 to 95:5) to afford the title compound as a yellow oil, 324 mg.

¹H-nmr (CDCl₃, 400 MHz) δ: 1.68 (d, 1H), 1.88 (d, 1H), 2.65 (d, 1H), 2.78 (m, 2H), 2.89 (d, 1H), 2.97 (m, 2H), 3.40 (s, 1H), 3.59 (s, 2H), 3.65 (m, 3H), 3.80 (dd, 2H), 4.06 (d, 1H), 4.38 (s, 1H), 6.79 (d, 1H), 7.30 (m, 5H), 8.22 (d, 1H). LRMS: m/z (ES⁺) 358 [MNa⁺]

Preparation 64

5-(7-Azabicyclo[2.2.1]hept-7-ylmethyl)-2-benzyl-1,2,3,4-tetrahydro[2,6]naphthyridine

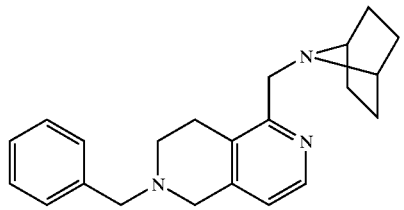

Diisopropylethylamine (720 μl, 4.13 mmol) was added to a solution of 7-azabicyclo[2.2.1]heptane (Can. J. Chem. 1970; 48(13); 2065) (500 mg, 3.75 mmol) in dichloromethane (7 mL), and the solution stirred for 40 minutes. A solution of the aldehyde from preparation 35 (650 mg, 2.57 mmol) in dichloromethane (2 mL) was added, followed by acetic acid (300 μl, 5.16 mmol), and the solution stirred for a further 2 hours. Sodium triacetoxyborohydride (1.1 g, 5.16 mmol) was added, and the reaction stirred at room temperature for 18 hours. The mixture was quenched by the addition of 2N hydrochloric acid (3 mL), then basified using 1N sodium hydroxide solution (20 mL). The mixture was extracted with dichloromethane (2×), the combined organic extracts dried (Na₂SO₄) and evaporated under reduced pressure. The crude product was purified by column chromatography on silica gel using an elution gradient of dichloromethane:methanol:0.88 ammonia (100:0:0 to 94:5:1) to afford the title compound as a brown oil.

¹H-nmr (CDCl₃, 400 MHz) δ: 1.25 (m, 4H), 1.80 (m, 4H), 2.78 (t, 2H), 3.05 (t, 2H), 3.25 (m, 2H), 3.58 (s, 2H), 3.61 (m, 2H), 3.67 (s, 2H), 6.79 (d, 1H), 7.30 (m, 5H), 8.22 (d, 1H). LRMS: m/z (ES⁺) 334 [MH⁺]

Preparation 65 tert-Butyl 4-(6-benzyl-5,6,7,8-tetrahydro[2,6]naphthyridin-1-yl)-1-piperidinecarboxylate

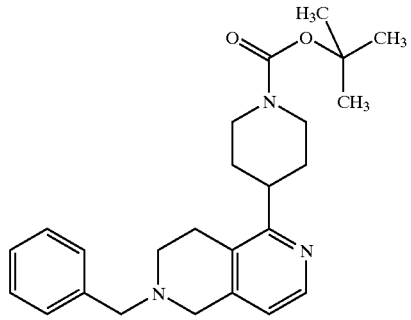

Zinc (809 mg, 12.4 mmol) was stirred in 1N hydrochloric acid (5 mL) for 5 minutes, the mixture filtered, and the collected zinc washed with water, ethanol and diethyl ether, then dried at 100° C. for 5 hours.

Dibromoethane (28 μl, 0.33 mmol) was added to a suspension of the zinc in N,N-dimethylformamide (12 mL), and the mixture heated at 50° C. for 4 minutes, then cooled. Trimethylsilyl chloride (54 mg, 0.50 mmol) was added, the mixture again heated at 50° C. for 5 minutes, tert-butyl 4-iodo-1-piperidinecarboxylate (EP 1078928) (2.57 g, 8.25 mmol) added and stirring continued for 5 minutes. A solution of the bromide from preparation 34 (1.0 g, 3.3 mmol) in N,N-dimethylformamide (2.5 mL), tris(dibenzylideneacetone)dipalladium (0) (38 mg, 0.07 mmol) and tri(o-furyl)phosphine (31 mg, 0.13 mmol) were added, and the reaction mixture heated at 60° C. for 1 hour. The cooled mixture was partitioned between dichloromethane (50 mL) and water (20 mL), and the phases separated. The aqueous layer was extracted with further dichloromethane (2×50 mL), and the combined organic extracts were dried (MgSO₄), filtered through Arbocel® and evaporated under reduced pressure. The residual orange oil was purified by column chromatography on silica gel using an elution gradient of dichloromethane:methanol (100:0 to 96:4) to give the title compound, as an oil, 1.0 g.

¹H-nmr (CDCl₃, 400 MHz) δ: 1.45 (s, 9H), 1.65 (m, 2H), 1.85 (m, 4H), 2.78 (m, 4H), 2.86 (m, 2H), 3.02 (m, 1H), 3.58 (s, 2H), 3.67 (s, 2H), 6.74 (d, 1H), 7.24–7.37 (m, 5H), 8.25 (d, 1H). LRMS: m/z (ES⁺) 408 [MH⁺]

Preparation 66

2-Benzyl-5-(4-piperidinyl)-1,2,3,4-tetrahydro[2,6]naphthyridine trihydrochloride

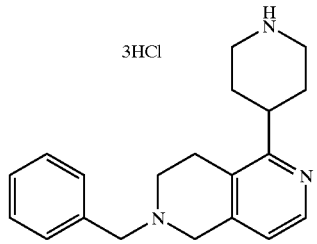

A solution of the protected amine from preparation 65 (990 mg, 2.43 mmol) in dry dichloromethane (30 mL) was cooled in an ice/acetone bath and hydrogen chloride gas bubbled through, until saturation. The solution was stirred for a further 2 hours, then evaporated under reduced pressure to afford the title compound as a cream foam, 924 mg.

$^1$H-nmr (CD$_3$OD, 400 MHz) δ: 1.74 (m, 1H), 2.00 (m, 1H), 2.20 (m, 4H), 3.09 (m, 1H), 3.29 (m, 2H), 3.45 (m, 2H), 3.56 (m, 2H), 4.60 (s, 2H), 4.67 (s, 2H), 7.53 (m, 3H), 7.68 (m, 3H), 8.58 (d, 1H). LRMS: m/z (ES$^+$) 308 [MH$^+$]

Preparation 67

2-Benzyl-5-(1-methyl-4-piperidinyl)-1,2,3,4-tetrahydro[2,6]naphthyridine

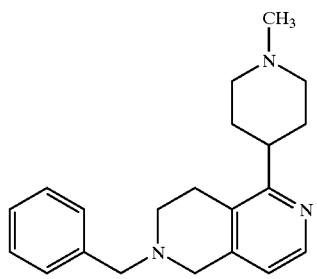

Triethylamine (675 μl, 4.81 mmol) was added to a solution of the amine from preparation 66 (914 mg, 2.40 mmol) in acetonitrile (10 mL), followed by dropwise addition of formaldehyde (37% aq., 390 mg, 4.81 mmol), and the solution stirred at room temperature for 1 hour. Sodium triacetoxyborohydride (2.546 g, 12.02 mmol) was added portionwise and the reaction stirred at room temperature for 72 hours. The mixture was diluted with water (10 mL), then neutralised using sodium bicarbonate solution and extracted with 5% methanol in dichloromethane solution (3×30 mL). The combined organic extracts were evaporated under reduced pressure and the residual orange oil, purified by column chromatography on silica gel using an elution gradient of dichloromethane:methanol:0.88 ammonia (96:4:0 to 90:10:0.5) to give the title compound as an orange oil, 690 mg.

$^1$H-nmr (CDCl$_3$, 400 MHz) δ: 1.77 (m, 2H), 2.07 (m, 4H), 2.33 (s, 3H), 2.77 (m, 3H), 2.84 (t, 2H), 3.01 (m, 2H), 3.57 (s, 2H), 3.67 (s, 2H), 6.72 (d, 1H), 7.25–7.35 (m, 5H), 8.27 (d, 1H). LRMS: m/z (ES$^+$) 322 [MH$^+$]

Preparation 68

N,6-Dibenzyl-5,6,7,8-tetrahydro[2,6]naphthyridin-1-amine

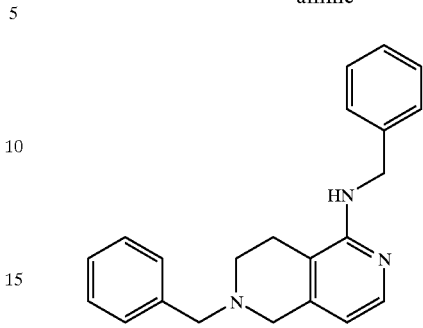

A mixture of the bromide from preparation 34 (303 mg, 1 mmol) and benzylamine (3 mL) was stirred at 160° C. for 12 hours. The cooled mixture was poured into ethyl acetate, washed with water, then dried (MgSO$_4$) and evaporated under reduced pressure. The residue was purified by column chromatography on silica gel using an elution gradient of dichloromethane:ethyl acetate (100:0 to 60:40) to afford the title compound as a pale yellow oil, 249 mg.

$^1$H-nmr (CDCl$_3$, 400 MHz) δ: 2.42 (t, 2H), 2.80 (t, 2H), 3.54 (s, 2H), 3.66 (s, 2H), 4.26 (m, 1H), 4.67 (d, 2H), 6.29 (d, 1H), 7.20–7.40 (m, 10H), 7.94 (d, 1H). LRMS: m/z (ES$^+$) 330 [MH$^+$]

Preparation 69 tert-Butyl 2-(1-pyrrolidinylmethyl)-7,8-dihydropyrido[4,3-d]pyrimidine-6(5H)-carboxylate

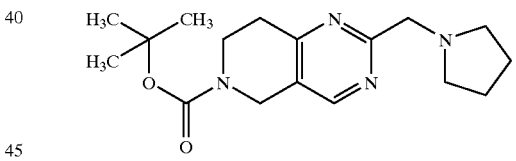

Triethylamine (0.36 mL, 2.6 mmol), followed by methanesulphonyl chloride (0.22 mL, 2.9 mmol) were added to an ice-cold solution of the alcohol from preparation 37 (600 mg, 2.4 mmol) in dichloromethane (6 mL), and the solution stirred at room temperature for 3 hours. The mixture was evaporated under reduced pressure, and the residue re-dissolved in tetrahydrofuran (6 mL). Pyrrolidine (0.99 mL, 11.9 mmol) was added, and the reaction stirred at room temperature for 18 hours. The mixture was partitioned between dichloromethane (50 mL) and water (50 mL), the layers separated and the organic phase dried (MgSO$_4$) and evaporated under reduced pressure. The residual yellow oil was purified by column chromatography using an elution gradient of dichloromethane:methanol:0.88 ammonia (98:2:0.2 to 95:5:0.5) to afford the title compound, 600 mg.

$^1$H-nmr (DMSOd$_6$, 400 MHz) δ: 1.49 (s, 9H), 1.81 (m, 4H), 2.65 (m, 4H), 2.95 (t, 2H), 3.73 (t, 2H), 3.87 (s, 2H), 4.56 (s, 2H), 8.42 (s, 1H). LRMS: m/z (ES$^+$) 319 [MH$^+$]

Preparation 70 tert-Butyl 2-{[(2-methoxnethyl)(methyl)amino]methyl}-7,8-dihydropyrido[4,3-d]pyrimidine-6(5H)-carboxylate

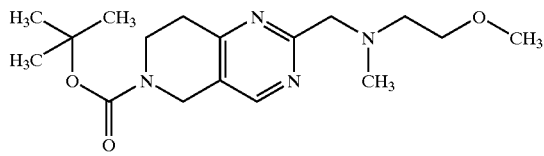

Diisopropylethylamine (388 mg, 3 mmol) was added to an ice-cold solution of the alcohol from preparation 37 (530 mg, 2 mmol) in dichloromethane (10 mL). Methanesulphonyl chloride (267 mg, 2.33 mmol) was added, and the reaction stirred at room temperature for 1 hour. 2-Methoxyethylmethylamine (890 mg, 10 mmol) was added and the reaction stirred at room temperature for a further 18 hours. The mixture was poured into water, then extracted with dichloromethane (3×40 mL), the combined organic extracts dried (MgSO$_4$) and evaporated under reduced pressure. The crude product was purified by column chromatography on silica gel using an elution gradient of dichloromethane:methanol (100:0 to 97:3) to afford the title compound as a yellow oil, 285 mg.

$^1$H-nmr (CDCl$_3$, 400 MHz) δ: 1.49 (s, 9H), 2,40 (s, 3H), 2,75 (t, 2H), 2,95 (t, 2H), 3.34 (s, 3H), 3.58 (t, 2H), 3.76 (t, 2H), 3.83 (s, 2H), 4.59 (s, 2H), 8.42 (s, 1H). LRMS: m/z (ES$^+$) 359 [MNa$^+$]

Preparation 71 tert-Butyl 2-[(dimethylamino)methyl]-7,8-dihydropyrido[4,3-d]pyrimidine-6(5H)-carboxylate

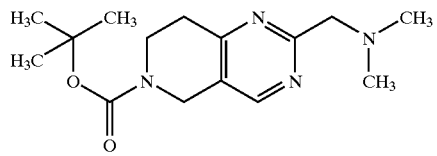

The title compound was obtained as an orange oil, from the alcohol from preparation 37 and dimethylamine (2M in tetrahydrofuran), using a similar procedure to that described in preparation 70.

$^1$H-nmr (CDCl$_3$, 400 MHz) δ: 1.49 (s, 9H), 2.38 (s, 6H), 2.98 (t, 2H), 3.66 (s, 2H), 3.74 (t, 2H), 4.58 (s, 2H), 8.44 (s, 1H). LRMS: m/z (ES$^+$) 315 [MNa$^+$]

Preparation 72 tert-Butyl 2-(1-piperidinlmethyl)-7,8-dihydropyrido[4,3-d]pyrimidine-6(5H)-carboxylate

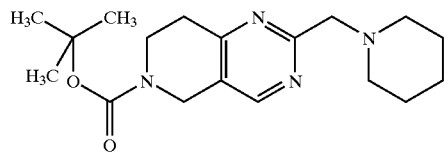

The title compound was obtained as a yellow oil in 54% yield from the alcohol from preparation 37 and piperidine, using a similar method to that described in preparation 70.

$^1$H-nmr (CDCl$_3$, 400 MHz) δ: 1.44 (m, 11H), 1.60 (m, 4H), 2.45 (m, 4H), 2.97 (t, 2H), 3.74 (m, 4H), 4.58 (s, 2H), 8.44 (s, 1H). LRMS: m/z (ES$^+$) 355 [MNa$^+$]

Preparation 73 tert-Butyl 2-{[2-(4-morpholinyl)ethoxy]methyl}-7,8-dihydropyrido[4,3-d]pyrimidine-6(5H)-carboxylate

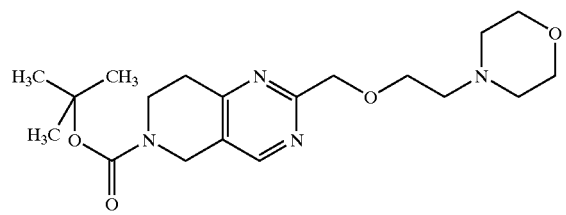

Triethylamine (305 µl, 2.19 mmol) and methanesulphonyl chloride (185 µl, 2.39 mmol) were added to an ice-cold solution of the alcohol from preparation 37 (500 mg, 1.99 mmol) in dichloromethane (5 mL), and the solution stirred at room temperature for 2 hours.

4-(2-Hydroxyethyl)morpholine (730 µl, 5.98 mmol) was added dropwise to an ice-cooled suspension of sodium hydride (265 mg, 60% dispersion in mineral oil, 6.57 mmol) in tetrahydrofuran (5 mL), and once addition was complete, the mixture was stirred at room temperature for 1.5 hours.

The first solution was concentrated under reduced pressure, the residual yellow oil redissolved in tetrahydrofuran (2 mL), and the prepared solution of 2-hydroxyethylmorpholine anion, added dropwise. The resulting mixture was stirred at room temperature for 18 hours, then partitioned between water (30 mL) and dichloromethane (30 mL). The layers were separated, the aqueous phase extracted with further dichloromethane (30 mL), and the combined organic solutions dried (Na$_2$SO$_4$) and evaporated under reduced pressure. The residual brown oil was purified by column chromatography on silica gel using dichloromethane:methanol:0.88 ammonia (98:2:1) as eluant to afford the title compound as a yellow oil, 600 mg.

$^1$H-nmr (CDCl$_3$, 400 MHz) δ: 1.49 (s, 9H), 2.52 (m, 4H), 2.68 (t, 2H), 2.95 (t, 2H), 3.60 (m, 2H), 3.75 (m, 6H), 4.58 (s, 2H), 4.71 (s, 2H), 8.45 (s, 1H). LRMS: m/z (ES$^+$) 401 [MNa$^+$]

Preparation 74

7-Benzyl-4-(1-pyrrolidinylmethyl)-5,6,7,8-tetrahydropyrdor[3,4-d]pyrimidine

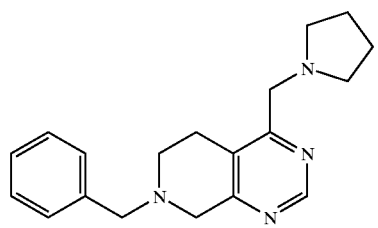

Pyrrolidine (322 mg, 4.54 mmol) and acetic acid (420 mg, 7 mmol) were added to a solution of the aldehyde from preparation 40 (574 mg, 2.27 mmol) in tetrahydrofuran (25 mL), and the solution stirred at room temperature for 30 minutes. Sodium triacetoxyborohydride (1.48 g, 7 mmol) was added, and the reaction stirred for a further 4 hours. The mixture was basified using saturated sodium bicarbonate solution, and extracted using dichloromethane (3×50 mL). The combined organic extracts were dried (MgSO₄) and evaporated under reduced pressure. The crude product was purified using column chromatography on silica gel using an elution gradient of dichloromethane:methanol (100:0 to 85:5) to afford the title compound as a yellow oil, 401 mg.

¹H-nmr (CDCl₃, 400 MHz) δ: 1.78 (m, 4H), 2.59 (m, 4H), 2.78 (t, 2H), 2.91 (t, 2H), 3.68 (s, 2H), 3.69 (s, 2H), 3.71 (s, 2H), 7.25–7.35 (m, 5H), 8.87 (s, 1H). LRMS: m/z (ES⁺) 309 [MH⁺]

Preparation 75

7-Benzyl-4-(1-piperidinylmethyl)-5,6,7,8-tetrahydropyrido[3,4-d]pyrimidine

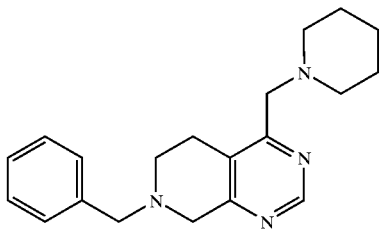

The title compound was obtained as colourless crystals in 52% yield from the aldehyde from preparation 40 and piperidine, following a similar procedure to that described in preparation 74.

¹H-nmr (CDCl₃, 400 MHz) δ: 1.43 (m, 2H), 1.56 (m, 4H), 2.40 (m, 4H), 2.77 (t, 2H), 2.95 (t, 2H), 3.49 (s, 2H), 3.68 (s, 2H), 3.71 (s, 2H), 7.35 (m, 5H), 8.86 (s, 1H). LRMS: m/z (ES⁺) 345 [MNa⁺]

Preparation 76

7-Benzyl-4-[(4-methoxy-1-piperidinyl)methyl]-5,6,7,8-tetrahydropyrido[3,4-d]pyrimidine

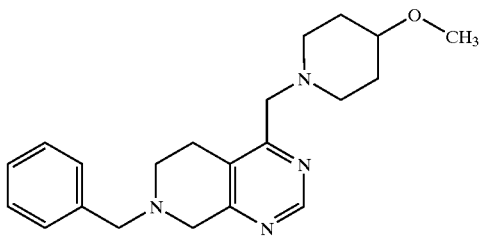

The title compound was obtained as a yellow oil in 44% yield, from the aldehyde from preparation 40 and the amine hydrochloride from preparation 94, following a similar procedure to that described in preparation 74, except, 1.2 eq of diisopropylethylamine was also used in the reaction.

¹H-nmr (CDCl₃, 400 MHz) δ: 1.56 (m, 2H), 1.88 (m, 2H), 2.22 (m, 2H), 2.70 (m, 2H), 2.77 (t, 2H), 2.94 (t, 2H), 3.22 (m, 1H), 3.32 (s, 3H), 3.52 (s, 2H), 3.68 (s, 2H), 3.71 (s, 2H), 7.25–7.36 (m, 5H), 8.86 (s, 1H). LRMS: m/z (ES⁺) 375 [MNa⁺]

Preparation 77

2-[Benzyl(1H-imidazol-4-ylmethyl)amino]ethanol

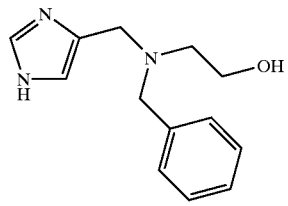

A suspension of 4-imidazolecarboxaldehyde (14 g, 145.7 mmol) and N-benzylethanolamine (26.4 g, 174.8 mmol) in tetrahydrofuran (200 mL) was stirred at room temperature for 1 hour. Sodium triacetoxyborohydride (37.06 g, 174.8 mmol) was added portionwise over 40 minutes, and the reaction stirred at room temperature for 18 hours. The reaction was quenched by the addition of water (150 mL), the mixture neutralised using saturated sodium bicarbonate solution, and then extracted with dichloromethane (3×300 mL). The combined organic extracts were dried (MgSO₄) and evaporated under reduced pressure to give a yellow oil. This was purified by column chromatography on silica gel using an elution gradient of dichloromethane:methanol:0.88 ammonia (95:5:0 to 90:10:1) to afford the title compound, 18.1 g.

¹H-nmr (CDCl₃, 400 MHz) δ: 2.73 (t, 2H), 3.63 (t, 2H), 3.67 (s, 2H), 3.71 (s, 2H), 6.88 (s, 1H), 7.25–7.31 (m, 5H), 7.57 (s, 1H). LRMS: m/z (ES⁻) 230 [M–H]⁻

Preparation 78

N-Benzyl-N-(2-chloroethyl)-N-(1H-imidazol-4-ylmethyl)amine dihydrochloride

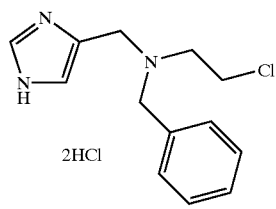

Thionyl chloride (11.35 mL, 155.6 mmol) was added to a solution of the alcohol from preparation 77 (9.0 g, 38.9 mmol) in dichloromethane (200 mL) over 20 minutes. The solution was then stirred under reflux for 3 hours, and allowed to cool. The mixture was concentrated under reduced pressure and azeotroped with acetonitrile (2×) and dried in vacuo, to afford the title compound as a solid, 11.14 g.

¹H-nmr (CD₃OD, 400 MHz) δ: 3.24 (m, 2H), 3.78 (m, 2H), 4.15 (s, 2H), 4.25 (s, 2H), 7.40 (m, 3H), 7.46 (m, 2H), 7.64 (s, 1H), 8.88 (s, 1H). LRMS: m/z (ES⁺) 250 [MH⁺]

Preparation 79

7-Benzyl-5,6,7,8-tetrahydroimidazo[1,5-a]pyrazine

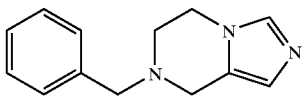

Triethylamine (19.55 mL, 140 mmol) was added to a solution of the chloride from preparation 78 (11.12 g, 38.9 mmol) in acetonitrile (150 mL) over 20 minutes, and the reaction heated under reflux for 6 hours. The cooled mixture was filtered, and the filtrate concentrated under reduced pressure. The residual oil was partitioned between dichloromethane (300 mL) and saturated sodium bicarbonate solution (150 mL) and the phases separated. The aqueous layer was extracted with further dichloromethane (2×300 mL), and the combined organic extracts dried (MgSO$_4$) and evaporated under reduced pressure. The crude product was purified by column chromatography on silica gel using an elution gradient of dichloromethane:methanol (100:0 to 95:5) to afford the title compound as an orange solid, 3.62 g.

$^1$H-nmr (CDCl$_3$, 400 MHz) δ: 2.84 (t, 2H), 3.67 (s, 2H), 3.70 (s, 2H) 4.02 (t, 2H), 6,73 (s, 1H), 7.25–7.35 (m, 6H). LRMS: m/z (ES$^+$) 214 [MH$^+$]

Preparation 80

7-Benzyl-3-ethyl-5,6,7,8-tetrahydroimidazo[1,5-a]pyrazine

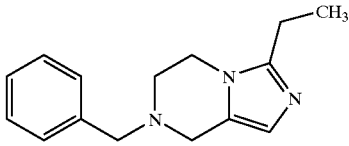

n-Butyllithium (3.3 mL, 1.6M in hexanes, 5.28 mmol) was added dropwise to a cooled (−78° C.) solution of the compound from preparation 79 (1.0 g, 4.69 mmol) in tetrahydrofuran (10 mL), so as to maintain the temperature below −70° C., and the solution then allowed to warm to 0° C. over 30 minutes. Ethyl iodide (1.22 mL, 15.0 mmol) was added, and the mixture stirred at 0° C. for 45 minutes. The reaction was allowed to warm to room temperature, then partitioned between ethyl acetate (30 mL) and saturated sodium bicarbonate solution (6 mL). The phases were separated, the aqueous layer extracted with further ethyl acetate, and the combined organic extracts dried (MgSO$_4$) and evaporated under reduced pressure. The residual orange oil was purified by column chromatography on silica gel using an elution gradient of dichloromethane:methanol (99:1 to 90:10) to afford the title compound as an orange oil, 552 mg.

$^1$H-nmr (CDCl$_3$, 400 MHz) δ: 1.30 (t, 3H), 2.62 (q, 2H), 2.84 (t, 2H), 3.63 (s, 2H), 3.68 (s, 2H), 3.85 (t, 2H), 6.62 (s, 1H), 7.24–7.34 (m, 5H). LRMS: m/z (ES$^+$) 242 [MH$^+$]

Preparation 81

7-Benzyl-3-methyl-5,6,7,8-tetrahydroimidazo[1,5-a]pyrazine

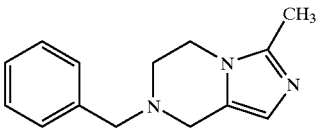

The title compound was obtained as an orange oil in 89% yield from the compound from preparation 79 and methyl iodide, following the procedure described in preparation 80.

$^1$H-nmr (CDCl$_3$, 400 MHz) δ: 2.30 (s, 3H), 2.84 (t, 2H), 3.62 (s, 2H), 3.68 (s, 2H), 3.83 (t, 2H), 6.59 (s, 1H), 7.25–7.34 (m, 5H). LRMS: m/z (ES$^+$) 228 [MH$^+$].

Preparation 82

2-(7-Benzyl-5,6,7,8-tetrahydroimidazo[1,5-a]pyrazin-3-yl)-2-propanol

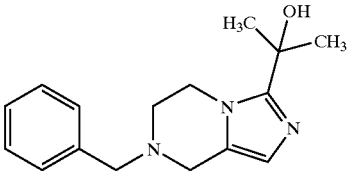

n-Butyllithium (6.21 mL, 1.6M in hexanes, 9.94 mmol) was added dropwise to a cooled (−78° C.) solution of the compound from preparation 79 (2.0 g, 9.38 mmol) in tetrahydrofuran (20 mL), so as to maintain the temperature below −70° C., and the solution then allowed to warm to 0° C. over 30 minutes. Acetone (2.06 mL, 28.13 mmol) was added, and the mixture stirred at 0° C. for 45 minutes. The reaction was allowed to warm to room temperature, then quenched by the addition of water (10 mL), then neutralised using 2N hydrochloric acid. The mixture was extracted with ethyl acetate (3×50 mL), and the combined organic extracts dried (MgSO$_4$) and evaporated under reduced pressure. The residual orange oil was purified by column chromatography on silica gel using an elution gradient of dichloromethane:methanol (99:1 to 94:6) to afford the title compound as a solid, 1.21 g.

$^1$H-nmr (CDCl$_3$, 400 MHz) δ: 1.63 (s, 6H), 2.80 (t, 2H), 3.63 (s, 2H), 3.67 (s, 2H), 4.23 (t, 2H), 6.60 (s, 1H), 7.25–7.39 (m, 5H). LRMS: m/z (ES$^+$) 272 [MH$^+$]

Preparation 83

7-Benzyl-3-bromo-5,6,7,8-tetrahydroimidazo[1,5-a]pyrazine

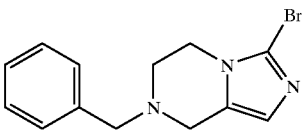

n-Butyllithium (2.2 mL, 2.5M in hexane, 5.5 mmol) was added dropwise to a cooled (−78° C.) solution of the compound from preparation 79 (1.07 g, 5 mmol) in tetrahydrofuran (20 mL), and the solution stirred for 15 minutes. Bromine (880 mg, 5.5 mmol) was then added dropwise, the reaction stirred for a further 15 minutes, then poured into water. The mixture was extracted with dichloromethane (3×50 mL), the combined organic extracts dried (MgSO$_4$) and concentrated under reduced pressure. The crude product was purified by column chromatography using an elution gradient of dichloromethane:methanol (100:0 to 95:5), then repeated using dichloromethane:ethyl acetate (100:0 to 60:40), to afford the title compound as a pale yellow crystalline solid, 979 mg.

$^1$H-nmr (CDCl$_3$, 400 MHz) δ: 2.86 (t, 2H), 3.62 (s, 2H), 3.69 (s, 2H), 3.86 (t, 2H), 6.71 (s, 1H), 7.25–7.34 (m, 5H). LRMS: m/z (ES$^+$) 314, 316 [MNa$^+$]

Preparation 84

3-Azido-7-benzyl-5,6,7,8-tetrahydroimidazo[1,5-a]pyrazine

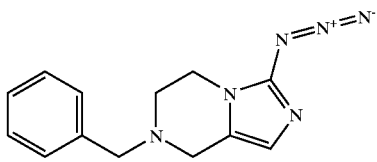

n-Butyllithium (1.23 mL, 2.5M in hexanes, 3.09 mmol) was added to a cooled (−78° C.) solution of the compound from preparation 79 (548 mg, 2.57 mmol) in tetrahydrofuran (10 mL), and the mixture stirred for 10 minutes. p-Toluenesulphonyl azide (WO 9824759) (609 mg, 3.09 mmol) was added, the reaction stirred for a further 10 minutes, and then saturated sodium bicarbonate solution (4 mL) added. The mixture was warmed to room temperature, diluted with brine, and extracted with dichloromethane (2×60 mL). The combined organic solutions were dried (MgSO$_4$), and evaporated under reduced pressure. The residue was purified by column chromatography on silica gel using an elution gradient of dichloromethane:ethyl acetate (100:0 to 60:40) to afford the title compound as a yellow-orange oil, 154 mg.

$^1$H-nmr (CDCl$_3$, 400 MHz) δ: 2.79 (t, 2H), 3.58 (s, 2H), 3.66 (s, 2H), 3.70 (t, 2H), 6.56 (s, 1H), 7.25–7.36 (m, 5H). LRMS: m/z (ES$^+$) 277 [MNa$^+$]

Preparation 85

N-(7-Benzyl-5,6,7,8-tetrahydroimidazo[1,5-a]pyrazin-3-yl)-N,N-dimethylamine

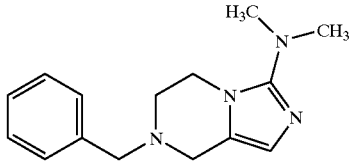

A solution of the bromide from preparation 83 (950 mg, 3.25 mmol) in ethanolic dimethylamine (33%, 12 mL) was heated at 140° C. in a sealed vessel for 4 days. The cooled mixture was poured into water, and extracted with dichloromethane (3×50 mL). The combined organic extracts were dried (MgSO$_4$) and evaporated under reduced pressure. The residue was purified by column chromatography on silica gel, using an elution gradient of dichloromethane:methanol (100:0 to 95:5) and repeated using ethyl acetate:methanol (100:0 to 95:5) to afford the title compound as an orange oil, 172 mg.

$^1$H-nmr (CDCl$_3$, 400 MHz) δ: 2.75 (s, 6H), 2.79 (t, 2H), 3.60 (s, 2H), 3.67 (s, 2H), 3.80 (t, 2H), 6.44 (s, 1H), 7.25–7.38 (m, H). LRMS: m/z (ES$^+$) 257 [MH$^+$]

Preparation 86

7-Benzyl-N-(2-methoxyethyl)-N-methyl-5,6,7,8-tetrahydroimidazo[1,5-a]pyrazin-3-amine

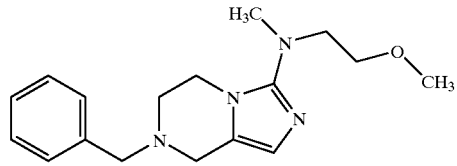

A solution of the bromide from preparation 83 (52 mg, 0.18 mmol) in N-(2-methoxyethyl)methylamine (3 mL) was heated at 140° C. for 18 hours in a sealed vessel. The reaction was heated to 185° C. for a further 5 hours, then cooled and partitioned between 0.1N sodium hydroxide solution and dichloromethane. The layers were separated, the aqueous phase extracted with further dichloromethane (2×50 mL), and the combined organic solutions dried (MgSO$_4$) and evaporated under reduced pressure. The residue was purified by column chromatography on silica gel using ethyl acetate:methanol:0.88 ammonia (100:0:0 to 93:7:0.7) to afford the title compound as a yellow oil, 75 mg.

$^1$H-nmr (CDCl$_3$, 400 MHz) δ: 2.76 (m, 5H), 3.18 (t, 2H), 3.32 (s, 3H), 3.48 (t, 2H), 3.59 (s, 2H), 3.66 (s, 2H), 3.82 (t, 2H), 6.46 (s, 1H), 7.25–7.36 (m, 5H). LRMS: m/z (ES$^+$) 323 [MNa$^+$]

Preparation 87

1-(7-Benzyl-5,6,7,8-tetrahydroimidazo[1,5-a]pyrazin-3-yl)-1-methylethyl acetate and Preparation 88

7-Benzyl-3-isopropenyl-5,6,7,8-tetrahydroimidazo[1,5-a]pyrazine

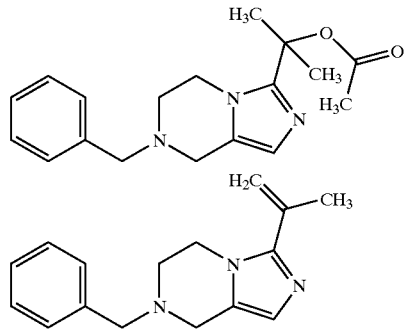

Acetic anhydride (541 μl, 5.74 mmol) was added dropwise to a solution of the alcohol from preparation 82 (1.25 g, 4.59 mmol) in pyridine (20 mL), containing 4-dimethylaminopyridine (70 mg, 0.57 mmol). The solution was stirred at room temperature for 72 hours then evaporated under reduced pressure. The residual orange oil was partitioned between ethyl acetate (100 mL) and 10% sodium bicarbonate solution (50 mL), and the layers separated. The organic phase was washed with water (2×50 mL), dried (MgSO₄) and evaporated under reduced pressure. The crude product was purified by column chromatography on silica gel using an elution gradient of dichloromethane:methanol (100:0 to 94:6) to afford the title compound as an orange oil, 471 mg.

¹H-nmr (CDCl₃, 400 MHz) (2:3 mixture of compounds) δ: 1.84 (s, 6H), 2.02 (s, 3H), 2.19 (s, 3H), 2.80 (t, 2H), 2.80 (t, 2H), 3.65 (2xs, 4H), 3.70 (2xs, 4H), 4.04 (m, 2H), 4.04 (m, 2H), 5.29 (s, 2H), 6.64 (s, 1H), 6.77 (s, 1H), 7.27–7.37 (m, 5H), 7.27–7.37(m, 5H). LRMS: m/z (ES⁺) 336 [MNa⁺] (preparation 87) LRMS: m/z (ES⁺) 254 [MH⁺] (preparation 88)

Preparation 89

Formyl(2-oxobutyl)formamide

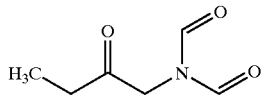

A mixture of bromobutan-2-one (10 g, 66 mmol), and sodium diformylamide (6.8 g, 72 mmol) in acetonitrile (50 mL) was stirred at room temperature for 3 hours, then warmed to 35° C. for 2 hours. The mixture was stirred for a further 48 hours at room temperature, then filtered, washing through with additional acetonitrile (50 mL). The filtrate was evaporated under reduced pressure to afford the title compound as a clear oil, 9.1 g.

¹H-nmr (CDCl₃, 400 MHz) δ: 1.10 (t, 3H), 2.50 (q, 2H), 4.42 (s, 2H), 8.90 (bs, 2H).

Preparation 90

1-Amino-2-butanone hydrochloride

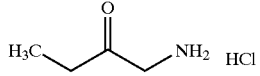

A solution of the compound from preparation 89 (9.1 g, 63.6 mmol) in ethanolic hydrochloric acid (5%, 175 mL) was stirred at room temperature for 48 hours. The reaction was then evaporated under reduced pressure to afford the title compound as a tan-coloured solid, 6.3 g.

¹H-nmr (DMSOd₆, 400 MHz) δ: 1.96 (t, 3H), 2.50 (q, 2H), 3.84 (bs, 2H), 8.38 (bs, 3H). LRMS: m/z (ES⁺) 175 [2M+H]⁺

Preparation 91

Benzyl 3-thioxo-1-piperazinecarboxylate

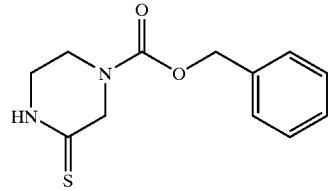

Lawesson's reagent (10.1 g, 20 mmol) was added to a solution of benzyl 3-oxo-1-piperazinecarboxylate (10 g, 43 mmol) in tetrahydrofuran (110 mL), and the reaction heated under reflux for 4 hours. The cooled mixture was concentrated under reduced pressure and the residue partitioned between 1N sodium hydroxide solution (150 mL) and ethyl acetate (250 mL), and the layers separated. The organic extract was washed with 1N sodium hydroxide solution (2×100 mL), then brine (100 mL), and the combined aqueous solutions extracted with ethyl acetate (200 mL). The combined organic solutions were dried (MgSO₄) and concentrated under reduced pressure. The crude product was purified by column chromatography on silica gel using dichloromethane:methanol (98:2) as eluant to afford the title compound as a tan-coloured solid, 6.7 g.

¹H-nmr (DMSOd₆, 400 MHz) δ: 3.24–3.34 (m, 2H), 3.58 (m, 2H), 4.36 (s, 2H), 5.10 (s, 2H), 7.30–7.40 (m, 5H). LRMS: m/z (ES⁺) 273 [MNa⁺]

Preparation 92

Benzyl 3-ethyl-5,6-dihydroimidazo[1,2-a]pyrazine-7(8H)-carboxylate

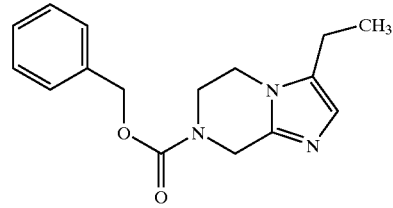

Methyl iodide (2.18 mL, 35 mmol) was added to a solution of the compound from preparation 91 (1 g, 3.5 mmol) in tetrahydrofuran (15 mL), and the reaction stirred at room temperature for 18 hours. The mixture was concentrated under reduced pressure, the residue re-dissolved in tetrahydrofuran (15 mL), diisopropylethylamine (1 mL) and the compound from preparation 90 (500 mg, 4 mmol) added, and the solution stirred at room temperature for 18 hours, followed by a further 2 hours under reflux. Acetic acid (15 mL) was added, the mixture concentrated under reduced pressure to a volume of about 15 mL, then heated under reflux for 1 hour. The reaction was evaporated under reduced pressure and the residue purified by column chromatography on silica gel using dichloromethane:methanol (95:5) as eluant to afford the title compound as a pale orange solid, 620 mg.

¹H-nmr (DMSOd₆, 400 MHz) δ: 1.14 (t, 3H), 3.10 (q, 2H), 3.60 (m, 2H), 3.82 (m, 2H), 4.60 (bs, 2H), 5.12 (s, 2H), 6.64 (s, 1H), 7.36 (m, 5H). LRMS: m/z (ES⁺) 286 [MH⁺]

Preparation 93 tert-Butyl 4-methoxy-1-piperidinecarboxylate

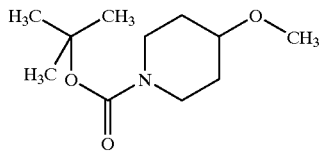

Sodium hydride (1.19 g, 60% in mineral oil, 29.7 mmol) was added portionwise to a cooled (10° C.) solution of tert-butyl 4-hydroxy-1-piperidinecarboxylate (Bioorg. Med. Chem. Lett. 10; 24; 2000; 2815) in tetrahydrofuran (80 mL), and the suspension stirred at room temperature for 1 hour. Iodomethane (1.85 mL, 29.7 mmol) was added, and the reaction stirred at 50° C. for 20 hours. The mixture was diluted with water (50 mL), extracted with ethyl acetate (2×150 mL) and the combined organic extracts washed with saturated sodium bicarbonate solution (50 mL), dried (MgSO$_4$) and evaporated under reduced pressure, to afford the title compound as a golden oil, 5.24 g.

$^1$H-nmr (CDCl$_3$, 400 MHz) δ: 1.47 (s, 9H), 1.50 (m, 2H), 1.80 (m, 2H), 3.08 (m, 2H), 3.34 (m, 4H), 3.75 (m, 2H). LRMS: m/z (ES$^+$) 238 [MNa$^+$]

Preparation 94

4-Methoxypiperidine hydrochloride

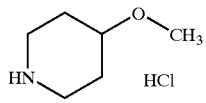

Hydrogen chloride was bubbled through an ice-cooled solution of the compound from preparation 93 (5.2 g, 24.2 mmol) in dichloromethane (100 mL), and the reaction stirred for 1.5 hours. The solution was purged with nitrogen, then evaporated under reduced pressure to afford the title compound as an off-white solid, 3.67 g.

$^1$H-nmr (DMSOd$_6$, 400 MHz) δ: 1.87 (m, 2H), 1.99 (m, 2H), 3.10 (m, 2H), 3.28 (m, 2H), 3.36 (s, 3H), 3.54 (m, 1H). LRMS: m/z (ES$^+$) 231 [2MH$^+$]

Preparation 95

N-(1,2,3,4-Tetrahydro-5-isoquinolinylmethyl) cyclopropanamine dihydrochloride

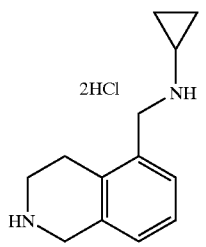

Hydrogen chloride was bubbled through an ice-cooled solution of the protected amine from preparation 29 (1.17 g, 3.87 mmol) in dichloromethane (35 mL), for 20 minutes. The reaction was then stirred for a further 30 minutes at room temperature and evaporated under reduced pressure to afford the title compound as a white solid, 1.15 g.

$^1$Hnmr (DMSOd$_6$, 400 MHz) δ: 0.83 (m, 2H), 0.95 (m, 2H), 2.67 (m, 1H), 3.10 (t, 2H), 3.34 (m, 2H), 4.17 (s, 2H), 4.26 (s, 2H), 7.26 (m, 2H), 7.48 (d, 1H), 9.60 (bs, 4H). LRMS: m/z (ES$^+$) 203 [MH$^+$]

Preparations 96 to 99

The following compounds of general structure:

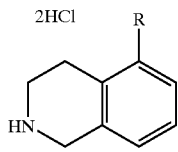

were prepared from the corresponding protected amines, following the procedure described in preparation 95:

| Prep no | R | Form | Data |
|---|---|---|---|
| 96 | -cyclopropyl) | White solid | $^1$Hnmr(DMSOd$_6$, 400MHz) (rotamers) δ: 0.70(m, 4H), 1.15(m, 1H), 2.67(2xs, 3H), 2.90(m, 1H), 3.33(m, 2H), 4.20(s, 2H), 4.40(2xs, 2H), 7.30(m, 2H), 7.60(m, 1H), 9.63(bs, 2H), 10.76(bs, 1H). LRMS: m/z(ES$^+$) 217[MH$^+$] |
| 97 | ![](bicyclic N) | White foam | $^1$Hnmr(DMSOd$_6$, 400MHz) δ: 0.59(m, 1H), 1.34(m, 1H), 1.72(m, 2H), 3.18(m, 2H), 3.36(m, 6H), 4.21(s, 2H), 4.34(d, 2H), 7.24(m, 2H), 7.73(m, 1H), 9.58(bs, 2H), 10.95(bs, 1H). LRMS: m/z(ES$^+$) 229[MH$^+$] |
| 98 | | White foam | $^1$Hnmr(DMSOd$_6$, 400MHz) δ: 3.01–3.40(m, 7H), 3.90(bs, 1H), 4.01(bs, 1H), 4.22(m, 6H), 4.40(s, 2H), 7.28(m, 2H), 7.43(m, 1H), 9.40–9.56 (m, 2H). LRMS: m/z(ES$^+$) 234[MH$^+$] |
| 99 | | White solid | $^1$Hnmr(DMSOd$_6$, 400MHz) δ: 3.20(m, 4H), 3.37(m, 2H), 3.62(m, 2H), 3.90(m, 4H), 4.22(m, 2H), 4.32(s, 2H), 7.30(m, 2H), 7.62(m, 1H), 9.58(bs, 2H), 11.40(bs, 1H). LRMS: m/z(ES$^+$) 233[MH$^+$] |

(a)-isolated as the trihydrochloride salt

Preparation 100

5-[(4-Methyl-1-piperazinyl)methyl]-1,2,3,4-tetrahydroisoquinoline trifluoroacetate

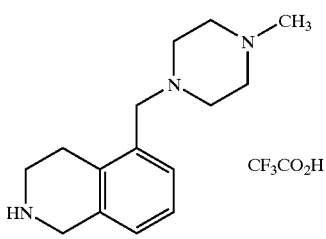

Trifluoroacetic acid (1 mL) was added to an ice-cooled solution of the protected amine from preparation 44 (200 mg, 0.58 mmol) in dichloromethane (3 mL), and the reaction stirred at room temperature for 3 hours. The mixture was concentrated under reduced pressure and the residue azeotroped with toluene (2×) and dichloromethane (3×) to afford the title compound.

$^1$Hnmr (DMSOd$_6$, 400 MHz) δ: 2.79 (s, 3H), 2.81–3.04 (m, 6H), 3.38 (m, 4H), 3.58 (m, 2H), 4.28 (t, 2H), 7.16 (m, 1H), 7.24 (m, 2H), 9.03 (bs, 2H). LRMS: m/z (ES$^+$) 246 [MH$^+$]

Preparation 101

5-[(1-Methyl-4-piperidinyl)oxy]-1,2,3,4-tetrahydroisoquinoline

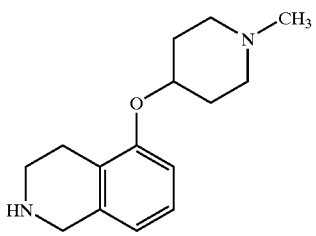

Trifluoroacetic acid (5 mL) was added dropwise to a solution of the protected amine from preparation 47 (420 mg, 1.21 mmol) in dichloromethane (5 mL), and the solution stirred at room temperature for 4 hours. The solution was concentrated under reduced pressure and azeotroped twice with toluene. The residual oil was purified by column chromatography on silica gel using an elution gradient of dichloromethane:methanol:0.88 ammonia (97:3:0.2 to 90:10:1) to afford the title compound as a colourless oil, 198 mg.

$^1$Hnmr (CDCl$_3$, 400 MHz) δ: 1.73 (m, 1H), 1.87 (m, 2H), 1.98 (m, 2H), 2.30 (s, 3H), 2.33 (m, 2H), 2.62 (m, 2H), 2.68 (t, 2H), 3.13 (t, 2H), 3.97 (s, 2H), 4.35 (m, 1H), 6.61 (d, 1H), 6.66 (d, 1H), 7.07 (dd, 1H). LRMS: m/z (ES$^+$) 247 [MH$^+$].

Preparation 102

N,N-Dimethyl(5,6,7,8-tetrahydro[1,6]naphthyridin-2-yl)methanamine

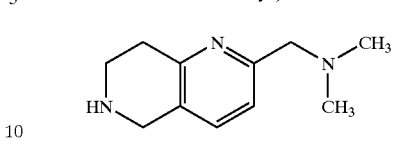

A solution of the protected naphthyridine from preparation 48 (600 mg, 2.13 mmol) in methanol (60 mL) was purged with argon, then heated to reflux. Immediately this was achieved, 10% palladium on charcoal (600 mg) and ammonium formate (268 mg, 4.26 mmol) were added, and the mixture stirred under reflux for 3 minutes. The reaction vessel was then immersed in cold water, and the cooled mixture then filtered through Arbocel®, washing through with ethanol. The filtrate was evaporated under reduced pressure and the residual oil was purified by column chromatography on silica gel using an elution gradient of dichloromethane:methanol:0.88 ammonia (97:3:0.2 to 90:10:1) to afford the title compound as a colourless oil, 259 mg.

$^1$H-nmr (CDCl$_3$, 400 MHz) δ: 2.28 (s, 6H), 2.96 (t, 2H), 3.21 (t, 2H), 3.56 (s, 2H), 3.98 (s, 2H), 7.18 (d, 1H), 7.25 (d, 1H). LRMS: m/z (ES$^+$) 214 [MNa$^+$].

Preparations 103 to 106

The following compounds of general structure:

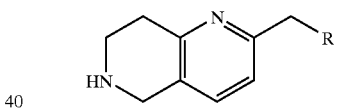

were prepared from the corresponding protected naphthryldines, following a similar procedure to that described in preparation 102.

| Prep. No. | R | Yield %/ Form | Data |
|---|---|---|---|
| 103 | ![pyrrolidinylmethyl] | 55 colourless oil | $^1$H-nmr(CDCl$_3$, 400MHz) δ: 1.78(m, 4H), 2.58(m, 4H), 2.94(t, 2H), 3.21(t, 2H), 3.73(s, 2H), 3.98(s, 2H), 7.17(d, 1H), 7.25(d, 1H). LRMS: m/z(ES$^+$) 218[MH$^+$] |
| 105 | ![4-methoxypiperidinyl] | 88 colourless oil | $^1$H-nmr(DMSOd$_6$, 400MHz) δ: 1.40(m, 2H), 1.80(m, 2H), 2.16(m, 2H), 2.64(m, 2H), 2.70(m, 2H), 2.98(m, 2H), 3.18(s, 3H), 3.20(m, 1H), 3.44(s, 2H), 3.80(s, 2H), 7.12(d, 1H), 7.38(d, 1H). LRMS: m/z(ES$^+$) 262[MH$^+$] |

-continued

| Prep. No. | R | Yield %/ Form | Data |
|---|---|---|---|
| 106 | 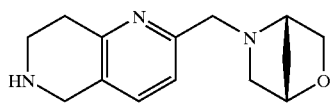 | 72 yellow oil | $^1$H-nmr(CDCl$_3$, 400MHz) δ: 2.55(m, 4H), 2.93(t, 2H), 3.21(t, 2H), 3.60(s, 2H), 3.71(m, 4H), 3.98(s, 2H), 7.19(d, 1H), 7.26(d, 1H). LRMS: m/z(ES$^+$) 234[MH$^+$] |

(a)-compound isolated without column chromatography

Preparation 107

(1S,4S)-5-(5,6,7,8-Tetrahydro[1,6]naphthyridin-2-ylmethyl)-2-oxa-5-azabicyclo[2.2.1]heptane

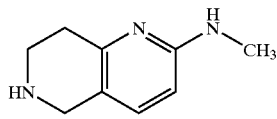

1-Chloroethyl chloroformate (79 mg, 0.55 mmol) was added to a solution of the compound from preparation 52 (168 mg, 0.5 mmol) in acetonitrile (5 mL), and the reaction warmed to 50° C., and the stirred for 30 minutes. The cooled mixture was concentrated under reduced pressure and the residue re-dissolved in methanol (5 mL), and the solution stirred under reflux for 45 minutes. The cooled solution was purified directly by column chromatography on silica gel using dichloromethane:methanol:0.88 ammonia (93:7:1) to afford the title compound as a pale orange oil, 66 mg.

$^1$H-nmr (CDCl$_3$, 400 MHz) δ: 1.80 (m, 1H), 1.99 (m, 1H), 2.71 (m, 1H), 3.01 (m, 1H), 3.04 (t, 2H), 3.32 (t, 2H), 3.59 (m, 1H), 3.67 (m, 1H), 3.94 (q, 2H), 4.11 (s, 2H), 4.16 (m, 1H), 4.44 (m, 1H), 7.35 (s, 2H); LRMS: m/z (APCl$^+$) 246 [MH$^+$]

Preparation 108

N-Methyl-5,6,7.8-tetrahydro[1,6]naphthyridin-2-amine

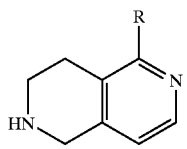

A mixture of the protected naphthyridine from preparation 54 (1.28 g, 5.05 mmol) and 10% palladium on charcoal (130 mg) in 1N hydrochloric acid (10.5 mL) was hydrogenated at 30° C. and 30 psi for 17 hours. The reaction mixture was filtered through Arbocel®, washing through with water and ethanol. The combined filtrate was evaporated under reduced pressure and the residual solid was suspended in a warm solution of water (20 mL) and 1N hydrochloric acid (4 mL) and the mixture filtered through Arbocel®. The filtrate was concentrated under reduced pressure and azeotroped with ethanol, ethyl acetate and diethyl ether. The product was recrystallised from methanol and ethyl acetate to afford the title compound as a solid, 300 mg.

$^1$H-nmr (D$_2$O, 400 MHz) δ: 2.95 (s, 3H), 3.15 (m, 2H), 3.57 (m, 2H), 4.20 (s, 2H), 6.84 (d, 1H), 7.59 (d, 1H). LRMS: m/z (ES$^+$) 164 [MH$^+$]

Preparation 109

2-(4-Morpholinyl)-5,6,7,8-tetrahydro[1,6]naphthyridine

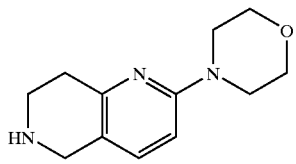

Ammonium formate (1.02 g, 16 mmol), followed by 10% palladium on charcoal (1 g) were added to a solution of the protected naphthyridine from preparation 55 (1 g, 3.2 mmol) in methanol (20 mL), and the reaction heated under reflux for 1.5 hours. The cooled mixture was filtered through Arbocel®, washing through with dichloromethane and methanol, and the filtrate evaporated under reduced pressure. The product was purified by column chromatography on silica gel using an elution gradient of dichloromethane:methanol:0.88 ammonia (98:2:0 to 94:5:1) to afford the title compound, 425 mg.

$^1$H-nmr (CDCl$_3$, 400 MHz) δ: 2.79 (t, 2H), 3.17 (t, 2H), 3.44 (m, 4H), 3.79 (m, 4H), 3.91 (s, 2H), 6.42 (d, 1H), 7.15 (d, 1H). LRMS: m/z (ES$^+$) 220 [MH$^+$]

Preparation 110

2-(4-Methyl-1-piperazinyl)-5,6,7,8-tetrahydro[1,6]naphthyridine

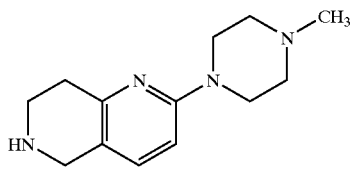

The title compound was obtained in 21% yield from the protected naphthyridine from preparation 56, following the procedure described in preparation 109.

$^1$H-nmr (CDCl$_3$, 400 MHz) δ: 2.32 (s, 3H), 2.49 (m, 4H), 2.72 (t, 2H), 3.15 (t, 2H), 3.51 (m, 4H), 3.83 (s, 2H), 6.43 (d, 1H), 7.10 (d, 1H). LRMS: m/z (ES$^+$) 233 [MH$^+$]

Preparations 111 to 118

Ammonium formate (5–25 eq) was added to a solution of the appropriate protected amines (1 eq) in methanol. 10% Palladium on charcoal (1:1 w/w eq.) was added portionwise, and the mixture stirred under reflux for 0.5 to 4 hours. The cooled mixture was filtered through Arbocel®, washing through with dichloromethane or dichloromethane:methanol (95:5) and the combined filtrates were evaporated under reduced pressure. The crude products were purified by column chromatography on silica gel using elution gradients of dichloromethane:methanol:0.88 ammonia, to afford the title compounds.

| Prep | R | Yield %/ Form | Data |
|---|---|---|---|
| 111 | H₃C-N(CH₃)-CH₂- | 41 clear oil | ¹H-nmr(CDCl₃, 400MHz) δ: 2.22(s, 6H), 2.84(t, 2H), 3.18 (t, 2H), 3.52(s, 2H), 3.98(s, 2H), 6.80(d, 1H), 8.24(d, 1H). LRMS: m/z(ES⁺) 192[MH⁺] |
| 113 | pyrrolidinylmethyl | 69 | ¹H-nmr(CDCl₃, 400MHz) δ: 1.78(m, 4H), 2.58(m, 4H), 2.86 (m, 2H), 3.18(m, 2H), 3.70(s, 2H), 3.97(s, 2H), 6.81(d, 1H), 8.24 (d, 1H). LRMS: m/z (ES⁺) 218[MH⁺] |
| 114 | piperidinylmethyl | 65 yellow gum | ¹H-nmr(CDCl₃, 400MHz) δ: 1.41(m, 2H), 1.53(m, 4H), 2.41 (m, 4H), 2.90(t, 2H), 3.16(t, 2H), 3.54(s, 2H), 3.98(s, 2H), 6.81 (d, 1H), 8.25(d, 1H). LRMS: m/z(ES⁺) 254[MNa⁺] |
| 115 | quinuclidinylmethyl | 24 colourless oil | ¹H-nmr(CDCl₃, 400MHz) δ: 1.25(m, 4H), 1.78(m, 4H), 2.92 (t, 2H), 3.16(t, 2H), 2.23(m, 2H), 3.59(s, 2H), 3.98(s, 2H), 6.80 (d, 1H), 8.24(d, 1H). LRMS: m/z(ES⁺) 244[MH⁺] |
| 116 | 4-hydroxypiperidinylmethyl | 84 orange oil | ¹H-nmr(CDCl₃, 400MHz) δ: 1.58(m, 4H), 1.85(m, 2H), 2.20 (m, 2H), 2.75(m, 2H), 2.90(m, 2H), 3.18(m, 4H), 3.59(s, 2H), 3.98 (s, 2H), 6.80(d, 1H), 8.24(d, 1H). LRMS: m/z(ES⁺) 262[MH⁺] |
| 117 | morpholinylmethyl | 75 colourless oil | ¹H-nmr(CDCl₃, 400MHz) δ: 2.48(m, 4H), 2.88(t, 2H), 3.18 (t, 2H), 3.60(s, 2H), 3.65(m, 4H), 3.98(s, 2H), 6.81(d, 1H), 8.24 (d, 1H). LRMS: m/z (ES⁺) 234[MH⁺] |
| 118 | oxabicyclic-N-methyl | 85 oil | ¹H-nmr(CDCl₃, 400MHz) δ: 1.90(d, 1H), 2.67(d, 1H), 2.88 (m, 4H), 3.18(m, 2H), 3.41(s, 1H), 3.61(d, 1H), 3.82(m, 2H), 3.98(s, 2H), 4.07(d, 1H), 4.37(s, 1H), 6.82 (d, 1H), 8.24(d, 1H). LRMS: m/z(ES⁺) 468[MNa⁺] |

Preparation 119

5,6,7,8-Tetrahydro[2,6]naphthyridin-1-amine

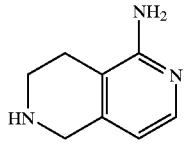

A mixture of the protected amine from preparation 68 (234 mg, 0.71 mol), ammonium formate (2.34 g, 37 mmol) and 10% palladium on charcoal (234 mg) in methanol (10 mL) was heated under reflux for 2 hours. Additional ammonium formate (2.34 g, 37 mmol) and 10% palladium on charcoal (234 mg) were added, and the mixture heated for a further 4 hours. The cooled mixture was diluted with dichloromethane (50 mL), filtered through Arbocel® and the filtrate concentrated under reduced pressure. The crude product was purified by column chromatography on silica gel using dichloromethane:methanol:0.88 ammonia (93:7:1) as eluant to afford the title compound, as a solid, 21 mg.

¹H-nmr (CDCl₃, 400 MHz) δ: 2.40 (t, 2H), 3.20 (t, 2H), 3.88 (s, 2H), 4.34 (bs, 2H), 6.38 (d, 1H), 7.82 (d, 1H). LRMS: m/z (ES⁺) 150 [MH⁺]

Preparation 120

5-(1-Methyl-4-piperidinyl)-1,2,3,4-tetrahydro[2,6] naphthyridine dihydrochloride

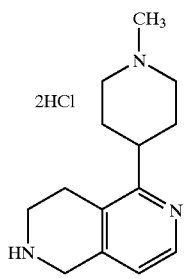

Formic acid (150 μl, 3.92 mmol) followed by 10% palladium on charcoal (150 mg) were added to a solution of the protected naphthyridine from preparation 67 (630 mg, 1.96 mmol) in methanol (10 mL), and the mixture heated under reflux for 4 hours. Additional 10% palladium on charcoal (350 mg) and formic acid (150 μl) were added, and the mixture stirred under reflux for a further 18 hours. The cooled reaction mixture was filtered through Arbocel®, washing through with methanol (300 mL), and the combined filtrates evaporated under reduced pressure. The residual oil was dissolved in 1N hydrochloric acid (6 mL), and the solution stirred under reflux for 1 hour. The cooled solution was concentrated under reduced pressure, azeotroped with methanol and dichloromethane to afford the title compound as a pale yellow foam, 590 mg.

¹H-nmr (CD₃OD, 40 MHz) δ: 2.18 (m, 2H), 2.26 (m, 2H), 2.95 (s, 3H), 3.30 (m, 4H), 3.50 (m, 1H), 3.62 (m, 4H), 4.58 (s, 2H), 7.56 (d, 1H), 8.57 (d, 1H). LRMS: m/z (ES⁺) 232 [MH⁺]

Preparation 121

N,N-Dimethyl(5,6,7,8-tetrahydropyrido[4,3-d]pyrimidin-2-yl)methanamine

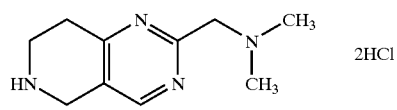

Hydrogen chloride gas was bubbled through an ice-cooled solution of the protected amine from preparation 71 (267 mg, 0.91 mmol) in dichloromethane (15 mL), for 10 minutes, and the reaction then stirred for a further 20 minutes at room temperature. The solution was evaporated under reduced pressure, dissolved in methanol (5 mL), and diluted with ethyl acetate (40 mL). The solution was evaporated under reduced pressure to afford the title compound as a buff-coloured solid.

$^1$H-nmr (DMSOd$_6$, 400 MHz) δ: 2.96 (s, 6H), 3,17 (t, 2H), 3.45 (t, 2H), 4.37 (s, 2H), 4.60 (s, 2H), 8.79 (s, 1H), 10.00–10.20 (bs, 3H). LRMS: m/z (ES$^+$) 193 [MH$^+$]

Preparations 122 to 125

The following compounds of general structure:

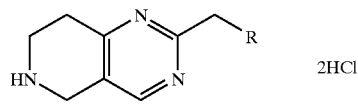

were prepared from the appropriate protected amines following a similar procedure to that described in preparation 121.

| Prep | R | Form | Data |
|---|---|---|---|
| 122 | -CH₂N(CH₃)CH₂CH₂OCH₃ | Brown solid | $^1$H-nmr(DMSOd$_6$, 400MHz) δ: 2.90(s, 3H), 3.17(t, 2H), 3.25(s, 3H), 3.37–3.60(m, 4H), 3.72 (t, 2H), 4.36(s, 2H), 4.60 (bd, 2H), 8.78(s, 1H), 10.00(bs, 2H), 10.20(bs, 1H). LRMS: m/z(ES$^+$) 237[MH$^+$] |
| 124 | -CH₂-piperidinyl | Tan solid | $^1$H-nmr(DMSOd$_6$, 400MHz) δ: 1.60–1.80 (m, 6H), 3.15(m, 2H), 3.17(t, 2H), 3.45(m, 4H), 4.38(s, 2H), 4.58(s, 2H), 8.79(s, 1H), 9.96–10.17 (m, 3H). LRMS: m/z(ES$^+$) 233[MH$^+$] |
| 125 | -CH₂-morpholinyl-CH₂CH₂O- | solid | $^1$H-nmr(DMSOd$_6$+dropTFAd, 400MHz) δ: 3.10(m, 4H), 3.36(m, 2H), 3.52(m, 2H), 3.81 (m, 4H), 3.94(m, 4H), 4.30(m, 2H), 4.69(s, 2H), 8.67(s, 1H), 9.85 (bs, 2H). LRMS: m/z (ES$^+$) 279[MH$^+$] |

(a)-compound azeotroped with dichloromethane

Preparation 126

4-(1-Pyrrolidinylmethyl)-5,6,7,8-tetrahydropyrido[3,4-d]pyrimidine

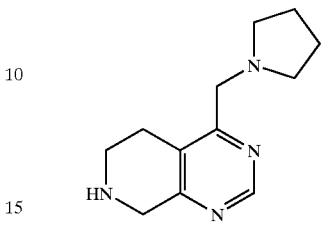

A solution of the protected amine from preparation 69 (395 mg, 1.28 mmol) in methanol (25 mL), was allowed to stand under a nitrogen atmosphere. 10% Palladium on charcoal (395 mg), followed by ammonium formate (1.0 g, 15.9 mmol) was added, and the mixture stirred vigorously under reflux for 30 minutes. The cooled mixture was diluted with dichloromethane (100 mL), filtered through Arbocel® and the filtrate concentrated under reduced pressure. The crude product was purified by column chromatography using dichloromethane:methanol:0.88 ammonia (97:3:1) as eluant to afford the title compound as a colourless oil, that crystallised on standing, 174 mg.

$^1$H-nmr (CDCl$_3$, 400 MHz) δ: 1.78 (m, 4H), 2.57 (m, 4H), 2,85 (t, 2H), 3,15 (t, 2H), 3.68 (s, 2H), 4.04 (s, 2H), 8.89 (s, 1H). LRMS: m/z (ES$^+$) 219 [MH$^+$]

Preparation 127

4-(1-Piperidinylmethyl)-5,6,7,8-tetrahydropyrido[3,4-d]pyrimidine

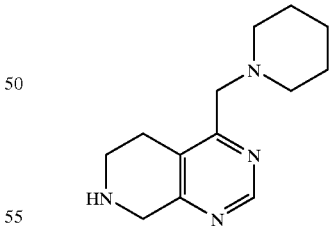

The title compound was obtained as an orange oil in 43% yield from the protected amine from preparation 72, following the procedure described in preparation 126.

$^1$H-nmr (CDCl$_3$, 400 MHz) δ: 1.42 (m, 2H), 1.55 (m, 4H), 2.41 (m, 4H), 2.89 (t, 2H), 3.14 (t, 2H), 3.50 (s, 2H), 4.05 (s, 2H), 8.87 (s, 1H). LRMS: m/z (ES$^+$) 233 [MH$^+$]

Preparation 128

4-[(4-Methoxy-1-piperidinyl)methyl]-5,6,7,8-tetrahydropyrido[3,4-d]pyrimidine

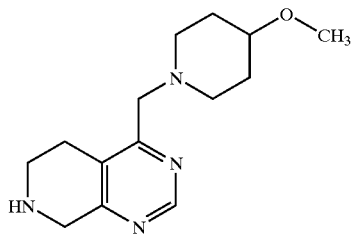

The title compound was obtained in 42% yield as a yellow oil, from the protected amine from preparation 76, following a similar procedure to that described in preparation 126.

$^1$H-nmr (CDCl$_3$, 400 MHz) δ: 1.56 (m, 2H), 1.84 (m, 2H), 2.24 (m, 2H), 2.73 (m, 2H), 2.88 (t, 2H), 3.15 (t, 2H), 3.20 (m, 1H), 3.32 (s, 3H), 3.53 (s, 2H), 4.05 (s, 2H), 8.87 (s, 1H). LRMS: m/z (ES$^+$) 263 [MH$^+$]

Preparation 129

5,6,7,8-Tetrahydroimidazo[1,5-a]pyrazine hydrochloride

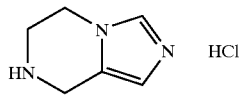

10% Palladium on charcoal (100 mg) was added portionwise to a solution of the protected amine from preparation 79 (900 mg, 4.22 mmol) in methanol (10 mL), followed by formic acid (0.25 mL), and the reaction stirred under reflux for 5 hours. The cooled mixture was diluted with water (5 mL), filtered through Arbocel®, and washed through with methanol (200 mL). The filtrate was concentrated under reduced pressure and azeotroped with dichloromethane. The residual oil was dissolved in 1N hydrochloric acid (10 mL), and the solution stirred under reflux for 2 hours. The cooled solution was evaporated under reduced pressure and the resulting solid recrystallised from methanol to afford the title compound as a white solid, 500 mg.

$^1$H-nmr (DMSOd$_6$, 400 MHz) δ: 3.58 (t, 2H), 4.40 (s, 2H), 4.50 (t, 2H), 7.56 (s, 1H), 9.10 (s, 1H). LRMS: m/z (ES$^+$) 125 [MH$^+$]

Preparation 130

3-Methyl-5,6,7,8-tetrahydroimidazo[1,5-a]pyrazine hydrochloride

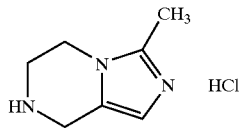

Ammonium formate (3.33 g, 52.8 mmol) and 10% palladium on charcoal (800 mg) were added to a solution of the protected amine from preparation 81 (800 mg, 3.52 mmol) in methanol (10 mL) and 2N hydrochloric acid (0.5 mL), and the reaction heated under reflux for 25 hours. The cooled mixture was diluted with water (5 mL), then filtered through Arbocel®. The filtrate was evaporated under reduced pressure, and the residual solid purified by column chromatography on silica gel using an elution gradient of dichloromethane:methanol:0.88 ammonia (100:0:0 to 90:10:1) to give a solid. This was dissolved in 2N hydrochloric acid (10 mL), the solution heated under reflux for 2 hours, then cooled and evaporated under reduced pressure, azeotroping with dichloromethane, to afford the title compound as a white solid, 536 mg.

$^1$H-nmr (CD$_3$OD, 400 MHz) δ: 2.66 (s, 3H), 3.81 (t, 2H), 4.44 (t, 2H), 4.57 (s, 2H), 7.46 (s, 1H). LRMS: m/z (ES$^+$) 138 [MH$^+$]

Preparation 131

3-Ethyl-5,6,7,8-tetrahydroimidazo[1,5-a]pyrazine

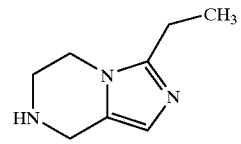

Ammonium formate (2.12 g, 33.6 mmol) and 10% palladium on charcoal (550 mg) were added to a solution of the protected amine from preparation 80 (541 mg, 2.24 mmol) in methanol (15 mL) and 2N hydrochloric acid (0.5 mL), and the reaction heated under reflux for 26 hours. The cooled mixture was diluted with water (5 mL), then filtered through Arbocel®, washing through with dichloromethane:methanol solution (1:1, 300 mL). The filtrate was evaporated under reduced pressure, and the residual solid was dissolved in 2N hydrochloric acid (10 mL), the solution heated under reflux for 2 hours, then cooled and evaporated under reduced pressure. The residual orange gum was purified by column chromatography on silica gel using an elution gradient of dichloromethane:methanol:0.88 ammonia (97:3:0 to 90:10:1) to give the title compound as an orange solid, 68 mg.

$^1$H-nmr (CD$_3$OD, 400 MHz) δ: 1.24 (t, 3H), 2.67 (q, 2H), 3.15 (t, 2H), 3.88 (t, 2H), 3.95 (s, 2H), 6.59 (s, 1H). LRMS: m/z (ES$^+$) 138 [MH$^+$]

Preparation 132

N,N-Dimethyl-5,6,7,8-tetrahydroimidazo[1,5-a]pyrazin-3-amine

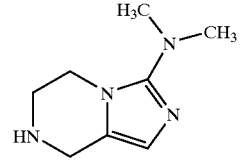

Ammonium formate (2.0 g, 31.7 mmol) and 10% palladium on charcoal (200 mg) were added to a solution of the protected amine from preparation 85 (170 mg, 0.66 mmol) in ethereal hydrochloric acid (2 mL, 1M) and methanol (20 mL), and the mixture heated under reflux for 20 minutes. The cooled mixture was diluted with dichloromethane (50 mL), filtered through Arbocel®, and, the filtrate concentrated under reduced pressure. The residue was purified by column chromatography on silica gel using dichloromethane:methanol:0.88 ammonia (93:7:1) as eluant to afford the title compound as a colourless gum, 72 mg.

¹H-nmr (CDCl₃, 400 MHz) δ: 1.70 (bs, 1H), 2.74 (s, 6H), 3.13 (t, 2H), 3.73 (t, 2H), 3.98 (s, 2H), 6.46 (s, 1H). LRMS: m/z (ES⁺) 167 [MH⁺]

Preparation 133

N-(2-Methoxyethyl)-N-methyl-5,6,7,8-tetrahydroimidazo[1,5-a]pyrazin-3-amine

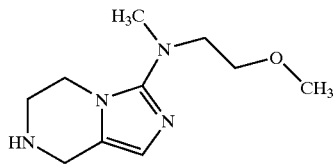

The title compound was obtained as a yellow oil, from the protected amine from preparation 86, following the procedure described in preparation 132.

¹H-nmr (CDCl₃, 400 MHz) δ: 2.78 (s, 3H), 3.13 (t, 2H), 3.18 (t, 2H), 3.32 (s, 3H), 3.48 (t, 2H), 3.76 (t, 2H), 3.97 (t, 2H), 6.48 (s, 1H). LRMS: m/z (ES⁺) 211 [MH⁺]

Preparation 134

3-Isopropyl-5,6,7,8-tetrahydroimidazo[1,5-a]pyrazine dihydrochloride and

Preparation 135

2-(5,6,7,8-Tetrahydroimidazo[1,5-a]pyrazin-3-yl)-2-propanol dihydrochloride

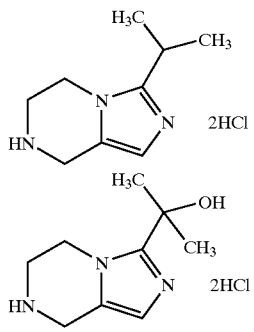

A mixture of the compounds from preparations 87 and 88 (460 mg, 1.47 mmol), glacial acetic acid (0.5 mL) and 10% palladium on charcoal (300 mg) was hydrogenated at 50 psi and 70° C. for 36 hours. The cooled mixture was diluted with water (10 mL), filtered through Arbocel®, washing through with methanol (500 mL). The filtrate was evaporated under reduced pressure, and the residual oil was purified by column chromatography on silica gel using an elution gradient of dichloromethane:methanol:0.88 ammonia (97:3:0 to 92:8:1) to give an orange oil. This was dissolved in methanol, 1N ethereal hydrochloric acid added, and the mixture evaporated under reduced pressure to give a mixture of the title compounds as a light brown foam, 165 mg.

¹H-nmr (CD₃OD, 400 MHz) δ: 1.42 (d, 6H), 1.71 (s, 6H), 3.45 (m, 1H), 3.78 (m, 2H), 3.78 (m, 2H), 4.50 (m, 2H), 4.58 (m, 2H), 4.58 (m, 2H), 4.80 (m, 2H), 7.46 (s, 1H).

Preparation 136

5,6,7,8-Tetrahydroimidazo[1,5-a]pyrazin-3-amine

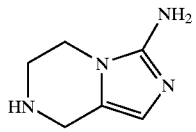

10% Palladium on charcoal (200 mg) and ammonium formate (2 g) were added carefully to a solution of the compound from preparation 84 (152 mg, 0.6 mmol) in 1N ethereal hydrochloric acid (2 mL) and methanol (20 mL). The mixture was heated under reflux for 1.5 hours, then cooled. Additional 1N ethereal hydrochloric acid (1 mL), 10% palladium on charcoal (200 mg) and ammonium formate (2 g) were added, and the mixture heated under reflux for a further 20 minutes. The cooled mixture was diluted with dichloromethane (50 mL), filtered through Arbocel®, and the filtrate concentrated under reduced pressure. The residue was purified by column chromatography on silica gel using dichloromethane:methanol:0.88 ammonia (93:7:1 to 80:20:2) to afford the title compound as an oil, 35 mg.

¹H-nmr (DMSOd₆, 400 MHz) δ: 3.12 (t, 2H), 3.57 (t, 2H), 3.87 (s, 2H), 6.27 (s, 1H). LRMS: m/z (ES⁺) 139 [MH⁺]

Preparation 137

3-Ethyl-5,6,7,8-tetrahydroimidazo[1,2-a]pyrazine dihydrochloride

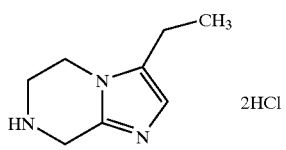

A mixture of the protected amine from preparation 92 (605 mg, 2.12 mmol), acetic acid (8 mL), and 1N ethereal hydrobromic acid (30 mL) in toluene (25 mL) was stirred at 100° C. for 4 hours. The mixture was cooled, concentrated under reduced pressure, and azeotroped with toluene (2×25 mL). The residue was dissolved in 1 N ethereal hydrochloric acid, then evaporated under reduced pressure to afford the title compound as a tan coloured solid, 405 mg.

¹H-nmr (DMSOd₆, 400 MHz) δ: 1.10 (t, 3H), 2.60 (m, 2H), 3.60 (m, 2H), 4.32 (m, 2H) 4.62 (s, 2H), 7.50 (s, 1H). LRMS: m/z (ES⁺) 152 [MH⁺]

Preparation 138

7-Benzyl-5,6,7,8-tetrahydro-imidazo[1,5-a]pyrazine-3-carbaldehyde

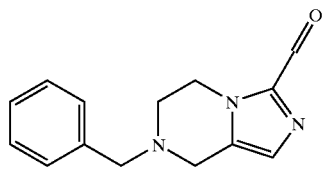

n-Butyllithium (1.6M in hexane, 9 ml, 14.4 mmol) was added to the imidazopyrazine from preparation 79 (2.8 g, 13.13 mmol) in tetrahydrofuran (20 ml) under a nitrogen atmosphere at −78° C. at a rate that maintained the reaction temperature below −70° C. The mixture was warmed to 0° C. and was stirred for 10 minutes and then cooled to −78° C. N,N-Dimethylformamide (1.5 ml, 19.4 mmol) was added dropwise and the mixture was warmed to 0° C. and was stirred for 10 minutes. Saturated sodium hydrogen carbonate solution (40 ml), then water (100 ml) were added and the aqueous solution was extracted with ethyl acetate (100 ml). The organic solution was washed with water (50 ml), then brine (50 ml), dried over magnesium sulphate and evaporated under reduced pressure. The residue was purified by chromatography on silica gel using ethyl acetate in pentane as eluant (gradient from 70:30 to 90:10) to give the title compound as a yellow solid (2.67 g).

$^1$H-nmr (CDCl$_3$, 400 MHz) δ: 2.89 (t, 2H), 3.72 (m, 4H), 4.44 (t, 2H), 7.02 (s, 1H), 7.35 (m, 5H), 9.72 (s, 1H) LRMS: m/z (ES$^+$) 264 [MNa$^+$]

Preparation 139

7-Benzyl-3-morpholin-4-ylmethyl-5,6,7,8-tetrahydro-imidazo[1,5-a]pyrazine

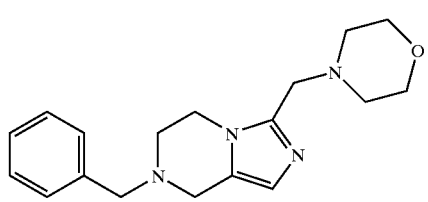

Morpholine (260 μl, 3.0 mmol) was added to the aldehyde from preparation 138 in tetrahydrofuran (10 ml) under a nitrogen atmosphere and the mixture was stirred for 1 hour. Sodium triacetoxyborohydride (790 mg, 3.73 mmol) was added portionwise and the reaction mixture was stirred at room temperature for 16 hours. Water (20 ml) was added and the solution was extracted with ethyl acetate (2×100 ml). The combined organic solutions were dried over magnesium sulphate and evaporated under reduced pressure. The residue was purified by chromatography on silica gel using methanol in dichloromethane as eluant (gradient from 1:99 to 5:95) to give the title compound as a golden oil (680 mg).

$^1$H-nmr (CDCl$_3$, 400 MHz) δ: 2.46 (m, 4H), 2.84 (t, 2H), 3.55 (s, 2H), 3.66 (m, 4H), 4.06 (t, 2H), 6.65 (s, 1H), 7.31 (m, 5H) LRMS: m/z (ES$^+$) 335 [MNa$^+$]

Preparation 140

(7-Benzyl-5,6,7,8-tetrahydro-imidazo[1,5-a]pyrazin-3-yl)-methanol

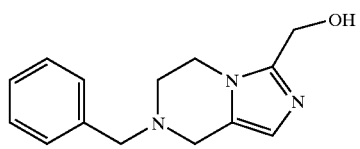

Sodium borohydride (250 mg, 6.6 mmol) was added portionwise to the aldehyde from preparation 138 (1.45 g, 6 mmol) in methanol (25 ml) under a nitrogen atmosphere. The mixture was stirred at room temperature for 1 hour and further sodium borohydride (45 mg, 2 mmol) was added. The mixture was stirred at room temperature for 30 minutes and saturated sodium hydrogen carbonate solution (40 ml) and water (40 ml) were added. The aqueous mixture was extracted with ethyl acetate (3×100 ml) and the combined organic solutions were dried over magnesium sulphate and evaporated under reduced pressure. The residue was co-evaporated with dichloromethane (×2) and the residue was dried under vacuum to give the title compound as a gum (1.45 g)

$^1$H-nmr (CDCl$_3$, 400 MHz) δ: 2.86 (t, 2H), 3.62 (s, 2H), 3.70 (s, 2H), 4.07 (t, 2H), 4.61 (s, 2H), 6.62 (s, 1H), 7.32 (m, 5H) LRMS: m/z (ES$^+$) 266 [MNa$^+$]

Preparation 141

7-Benzyl-3-(4-methoxy-piperidin-1-yl)-5,6,7,8-tetrahydro-imidazo[1,5-a]pyrazine

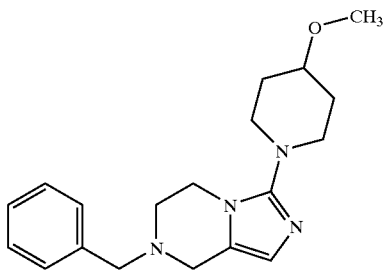

A stirred mixture of the bromo compound from preparation 83 (584 mg, 2 mmol) 4-methoxypiperidine (3 g, 26 mmol) and tetrakis(triphenylphosphine)palladium(0) (46 mg, 0.04 mmol) was purged with argon and then heated to 150° C. for 17 hours. The reaction mixture was cooled to room temperature and partitioned between dichloromethane (100 ml) and water (100 ml). The organic phase was separated, dried over magnesium sulphate and evaporated under reduced pressure. The residue was purified by chromatography on silica gel using methanol in ethyl acetate as eluant (gradient from 2:98 to 6:94). The material obtained was dissolved in dichloromethane (50 ml), washed with 5% sodium carbonate solution (50 ml), water (50 ml) dried over magnesium sulphate and evaporated under reduced pressure. The residue was purified by chromatography on silica gel using methanol in ethyl acetate as eluant (gradient from 2:98 to 6:94) to give the title compound as a yellow oil (202 mg).

$^1$H-nmr (CDCl$_3$, 400 MHz) δ: 1.65 (m, 2H), 2.02 (m, 2H), 2.78 (t, 2H), 2.88 (m, 2H), 3.25 (m, 3H), 3.37 (s, 3H), 3.62 (s, 2H), 3.67 (s, 2H), 3.79 (t, 2H), 6.45 (s, 1H), 7.30 (m, 5H) LRMS: m/z (ES$^+$) 327 [MH$^+$]

Preparation 142

N'-(6-Benzyl-5,6,7,8-tetrahydro-[2,6]naphthyridin-1-yl)-N,N-dimethyl-ethane-1,2-diamine

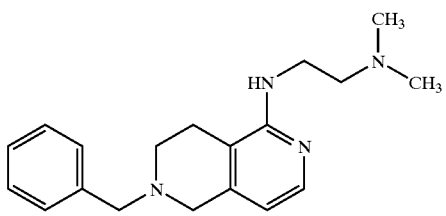

A mixture of the bromo compound from preparation 34 (1 g, 3.3 mmol) and N,N-dimethylethylenediamine (5 ml) were heated at 140° C. in an autoclave for 20 hours. The mixture was cooled to room temperature and was added to 0.05M sodium hydroxide solution. The solution was extracted with dichloromethane (3×60 ml) The combined organic solutions were dried over magnesium sulphate and evaporated under reduced pressure. The residue was purified by chromatography on silica gel using methanol and ammonium hydroxide in dichloromethane as eluant (gradient from 0:1:99 to 20:1:79) to give the title compound as a yellow oil (971 mg).

$^{1}$H-nmr (CDCl$_{3}$, 400 MHz) δ: 2.26 (s, 6H), 2.47 (t, 2H), 2.55 (t, 2H), 2.80 (t, 2H), 3.50 (m, 4H), 3.68 (s, 2H), 4.80 (s, 1H), 6.23 (d, 1H), 7.33 (m, 5H), 7.88 (d, 1H) LRMS: m/z (ES$^{+}$) 311 [MH$^{+}$]

Preparation 143

(6-Benzyl-5,6,7,8-tetrahydro-[2,6]naphthyridin-1-yl)-pyridin-2-ylmethyl-amine

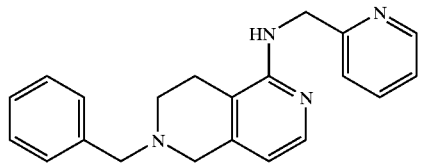

The bromo compound from preparation 34 (303 mg, 1 mmol) was mixed with 2-aminomethylpyrimidine (2 ml) and the mixture was heated at 170° C. under a nitrogen atmosphere for 5 hours. The reaction mixture was cooled and partitioned between ethyl acetate and 0.02 M sodium hydroxide solution. The organic solution was dried over magnesium sulphate and evaporated under reduced pressure. The residue was purified by chromatography on silica gel using dichloromethane and ethyl acetate and then methanol in ethyl acetate as eluant (gradient from 100:0 to 0:100 dichloromethane and ethyl acetate followed by methanol in ethyl acetate 0:100 to 5:95) to give the title compound as a pale yellow oil that crystallised on standing (216 mg).

LRMS: m/z (ES$^{+}$) 331 [MH$^{+}$]

Preparation 144

(6-Benzyl-5,6,7,8-tetrahydro-[2,6]naphthyridin-1-ylmethyl)-(2-methoxy-ethyl)-methyl-amine

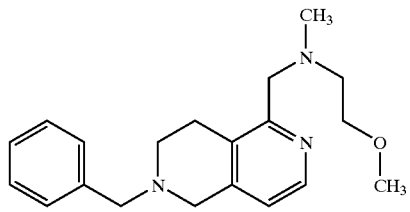

Acetic acid (480 mg, 8 mmol) was added to a solution of the aldehyde from preparation 35 and N-(2-methoxyethyl) methylamine (356 mg, 4 mmol) in tetrahydrofuran (20 ml) and the mixture was stirred for 10 minutes. Sodium triacetoxyborohydride (2.12 g, 10 mmol) was added and the mixture was stirred at room temperature for 2.5 hours. 2M Hydrochloric acid was added and the mixture was basified with 1M sodium hydroxide and extracted with ethyl acetate. The combined organic solutions were dried over magnesium sulphate and evaporated under reduced pressure. The residue was purified by chromatography on silica gel using methanol in dichloromethane as eluant (gradient from 0:100 to 10:90) to give the title compound as a yellow oil (544 mg).

$^{1}$H-nmr (CDCl$_{3}$, 400 MHz) δ: 2.27 (s, 3H), 2.66 (t, 2H), 2.79 (t, 2H), 3.00 (t, 2H), 3.28 (s, 3H), 3.48 (t, 2H), 3.60 (s, 2H), 3.66 (s, 2H), 3.68 (s, 2H), 6.80 (d, 1H), 7.34 (m, 5H), 8.25 (d, 1H) LRMS: m/z (ES$^{+}$) 326 [MH$^{+}$]

Preparation 145

(7-Benzyl-4-chloro-5,6,7,8-tetrahydro-pyrido[3,4-d] pyrimidin-2-yl)-dimethyl-amine

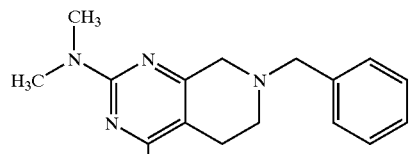

1-Benzyl-3-oxo-piperidine-4-carboxylic acid ethyl ester (10 g, 38.3 mmol) was added to a mixture of dimethyl guanidinium sulphate (4.6 g, 25 mmol) and potassium carbonate (9.28 g, 67 mmol) in methanol and the reaction mixture was stirred at room temperature for 48 hours. The mixture was filtered and the solid obtained was recrystallised from ethanol.

The material isolated was dissolved in phosphorous oxychloride (20 ml) and heated at 90° C. for 1 hour. The mixture was concentrated under reduced pressure and the residue was dissolved in dichloromethane (50 ml) and was added to sodium hydrogen carbonate solution. The aqueous layer was extracted with dichloromethane (2×50 ml) and the combined organic solutions were dried over magnesium sulphate and evaporated under reduced pressure to give the title compound as a brown oil (3.03 g).

$^{1}$H-nmr (CDCl$_{3}$, 400 MHz) δ: 2.70 (m, 4H), 3.12 (s, 6H), 3.48 (s, 2H), 3.68 (s, 2H), 7.33 (m, 5H) LRMS: m/z ES$^{+}$ 303, 305 [MH$^{+}$]

Preparation 146

7-Benzyl-N*2*, N*2*-dimethyl-5,6,7,8-tetrahydro-pyrido[3,4-d]pyrimidine-2,4-diamine

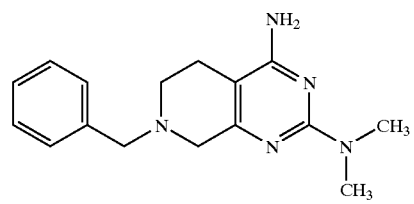

Ammonia was bubbled through a solution of the chloro compound from preparation 145 (1.51 g, 5 mmol) in dimethylsulphoxide (20 ml) to give a saturated solution and the mixture was heated at 140° C. in an autoclave for 18 hours. The reaction mixture was cooled to room temperature and was dissolved in ethyl acetate. The organic solution was washed with water and brine (×2) and then was dried over magnesium sulphate and evaporated under reduced pressure. The residue was purified by chromatography on silica gel using methanol in dichloromethane as eluant (gradient from 0:100 to 6:94) to give the title compound as a brown solid (0.54 g).

$^1$H-nmr (DMSOd$_6$, 400 MHz) δ: 2.40 (t, 2H), 2.73 (t, 2H), 3.05 (s, 6H), 3.41 (s, 2H), 3.67 (s, 2H), 4.45 (s, 2H), 7.33 (m, 5H) LRMS: m/z ES$^+$ 284 [MH$^+$]

Preparation 147

7-Benzyl-N*4*-(2-methoxy-ethyl)-N*2*,N*2*-dimethyl-5,6,7,8-tetrahydro-pyrido[3,4-d]pyrimidine-2,4-diamine

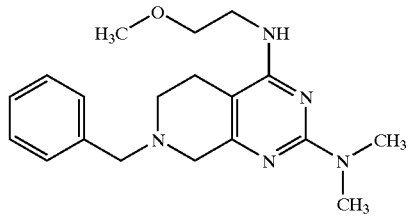

The chloro compound from preparation 145 (1.51 g, 5 mmol) and 2-methoxyethylamine (2 ml, 23 mmol) were dissolved in ethanol (20 ml) and the solution was heated under reflux for 48 hours. The solvent was evaporated under reduced pressure and the residue was diluted with 2-methoxyethylamine (6 ml, 69 mmol) and was heated under reflux for 8 hours. The reaction mixture was cooled to room temperature and was added to ethyl acetate. The solution was washed with 0.1M sodium hydroxide solution and brine, dried over magnesium sulphate and evaporated under reduced pressure to give the title compound (1.57 g).

$^1$H-nmr (CDCl$_3$, 400 MHz) δ: 2.35 (t, 2H), 2.73 (t, 2H), 3.07 (s, 6H), 3.35 (s, 3H), 3.40 (s, 2H), 3.53 (t, 2H), 3.66 (m, 4H), 4.62 (t, 1H), 7.23 (m, 1H), 7.31 (m, 2H), 7.35 (d, 2H) LRMS: m/z ES$^+$ 342 [MH$^+$]

Preparation 148

(6-Benzyl-5,6,7,8-tetrahydro-[1,6]naphthyridin-2-yl)-(2-methoxy-ethyl)-amine

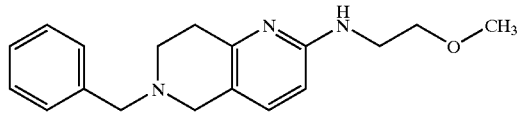

Copper (II) sulphate (200 mg) was added to a solution of 6-benzyl-2-chloro-5,6,7,8-tetrahydro-[1,6]naphthyridine (4.5 g, 17.4 mmol)(see reference WO9830560 Example 33 b) in 2-methoxyethylamine and the mixture was heated under reflux for 20 hours. The mixture was evaporated under reduced pressure and the residue was partitioned between dichloromethane (100 ml) and water (50 ml). The aqueous phase was extracted with dichloromethane (2×50 ml) and the combined organic phases were dried over magnesium sulphate and evaporated under reduced pressure. The residue was purified by chromatography on silica gel using methanol in dichloromethane as eluant (gradient from 1:99 to 3:97) to give the title compound as an orange oil (1.32 g).

LRMS: m/z ES$^+$ 298.2 [MH$^+$]

Preparation 149

(6-Benzyl-5,6,7,8-tetrahydro-[1,6]naphthyridin-2-yl)-pyridin-2-ylmethyl-amine

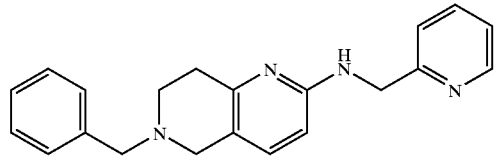

The title compound was obtained from 6-benzyl-2-chloro-5,6,7,8-tetrahydro-[1,6]naphthyridine(see reference WO9830560 Example 33b) and 2-aminomethylpyridine in 50% yield following the procedure described in preparation 148.

LRMS: m/z ES$^+$ 331.2 [MH$^+$]

Preparation 150

6-Benzyl-5,6,7,8-tetrahydro-[1,6]naphthyridine-2-carbonitrile

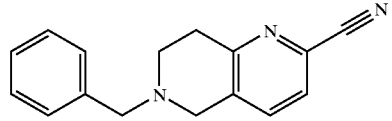

6-Benzyl-2-chloro-5,6,7,8-tetrahydro-[1,6]naphthyridine (129 mg, 0.5 mmol) (See Reference WO9830560 Example 33b) was added to zinc cyanide (58.7 mg, 0.5 mmol), lithium chloride (27 mg, 0.65 mmol) and tetrakis (triphenylphosphine)palladium (0) (35 mg, 0.03 mmol) in N,N-dimethylformamide (3 ml). The mixture was purged with argon and was heated at 100° C. for 17 hours. The reaction mixture was cooled to room temperature and a further quantity of tetrakis(triphenylphosphine)palladium (0) (35 mg, 0.03 mmol) was added and the mixture was heated at 125° C. for 3 hours. The reaction mixture was cooled to room temperature and a further quantity of tetrakis (triphenylphosphine)palladium (0) (35 mg, 0.03 mmol) was added and the mixture was heated at 125° C. for 3 hours. The reaction mixture was cooled to room temperature and was partitioned between ethyl acetate (40 ml) and water (40 ml). The phases were separated and the organic phase was washed with water (3×30 ml) dried over magnesium sulphate and evaporated under reduced pressure. The residue was purified by chromatography on silica gel using ethyl acetate in pentane as eluant (33:67) to give the title compound as a brown gum (97 mg).

$^1$H-nmr (CDCl$_3$, 400 MHz) δ: 2.88 (t, 2H), 3.09 (t, 2H), 3.68 (s, 2H), 3.73 (s, 2H), 7.23 (m, 7H) LRMS: m/z ES$^+$ 250 [MH$^+$].

Preparation 151

(6-Benzyl-5,6,7,8-tetrahydro-[1,6]naphthyridin-2-yl)-methylamine

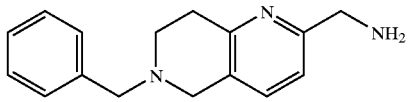

Anhydrous cobalt chloride (389 mg, 3 mmol) was added to the nitrile from preparation 150 (373 mg, 1.5 mmol) in methanol (10 ml) and the mixture was stirred at room temperature for 10 minutes. Sodium borohydride (567 mg, 15 mmol) was added portionwise over 15 minutes and the reaction mixture was stirred at room temperature for 1.5 hours. 3N Hydrochloric acid (7 ml) was added dropwise over 10 minutes and the mixture was stirred at room temperature for 20 minutes. The solution was neutralised by addition of concentrated aqueous ammonia and the mixture was stirred at room temperature for 72 hours. Silica gel (10 g) was added and the mixture was evaporated under reduced pressure. The residue was purified by chromatography on silica gel using ammonium hydroxide and methanol in dichloromethane as eluant (2:15:85). The material obtained was co evaporated with methanol and then with dichloromethane to give the title compound as a pale brown gum (135 mg).

$^1$H-nmr (CDCl$_3$, 400 MHz) δ: 2.86 (t, 2H), 3.00 (t, 2H), 3.60 (s, 2H), 3.70 (s, 2H), 3.90 (s, 2H), 7.30 (m, 7H) LRMS: m/z (ES$^+$) 254 [MH$^+$]

Preparation 152

(6-Benzyl-5,6,7,8-tetrahydro-[1,6]naphthyridin-2-ylmethyl)-carbamic acid tert-butyl ester

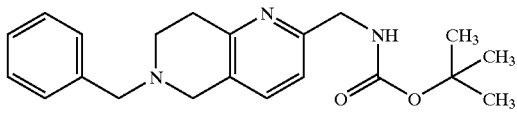

Di-tert-butyl dicarbonate (300 mg, 1.37 mmol) in dichloromethane (2 ml) was added to the amine from preparation 151 (288 mg, 1.14 mmol) in dichloromethane (10 ml) and the mixture was stirred at room temperature for 72 hours. The solvent was evaporated under reduced pressure and the residue was purified by chromatography on silica gel using ammonium hydroxide and methanol in dichloromethane as eluant (0.5:5:95). The material obtained was further purified by chromatography on silica gel using ammonium hydroxide and propan-2-ol in pentane as eluant (gradient from 0.5:10:90 to 0.7:15:85). The material isolated was co-evaporated with methanol to give the title compound as a colourless gum (251 mg).

$^1$H-nmr (CDCl$_3$, 400 MHz) δ: 1.46 (s, 9H), 2.95 (t, 2H), 3.00 (t, 2H), 3.60 (d, 2H), 3.71 (s, 2H), 4.35 (d, 2H), 5.41 (s, 1H), 7.00 (d, 1H), 7.30 (m, 6H) LRMS: m/z (ES$^+$) 354 [MH$^+$]

Preparation 153 tert-Butyl (2E)-3-(6-benzyl-5,6,7,8-tetrahydro[1,6]naphthyridin-2-yl)-2-propenoate

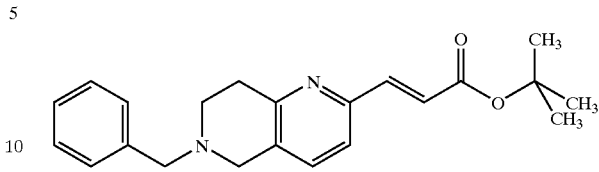

Tri-tert-butylphosphine (3.0 g, 15.28 mmol) was added to a solution of tris(dibenzylideneacetone)dipalladium (4.2 g, 4.63 mmol) in 1,4-dioxane (45 ml), under argon, and the solution stirred for 30 minutes at room temperature. This solution was then added to a mixture of 6-benzyl-2-chloro-5,6,7,8-tetrahydro[1,6]naphthyridine (WO 9830560 Example 33b) (12 g, 46.3 mmol) and tert-butylacrylate (20.3 ml, 139 mmol) in triethylamine (45 ml), and the reaction was stirred under reflux for 17 hours. The cooled mixture was concentrated under reduced pressure and the residue partitioned between ethyl acetate (300 ml) and water (300 ml) and this mixture filtered through Arbocel®. The pH of the mixture was adjusted to 8 using sodium bicarbonate, the phases separated, and the aqueous layer re-extracted with ethyl acetate (2×100 ml). The combined organic solutions were dried over magnesium sulphate and evaporated under reduced pressure. The crude product was pre-adsorbed onto silica gel, and purified by column chromatography using an elution gradient of cyclohexane: ethyl acetate (84:16 to 66:34) to afford the title compound as an orange-red oil, (15.8 g).

$^1$H-nmr (CDCl$_3$, 400 MHz) δ: 1.50 (s, 9H), 2.82 (t, 2H), 3.02 (t, 2H), 3.61 (s, 2H), 3.70 (s, 2H), 6.75 (d, 1H), 7.18 (d, 1H), 7.26 (m, 2H), 7.35 (m, 4H), 7.55 (d, 1H). LRMS: m/z (ES$^+$) 373 [MNa$^+$]

Preparation 154 tert-Butyl (2R,3R)-3-(6-benzyl-5,6,7,8-tetrahydro[1,6]naphthyridin-2-yl)-2,3-dihydroxypropanoate

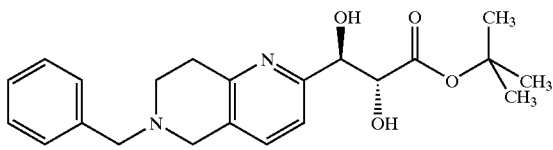

Osmium tetroxide (8.3 ml, 2.5% wt in tert-butanol) was added dropwise to a mixture of the compound from preparation 153 (11.3 g, 32.2 mmol), N-methylmorpholine N-oxide (4.15 g, 35.4 mmol) in water (80 ml) and acetone (160 ml), and the reaction was stirred at room temperature for 72 hours. The mixture was concentrated under reduced pressure, and the residue azeotroped with acetone. The crude product was purified by column chromatography on silica gel using an elution gradient of cyclohexane: ethyl acetate (80:25 to 25:75), to afford the title compound as a gum (7.2 g).

$^1$H-nmr (DMSOd$_6$, 400 MHz) δ: 1.38 (s, 9H), 2.77 (m, 2H), 2.81 (m, 2H), 3.52 (s, 2H), 3.62 (s, 2H), 4.20 (d, 1H), 4.78 (d, 1H), 4.82 (d, 1H), 5.40 (d, 1H), 7.22 (m, 2H), 7.30 (m, 4H), 7.38 (d, 1H). LRMS: m/z (ES$^+$) 407 [MNa$^+$]

Preparation 155

2-{[(6-Benzyl-5,6,7,8-tetrahydro[1,6]naphthyridin-2-yl)methyl]amino}ethanol

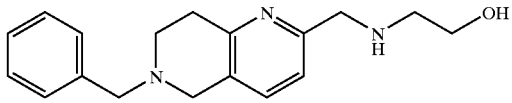

Acetic acid (368.7 mg, 6.14 mmol) and ethanolamine (187.5 mg, 3.07 mmol) were added dropwise to a solution of the aldehyde from preparation 29b (595 mg, 2.36 mmol), and the mixture purged with argon, then heated under reflux for 2 hours. Sodium triacetoxyborohydride (1 g, 4.72 mmol) was added to the cooled solution, and the reaction stirred at room temperature for 17 hours. 2M Hydrochloric acid (12 ml) was added, the solution stirred for 15 minutes, then partitioned between dichloromethane (150 ml) and water (150 ml), and the layers separated. The pH of the aqueous layer was adjusted to 12 using 5% aqueous sodium carbonate solution, re-partitioned with the separated organic phase, and further extracted with dichloromethane (3×60 ml). These combined organic solutions were dried over magnesium sulphate and evaporated under reduced pressure. The residual oil was purified by column chromatography on silica gel using an elution gradient of dichloromethane: methanol: 0.88 ammonia (97:3:0.2 to 90:10:10) to afford the title compound as a colourless oil (450 mg).

$^1$H-nmr (CDCl$_3$, 400 MHz) δ: 2.76 (m, 4H), 3.04 (t, 2H), 3.60 (s, 2H), 3.62 (t, 2H), 3.72 (s, 2H), 3.90 (s, 2H), 7.02 (d, 1H), 7.25 (m, 6H). LRMS: m/z (ES$^+$) 320 [MNa$^+$]

Preparation 156

N-[(6-Benzyl-5,6,7,8-tetrahydro[1,6]naphthyridin-2-yl)methyl]-2-methoxy-N-methylethanamine

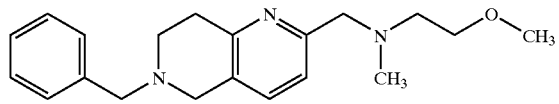

The title compound was obtained as a yellow oil in 89% yield from the aldehyde from preparation 29b and N-(2-methoxyethyl)methylamine, following a similar procedure to that described in preparation 155.

$^1$H-nmr (CDCl$_3$, 400 MHz) δ: 2.30 (s, 3H), 2.64 (t, 2H), 2.83 (t, 2H), 3.01 (t, 2H), 3.21 (s, 3H), 3.51 (t, 2H), 3.59 (s, 2H), 3.66 (s, 2H), 3.69 (s, 2H), 7.20–7.38 (m, 7H). LRMS: m/z (ES$^+$) 348 [MNa$^+$]

Preparation 157

6-Benzyl-5,6,7,8-tetrahydro[1,6]naphthyridin-2-yl trifluoromethanesulfonate

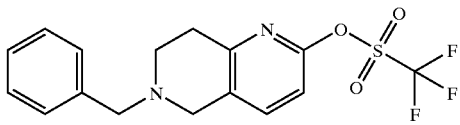

Trifluoromethanesulphonic anhydride (770 μl, 4.58 mmol) was added dropwise to a cooled (−30° C.) solution of the compound from preparation 27 (1 g, 4.16 mmol) and triethylamine (640 μl, 4.58 mmol) in dichloromethane (20 ml), so as to maintain the temperature below −20° C. The solution was then allowed to warm slowly to room temperature and stirred for a further 2 hours. The solution was diluted with dichloromethane (30 ml), washed with water (10 ml), dried over magnesium sulphate and evaporated under reduced pressure. The residual brown oil was purified by column chromatography on silica gel using an elution gradient of pentane: dichloromethane: methanol (5:95:0 to 0:100:0 to 0:97:3) to afford the title compound as an orange oil (980 mg).

$^1$H-nmr (CDCl$_3$, 400 MHz) δ: 2.84 (t, 2H), 3.00 (t, 2H), 3.62 (s, 2H), 3.71 (s, 2H), 6.91 (d, 1H), 7.25–7.40 (m, 5H), 7.43 (d, 1H). LRMS: m/z (ES$^+$) 373 [MH$^+$]

Preparation 158 tert-Butyl 4-(6-benzyl-5,6,7,8-tetrahydro[1,6]naphthyridin-2-yl)-1-piperidinecarboxylate

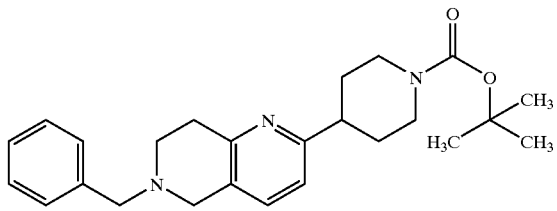

A mixture of 1,2-dibromoethane (22 μl, 0.26 mmol) and activated zinc (640 mg, 9.80 mmol) in N,N-dimethylformamide (1.5 ml) was heated to 50° C. for 5 minutes, then allowed to cool to room temperature. Trimethylsilylchloride (32.7 μl, 0.26 mmol) was added, the mixture heated again to 50° C., re-cooled to room temperature and tert-butyl 4-iodo-1-piperidinecarboxylate (EP 1078928 preparation 15–2) (2.0 g, 6.45 mmol) added. This mixture was re-heated to 50° C. for 5 minutes, cooled again, and a solution of the compound from preparation 157 (960 mg, 2.58 mmol) in N,N-dimethylformamide (1 ml), followed by tris(dibenzylideneacetone)dipalladium (0) (29.6 mg, 0.05 mmol) and tri(2-furyl)phosphine (24 mg, 0.10 mmol) added and the reaction mixture stirred at 60° C. for 2 hours. The cooled mixture was partitioned between water (15 ml) and dichloromethane (50 ml), filtered through Arbocel® and the filtrate separated. The aqueous phase was extracted with dichloromethane (30 ml), and the combined organic solutions dried over magnesium sulphate and evaporated under reduced pressure. The residual orange oil was purified by column chromatography on silica gel using an elution gradient of dichloromethane: methanol (100:0 to 96.5:3.5) to afford the title compound as an orange oil (717 mg).

$^1$H-nmr (CDCl$_3$, 400 MHz) δ: 1.45 (s, 9H), 1.63 (m, 2H), 1.87 (m, 2H), 2.84 (m, 4H), 3.00 (m, 2H), 3.58 (s, 2H), 3.69 (s, 2H), 3.83 (m, 1H), 4.22 (bs, 2H), 6.88 (d, 1H), 7.20 (d, 1H), 7.32 (m, 5H). LRMS: m/z (ES$^+$) 430 [MNa$^+$]

Preparation 159

6-Benzyl-2-(4-piperidinyl)-5,6,7,8-tetrahydro[1,6]naphthyridine dihydrochloride

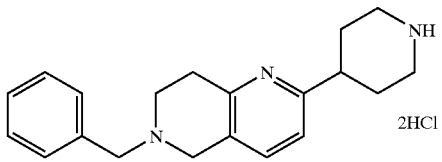

2HCl

An ice-cooled solution of the protected amine from preparation 158 (700 mg, 1.72 mmol) in dichloromethane (20 ml) was saturated with hydrogen chloride, and the solution then stirred for 2 hours at 0° C. The reaction mixture was then degassed under nitrogen and evaporated under reduced pressure to afford the title compound as an orange foam (654 mg).

$^1$H-nmr (CD$_3$OD, 400 MHz) δ: 2.10 (m, 2H), 2.22 (m, 2H), 3.18 (m, 2H), 3.33 (s, 2H), 3.53 (m, 4H), 3.80 (m, 1H), 4.58 (m, 4H), 7.53 (m, 4H), 7.63 (m, 3H).

LRMS: m/z (ES$^+$) 308 [MH$^+$]

Preparation 160

6-Benzyl-2-(1-methyl-4-piperidinyl)-5,6,7,8-tetrahydro[1,6]naphthyridine

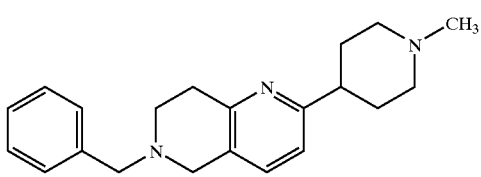

Triethylamine (471 μl, 3.37 mmol) and formaldehyde (37% w/w solution, 273 mg, 3.37 mmol) were added to a suspension of the amine from preparation 159 (641 mg, 1.69 mmol) in acetonitrile (10 ml), and the solution stirred at room temperature for 1 hour. Sodium triacetoxyborohydride (1.79 g, 3.37 mmol) was then added and the reaction stirred at room temperature for 18 hours. The mixture was neutralised using saturated sodium bicarbonate solution, then extracted using dichloromethane (3×50 ml). The combined organic solutions were dried over magnesium sulphate and evaporated under reduced pressure. The crude product was purified by column chromatography on silica gel using an elution gradient of dichloromethane: methanol: 0.88 ammonia (93:7:0.2 to 91:9:0.6) to afford the title compound as an orange solid (342 mg).

$^1$H-nmr (CDCl$_3$, 400 MHz) δ: 1.80–2.00 (m, 4H), 2.15 (m, 2H), 2.36 (s, 3H), 2.67 (m, 1H), 2.84 (t, 2H), 3.00 (m, 4H), 3.58 (s, 2H), 3.69 (s, 2H), 6.93 (d, 1H), 7.28 (m, 6H).
LRMS: m/z (ES$^+$) 322 [MH$^+$]

Preparation 161

1-tert-Butyl 2-ethyl (2R,4R)-4-hydroxy-1,2-pyrrolidinedicarboxylate

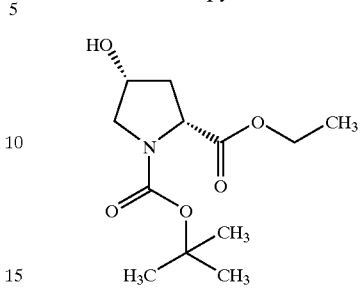

Triethylamine (0.27 ml, 2.05 mmol) followed by di-tert-butyl dicarbonate (223 mg, 1.02 mmol) were added to a solution of ethyl (2R,4R)-4-hydroxy-2-pyrrolidinecarboxylate hydrochloride (J. Org. Chem. 1990; 1684) (200 mg, 1.02 mmol) in 1,4-dioxane (5 ml) and water (5 ml), and the reaction stirred at room temperature for 4 hours. The mixture was extracted with ethyl acetate (50 ml), and the organic solution washed sequentially with 0.25M hydrochloric acid (50 ml), water (50 ml) and brine (50 ml). The solution was then dried over magnesium sulphate and evaporated under reduced pressure to afford the title compound (110 mg).

$^1$H-nmr (CDCl$_3$, 400 MHz) δ: 1.24 (t, 3H), 1.42 (s, 9H), 2.20 (m, 2H), 3.52 (m, 2H), 4.23 (q, 2H), 4.35 (m, 2H).
LRMS: m/z (ES$^+$) 282 [MNa$^+$]

Preparation 162 tert-Butyl (2R,4R)-4-hydroxy-2-(hydroxymethyl)-1-pyrrolidinecarboxylate

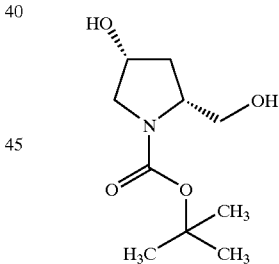

Lithium borohydride (1.4 ml, 2M in tetrahydrofuran, 2.8 mmol) was added dropwise to an ice-cooled solution of the ester from preparation 161 (210 mg, 0.81 mmol) in tetrahydrofuran (10 ml), the solution stirred for an hour at 0° C., and a further hour at room temperature. The solution was re-cooled to 0° C., water carefully added, followed by 2N hydrochloric acid. The mixture was then warmed to room temperature and extracted with ethyl acetate (3×100 ml). The combined organic solutions were washed with 1N sodium hydroxide solution, brine (100 ml), then dried over magnesium sulphate and evaporated under reduced pressure to afford the title compound (100 mg).

$^1$H-nmr (CDCl$_3$, 400 MHz) δ: 1.39 (s, 9H), 1.80 (m, 1H), 2.25 (m, 1H), 3.36 (m, 3H), 3.98 (dd, 2H), 4.23 (m,1H).
LRMS: m/z (ES$^-$) 216 [M–H$^-$]

Preparation 163 tert-Butyl (1R,4R)-2-oxa-5-azabicyclo[2.2.1]heptane-5-carboxylate

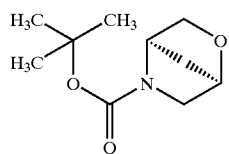

Diisopropyl azodicarboxylate (0.5 ml, 2.53 mmol) was added dropwise to an ice-cooled solution of the diol from preparation 162 (500 mg, 2.30 mmol) and triphenylphosphine (664 mg, 2.53 mmol) in dichloromethane (50 ml). Once addition was complete, the reaction was stirred at room temperature for 18 hours. The mixture was partitioned between dichloromethane (100 ml) and water (100 ml), and the layers separated. The aqueous phase was extracted with further dichloromethane (100 ml), and the combined organic solutions dried over magnesium sulphate and evaporated under reduced pressure. The residue was triturated with cyclohexane, the precipitate filtered, and the filtrate evaporated under reduced pressure. This product was purified by column chromatography on silica gel using an elution gradient of dichloromethane: methanol (100:0 to 91:9) to afford the title compound (200 mg).

$^1$H-nmr (CDCl$_3$, 400 MHz) δ: 1.43 (s, 9H), 1.82 (m, 2H), 3.29 (m, 2H), 3.83 (m, 2H), 4.48 (m, 2H). LRMS: m/z (ES$^+$) 222 [MNa$^+$]

Preparation 164

(1R,4R)-2-Oxa-5-azabicyclo[2.2.1]heptane hydrochloride

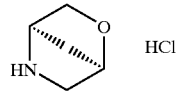

An ice-cooled solution of the compound from preparation 163 (200 mg, 1.0 mmol) in dichloromethane (10 ml) was saturated with hydrogen chloride, and the solution then stirred at room temperature for 1 hour. The mixture was concentrated under reduced pressure and the residue azeotroped with diethyl ether to afford the title compound.

$^1$H-nmr (DMSOd$_6$, 400 MHz) δ: 1.83 (d, 1H), 1.91 (d, 1H), 3.10 (s, 2H), 3.64 (d, 1H), 3.92 (d, 1H), 4.35 (s, 1H), 4.61 (s, 1H), 9.22 (s, 2H)

Preparation 165

(1R,4R)-5-[(6-benzyl-5,6,7,8-tetrahydro[2,6]naphthyridin-1-yl)methyl]-2-oxa-5-azabicyclo[2.2.1]heptane

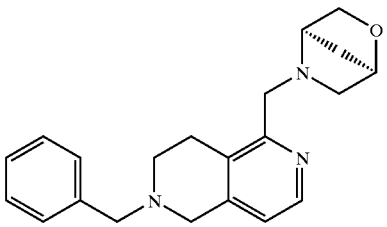

Sodium triacetoxyborohydride (418 mg, 1.98 mmol) was added to a solution of the aldehyde from preparation 35 (211 mg, 1.25 mmol), the amine hydrochloride from preparation 164 (170 mg, 1.25 mmol), sodium acetate (72 mg, 0.88 mmol), and acetic acid (50 μl, 8.7 mmol) in tetrahydrofuran (10 ml), and the reaction was stirred at room temperature for 4 hours. The solution was diluted with water (15 ml) and 0.88 ammonia (15 ml), and the mixture then extracted with ethyl acetate. The organic extract was washed with brine, dried over magnesium sulphate and concentrated under reduced pressure. The residual oil was purified by column chromatography on silica gel using dichloromethane: methanol (100:0 to 92.5:7.5) to afford the title compound as a yellow oil, 127 mg.

$^1$H-nmr (CDCl$_3$, 400 MHz) δ: 1.70 (dd, 1H), 1.94 (dd, 1H), 2.65 (d, 1H), 2.79 (t, 2H), 2.92 (dd, 1H), 2.99 (t, 2H), 3.42 (m, 1H), 3.60 (m, 3H), 3.70 (s, 2H), 3.81 (dd, 2H), 4.08 (d, 1H), 4.39 (s, 1H), 6.81 (d, 1H), 7.32 (m, 5H), 8.24 (d, 1H). LRMS: m/z (ES$^+$) 336 [MH$^+$]

Preparation 166

2-Benzyl-5-(3-methoxy-azetidin-1-ylmethyl)-1,2,3,4-tetrahydro-[2,6]naphthyridine

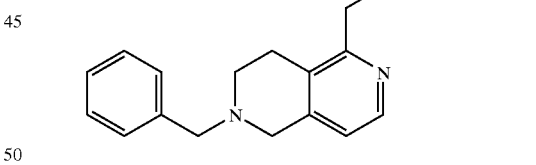

N,N-Diisopropylethylamine (517 mg, 4 mmol) was added to a solution of the amine hydrochloride from preparation 21 (494 mg, 4 mmol) and the aldehyde from preparation 35 (756 mg, 3 mmol) in tetrahydrofuran (20 ml), and the solution was stirred for 10 minutes. Acetic acid (480 mg, 8 mmol) was then added, followed by sodium triacetoxyborohydride (2.12 g, 10 mmol) and the reaction mixture was stirred at room temperature for 45 minutes. 2M Hydrochloric acid (5 ml) was added, the mixture then re-basified using 1N sodium hydroxide solution, and the mixture extracted with dichloromethane (3×50 ml). The combined organic solutions were dried over magnesium sulphate and evaporated under reduced pressure to give the final compound as a yellow oil (970 mg).

$^1$H-nmr (CDCl$_3$, 400 MHz) δ: 2.78 (m, 2H), 2.86 (m, 2H), 3.03 (m, 4H), 3.22 (s, 3H), 3.58 (s, 2H), 3.67 (m, 4H), 4.03

(m, 1H), 6.78 (d, 1H), 7.25 (m, 1H), 7.34 (m, 4H), 8.23 (d, 1H). LRMS: m/z (ES⁺) 324 [MH⁺]

Preparation 167 tert-Butyl (3S)-3-methoxy-1-pyrrolidinecarboxylate

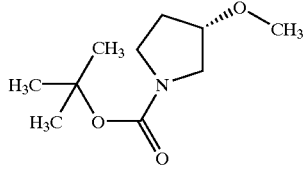

Sodium hydride (2.2 g, 80% dispersion in mineral oil, 73.2 mmol) was added to an ice-cooled solution of (3S)-N-tert-butoxycarbonylpyrrolidin-3-ol (U.S. Pat. No. 6,180,627 preparation 78), (12.5 g, 66.7 mmol) in tetrahydrofuran (330 ml), and the solution was stirred at room temperature for an hour. Iodomethane (14.5 g, 100 mmol) was then added and the reaction stirred for 18 hours. Water (100 ml) was added and the mixture concentrated under reduced pressure to remove the organic solvents. The solution was partitioned between water (750 ml) and ethyl acetate (750 ml) the layers separated, and the organic solution dried over magnesium sulphate and evaporated under reduced pressure to give the title compound.

¹Hnmr (CDCl₃, 400 MHz) δ: 1.42 (s, 9H), 1.84–2.00 (m, 2H), 3.32 (s, 3H), 3.40 (m, 4H), 3.92 (m, 1H).

Preparation 168

(3S)-3-Methoxypyrrolidine trifluoroacetate

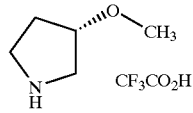

Hydrogen chloride was bubbled through an ice-cooled solution of the protected amine from preparation 167 (23.77 g, 118 mmol) in diethyl ether(591 ml), until saturated, and the solution was stirred for 1 hour at room temperature. The reaction was concentrated under reduced pressure and the residue re-suspended in diethyl ether. The mixture was stirred for 3 hours and the ether decanted off, the residue was evaporated under reduced pressure. The product was dissolved in ethanol, trifluoroacetic acid (16 ml) added, and the solution evaporated under reduced pressure to afford the title compound.

¹Hnmr (CDCl₃, 400 MHz) δ: 2.00 (m, 1H), 2.18 (m, 1H), 3.25–3.48 (m, 7H), 4.06 (m, 1H), 8.75 (s, 1H), 9.24 (s, 1H).

Preparation 169

2-Benzyl-5-{[(3S)-3-methoxypyrrolidinyl]methyl}-1,2,3,4-tetrahydro[2,6]naphthyridine

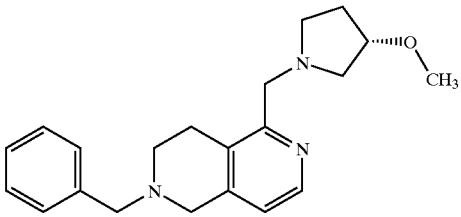

A solution of the aldehyde from preparation 35 (500 mg, 2 mmol) and the pyrrolidine from preparation 168 (385 mg, 2.8 mmol) in dichloromethane (10 ml) was stirred at room temperature for 30 minutes. Sodium triacetoxyborohydride (1.05 g, 5 mmol) was added and the reaction stirred at room temperature for 18 hours. The reaction was washed with sodium bicarbonate solution, and this aqueous solution extracted with further dichloromethane (2×). The combined organic solutions were dried over magnesium sulphate and evaporated under reduced pressure. The residual oil was purified by column chromatography on silica gel using an elution gradient of dichloromethane: methanol: 0.88 ammonia (98:2:0.2 to 90:10:1) to afford the title compound as an orange oil (290 mg).

¹H-nmr (CDCl₃, 400 MHz) δ: 1.82 (m, 1H), 2.13 (m, 1H), 2.60–2.82 (m, 5H), 3.00 (m, 3H), 3.27 (s, 3H), 3.60 (s, 2H), 3.70 (s, 2H), 3.80 (m, 2H), 3.97 (m, 1H), 6.81 (d, 1H), 7.22–7.40 (m, 5H), 8.24 (d, 1H). LRMS: m/z (ES⁺) 360 [MNa⁺]

Preparation 170

7-Benzyl-3-(4-morpholinyl)-5,6,7,8-tetrahydroimidazo[1,5-a]pyrazine

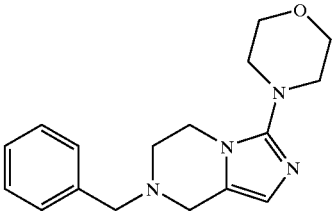

A mixture of the bromide from preparation 83 (292 mg, 1 mmol) and tetrakis(triphenylphosphine) palladium (0) (23 mg, 0.22 mmol) in morpholine (2 ml) was heated under reflux for 20 hours. The cooled mixture was poured into 0.1N sodium hydroxide solution and extracted with dichloromethane (3×50 ml). The combined organic extracts were dried over magnesium sulphate and evaporated under reduced pressure. The residue was purified by column chromatography on silica gel using an elution gradient of ethyl acetate: methanol (100:0 to 93:7) to afford the title compound as a yellow oil (182 mg).

¹H-nmr (CDCl₃, 400 MHz) δ: 2.80 (t, 2H), 3.07 (m, 4H), 3.62 (s, 2H), 3.68 (s, 2H), 3.81 (m, 6H), 6.49 (s, 1H), 7.32 (m, 5H). LRMS: m/z (ES⁺) 321 [MNa⁺]

Preparation 171

(7-Benzyl-5,6 7,8-tetrahydroimidazo[1,5-a]pyrazin-3-yl)(cyclopropyl)methanol

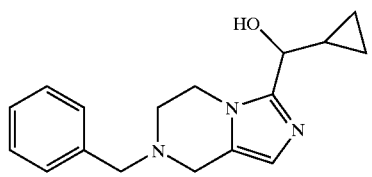

n-Butyl lithium (4.97 ml, 7.95 mmol) was added dropwise to a cooled (−78° C.) solution of the bromide from preparation 83 (1.60 g, 7.50 mmol) in tetrahydrofuran (16 ml), so as to maintain the temperature below −70° C., and once addition was complete, the solution was allowed to warm to 0° C. slowly. Cyclopropanecarboxaldehyde (1.68 ml, 22.5 mmol) was then added, the solution stirred for a further 20 minutes at 0° C., then quenched by the addition of water (10 ml). The mixture was neutralised using 2N hydrochloric acid, then extracted with ethyl acetate (3×50 ml) and methanol: dichloromethane (5:95, 3×50 ml). The combined organic solutions were dried over magnesium sulphate and concentrated under reduced pressure. The residual oil was purified by column chromatography on silica gel using an elution gradient of dichloromethane: methanol (100:0 to 95:5) to afford the title compound as an orange solid (1.18 g).

$^1$H-nmr (CDCl$_3$, 400 MHz) δ: 0.40 (m, 1H), 0.46 (m, 1H), 0.62 (m, 2H), 1.42 (m, 1H), 2.17 (s, 1H), 2.83 (t, 2H), 3.65 (s, 2H), 3.69 (s, 2H), 4.07 (m, 3H), 6.67 (s, 1H), 7.25–7.35 (m, 5H). LRMS: m/z (ES$^+$) 306 [MNa$^+$]

Preparation 172

(7-Benzyl-5,6,7,8-tetrahydroimidazo[1,5-a]pyrazin-3-yl)(cyclopropyl)methyl acetate

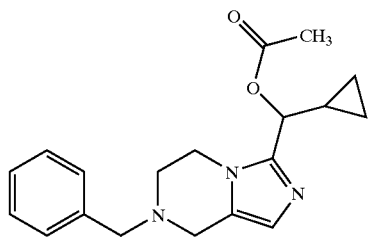

4-Dimethylaminopyridine (40.4 mg, 0.33 mmol), triethylamine (740 μl, 5.30 mmol) and acetic anhydride (499 μl, 5.29 mmol) were added to a solution of the alcohol from preparation 171 (750 mg, 2.64 mmol) in dichloromethane (20 ml), and the reaction stirred at room temperature for 18 hours. The solution was diluted with dichloromethane (30 ml), then washed with water (10 ml), saturated sodium bicarbonate solution (10 ml), dried over magnesium sulphate and evaporated under reduced pressure. The residual brown oil was purified by column chromatography on silica gel using an elution gradient of dichloromethane: methanol (100:0 to 95:5) to afford the title compound as an orange oil (492 mg).

$^1$H-nmr (CDCl$_3$, 400 MHz) δ; 0.37 (m, 1H), 0.50 (m, 1H), 0.65 (m, 2H), 1.72 (m, 1H), 2.07 (s, 3H), 2.82 (t, 2H), 3.64 (s, 2H), 3.68 (s, 2H), 3.94 (m, 1H), 4.02 (m, 1H) 5.21 (d, 1H), 6.75 (s, 1H), 7.31 (m, 5H). LRMS: m/z (ES$^+$) 348 [MNa$^+$]

Preparation 173

3-Morpholin-4-ylmethyl-5,6,7,8-tetrahydro-imidazo[1,5-a]pyrazine

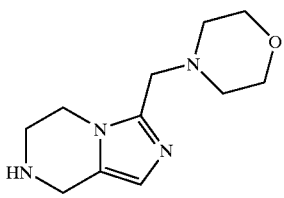

The title compound was obtained from the benzyl compound from preparation 139 (650 mg, 2.1 mmol) in 96% yield following the procedure described in preparation 109.

$^1$H-nmr (CDCl$_3$, 400 MHz) δ: 2.45 (m, 4H), 3.21 (t, 2H), 3.58 (m, 2H), 3.67 (m, 4H), 4.02 (t, 2H) 4.06 (s, 2H), 6.67 (s, 1H) LRMS: m/z (ES$^+$) 245 [MNa$^+$]

Preparations 174 to 190

The compounds of the following tabulated preparations, were prepared by a similar method to that of preparation 173 using the appropriate benzyl protected amine.

| Prep | Structure | Spectroscopic Data |
| --- | --- | --- |
| 174 | 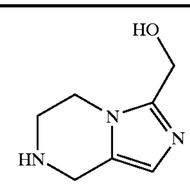 | $^1$H-nmr(CDCl$_3$, 400MHz) δ: 3.00(s, 2H), 3.22(t, 2H), 4.01(m, 4H), 4.62(s, 2H), 6.66(s, 1H) LRMS: m/z(ES$^+$) 154[MH$^+$] |
| 175 | 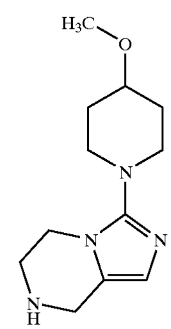 | $^1$H-nmr(CDCl$_3$, 400MHz) δ: 1.65(m, 3H), 2.03(m, 2H), 2.90(m, 2H), 3.15(t, 2H), 3.26(m, 2H), 3.33(m, 1H), 3.39(s, 3H), 3.74(t, 2H), 4.01(s, 2H), 6.50(s, 1H) LRMS: m/z (ES$^+$) 237[MH$^+$] |
| 176 | 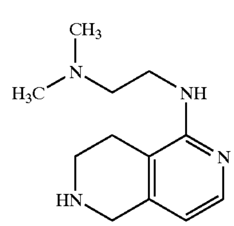 | $^1$H-nmr(CDCl$_3$, 400MHz) δ: 2.28(s, 6H), 2.34(m, 2H), 2.53(t, 2H), 3.19(t, 2H), 3.50(m, 2H), 3.85(s, 2H), 4.79(s, 1H), 6.25(d, 1H), 7.90(d, 1H) LRMS: m/z(ES$^+$) 221[MH$^+$] |
| 177 | 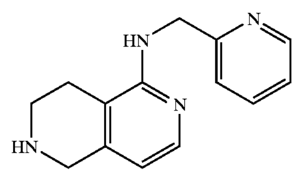 | LRMS: m/z ES$^+$ 241[MH$^+$] |

-continued

| Prep | Structure | Spectroscopic Data |
|---|---|---|
| 178 | 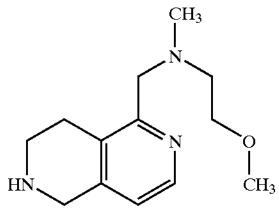 | ¹H-nmr(CDCl₃, 400MHz) δ: 2.28(s, 3H), 2.66(t, 2H), 2.90(t, 2H), 3.17(t, 2H), 3.30(s, 3H), 3.50(t, 2H), 3.66(s, 2H), 3.98(s, 2H), 6.81(d, 1H), 8.27(d, 1H) LRMS: m/z ES⁺ 258[MNa⁺] |
| 179 | 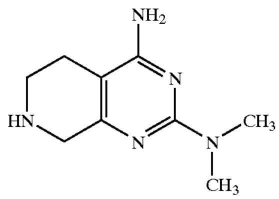 | ¹H-nmr(CDCl₃, 400MHz) δ: 2.29(t, 2H), 3.08(s, 6H), 3.12(t, 2H), 3.74(s, 2H), 4.47(s, 2H) LRMS: m/z ES⁺ 194[MH⁺] |
| 180 | 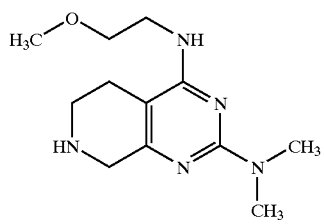 | ¹H-nmr(CDCl₃, 400MHz) δ: 2.25(t, 2H), 3.10(m, 8H), 3.38(s, 3H), 3.57(t, 2H), 3.66(q, 2H), 3.73(s, 2H), 4.68(t, 1H) LRMS: m/z ES⁺ 252[MH⁺] |
| 181 | 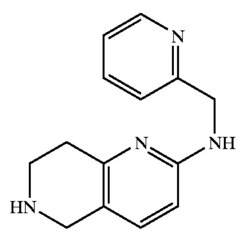 | ¹H-nmr(CDCl₃, 400MHz) δ: 2.80(t, 2H), 3.20(t, 2H), 3.89(s, 2H), 4.60(d, 2H), 5.40(s, 1H), 6.29(d, 1H), 7.07(d, 1H), 7.15(m, 1H), 7.25(d, 1H), 7.61(m, 1H), 8.55(d, 1H) LRMS: m/z ES⁺ 241.3[MH⁺] |
| 182 | 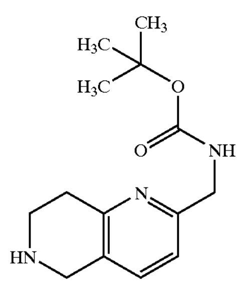 | ¹H-nmr(ODCl₃, 400MHz) δ: 1.47(s, 9H), 1.60(s, 1H), 2.91(t, 2H), 3.20(t, 2H), 3.97(s, 2H), 4.35(d, 2H), 5.41(s, 1H), 7.02(d, 1H), 7.26(s, 1H) LRMS: m/z ES⁺ 286[MNa⁺] |
| 183 | 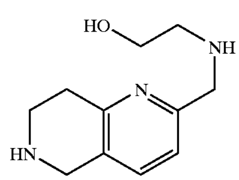 | ¹H-nmr(DMSOd₆, 400MHz) δ: 2.58(t, 2H), 2.73(t, 2H), 3.00(t, 2H), 3.45(t, 2H), 3.70(s, 2H), 3.83(s, 2H), 7.13(d, 1H), 7.33(d, 1H). LRMS: m/z(ES⁺) 208[MH⁺] |
| 184 | 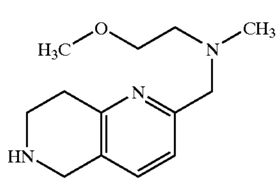 | LRMS: m/z(ES⁺) 258[MNa⁺] |
| 185 | | ¹H-nmr(CD₃OD, 400MHz) δ: 2.04(m, 4H), 2.70(s, 3H), 2.77–2.96(m, 3H), 3.04(m, 2H), 3.37(m, 4H), 4.15(s, 2H), 7.18(d, 1H), 7.53(d, 1H). LRMS: m/z(ES⁺) 232[MH⁺] |
| 186 | | LRMS: m/z(ES⁺) 258[MNa⁺] |
| 187 | | ¹H-nmr(CDCl₃, 400MHz) δ: 2.78(m, 2H), 3.03(m, 2H), 3.17(t, 2H), 3.21(s, 3H), 3.63(m, 2H), 3.72(s, 2H), 3.96(s, 2H), 4.02(m, 1H), 6.80(d, 1H), 8.24(d, 1H). LRMS: m/z (ES⁺) 234[MH⁺] |
| 188 | | ¹H-nmr(CDCl₃, 400MHz) δ: 1.80(m, 1H), 2.10(m, 1H), 2.45(s, 1H), 2.63(dd, 1H), 2.74(m, 2H), 2.94(m, 2H), 2.98(dd, 1H), 3.20(t, 2H), 3.26(s, 3H), 3.79(s, 2H), 3.96(m, 1H), 4.01(s, 2H), 6.84(d, 1H), 8.28(d, 1H). LRMS: m/z (ES⁺) 248[MH⁺] |
| 189 | | ¹H-nmr(CDCl₃, 400MHz) δ: 3.08(m, 4H), 3.18(t, 2H), 3.77(m, 2H), 3.80(m, 4H), 4.02(s, 2H), 6.52(s, 1H). LRMS: m/z(ES⁺) 231[MNa⁺] |
| 190 | | ¹H-nmr(CD₃OD, 400MHz) δ: 0.38–0.84(m, 4H), 1.30(m, 1H), 3.46(s, 2H), 3.80(m, 2H), 4.60(m, 4H), 7.58(s, 1H). LRMS: m/z (ES⁺) 178[MH⁺] |

Preparation 191

Methoxy-ethyl)-(5,6,7,8-tetrahydro-[1,6]naphthyridin-2-yl)-amine hydrochloride

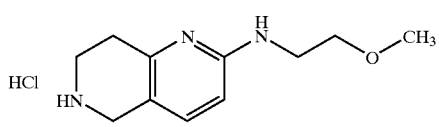

10% Palladium on activated carbon (800 mg) was added to a solution of the N-benzyl compound from preparation 148 (1.31 g, 4.4 mmol) and ammonium formate (1.39 g, 22 mmol) in methanol (50 ml). The mixture was heated under reflux for 1 hour, cooled to room temperature and then filtered through Arbocel®. The filter cake was washed with dichloromethane/methanol (50:50, 400 ml) and the combined filtrates were evaporated under reduced pressure. The residue was purified by chromatography on silica gel using methanol and ammonium hydroxide in dichloromethane as eluant (gradient from 3:0.5:97 to 10:1:90). The material isolated was azeotroped with dichloromethane and dried under vacuum. The residue was dissolved in dichloromethane (5 ml) and hydrogen chloride (1M in diethyl ether) was added. The solid formed was isolated by filtration and was dried at 60° C. under vacuum to give the title compound as a pale yellow solid (832 mg).

LRMS: m/z ES$^+$ 208.3 [MH$^+$]

Preparation 192

2-Methanesulfonyloxymethyl-7,8-dihydro-5H-pyrido[4,3-d]pyrimidine-6-carboxylic acid

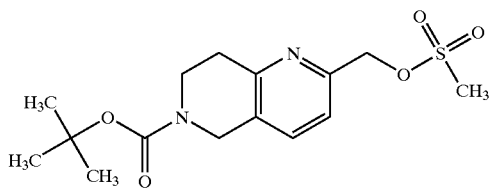

Methane sulphonyl chloride (140 µl, 1.8 mmol) was added to a solution of the alcohol from preparation 37 (400 mg, 1.5 mmol) and triethylamine (229 µl, 1.6 mmol) in tetrahydrofuran (10 ml) at 0° C. The mixture was warmed to room temperature and was stirred for 3 hours. The solvent was evaporated under reduced pressure and the residue was redissolved in tetrahydrofuran (10 ml) and partitioned between water (50 ml) and dichloromethane (50 ml). The organic layer was separated, dried over magnesium sulphate and evaporated under reduced pressure to give the title compound as an oil (622 mg).

$^1$H-nmr (CDCl$_3$, 400 MHz) δ: 1.42 (s, 9H), 2.96 (m, 2H), 3.75 (m, 4H), 4.59 (s, 3H), 4.68 (s, 2H), 8.48 (s, 1H) LRMS: m/z (ES$^+$) 366 [MNa$^+$]

Preparation 193

2-Morpholin-4-ylmethyl-7,8-dihydro-5H-pyrido[4,3-d]pyrimidine-6-carboxylic acid tert-butyl ester

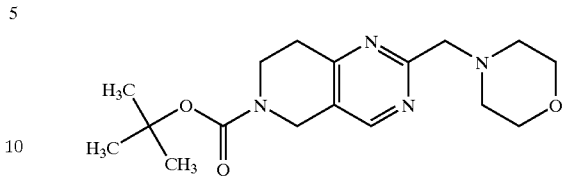

The mesylate from preparation 192 (300 mg, 0.88 mmol) was dissolved in morpholine (5 ml) containing N,N-diisopropylethylamine (150 µl, 0.88 mmol) and the mixture was stirred at room temperature for 16 hours. The reaction mixture was partitioned between dichloromethane (50 ml) and water (50 ml) and the organic layers were dried over magnesium sulphate and evaporated under reduced pressure. The residue was purified by chromatography on silica gel using methanol and ammonium hydroxide in dichloromethane as eluant (gradient from 2:0.2:98 to 5:0.5:95) to give the title compound as a yellow oil (260 mg).

$^1$H-nmr (CDCl$_3$, 400 MHz) δ: 1.50 (s, 9H), 2.59 (m, 4H), 2.96 (m, 2H), 3.74 (m, 8H), 4.58 (s, 2H), 8.45 (s, 1H) LRMS: m/z (ES$^+$) 357 (MNa$^+$]

Preparation 194 tert-Butyl 5-{[(3R)-1-benzylpyrrolidinyl]oxy}-3,4-dihydro-2(1H)-isoquinolinecarboxylate

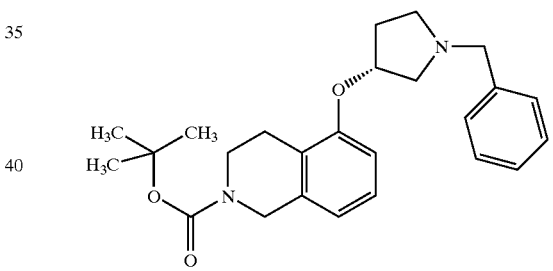

A solution of diethylazodicarboxylate (731 mg, 4.2 mmol) in dichloromethane (5 ml) was added to an ice-cooled solution of the alcohol from preparation 22 (498 mg, 2 mmol) and triphenylphosphine (1.18 g, 4.5 mmol) in dichloromethane (35 ml), and the solution stirred for 30 minutes. (S)-1-Benzyl-3-pyrrolidinol (885 mg, 5 mmol) was added, the mixture allowed to warm to room temperature and the reaction stirred for a further 72 hours. The mixture was diluted with dichloromethane (50 ml), washed with water (2×50 ml), dried over magnesium sulphate and concentrated under reduced pressure. The residual oil was purified by column chromatography on silica gel twice, using an elution gradient of cyclohexane: propan-2-ol: 0.88 ammonia (95:6:0.2 to 90:10:0.4). The product was azeotroped with methanol to afford the title compound as a colourless oil, 718 mg.

$^1$H-nmr (CDCl$_3$, 400 MHz) δ: 1.48 (s, 9H), 1.97 (m, 1H), 2.27 (m, 1H), 2.65 (m, 3H), 2.75 (t, 2H), 3.03 (dd, 1H), 3.61 (t, 2H), 3.66 (dd, 2H), 4.53 (s, 2H), 4.80 (m, 1H), 6.56 (d, 1H), 6.68 (d, 1H), 7.07 (dd, 1H), 7.22–7.37 (m, 5H). LRMS: m/z (ES$^+$) 431 [MNa$^+$]

Preparation 196 tert-Butyl 5-{[(3S)-1-benzylpyrrolidinyl]oxy}-3,4-dihydro-2(1H)-isoquinolinecarboxylate

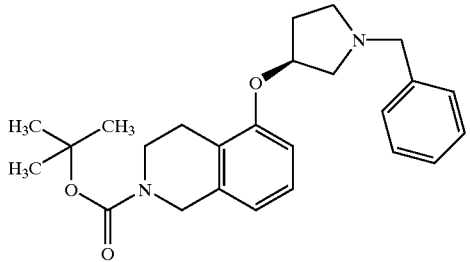

The title compound was obtained as a colourless oil in 82% yield from (R)-1-benzyl-3-pyrrolidinol and the alcohol from preparation 22, according to the method described in preparation 194.

$^1$H-nmr (CDCl$_3$, 400 MHz) δ: 1.48 (s, 9H), 1.97 (m, 1H), 2.27 (m, 1H), 2.65 (m, 3H), 2.75 (t, 2H), 3.05 (dd, 1H), 3.62 (t, 2H), 3.66 (dd, 2H), 4.54 (s, 2H), 4.80 (m, 1H), 6.57 (d, 1H), 6.65 (d, 1H), 7.07 (dd, 1H), 7.22–7.37 (m, 5H). LRMS: m/z (ES$^+$) 431 [MNa$^+$]

Preparation 196 tert-Butyl 5-({(2S)-1-[(benzyloxy)carbonyl]pyrrolidinyl}methoxy)-3,4-dihydro-2(1H)-isoguinolinecarboxylate

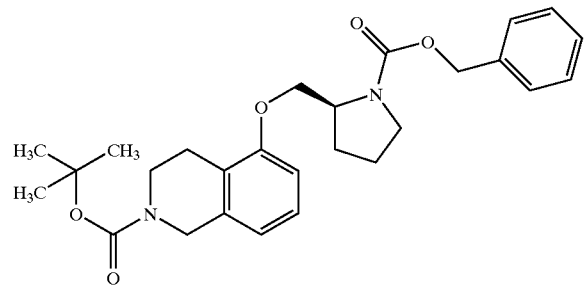

The title compound was obtained as a colourless oil in 79% yield from the alcohol from preparation 22 and benzyl (2S)-2-(hydroxymethyl)-1-pyrrolidinecarboxylate (J. Chem. Soc. Perkin Trans. 1; EN; 19; 1997; 2891) (823 mg, 2.53 mol), following a similar procedure to that described in preparation 195, except cyclohexane: ethyl acetate (91:9 to 75:25) was used as the elution gradient.

$^1$H-nmr (CDCl$_3$, 400 MHz) δ: 1.46 (s, 9H), 1.88 (m, 1H), 2.05 (m, 3H), 2.70 (m, 2H), 3.48 (m, 2H), 3.60 (m, 3H), 4.00 (m, 2H), 4.53 (m, 2H), 5.14 (m, 2H), 6.65 (m, 2H), 7.09 (m, 1H), 7.33 (m, 5H). LRMS: m/z (ES$^+$) 490 [MNa$^+$]

Preparation 197 tert-Butyl 5-({(2R)-1-[(benzyloxy)carbonyl]pyrrolidinyl}methoxy)-3,4-dihydro-2(1H)-isoquinolinecarboxylate

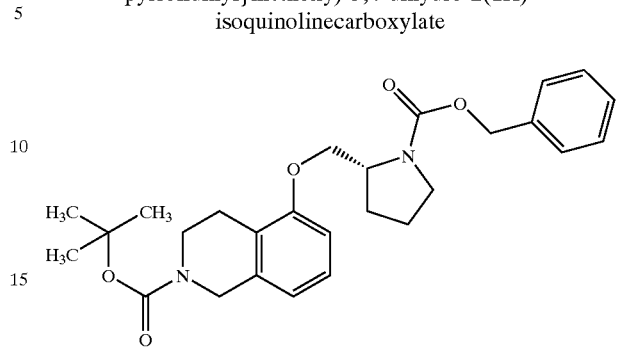

The title compound was obtained as a colourless oil in 83% yield from the alcohol from preparation 22 and benzyl (2R)-2-(hydroxymethyl)-1-pyrrolidinecarboxylate (Tet. Lett. 33; 52; 1992; 8011), following a similar procedure to that described in preparation 195.

$^1$H-nmr (DMSOd$_6$ 400 MHz) δ: 1.39 (s, 9H), 1.80 (m, 1H), 2.00 (m, 3H), 2.58 (m, 2H), 3.38 (m, 2H), 3.50 (m, 2H), 3.90–4.10 (m, 3H), 4.22 (s, 2H), 5.05 (s, 2H), 6.65–7.10 (m, 3H), 7.26 (m, 5H). LRMS: m/z (ES$^+$) 489 [MNa$^+$]

Preparation 198 tert-Butyl 5-[(3R)-pyrrolidinyloxy]-3,4-dihydro-2(1H)-isoquinolinecarboxylate

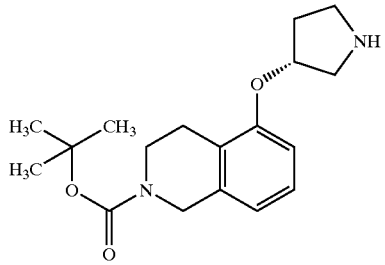

A solution of the compound from preparation 195 (662 mg, 1.62 mmol) in methanol (60 ml) was purged with argon, then heated under reflux, and allowed to cool slightly. 10% Palladium on carbon (330 mg) and ammonium formate (204 mg, 3.25 mmol) were added, and the mixture heated at reflux for 10 minutes, then cooled rapidly to room temperature. The mixture was filtered through Arbocel®, washing through with ethanol, and the combined filtrate evaporated under reduced pressure. The residual oil was purified by column chromatography on silica gel using an elution gradient of dichloromethane: methanol: 0.88 ammonia (95:5:0.5 to 93:7:0.7) to afford the title compound as a colourless oil, 420 mg.

$^1$H-nmr (CDCl$_3$, 400 MHz) δ: 1.47 (s, 9H), 1.67 (s, 2H), 1.96 (m, 1H), 2.06 (m, 1H), 2.70 (t, 2H), 2.91 (m, 1H), 3.04 (dd, 1H), 3.15 (m, 1H), 3.61 (t, 2H), 4.53 (s, 2H), 4.81 (m, 1H), 6.64 (d, 1H), 6.69 (d, 1H), 7.10 (dd, 1H). LRMS: m/z (ES$^+$) 319 [MH$^+$]

Preparation 199 tert-Butyl 5-[(3S)-pyrrolidinyloxy]-3,4-dihydro-2(1H)-isoquinolinecarboxylate

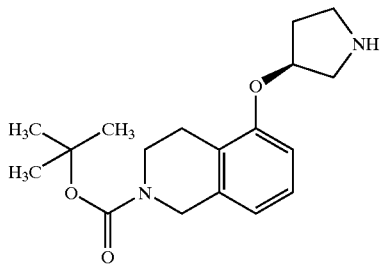

The title compound was obtained as a colourless oil in 89% yield from the compound from preparation 196, following the procedure described in preparation 198.

$^1$H-nmr (CDCl$_3$, 400 MHz) δ: 1.47 (s, 9H), 1.67 (s, 2H), 1.96 (m, 1H), 2.06 (m, 1H), 2.70 (t, 2H), 2.90 (m, 1H), 3.04 (dd, 1H), 3.15 (m, 1H), 3.62 (t, 2H), 4.53 (s, 2H), 4.81 (m, 1H), 6.64 (d, 1H), 6.69 (d, 1H), 7.10 (dd, 1H). LRMS: m/z (ES$^+$) 319 [MH$^+$]

Preparation 200 tert-Butyl 5-[(2S)-pyrrolidinylmethoxy]-3,4-dihydro-2(1H)-isoquinolinecarboxylate

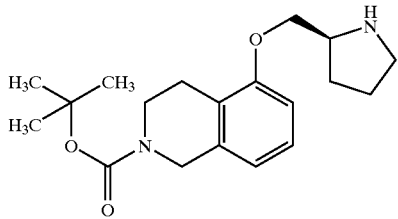

The title compound was obtained as a colourless oil in 90% yield from the compound from preparation 196, following the procedure described in preparation 198.

$^1$H-nmr (CDCl$_3$, 400 MHz) δ: 1.47 (s, 9H), 1.60 (m, 1H), 1.66 (m, 1H), 1.80 (m, 2H), 1.95 (m, 1H), 2.75 (t, 2H), 2.94 (m, 1H), 3.02 (m, 1H), 3.52 (m, 1H), 3.61 (t, 2H), 3.90 (m, 2H), 4.54 (s, 2H), 6.70 (m, 2H), 7.10 (dd, 1H). LRMS: m/z (ES$^+$) 333 [MH$^+$]

Preparation 201 tert-Butyl 5-[(2R)-pyrrolidinylmethoxy]-3,4-dihydro-2(1H)-isoquinolinecarboxylate

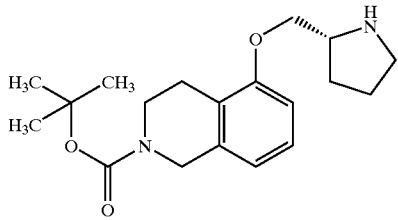

The title compound was obtained as a colourless oil in 87% yield from the compound from preparation 197, following the procedure described in preparation 198.

$^1$H-nmr (CDCl$_3$, 400 MHz) δ: 1.47 (s, 9H), 1.60 (m, 1H), 1.66 (m, 1H), 1.80 (m, 2H), 1.95 (m, 1H), 2.75 (t, 2H), 2.94 (m, 1H), 3.02 (m, 1H), 3.52 (m, 1H), 3.61 (t, 2H), 3.90 (m, 2H), 4.54 (s, 2H), 6.69 (m, 2H), 7.10 (dd, 1H). LRMS: m/z (ES$^+$) 333 [MH$^+$]

Preparation 202 tert-Butyl 5-{[(3R)-1-methylpyrrolidinyl]oxy}-3,4-dihydro-2(1H)-isoquinolinecarboxylate

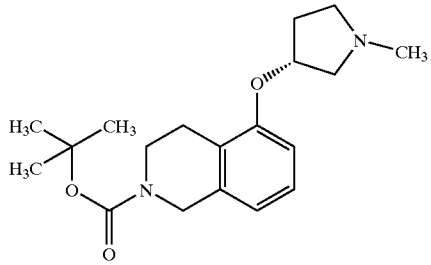

Acetic acid (156 mg, 2.6 mmol) was added dropwise to a solution of the pyrrolidine from preparation 198 (395 mg, 1.24 mmol) in tetrahydrofuran (10 ml), followed by formaldehyde (210 μl, 37%, 2.6 mmol), and the solution stirred for 20 minutes. Sodium triacetoxyborohydride (788 mg, 3.72 mmol) was added, and the reaction stirred at room temperature for 72 hours. The mixture was partitioned between dichloromethane (75 ml) and water (75 ml), and the layers separated. The aqueous phase was basified using 10% aqueous sodium carbonate solution and extracted with further dichloromethane (2×50 ml). The combined organic solutions were dried over magnesium sulphate and evaporated under reduced pressure. The residual oil was purified by column chromatography on silica gel using an elution gradient of dichloromethane: methanol: 0.88 ammonia (97:3:0.2 to 93:7:0.7), then azeotroped with methanol to afford the title compound as a pale yellow oil (378 mg).

$^1$H-nmr (CDCl$_3$, 400 MHz) δ: 1.47 (s, 9H), 1.98 (m, 1H), 2.29 (m, 1H), 2.38 (s, 3H), 2.52 (m, 1H), 2.74 (m, 4H), 2.91 (m, 1H), 3.59 (dd, 2H), 4.53 (s, 2H), 4.80 (m, 1H), 6.57 (d, 1H), 6.68 (d, 1H), 7.09 (dd, 1H). LRMS: m/z (ES$^+$) 333 [MH$^+$]

Preparation 203 tert-Butyl 5-{[(3S)-1-methylpyrrolidinyl]oxy}-3,4-dihydro-2(1H)-isoquinolinecarboxylate

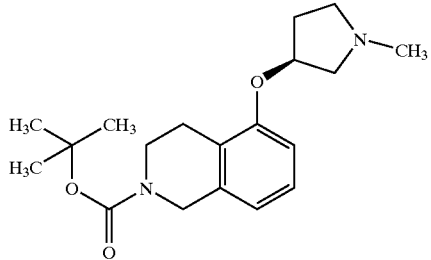

The title compound was obtained as a pale yellow oil in 94% yield from the compound from preparation 199 and formaldehyde following the procedure described in preparation 202.

$^1$H-nmr (CDCl$_3$, 400 MHz) δ: 1.47 (s, 9H), 1.98 (m, 1H), 2.29 (m, 1H), 2.38 (s, 3H), 2.52 (m, 1H), 2.74 (m, 4H), 2.91

(m, 1H), 3.59 (dd, 2H), 4.53 (s, 2H), 4.80 (m, 1H), 6.57 (d, 1H), 6.68 (d, 1H), 7.09 (dd, 1H). LRMS: m/z (ES⁺) 333 [MH⁺]

Preparation 204 tert-Butyl 5-{[(2S)-1-methylpyrrolidinyl]methoxy}-3,4-dihydro-2(1H)-isoquinolinecarboxylate

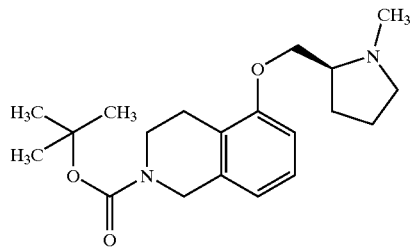

The title compound was obtained as a pale yellow oil in 94% yield from the pyrrolidine from preparation 200 and formaldehyde, following the procedure described in preparation 202.

¹H-nmr (CDCl₃, 400 MHz) δ: 1.47 (s, 9H), 1.68 (m, 1H), 1.79 (m, 2H), 2.03 (m, 1H), 2.30 (m, 1H), 2.48 (s, 3H), 2.66 (m, 1H), 2.74 (m, 2H), 3.09 (m, 1H), 3.60 (m, 2H), 3.84 (m, 1H), 3.98 (m, 1H), 4.54 (s, 2H), 6.68 (m, 2H), 7.10 (dd, 1H). LRMS: m/z (ES⁺) 347 [MH⁺]

Preparation 204 tert-Butyl 5-{[(2S)-1-methylpyrrolidinyl]methoxy}-3,4-dihydro-2(1H)-isoquinolinecarboxylate

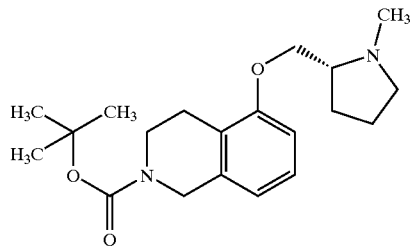

The title compound was obtained as a pale yellow oil in 90% yield from the pyrrolidine from preparation 201 and formaldehyde, following the procedure described in preparation 202.

¹H-nmr (CDCl₃, 400 MHz) δ: 1.47 (s, 9H), 1.68 (m, 1H), 1.79 (m, 2H), 2.03 (m, 1H), 2.30 (m, 1H), 2.48 (s, 3H), 2.66 (m, 1H), 2.74 (m, 2H), 3.09 (m, 1H), 3.60 (m, 2H), 3.84 (m, 1H), 3.98 (m, 1H), 4.54 (s, 2H), 6.68 (m, 2H), 7.10 (dd, 1H). LRMS: m/z (ES⁺) 347 [MH⁺]

Preparation 205 tert-Butyl 2-formyl-7,8-dihydropyrido[4,3-d]pyrimidine-6(5H)-carboxylate

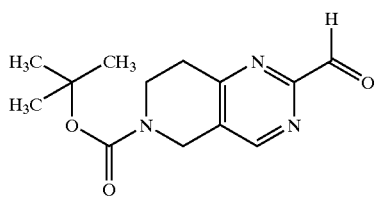

A solution of dimethylsulphoxide (1.41 ml, 19.9 mmol) in dichloromethane (2 ml) was added to a cooled (−65° C.) solution of trifluoroacetic anhydride (2.08 ml, 14.9 mmol) in dichloromethane (40 ml), and the solution stirred for 30 minutes. A solution of the alcohol from preparation 37 (2.5 g, 9.96 mmol) in dichloromethane (10 ml) was added dropwise, so as to maintain the temperature below −60° C., and once addition was complete, the solution was stirred for a further 30 minutes. Triethylamine (6.94 ml, 49.8 mmol) was slowly added, the reaction stirred for a further hour at −65° C., and then poured into ethyl acetate (200 ml) and water (100 ml). The phases were separated, the organic phase washed with water (150 ml), 10% aqueous citric acid solution (150 ml) and brine (150 ml), then dried over magnesium sulphate and evaporated under reduced pressure. The crude product was purified by column chromatography on silica gel using ethyl acetate as eluant, to afford the title compound, 1.3 g.

LRMS: m/z (ES⁺) 286 [MNa⁺]

Preparation 206 tert-Butyl 2-{[(2-methoxyethyl)amino]methyl}-7,8-dihydropyrido[4,3-d]pyrimidine-6(5H)-carboxylate

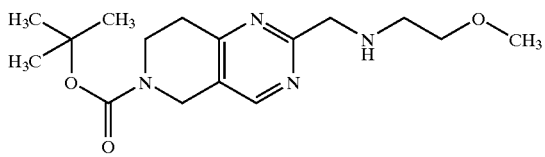

2-Methoxyethylamine (0.21 ml, 2.45 mmol) and acetic acid (0.10 ml, 1.79 mmol) were added to a solution of the aldehyde from preparation 205 (430 mg, 1.63 mmol) in tetrahydrofuran (10 ml), and the solution stirred at room temperature for 1 hour. Sodium triacetoxyborohydride (0.87 g, 4.08 mmol) was added and the reaction stirred at room temperature for 18 hours. The mixture was concentrated under reduced pressure and the residue partitioned between 0.88 ammonia and ethyl acetate, and the layers separated. The organic phase was washed with brine, dried over magnesium sulphate and evaporated under reduced pressure. The crude product was purified by column chromatography on silica gel using an elution gradient of dichloromethane:methanol (98:2 to 95:5) to afford the title compound (282 mg).

¹H-nmr (CDCl₃, 400 MHz) δ: 1.48 (s, 9H), 2.86 (t, 2H), 2.92 (t, 2H), 3.37 (s, 3H) 3.55 (t, 2H), 3.72 (t, 2H), 4.02 (s, 2H), 4.57 (s, 2H), 8.41 (s, 1H).

Preparation 207 tert-Butyl 2-({[(1S)-2-methoxy-1-methylethyl]amino}methyl)-7,8-dihydropyrido[4,3-d]pyrimidine-6(5H)-carboxylate

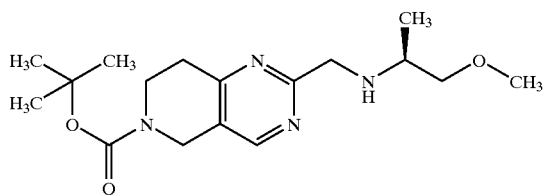

The title compound was obtained, quantitatively from the aldehyde from preparation 205 and (S)-(+)-1-methoxy-2-propylamine, following a similar procedure to that described in preparation 206, except the compound was isolated without column chromatography.

$^1$H-nmr (CDCl$_3$, 400 MHz) δ: 1.07 (d, 3H), 1.45 (s, 9H), 2.94 (m, 2H), 3.35 (m, 6H), 3.74 (t, 2H), 3.96–4.10 (dd, 2H), 4.57 (s, 2H), 8.40 (s, 1H). LRMS: m/z (ES$^+$) 359 [MNa$^+$]

Preparation 208 tert-Butyl 2-{[[(1S)-2-methoxy-1-methylethyl](methyl)amino]methyl}-7,8-dihydropyrido[4,3-d]pyrimidine-6(5H)-carboxylate

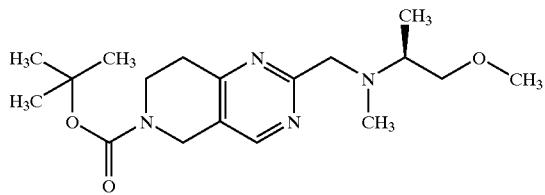

Formaldehyde (608 μl, 7.5 mmol), followed by sodium triacetoxyborohydride (2.12 g, 10 mmol) were added to a solution of the amine from preparation 207 (842 mg, 2.5 mmol) in dichloromethane (40 ml), and the reaction was stirred at room temperature for 18 hours. The mixture was partitioned between dichloromethane (100 ml) and 0.88 ammonia (100 ml), and the layers separated. The organic phase was washed with brine (100 ml), dried over sodium sulphate and evaporated under reduced pressure. The crude product was purified by column chromatography on silica gel using an elution gradient of dichloromethane: methanol (100:0 to 97:3) to afford the title compound, 523 mg.

$^1$H-nmr (CDCl$_3$, 400 MHz) δ: 1.08 (d, 3H), 1.46 (s, 9H), 2.38 (s, 3H), 2.95 (m, 2H), 3.00 (m, 1H), 3.35 (s, 3H), 3.44 (s, 2H), 3.75 (m, 2H), 3.85 (s, 2H), 4.58 (s, 2H). LRMS: m/z (ES$^+$) 373 [MNa$^+$]

Preparation 209 tert-Butyl 2-{[ethyl(2-methoxyethyl)amino]methyl}-7,8-dihydropyrido[4,3-d]pyrimidine-6(5H)-carboxylate

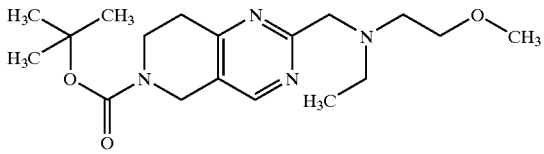

Acetaldehyde (0.21 ml, 3.8 mmol) was added to a solution of the amine from preparation 206 (282 mg, 0.97 mmol) in dichloromethane (10 ml) and the solution stirred for 1 hour at room temperature. Sodium triacetoxyborohydride (1.03 g, 4.8 mmol) was added and the reaction was stirred at room temperature for 18 hours. The mixture was concentrated under reduced pressure and the residue partitioned between 0.88 ammonia (100 ml) and ethyl acetate (100 ml) and the layers separated. The organic phase was washed with brine (100 ml), dried over magnesium sulphate and evaporated under reduced pressure. The crude product was purified by column chromatography on silica gel using an elution gradient of dichloromethane: methanol (99:1 to 96:4) to afford the title compound, 90 mg.

$^1$H-nmr (CDCl$_3$, 400 MHz) δ: 1.08 (t, 3H), 1.48 (s, 9H), 2.72 (q, 2H), 2.81 (t, 2H), 2.91 (t, 2H), 3.33 (s, 3H), 3.54 (t, 2H), 3.75 (t, 2H), 3.92 (s, 2H), 4.57 (s, 2H), 8.44 (s, 1H). LRMS: m/z (ES$^+$) 373 [MNa$^+$]

Preparation 210 tert-Butyl 2-[(4-methoxy-1-piperidinyl)methyl]-7,8-dihydropyrido[4,3-d]pyrimidine-6(5H)-carboxylate

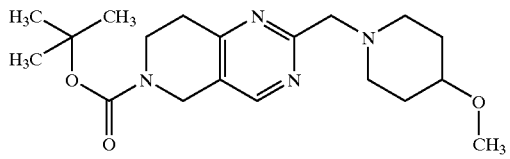

Triethylamine (305 μl, 2.19 mmol) and methanesulphonyl chloride (185 μl, 2.39 mmol) were added to a solution of the alcohol from preparation 37 (500 mg, 1.99 mmol) in dichloromethane (5 ml), and the solution stirred at room temperature for 3 hours. The mixture was evaporated under reduced pressure and the residue re-dissolved in tetrahydrofuran (5 ml) and 4-methoxypiperidine (J. Chem. Soc. 1984, (4), 737, Example 13) (1 g, 5.98 mmol) added, and the reaction mixture was stirred at room temperature for 18 hours. The mixture was partitioned between dichloromethane (30 ml) and water (30 ml), the layers separated, and the aqueous phase extracted with dichloromethane (30 ml). The combined organic solutions were dried over sodium sulphate and evaporated under reduced pressure to give a brown oil. This was purified by column chromatography on silica gel using an elution gradient of dichloromethane: methanol: 0.88 ammonia (98:2:1 to 96:4:1) to afford the title compound as a yellow gum (350 mg).

$^1$H-nmr (CDCl$_3$, 400 MHz) δ: 1.49 (s, 9H), 1.68 (m, 2H), 1.89 (m, 2H), 2.28 (m, 2H), 2.81 (m, 2H), 2.95 (t, 2H), 3.21 (m, 1H), 3.32 (s, 3H), 3.73 (m, 4H), 4.57 (s, 2H), 8.45 (s, 1H). LRMS: m/z (ES$^+$) 363 [MH$^+$]

Preparation 211

(2-Methoxy-ethyl)-methyl-(5,6,7,8-tetrahydro-[1,6]naphthyridin-2-ylmethyl)-amine

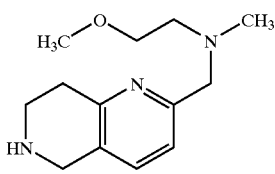

The title compound was obtained as a pale yellow oil from the benzyl compound from preparation 156 (832 mg, 2.55 mmol) following the procedure described in preparation 109.

LRMS: m/z (ES$^+$) 258 [MNa$^+$]

Preparation 212

2-Morpholin-4-ylmethyl-5,6,7,8-tetrahydro-pyrido[4,3-d]pyrimidine dihydrochloride

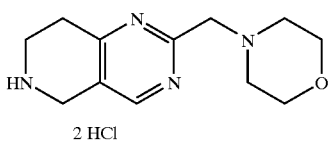

2 HCl

The protected amine from preparation 210 (243 mg, 0.72 mmol) was dissolved in dichloromethane (15 ml) at 0° C. and hydrogen chloride gas was bubbled through the solution for 10 minutes. The solvent was removed under reduced pressure to give the title compound as a white solid (200 mg)

$^1$H-nmr (DMSOd$_6$ 400 MHz) δ: 2.48 (m, 4H), 3.13 (m, 2H), 3.49 (m, 2H), 3.90 (m, 4H), 4.35 (s, 2H), 4.63 (s, 2H), 8.79 (s, 1H), 9.95 (s, 2H) LRMS: m/z (ES$^+$) 235 [MH$^+$]

Preparations 213 to 215

The compounds of the following tabulated preparations, of the general formula

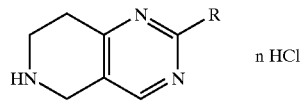

n HCl were prepared by a similar method to that of preparation 212 using the appropriate protected amine.

| Prep | Structure | Spectroscopic Data |
|---|---|---|
| 213 | ![structure] | $^1$H-nmr (CDCl$_3$, 400MHz) δ: 1.22(t, 3H), 2.46(m, 2H), 3.12(t, 2H), 3.22(s, 3H), 3.42(m, 2H), 3.44(m, 2H), 3.68(t, 2H), 4.35(s, 2H), 4.60(s, 2H), 8.75(s, 1H). LRMS: m/z(ES$^+$) 251[MH$^+$] |
| 214 | ![structure] | $^1$H-nmr(DMSOd$_6$, 400MHz) δ: 1.23(m, 3H), 2.82(s, 3H), 3.14(t, 2H), 3.24(m, 3H), 3.46(m, 2H), 3.60(m, 2H), 3.77(m, 1H), 4.38(s, 2H), 4.50(m, 1H), 4.64(m, 1H), 8.79(s, 1H), 10.07(m, 1H). LRMS: m/z(ES$^+$) 251[MH$^+$] |
| 215 | ![structure] | $^1$H-nmr(DMSOd$_6$, 400MHz) δ: 1.70(m, 1H), 1.98(m, 2H), 2.15 (m, 1H), 3.12–3.25(m, 8H), 3.38 (m, 2H), 3.47(m, 2H), 3.57(m, 2H), 4.35(s, 2H), 4.60(s, 2H), 8.80(s, 1H). LRMS: m/z(ES$^+$) 275[MNa$^+$] |

Preparation 216

5-{[(3R)-1-Methylpyrrolidinyl]oxy}-1,2,3,4-tetrahydroisoquinoline

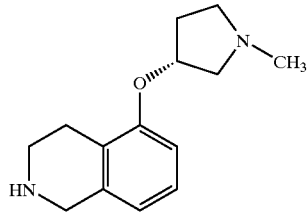

Trifluoroacetic acid (5 ml) was added dropwise to a solution of the protected amine from preparation 202 (354 mg, 1.06 mmol) in dichloromethane (5 ml), and the solution then stirred at room temperature for 3.5 hours. The reaction mixture was concentrated under reduced pressure and the residue azeotroped with toluene. The crude product was purified by column chromatography on silica gel using an elution gradient of dichloromethane: methanol: 0.88 ammonia (97:3:0.2 to 90:10:1) to afford the title compound as a colourless oil (220 mg).

$^1$H-nmr (CDCl$_3$, 400 MHz) δ: 1.98 (m, 2H), 2.28 (m, 1H), 2.38 (s, 3H), 2.52 (m, 1H), 2.65 (t, 2H), 2.69 (m, 2H), 2.93 (m, 1H), 3.11 (t, 2H), 3.96 (s, 2H), 4.80 (m, 1H), 6.55 (d, 1H), 6.60 (d, 1H), 7.04 (dd, 1H). LRMS: m/z (ES$^+$) 233 [MH$^+$]

Preparations 217 to 219

The compounds of the following tabulated preparations were prepared by a similar method to that of preparation 216 from the appropriate protected amines.

| Prep | Structure | Spectroscopic Data |
|------|-----------|--------------------|
| 217 | ![structure] | ¹H-nmr(CDCl₃, 400MHz) δ: 1.98(m, 2H), 2.28(m, 1H), 2.38(s, 3H), 2.52(m, 1H), 2.65(t, 2H), 2.69 (m, 2H), 2.93(m, 1H), 3.11(t, 2H), 3.96(s, 2H), 4.80(m, 1H), 6.55(d, 1H), 6.60(d, 1H), 7.04(dd, 1H). LRMS: m/z(ES⁺) 233[MH⁺] |
| 218 | ![structure] | ¹H-nmr(CDCl₃, 400MHz) δ: 1.68(m, 1H), 1.80(m, 2H), 1.95(m, 1H), 2.03(m, 1H), 2.30(dd, 1H), 2.50(s, 3H), 2.67(m, 3H), 3.11(m, 3H), 3.84(m, 1H), 3.96(m, 3H), 6.63(m, 2H), 7.06(dd, 1H). LRMS: m/z(ES⁺) 247[MH⁺] |
| 219 | ![structure] | ¹H-nmr(CDCl₃, 400MHz) δ: 1.68(m, 1H), 1.80(m, 2H), 2.01(m, 1H), 2.30(dd, 1H), 2.49(s, 3H), 2.67 (m, 3H), 3.11(m, 3H), 3.84(m, 1H), 3.96(s, 2H), 3.99(m, 1H), 6.63(m, 2H), 7.06(dd, 1H). LRMS: m/z(ES⁺) 247[MH⁺] |

Preparation 220

{tert-Butoxycarbonylimino-[2-(2-methoxy-ethylamino)-7,8-dihydro-5H-[1,6]naphthyridin-6-yl]-methyl}-carbamic acid tert-butyl ester

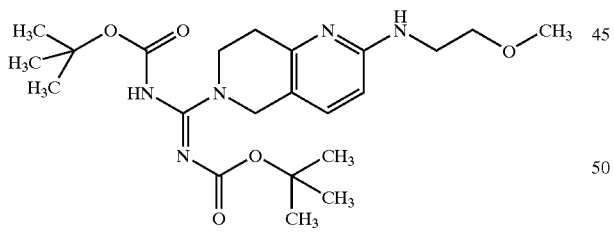

Mercury (II) chloride (1.29 g, 4.78 mmol) was added to the amine from preparation 191 (0.9 g, 4.34 mmol), triethylamine (1.67 ml, 12 mmol) and 1,3-bis(tert-butoxycarbonyl)-2-methyl-2-thiopseudourea (1.39 g, 4.78 mmol) in dichloromethane (25 ml) and the mixture was stirred at room temperature for 16 hours. The reaction mixture was diluted with dichloromethane and filtered through Arbocel® and the filtrate was evaporated under reduced pressure. The residue was purified by chromatography on silica gel using ethyl acetate in pentane as eluant (50:50) to give the title compound as a white solid (1.5 g).

¹H-nmr (CDCl₃, 400 MHz) δ: 1.50 (s, 18H), 2.93 (m, 2H), 3.36 (s, 3H), 3.48 (m, 2H), 3.55 (m, 2H), 3.80 (m, 2H), 4.57 (s, 2H), 4.68 (d, 1H), 6.24 (d, 1H), 7.11 (d, 1H), 10.08 (s, 1H) LRMS: m/z (ES⁻) 448 [M–H]⁻

Preparations 221 to 223

The compounds of the following tabulated preparations, of the general formula:

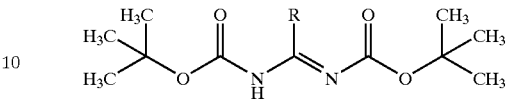

were prepared by a similar method to that of preparation 220 using the appropriate amine.

| Prep | R | Spectroscopic Data |
|------|---|--------------------|
| 221 | ![structure] | ¹H-nmr(CDCl₃, 400MHz) δ: 1.50(s, 18H), 3.17(t, 2H), 3.85(t, 2H), 4.72(s, 2H), 7.09 (m, 1H), 7.40(d, 1H), 8.43(d, 1H), 10.12(s, 1H) LRMS: m/z ES⁺ 399[MNa⁺] |
| 222 | ![structure] | ¹H-nmr(CDCl₃, 400MHz) δ: 1.48(s, 18H), 2.61(m, 2H), 3.38(s, 3H), 3.59(m, 2H), 3.67(m, 2H), 3.80(m, 2H), 4.50(s, 1H), 4.59(s, 2H), 6.33 (d, 1H), 7.91(d, 1H), 10.17(s, 1H) LRMS: m/z ES⁺ 450[MH⁺] |
| 223 | ![structure] | ¹H-nmr(CDCl₃, 400MHz) δ: 1.52(s, 18H), 2.74(s, 2H), 3.83(s, 2H), 4.60(s, 2H), 4.79 (s, 2H), 5.57(s, 1H), 6.37(d, 1H), 7.17(m, 1H), 7.30(d, 1H), 7.63(m, 1H), 7.96(s, 1H), 8.55(d, 1H), 10.18(s, 1H) LRMS: m/z ES⁺ 505[MNa⁺] |

Preparation 224

2-(2-Methoxy-ethylamino)-7,8-dihydro-5H-[1,6]naphthyridine-6-carboxamidine dihydrochloride

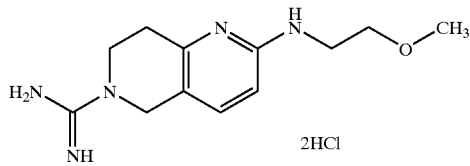

Hydrogen chloride gas was bubbled into a solution of the protected amidine from preparation 220 (1.5 g, 3.34 mmol) in dichloromethane for 10 minutes. The mixture was stirred at room temperature for 1 hour. The solvent was evaporated under reduced pressure to give the title compound as a white solid (1 g).

¹H-nmr (DMSOd₆ 400 MHz) δ: 3.04 (m, 2H), 3.27 (s, 3H), 3.52 (t, 2H), 3.63 (t, 2H), 3.74 (m, 2H), 4.51 (s, 2H), 7.01 (d, 1H), 7.60 (d, 1H), 7.79 (s, 4H) LRMS: m/z (ES⁺) 292 [MH]⁺

Preparations 225 to 227

The compounds of the following tabulated preparations, of the general formula:

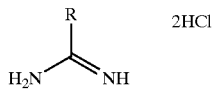

2HCl were prepared by a similar method to that of preparation 224 using the appropriate amidine.

| Prep | R | Spectroscopic Data |
|---|---|---|
| 225ᴬ | ![structure] | ¹H-nmr(DMSOd₆ 400MHz) δ: 3.01(t, 2H), 3.75(t, 2H), 4.64 (s, 2H), 7.45(s, 5H), 7.59(d, 1H), 8.43(d, 1H) LRMS: m/z ES⁺ 177[MH⁺] |
| 226 | ![structure] | ¹H-nmr(CD₃OD, 400MHz) δ: 2.78(m, 2H), 3.36(s, 3H), 3.68(m, 4H), 3.82(t, 2H), 4.68 (s, 2H), 6.76(d, 1H), 6.73(d, 1H) LRMS: m/z ES⁺ 251[MH⁺] |
| 227 | ![structure] | ¹H-nmr(CD₃OD, 400MHz) δ: 2.94(m, 2H), 3.88(m, 2H), 4.73(s, 2H), 5.20(s, 2H), 6.90 (d, 1H), 7.81(m, 1H), 7.91(m, 1H), 8.01(d, 1H), 8.48(m, 1H), 8.79(d, 1H) LRMS: m/z ES⁺ 505[MNa⁺] |

ᴬ Trifluoroacetic acid was used for the deprotection; the product was isolated as the ditrifluoroacetate salt Preparation 228-A 1-(2-Pyrrolidin-1-yl-ethyl)-1,4,6,7-tetrahydro-pyrazolo[4,3-c]pyridine-5-carboxylic acid tert-butyl ester

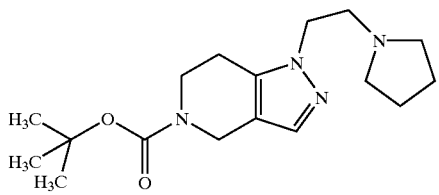

Preparation 228-B 2-(2-Pyrrolidin-1-yl-ethyl)-2,4,6,7-tetrahydro-pyrazolo[4,3-c]pyridine-5-carboxylic acid tert-butyl ester

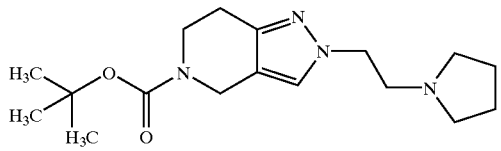

1,4,6,7-Tetrahydro-pyrazolo[4,3-c]pyridine-5-carboxylic acid tert-butyl ester (1.8 g, 8.06 mmol)(EP1057814, Example 2c) was added to 1-(2-chloro-ethyl)-pyrrolidine hydrochloride (1.65 g, 9.67 mmol) and potassium carbonate (3.34 g, 24.2 mmol) in N,N-dimethylformamide (35 ml) and the mixture was heated at 65° C. for 26 hours, then cooled to room temperature and stirred for 72 hours. The solvent was evaporated under reduced pressure and the residue was dissolved in 2N sodium hydroxide solution. The aqueous mixture was extracted with ethyl acetate (×2) and the combined organic layers were dried over magnesium sulphate and evaporated under reduced pressure. The residue was purified by chromatography on silica gel using ammonium hydroxide, methanol and ethyl acetate in dichloromethane as eluant (gradient from 0:0:50:50 to 0:0.1:50:50 to 0.5:5:0:95) to give the title compounds from preparation 228-A and preparation 228-B as a mixture of isomers (300 mg). LRMS: m/z ES⁺ 321 [MH⁺]

Preparation 229-A 1-(2-Pyrrolidin-1-yl-ethyl)-4,5,6 7-tetrahydro-1H-pyrazolo[4,3-c]pyridine ditrifluoroacetate

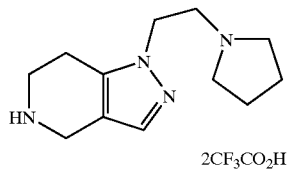

2CF₃CO₂H

Preparation 229-B 2-(2-Pyrrolidin-1-yl-ethyl)-2,4,6,7-tetrahydro-pyrazolo[4,3-c]pyridine ditrifluoroacetate

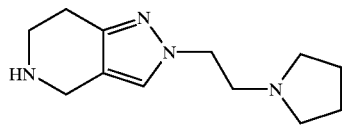

2CF₃CO₂H

Trifluoroacetic acid (2 ml) was added to the product from preparation 228 (equimolar mixture preparation 228-A and preparation 228-B, 300 mg, 0.94 mmol) in dichloromethane under a nitrogen atmosphere. The mixture was stirred at room temperature for 1.5 hours and then the solvent was evaporated under reduced pressure. Residual trifluoroacetic acid was removed by dichloromethane azeotrope (×3) to give a mixture of the title compound from preparation 232-A containing 40% by weight the title compound from preparation 232-B as a brown gum (792 mg).

LRMS: m/z ES⁺ 221 [MH⁺]

Preparation 230

2-[2-Fluoro-4-methoxy-6-(tetrahydro-pyran-4-yl)-phenyl]-4,4-dimethyl-4,5-dihydro-oxazole

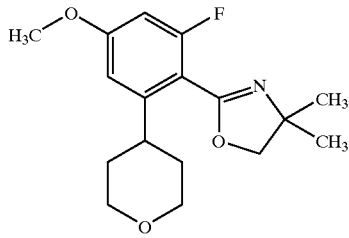

Magnesium turnings (2.4 g, 100 mmol) were added to 4-chlorotetrahydropyran (12 g, 100 mmol) in tetrahydrofuran (100 ml) followed by a crystal of iodine. After initiation of the reaction the mixture reached reflux without external heating. When the reaction had subsided, the mixture was stirred at room temperature for 2 hours. The above tetrahydropyran-4-yl magnesium chloride solution (50 ml) was added dropwise to the fluoro compound from preparation 2 (4.82 g, 20 mmol) in tetrahydrofuran (20 ml) at 0° C. and the mixture was warmed to room temperature and was stirred for 2 hours. The reaction mixture was diluted with water and filtered through Arbocel®. The solution was extracted with ethyl acetate and the organic layer was washed with brine and dried over magnesium sulphate and evaporated under reduced pressure. The residue was purified by chromatography on silica gel using ethyl acetate in dichloromethane as eluant (gradient from 0:100 to 40:60) to give the title compound as a white solid (6.5 g).

¹H-nmr (CDCl₃, 400 MHz) δ: 1.40 (s, 6H), 1.95 (m, 4H), 3.14 (m, 1H), 3.46 (m, 2H), 3.79 (s, 3H), 4.05 (m, 2H), 4.10 (s, 2H), 6.50 (d, 1H), 6.62 (s, 1H) LRMS: m/z (ES⁺) 330 [MNa⁺]

Preparation 231

2-Fluoro-4-methoxy-6-(tetrahydro-pyran-4-yl)-benzonitrile

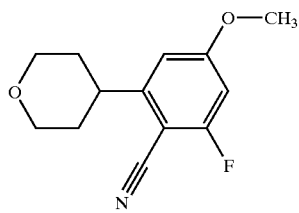

Phosphorous oxychloride (6.14 g, 40 mmol) was added to the oxazolidine from preparation 230 (6.42 g, 21 mmol) in ethyl acetate (75 ml) and pyridine (15.8 g, 0.2 mol) and the mixture was heated under reflux for 9 hours. The reaction mixture was cooled to room temperature and was added to ice and water. The mixture was extracted with ethyl acetate and the organic layer was washed with 2N hydrochloric acid (40 ml), brine (30 ml) and dried over magnesium sulphate and evaporated under reduced pressure. The residue was purified by chromatography on silica gel using ethyl acetate in dichloromethane as eluant (gradient from 0:100 to 10:90) to give the title compound as a white solid (4.3 g).

¹H-nmr (CDCl₃, 400 MHz) δ: 1.80 (m, 4H), 3.17 (m, 1H), 3.59 (m, 2H), 3.85 (s, 3H), 4.08 (m, 2H), 6.57 (d, 1H), 6.68 (s, 1H) LRMS: m/z (ES⁺) 258 [MNa⁺]

Preparation 232

2-(2-Fluoro-6-isopropyl-4-methoxy-phenyl)-4,4-dimethyl-4,5-dihydro-oxazole

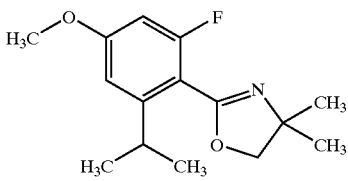

Isopropyl magnesium chloride (2M in tetrahydrofuran, 0.5 ml, 1 mmol) was added dropwise to the fluoro compound from preparation 2 (241 mg, 1 mmol) in tetrahydrofuran (5 ml) at 0° C. The reaction mixture was stirred at 0° C. for 15 minutes and then was stirred at room temperature for 16 hours. The reaction mixture was added to water and the solution was extracted with dichloromethane (3×30 ml). The combined organic solutions were dried over magnesium sulphate and evaporated under reduced pressure. The residue was purified by chromatography on silica gel using ethyl acetate in hexane as eluant (gradient from 0:100 to 30:70) to give the title compound as a colourless oil (110 mg).

¹H-nmr (CDCl₃, 400 MHz) δ: 1.21 (d, 6H), 1.39 (s, 6H), 3.28 (m, 1H), 3.80 (s, 3H), 4.08 (s, 2H), 6.47 (d, 1H), 6.65 (s, 1H) LRMS: m/z (ES⁺) 266 [MH⁺]

Preparation 233

2-Fluoro-6-isopropyl-4-methoxy-benzonitrile

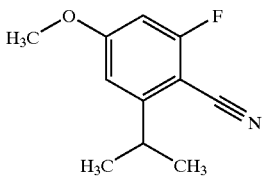

The title compound was obtained from the compound from preparation 232 (2.43 g, 9.17 mmol) in 95% yield following the procedure described in preparation 231.

¹H-nmr (CDCl₃, 400 MHz) δ: 1.30 (d, 6H), 3.31 (m, 1H), 6.83 (s, 3H), 6.55 (d, 1H), 6.67 (s, 1H) LRMS: m/z (ES⁺) 216 [MNa⁺]

Preparation 234

2-Fluoro-4-methoxy-6-(tetrahydro-furan-3-yloxy)-benzonitrile

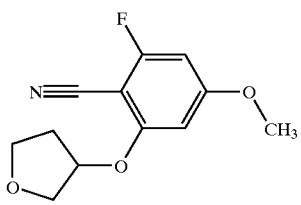

Sodium hydride (60% in mineral oil, 0.83 g, 21 mmol) was added portionwise to 3-hydroxytetrahydrofuran (1.82 g, 21 mmol) in tetrahydrofuran (40 ml) at 0° C. under a nitrogen atmosphere. The suspension was warmed to room temperature and was stirred for 1 hour. The mixture formed was added over 30 minutes to 2,6-difluoro-4-methoxy-benzonitrile (Mol. Cryst. Liq. Cryst. 1989, 172) (3.5 g, 21 mmol) in tetrahydrofuran (50 ml) and the resulting solution was held at room temperature for 16 hours. Water (75 ml) was added and the aqueous mixture was extracted with ethyl acetate (3×200 ml) The combined organic solutions were dried over magnesium sulphate and evaporated under reduced pressure. The material obtained was dried under vacuum to give the title compound as a brown solid (5.1 g).

$^1$H-nmr (CDCl$_3$, 400 MHz) δ: 2.20 (m, 2H), 3.84 (s, 3H), 4.00 (m, 4H), 4.95 (m, 1H), 6.18 (s, 1H), 6.32 (d, 1H) LRMS: m/z ES$^+$ 260 [MNa$^+$]

Preparation 235

2-Fluoro-6-isopropoxy-4-methoxy-benzonitrile

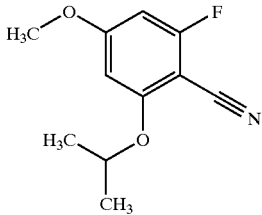

The title compound was obtained from 2,6-difluoro-4-methoxy-benzonitrile (Mol. Cryst. Liq. Cryst. 1989, 172) in 49% yield following the procedure described in preparation 234.

$^1$H-nmr (CDCl$_3$, 400 MHz) δ: 1.40 (d, 6H), 3.85 (s, 3H), 4.59 (m, 1H), 6.24 (m, 2H) LRMS: m/z ES$^+$ 210 [MH$^+$]

Preparation 236

2-Cyclobutoxy-6-fluoro-4-methoxy-benzonitrile

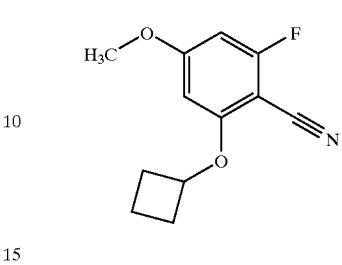

The title compound was obtained from 2,6-difluoro-4-methoxy-benzonitrile (Mol. Cryst. Liq. Cryst. 1989, 172) in 80% yield following the procedure described in preparation 234.

$^1$H-nmr (CDCl$_3$, 400 MHz) δ: 1.68 (m, 1H), 1.88 (m, 1H), 2.23 (m, 2H), 2.42 (m, 2H), 3.78 (s, 3H), 4.65 (m, 1H), 6.06 (s, 1H), 6.24 (d, 1H) LRMS: m/z (ES$^+$) 244 [MNa$^+$]

Preparation 237

2-Fluoro-4-methoxy-6-(2-methoxy-ethoxy)-benzonitrile

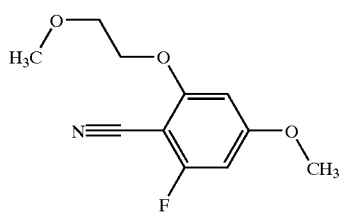

Sodium hydride (60% in mineral oil, 0.88 g, 22 mmol) was added to 2-methoxyethanol (1.84 g, 24 mmol) in tetrahydrofuran (20 ml) and the mixture was stirred at room temperature for 20 minutes. 2,6-Difluoro-4-methoxy-benzonitrile (Mol. Cryst. Liq. Cryst. 1989, 172) (3.38 g, 20 mmol) was added and the mixture was stirred at room temperature for 1 hour. The reaction mixture was poured into water and the solution was extracted with dichloromethane (3×50 ml). The combined organic solutions were dried over magnesium sulphate and evaporated under reduced pressure. The residue was purified by chromatography on silica gel using methanol in dichloromethane as eluant (gradient from 0:100 to 3:97) to give the title compound (3.8 g).

$^1$H-nmr (CDCl$_3$, 400 MHz) δ: 3.46 (s, 3H), 3.78 (t, 2H), 3.81 (s, 3H), 4.20 (t, 2H), 6.30 (m, 2H) LRMS: m/z ES$^+$ 248 [MNa$^+$]

Preparation 238

2-Azido-4-methoxy-6-(2-methoxy-ethoxy)-benzonitrile

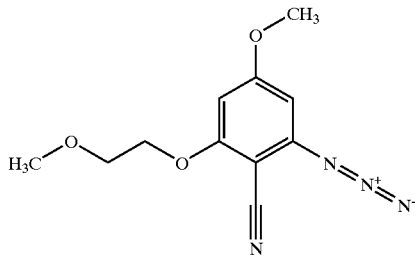

The fluoro compound from preparation 237 (3.6 g, 16 mmol) was added to sodium azide (1.56 g, 24 mmol) in N,N-dimethylformamide (25 ml) and the mixture was heated at 100° C. for 8 hours. The reaction mixture was cooled to room temperature and was added to water. The aqueous mixture was extracted with dichloromethane (3×60 ml) and the combined organic solutions were dried over magnesium sulphate and evaporated under reduced pressure. The residue was purified by chromatography on silica gel using ethyl acetate in dichloromethane as eluant (gradient from 0:100 to 20:80) to give the title compound (3.51 g).

$^1$H-nmr (CDCl$_3$, 400 MHz) δ: 3.47 (s, 3H), 3.79 (t, 2H), 3.86 (s, 3H), 4.20 (t, 2H), 6.30 (2×s, 2H) LRMS: m/z ES$^+$ 248 [MNa$^+$]

Preparation 239

2-Amino-4-methoxy-6-(2-methoxy-ethoxy)-benzonitrile

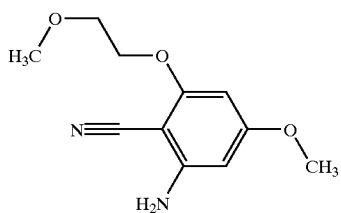

The azide from preparation 238 (3.50 g, 14.1 mmol) was suspended in methanol (100 ml) and magnesium turnings (1.68 g, 70 mmol) were added. The mixture was stirred for 18 hours and then 1N citric acid was added. The aqueous mixture was extracted with dichloromethane (3×100 ml) and the combined organic solutions were dried over magnesium sulphate and evaporated under reduced pressure. The residue was purified by chromatography on silica gel using methanol in dichloromethane as eluant (gradient from 0:100 to 5:95). The material obtained was triturated with diethyl ether to give the title compound as a white solid (1.78 g).

$^1$H-nmr (CDCl$_3$, 400 MHz) δ: 3.43 (s, 3H), 3.77 (m, 5H), 4.12 (t, 2H), 4.37 (s, 2H), 5.82 (s, 1H), 5.86 (s, 1H) LRMS: m/z ES$^+$ 245 [MNa$^+$]

Preparation 240

2-Chloro-6-fluoro-4-methoxy-benzonitrile

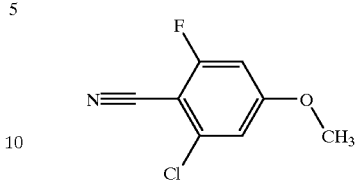

A solution of sodium nitrite (3.73 g, 54 mmol) in water (20 ml) was added to the amino compound from preparation 291 (8.3 g, 50 mmol) in concentrated hydrochloric acid at −10° C. at a rate that maintained the temperature below −5° C. The solution was stirred at −5° C. for 1 hour and then was added dropwise to copper (I) chloride (9.9 g, 0.1 mol) in water (100 ml) at −10° C. The reaction mixture was warmed to room temperature and was stirred for 16 hours and then the aqueous mixture was extracted with dichloromethane (×3). The combined organic solutions were washed with 1M sodium hydroxide solution (2×250 ml) and water (250 ml) then dried over sodium sulphate and evaporated under reduced pressure. The residue was purified by chromatography on silica gel using cyclohexane in dichloromethane as eluant (25:75) to give the title compound as a white solid (6.5 g).

$^1$H-nmr (CDCl$_3$, 400 MHz) δ: 3.87 (s, 3H), 6.65 (dd, 1H), 6.85 (d, 1H) LRMS: m/z (ES$^+$) 208 [MNa$^+$]

Preparation 241

2-Fluoro-6-iodo-4-methoxy-benzonitrile

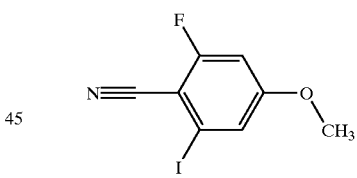

Sodium nitrite (227 mg, 3.3 mmol) in water (1 ml) was added dropwise to the amino compound from preparation 291 (500 mg, 3 mmol) in concentrated hydrochloric acid (10 ml) at −10° C. The mixture was stirred at −10° C. for 1 hour and then was added dropwise to potassium iodide (996 mg, 6 mmol) in water (5 ml) at −10° C. The reaction mixture was warmed to room temperature and was stirred for 72 hours. The reaction mixture was extracted with dichloromethane (3×50 ml) and the combined organic extracts were washed with 10% sodium metabisulphite solution (100 ml), 1M sodium hydroxide solution (100 ml) and water (100 ml) The organic solution was dried over magnesium sulphate and evaporated under reduced pressure to give the title compound as a yellow solid (751 mg).

$^1$H-nmr (DMSOd$_6$ 400 MHz) δ: 3.85 (s, 3H), 7.15 (d, 1H), 7.45 (s, 1H) LRMS: m/z ES$^+$ 300 [MNa$^+$]

Preparation 242

2-Amino-4-methoxy-6-(tetrahydro-pyran-4-yl)-benzonitrile

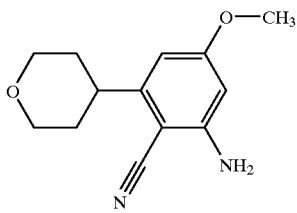

Ammonia gas was bubbled into dimethylsulphoxide (30 ml) for 20 minutes and the fluoro compound from preparation 231 (4.2 g, 17.9 mmol) was added and the mixture was heated at 150° C. for 18 hours. The reaction mixture was cooled to room temperature and was added to ethyl acetate (200 ml). The organic solution was washed with water (100 ml), 1N citric acid (40 ml) and brine (40 ml), then dried over magnesium sulphate and evaporated under reduced pressure. The residue was purified by chromatography on silica gel using ethyl acetate in dichloromethane as eluant (gradient from 0:100 to 25:75) to give the title compound as a white solid (1.64 g).

$^1$H-nmr (CDCl$_3$, 400 MHz) δ: 1.79 (m, 4H), 3.06 (m, 1H), 3.57 (m, 1H), 3.79 (s, 3H), 4.06 (m, 2H), 4.39 (s, 2H), 6.08 (d, 1H), 6.23 (s, 1H) LRMS: m/z (ES$^+$) 255 [MNa$^+$]

Preparations 243 to 248

The compounds of the following tabulated preparations, of the general formula:

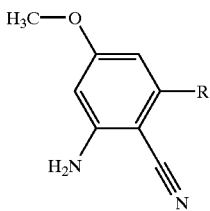

were prepared by a similar method to that of preparation 242 from the appropriate fluoro compound.

| Prep | R | Spectroscopic Data |
|---|---|---|
| 243 | CH(CH$_3$)$_2$ | $^1$H-nmr(CDCl$_3$, 400 MHz) δ: 1.28(d, 6H), 3.19(m, 1H), 3.75(s, 3H), 4.35(s, 2H), 6.06(s, 1H), 6.24(s, 1H) LRMS: m/z(ES$^+$) 213[MNa$^+$] |
| 244 | tetrahydrofuran-3-yloxy | $^1$H-nmr(CDCl$_3$, 400 MHz) δ: 2.18(m, 2H), 3.75(s, 3H), 3.98(m, 4H), 4.38(s, 2H), 4.90(m, 1H), 5.72(s, 1H), 5.81(s, 1H) LRMS: m/z ES$^+$ 257[MNa$^+$] |
| 245 | OCH(CH$_3$)$_2$ | $^1$H-nmr(CDCl$_3$, 400 MHz) δ: 1.36(d, 6H), 3.77(s, 3H), 4.35(s, 2H), 4.53(m, 1H), 5.81(m, 2H) LRMS: m/z ES$^+$ 229[MNa$^+$] |
| 246 | Cl | $^1$H-nmr(CDCl$_3$, 400 MHz) δ: 3.78(s, 3H), 4.50(s, 2H), 6.09(s, 1H), 6.39(s, 1H) LRMS: m/z(ES$^-$) 181, 183[M$^-$H] |
| 247 | cyclobutyloxy | $^1$H-nmr(CDCl$_3$, 400 MHz) δ: 1.67(m, 1H), 1.87(m, 1H), 2.21(m, 2H), 2.40(m, 2H), 3.74(s, 3H), 4.35(s, 2H), 4.61(m, 1H), 4.65(s, 1H), 5.79(s, 1H) LRMS: m/z(ES$^+$) 241[MNa$^+$] |
| 248 | I | $^1$H-nmr(CDCl$_3$, 400 MHz) δ: 3.77(s, 3H), 4.43(s, 2H), 6.15(s, 1H), 6.80(s, 1H) LRMS: m/z ES$^+$ 297[MNa$^+$] |

Preparation 249

2-Amino-6-(4,5-dihydro-furan-2-yl)-4-methoxy-benzonitrile

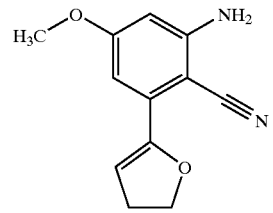

The iodo compound from preparation 248 (2.1 g, 7.7 mmol) in 1,4-dioxane (15 ml) was added to a solution of tris-(dibenzylideneacetone)dipalladium(0) (174 mg, 0.19 mmol) and tri-furan-2-yl-phosphine (88.2 mg, 0.38 mmol) in 1,4-dioxane (15 ml) under an argon atmosphere. Tributyl-(4,5-dihydro-furan-2-yl)-stannane (5.5 kg, 15.3 mmol) was added and the mixture was heated under reflux for 1.25 hours and then was cooled to room temperature. 1M Potassium fluoride solution (22 ml) was added and the mixture was stirred at room temperature for 30 minutes. The mixture was filtered and the filter cake was washed with ethyl acetate (75 ml). The filtrate was diluted with water and extracted with ethyl acetate (2×75 ml), the combined organic solutions were dried over magnesium sulphate and evaporated under reduced pressure. The residue was purified by chromatography on silica gel using ethyl acetate in cyclohexane as eluant (10:90). The material obtained was dissolved in acetonitrile and was washed with hexane (2×60 ml). The acetonitrile layer was separated and evaporated under reduced pressure to give the title compound as a yellow solid (1.34 g).

$^1$H-nmr (DMSOd$_6$ 400 MHz) δ: 2.78 (m, 2H), 3.72 (s, 3H), 4.37 (t, 2H), 5.76 (t, 1H), 5.84 (s, 2H), 6.33 (s, 1H), 6.39 (s, 1H) LRMS: m/z ES$^+$ 239 [MNa$^+$]

Preparation 250

2-Amino-4-methoxy-6-(tetrahydro-furan-2-yl)-benzonitrile

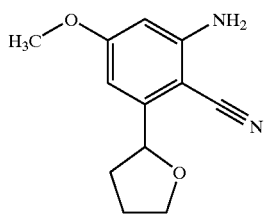

The dihydrofuran from preparation 249 (1.29 g, 5.96 mmol) was dissolved in methanol (125 ml) and the solution was purged with argon. 10% Palladium on active carbon (1.29 g) and ammonium formate (12.9 g, 0.2 mol) were added and the mixture was heated under reflux for 15 minutes. The mixture was cooled and filtered through Arbocel®. The filter cake was washed with ethanol. The combined organic solutions were evaporated under reduced pressure and the residue was partitioned between ethyl acetate (200 ml) and water (200 ml). Sodium carbonate was added to give pH10 and the phases were separated. The aqueous phase was extracted with ethyl acetate (2×50 ml) and the combined organic solutions were dried over magnesium sulphate and evaporated under reduced pressure. The residue was purified by chromatography on silica gel using ethyl acetate in cyclohexane as eluant (10:90) and the material obtained was co-evaporated with diethyl ether to give the title compound as a white solid (473 mg).

$^1$H-nmr (CDCl$_3$, 400 MHz) δ: 1.75 (m, 1H), 2.00 (m, 2H), 2.51 (m, 1H), 3.79 (s, 3), 3.94 (q, 1H), 4.13 (q, 1H), 4.35 (s, 2H), 5.02 (t, 1H), 6.10 (s, 1H), 6.48 (s, 1H) LRMS: m/z ES$^+$ 241 [MNa$^+$]

Preparation 251

7-Methoxy-5-(tetrahydro-pyran-4-yl)-1H-quinazoline-2,4-dione

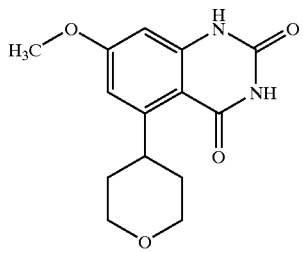

1,8-Diazabicyclo[5.4.0]undec-7-ene (3 ml) was added to the nitrile from preparation 242 (1.6 g, 6.9 mmol) in N,N-dimethylformamide (15 ml) and the solution was cooled to −78° C. and solid carbon dioxide (6 g) was added. The mixture was heated at 140° C. and 600 psi for 18 hours and then cooled to room temperature and added to water. The aqueous solution was acidified with 2N hydrochloric acid and the solid formed was isolated by filtration. The filter cake was washed with water and dried at 100° C. under vacuum to give the title compound as a white solid (1.81 g).

$^1$H-nmr (DMSOd$_6$ 400 MHz) δ: 1.61 (m, 4H), 3.40 (m, 2H), 3.79 (s, 3H), 3.92 (m, 1H), 6.52 (d, 1H), 6.60 (s, 1H) LRMS: m/z (ES$^+$) 299 [MNa$^+$]

Preparations 252 to 257

The compounds of the following tabulated preparations of the general formula:

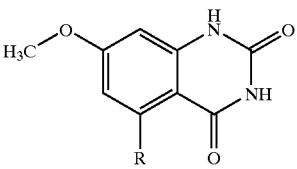

were prepared by a similar method to that of preparation 251 from the appropriate nitrile compound.

| Prep | R | Spectroscopic Data |
|---|---|---|
| 252 | ![CH(CH3)2] | $^1$H-nmr(DMSOd$_6$, 400 MHz) δ: 1.13(d, 6H), 3.79(s, 3H), 4.49(m, 1H), 6.52(d, 1H), 6.61(d, 1H) LRMS: m/z(ES$^+$) 491[2MNa$^+$] |
| 253 | ![tetrahydrofuran-3-yloxy] | $^1$H-nmr(DMSOd$_6$, 400 MHz) δ: 1.99(m, 1H), 2.15(m, 1H), 3.80(m, 7H), 5.01(m, 1H), 6.08(s, 1H), 6.23(s, 1H) LRMS: m/z ES$^+$ 301[MNa$^+$] |
| 254 | ![CH3OCH2CH2O] | $^1$H-nmr(DMSOd$_6$, 400 MHz) δ: 3.35(s, 3H), 3.66(t, 2H), 3.78(s, 3H), 4.10(m, 2H), 6.24(m, 2H) LRMS: m/z(ES$^+$) 555[2MNa$^+$] |
| 255 | ![(CH3)2CHO] | $^1$H-nmr(DMSOd$_6$, 400 MHz) δ: 1.28(d, 6H), 3.78(s, 3H), 4.59(m, 1H), 6.22(s, 2H) LRMS: m/z ES$^+$ 273[MNa$^+$] |
| 256 | Cl | $^1$H-nmr(DMSOd$_6$, 400 MHz) δ: 3.80(s, 3H), 6.59(s, 1H), 6.79(s, 1H) LRMS: m/z(ES$^-$) 225, 227[M$^-$H] |
| 257 | ![tetrahydrofuran-2-yl] | $^1$H-nmr(DMSOd$_6$, 400 MHz) δ: 1.47(m, 1H), 1.73(m, 1H), 1.83(m, 1H), 2.45(m, 1H), 3.80(m, 4H), 4.03(m, 1H), 5.75(t, 1H), 6.52(s, 1H), 6.80(s, 1H), 10.98(2xs, 2H) LRMS: m/z ES$^+$ 262[MNa$^+$] |

Preparation 258

4-Amino-5-cyclobutoxy-7-methoxy-1H-quinazolin-2-one

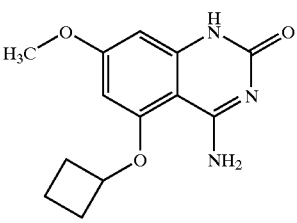

Trifluoroacetic acid (6.7 ml, 84 mmol) was added to a suspension of sodium cyanate (5.4 g, 84 mmol) in dichloromethane (120 ml) at 0° C. under a nitrogen atmosphere. The mixture was warmed to room temperature and was stirred for 45 minutes. The amino nitrile from preparation 247 (7.3 g, 33 mmol) was added in dichloromethane (100 ml) and the reaction mixture was stirred at room temperature for 4 hours. The solid formed was isolated by filtration and the filter cake was washed with water and then with diethyl ether. The residue was re-suspended in water and was stirred for 2 hours and then isolated by filtration. The filter cake was washed with water and diethyl ether then dried under vacuum to give the title compound as a white solid (5.9 g).

¹H-nmr (DMSOd₆ 400 MHz) δ: 1.59 (m, 1H), 1.78 (m, 1H), 2.00 (m, 2H), 3.74 (s, 3H), 4.77 (m, 1H), 6.05 (s, 1H), 6.21 (s, 2H), 7.34 (s, 1H), 8.20 (s, 1H) LRMS: m/z ES⁺ 284 [MNa⁺]

Preparation 259

2-Chloro-5-cyclobutoxy-7-methoxy-quinazolin-4-ylamine

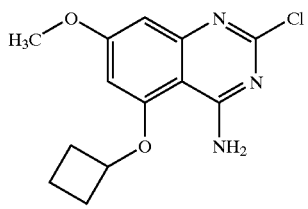

The quinazolinone from preparation 258 (3 g, 11 mmol) was suspended in acetonitrile (30 ml) and tetraethylammonium chloride (2.1 g, 11 mmol), N'N-dimethylaniline (1.46 ml, 11 mmol) and phosphorous oxychloride (5.35 ml, 57 mmol) were added. The mixture was heated to 75° C. over 20 minutes and then was cooled to room temperature. The mixture was added to ice and then saturated sodium carbonate solution was added to give pH 9. The solution was extracted with dichloromethane containing 5% methanol (×3). The combined organic solutions were dried over sodium sulphate and evaporated under reduced pressure. The residue was purified by chromatography on silica gel using methanol in dichloromethane as eluant (gradient from 0:100 to 10:90) to give the title compound as a white solid (1.11 g).

¹H-nmr (CDCl₃, 400 MHz) δ: 1.78 (m, 1H), 1.96 (m, 1H), 2.23 (m, 2H), 2.56 (m, 2H), 3.83 (s, 3H), 4.74 (m, 1H), 5.90 (s, 1H), 6.20 (s, 1H), 6.70 (s, 1H), 7.52 (s, 1H) LRMS: m/z ES⁺ 280, 282 [MH⁺]

Preparation 260

2,4-Dichloro-5-cyclobutoxy-7-methoxy-quinazoline

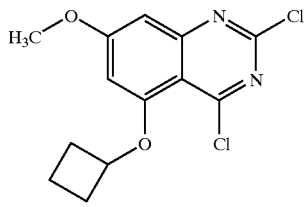

Antimony (III) chloride (4 g, 17.4 mmol) was added to a suspension of the amino compound from preparation 259 (2.43 g, 8.7 mmol) in dichloromethane (50 ml) and acetonitrile (50 ml) and the mixture was cooled to -10° C. and tert-butyl nitrite (3.6 ml, 30.4 mmol) was added dropwise. The mixture was stirred at -10° C. for 1 hour, at room temperature for 1.5 hours and under reflux for 16 hours. The reaction mixture was cooled to room temperature and was added to ice. The mixture was filtered and the phases were separated. The aqueous phase was extracted with dichloromethane (×2) and the combined organic solutions were dried over sodium sulphate and evaporated under reduced pressure. The residue was purified by chromatography on silica gel using ethyl acetate in pentane as eluant (gradient from 5:95 to 15:85) to give the title compound as an off white solid (200 mg).

¹H-nmr (CDCl₃, 400 MHz) δ: 1.79 (m, 1H), 1.98 (m, 1H), 2.33 (m, 3H), 2.55 (m, 2H), 3.93 (m, 1H), 6.40 (s, 1H), 6.88 (s, 1H) LRMS: m/z ES⁺ 321, 323 [MNa⁺]

Preparation 261

2,4-Dichloro-7-methoxy-5-(tetrahydro-pyran-4-yl)-quinazoline

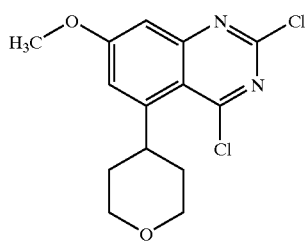

The quinazolinedione from preparation 251 (1.76 g) was suspended in phosphorous oxychloride (20 ml) and N,N-diisopropylethylamine (1.98 g, 15.3 mmol) was added dropwise. The mixture was heated at 90° C. for 2 hours and then was heated under reflux for 3 hours. The reaction mixture was cooled to room temperature and evaporated under reduced pressure. The residue was partitioned between water and ethyl acetate, the organic phase separated and washed with water and brine, then dried over magnesium sulphate and evaporated under reduced pressure. The residue was purified by chromatography on silica gel using ethyl acetate in dichloromethane as eluant (gradient from 0:100 to 25:75) to give the title compound as a white solid (1.2 g).

¹H-nmr (CDCl₃, 400 MHz) δ: 1.88 (m, 4H), 3.62 (m, 2H), 3.97 (s, 3H), 4.12 (m, 2H), 4.35 (m, 1H), 7.19 (dd, 1H), 7.22 (d, 1H) LRMS: m/z (ES⁺) 335, 337 [MNa⁺]

Preparations 262 to 267

The compounds of the following tabulated preparations of the general formula:

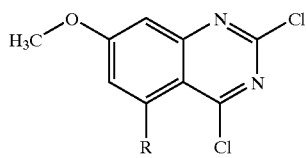

were prepared by a similar method to that of preparation 261 using the appropriate quinazolinedione compound.

| Prep | R | Spectroscopic Data |
|---|---|---|
| 262 |  | ¹H-nmr(CDCl₃, 400 MHz) δ: 1.38(d, 6H), 3.95(s, 3H), 4.52(m, 1H), 7.15(s, 1H), 7.29(d, 1H) LRMS: m/z(ES⁺) 271, 273[MNa⁺] |
| 263 | 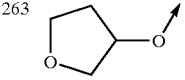 | ¹H-nmr(DMSOd₆, 400 MHz) δ: 2.10(m, 1H), 2.28(m, 1H), 3.90(m, 7H), 5.29(m, 1H), 6.80(s, 1H), 6.99(s, 1H) LRMS: m/z ES⁺ 337, 339[MNa⁺] |
| 264 |  | ¹H-nmr(CDCl₃, 400 MHz) δ: 3.48(s, 3H), 3.88(s, 2H), 3.94(s, 3H), 4.23(s, 2H), 6.59(s, 1H), 6.90(s, 1H) LRMS: m/z ES⁺ 303, 305[MH⁺] |
| 265 | 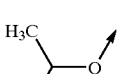 | ¹H-nmr(CDCl₃, 400 MHz) δ: 1.50(d, 6H), 3.93(s, 3H), 4.71(m, 1H), 6.55(s, 1H), 6.87(s, 1H) LRMS: m/z ES⁺ 197[MH⁺] |
| 266 | Cl | ¹H-nmr(CDCl₃, 400 MHz) δ: 3.95(s, 3H), 7.22(s, 1H), 7.27(s, 1H) |
| 267 |  | ¹H-nmr(CDCl₃, 400 MHz) δ: 1.91(m, 3H), 2.68(m, 1H), 3.99(m, 4H), 4.21(m, 1H), 6.18(m, 1H), 7.19(d, 1H), 7.64(d, 1H) LRMS: m/z ES⁺ 321[MNa⁺] |

Preparation 268

2-Chloro-7-methoxy-5-(tetrahydro-pyran-4-yl)-3H-quinazolin-4-one

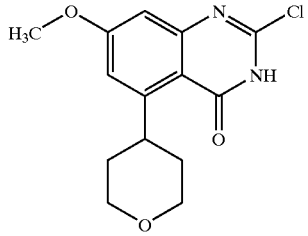

The dichloride from preparation 261 (1.17 g, 3.74 mmol) was added to 1,4-dioxane (20 ml) and 1M sodium hydroxide solution (20 ml) and the mixture was stirred at room temperature for 2 hours. The reaction mixture was acidified with 2M hydrochloric acid (15 ml) and was extracted with methanol in dichloromethane (10:90, 5×50 ml). The combined organic solutions were dried over magnesium sulphate and evaporated under reduced pressure. The residue was triturated with diethyl ether to give the title compound as a white solid (0.98 g).

¹H-nmr (DMSOd₆ 400 MHz) δ: 1.64 (m, 4H), 3.42 (m, 2H), 3.85 (s, 3H), 4.12 (m, 2H), 4.35 (m, 1H), 6.93 (s, 2H) LRMS: m/z (ES⁻) 293, 295 [M-H]⁻

Preparations 269 to 275

The compounds of the following tabulated preparations of the general formula:

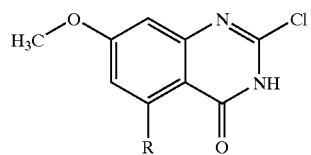

were prepared by a similar method to that of preparation 268 from the appropriate dichloro compound.

| Prep | R | Spectroscopic Data |
|---|---|---|
| 269 |  | ¹H-nmr(CDCl₃, 400 MHz) δ: 1.29(d, 6H), 3.92(s, 3H), 4.55(m, 1H), 6.93(d, 1H), 7.01(s, 1H) LRMS: m/z(ES⁺) 275, 277[MNa⁺] |
| 270 | 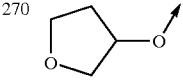 | ¹H-nmr(DMSOd₆, 400 MHz) δ: 2.00(m, 1H), 2.19(m, 1H), 3.80(m, 7H), 5.08(m, 1H), 6.52(s, 1H), 6.62(s, 1H) LRMS: m/z ES⁺ 319, 321[MNa⁺] |
| 271 | 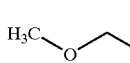 | ¹H-nmr(DMSOd₆, 400 MHz) δ: 3.33(s, 3H), 3.68(t, 2H), 3.83(s, 3H), 4.15(t, 2H), 6.56(d, 1H), 6.60(d, 1H) LRMS: m/z ES⁺ 307, 309[MH⁺] |
| 272 | 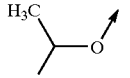 | ¹H-nmr(DMSOd₆, 400 MHz) δ: 1.30(d, 6H), 3.83(s, 3H), 4.66(m, 1H), 6.55(s, 1H), 6.60(s, 1H) LRMS: m/z ES⁺ 291[MNa⁺] |
| 273 | Cl | ¹H-nmr(CDCl₃, 400 MHz) δ: 3.88(s, 3H), 7.01(s, 1H), 7.13(s, 1H) LRMS: m/z(ES⁻) 243, 245[M-H] |
| 274 |  | ¹H-nmr(CDCl₃, 400 MHz) δ: 1.78(m, 1H), 1.92(m, 1H), 2.35(m, 2H), 2.52(m, 2H), 3.88(s, 3H), 4.73(m, 1H), 6.30(s, 1H), 6.69(s, 1H), 10.83(s, 1H) LRMS: m/z ES⁻ 279, 281[M-H] |
| 275 |  | ¹H-nmr(CDCl₃, 400 MHz) δ: 1.63(m, 1H), 1.94(m, 2H), 2.69(m, 1H), 3.90(s, 3H), 4.18(m, 1H), 6.00(t, 1H), 6.96(d, 1H), 7.38(d, 1H), 10.03(s, 1H) LRMS: m/z ES⁺ 303[MNa⁺] |

Preparation 276

2,6-Difluoro-4-methoxy-benzoic acid tert-butyl ester

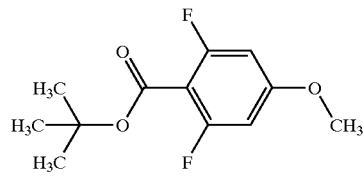

N,N-dimethylformamide di-tert-butyl acetal (75 ml, 0.31 mol) in toluene (60 ml) was added dropwise over 1.5 hours to 2,6-difluoro-4-methoxy-benzoic acid (15 g, 80 mmol) (Mol. Cryst. Liq. Cryst. 1989, 172) in toluene (120 ml) at 80° C. under a nitrogen atmosphere. The mixture was stirred at 80° C. for 30 minutes and then cooled to room temperature. Ethyl acetate (100 ml) was added and the organic solution was washed with saturated sodium hydrogen carbonate solution (2×150 ml), brine (150 ml), dried over magnesium sulphate and evaporated under reduced pressure. The residue was purified by chromatography on silica gel using diethyl ether in pentane as eluant (10:90) to give the title compound as an oil (17.91 g).

$^1$H-nmr (CDCl$_3$, 400 MHz) δ: 1.58 (s, 9H), 3.79 (s, 3H), 6.43 (d, 2H) LRMS: m/z ES$^+$ 267 [MNa$^+$]

Preparation 277

2-Butylsulfanyl-6-fluoro-4-methoxy-benzoic acid tert-butyl ester

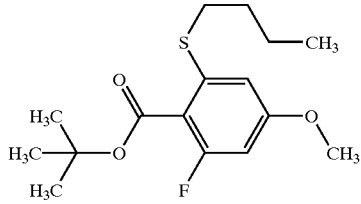

The ester from preparation 276 (488 mg, 2 mmol) was added to butane-1-thiol (321 µl, 3 mmol) and potassium carbonate (826 mg, 6 mmol) in 1-methyl-pyrrolidin-2-one (4 ml) and the mixture was heated at 120° C. for 23 hours. The reaction mixture was partitioned between water (20 ml) and diethyl ether/pentane (50:50, 100 ml) and the phases were separated. The organic layer was washed with 1M sodium hydroxide solution (2×10 ml) and water (10 ml), then dried over magnesium sulphate and evaporated under reduced pressure to give the title compound as an oil (562 mg).

$^1$H-nmr (CDCl$_3$, 400 MHz) δ: 0.93 (t, 3H), 1.42 (m, 2H), 1.59 (s, 9H), 1.68 (m, 2H), 2.71 (t, 2H), 3.79 (s, 3H), 6.40 (d, 1H), 6.65 (s, 1H)

Preparation 278

2-(Butane-1-sulfonyl)-6-fluoro-4-methoxy-benzoic acid tert-butyl ester

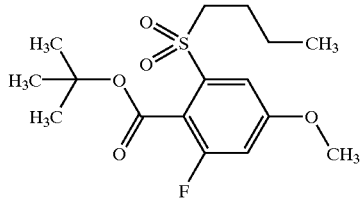

The thioether from preparation 277 (550 mg, 1.5 mmol) was dissolved in dichloromethane (15 ml) and 3-chloroperoxybenzoic (60–85% pure, 2.4 g) was added. The mixture was stirred for 2 hours and then was diluted with dichloromethane (50 ml). The mixture was washed with 30% potassium carbonate solution (2×50 ml) and brine (50 ml), then dried over magnesium sulphate and evaporated under reduced pressure. The residue was purified by chromatography on silica gel using diethyl ether in pentane as eluant (gradient from 10:90 to 20:80) to give the title compound as a gum (339 mg).

$^1$H-nmr (CDCl$_3$, 400 MHz) δ: 0.92 (t, 3H), 1.43 (m, 2H), 1.59 (s, 9H), 1.71 (m, 2H), 3.37 (m, 2H), 3.87 (s, 3H), 6.82 (d, 1H), 7.30 (s, 1H) LRMS: m/z ES$^+$ 369 [MNa$^+$]

Preparation 279

2-(Butane-1-sulfonyl)-6-fluoro-4-methoxy-benzoic acid

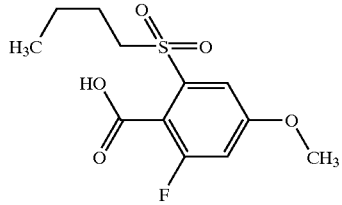

Trifluoroacetic acid (3 ml) was added to the ester from preparation 278 (320 mg, 0.92 mmol) in dichloromethane (3 ml) and the mixture was stirred for 2 hours at room temperature. The solvent was evaporated under reduced pressure and the last traces of trifluoroacetic acid were removed by dichloromethane azeotrope (3×10 ml) to give the title compound as a gum (288 mg).

$^1$H-nmr (CDCl$_3$, 400 MHz) δ: 0.92 (t, 3H), 1.44 (m, 2H), 1.76 (m, 2H), 3.40 (t, 2H), 3.92 (s, 3H), 6.88 (d, 1H), 7.37 (s, 1H) LRMS: m/z (ES$^-$) 289 [M–H]$^-$ Preparation 280

[2-(Butane-1-sulfonyl)-6-fluoro-4-methoxy-phenyl]-imidazol-1-yl-methanone

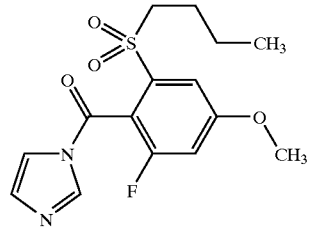

The carboxylic acid from preparation 279 (288 mg, 0.92 mmol) was dissolved in N,N-dimethylformamide (4 ml) and 1,1'-carbonyldiimidazole (164 mg, 1 mmol) was added under a nitrogen atmosphere. The reaction mixture was stirred at room temperature for 1.5 hours and then was diluted with N,N-dimethylformamide (2 ml). The resulting solution was used without further elaboration in Example 127 and Example 128.

Preparation 281

2-Fluoro-4-methoxy-6-pyridin-2-yl-benzonitrile

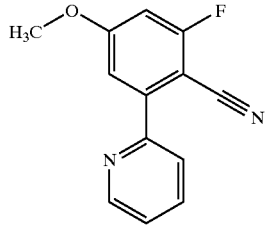

The iodo compound from preparation 241 (1 g, 3.6 mmol) was mixed with 2-tributylstannanyl-pyridine (2.66 g, 7.2 mmol), copper (I) iodide (137 mg, 0.72 mmol), lithium chloride (612 mg, 14.2 mmol) and tetrakis (triphenylphosphine)palladium(0) (400 mg, 0.34 mmol) in 1,4-dioxane (25 ml) and the mixture was heated under reflux for 4 hours. The reaction was cooled to room temperature and concentrated ammonium hydroxide solution (5 ml) was added. The solution was partitioned between brine and dichloromethane and the aqueous phase was extracted with dichloromethane. The combined organic solutions were dried over magnesium sulphate and evaporated under reduced pressure. The residue was purified by chromatography on silica gel using ethyl acetate in pentane as eluant (gradient from 50:50 to 100:0) to give the title compound as a pale yellow solid (0.95 g). LRMS: m/z ES$^+$ 229 [MH$^+$]

Preparation 282

2-Fluoro-4-methoxy-6-pyridin-2-yl-benzoic acid

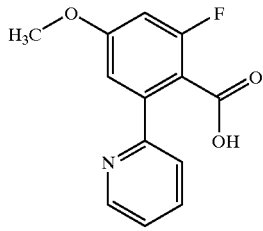

The nitrile from preparation 281 (500 mg) was added to concentrated hydrochloric acid (15 ml) and the mixture was heated under reflux for 6 hours. The reaction mixture was cooled to room temperature and adjusted to pH5 by addition of 5N sodium hydroxide. The solution was extracted with dichloromethane (3×50 ml) and ethyl acetate (3×10 ml) and the combined organic solutions were dried over magnesium sulphate and evaporated under reduced pressure to give the title compound (420 mg).

LRMS: m/z ES$^+$ 248 [MH$^+$]

Preparation 283

2-(3-Fluoro-5-methoxy-2-methoxycarbonyl-phenyl)-1-methyl-pyridinium iodide

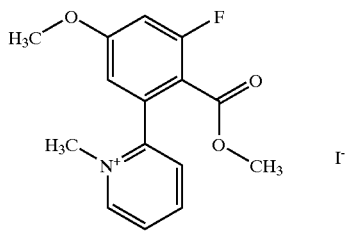

The pyridylbenzoic acid from preparation 282 (282 mg, 1.1 mmol) and iodomethane (1.42 g, 10 mmol) in acetonitrile (10 ml) were stirred at room temperature for 16 hours. N,N-Diisopropylethylamine (142 mg, 1.1 mmol) was added and the mixture was stirred at room temperature for 4 hours and then was heated under reflux for 2.5 hours. The reaction mixture was cooled to room temperature and was stirred for 16 hours. The solvent was evaporated under reduced pressure and the residue was purified by chromatography on silica gel using methanol in dichloromethane as eluant (10:90). The material obtained was triturated with diethyl ether to give the title compound as a yellow solid (416 mg).

$^1$H-nmr (DMSOd$_6$ 400 MHz) δ: 3.60 (s, 3H), 3.90 (s, 3H), 4.00 (s, 3H), 7.12 (s, 1H), 7.27 (d, 1H), 7.99 (d, 1H), 8.15 (m, 1H), 8.60 (m, 1H), 9.12 (d, 1H) LRMS: m/z ES$^+$ 291 [MNa$^+$]

Preparation 284

2-Fluoro-4-methoxy-6-(1-methyl-piperidin-2-yl)-benzoic acid methyl ester

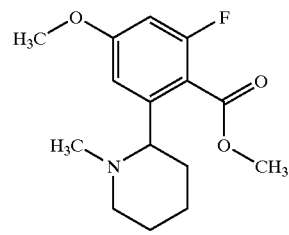

The pyridinium iodide from preparation 283 (410 mg, 1 mmol) was added to platinum oxide (100 mg) in methanol (50 ml) under a nitrogen atmosphere and ammonium formate (3.3 g) was added. The mixture was heated under reflux for 2 hours, cooled to room temperature and stirred for 16 hours. Additional platinum oxide (100 mg) and ammonium formate (3.3 g) were added and the mixture was heated under reflux for 1 hour. The reaction mixture was cooled to room temperature, diluted with dichloromethane (150 ml) and filtered through Arbocel®. The filter cake was washed with dichloromethane and water and the filtrate was diluted with water. The organic layer was separated, dried over magnesium sulphate and evaporated under reduced pressure. The residue was purified by chromatography on silica gel using methanol in dichloromethane as eluant (gradient from 0:100 to 4:96) to give the title compound as an orange oil (150 mg).

$^1$H-nmr (CDCl$_3$, 400 MHz) δ: 1.63 (m, 6H), 2.00 (s, 3H), 2.10 (m, 1H), 2.97 (m, 2H), 3.80 (s, 3H), 3.88 (s, 3H), 6.51 (d, 1H), 6.93 (s, 1H) LRMS: m/z ES$^+$ 282 [MH$^+$]

Preparation 285

2-Fluoro-4-methoxy-6-(1-methyl-piperidin-2-yl)-benzoic acid

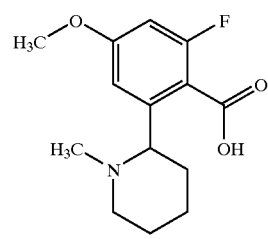

The methyl ester from preparation 284 (215 mg, 0.76 mmol) and 1M sodium hydroxide solution (0.8 ml, 0.8 mmol) were mixed in methanol (10 ml) and the solution was heated under reflux for 2 hours. Additional 2M sodium hydroxide solution (1 ml, 2 mmol) was added and the mixture was heated under reflux for a further 6 hours. The reaction mixture was cooled to room temperature and 2M hydrochloric acid (1.5 ml) was added. The mixture was evaporated under reduced pressure and the residue was purified by chromatography on silica gel using methanol and ammonium hydroxide in dichloromethane as eluant (10:1:90). The material obtained was triturated with diethyl ether to give the title compound as a white solid (173 mg).

$^1$H-nmr (DMSOd$_6$ 400 MHz) δ: 1.98 (m, 9H), 2.47 (m, 1H), 3.27 (m, 2H), 3.81 (s, 3H), 6.50 (s, 1H), 6.64 (d, 1H) LRMS: m/z ES$^+$ 268 [MH$^+$]

Preparation 286

N-[(7,8-Dihydro-5H-[1.6]naphthyridin-6-yl)-iminomethyl]-2-fluoro-4-methoxy-6-(1-methyl-piperidin-2-yl)-benzamide

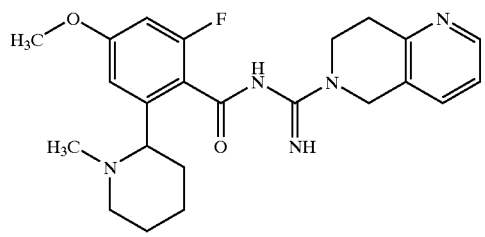

The guanidine from preparation 225 (121 mg, 0.3 mmol) was suspended in N,N-dimethylformamide (3 ml) and sodium hydride (60% in mineral oil, 60 mg, 1.5 mmol) was added and the mixture was stirred at room temperature for 20 minutes. The carboxylic acid from preparation 285 (80 mg, 0.3 mmol) was suspended in dichloromethane (4 ml) containing 1 drop of N,N-dimethylformamide. Oxalyl chloride (76 mg, 0.6 mmol) was added and the mixture was stirred for 10 minutes. The mixture was evaporated under reduced pressure and the residue was redissolved in dichloromethane (3 ml). The solution obtained was added to the guanidinium salt described above and the mixture was stirred at room temperature for 1 hour and then was acidified with 0.2N hydrochloric acid (50 ml). The solution was washed with dichloromethane (2×20 ml) and then basified with 1M sodium hydroxide. The aqueous mixture was extracted with dichloromethane (3×70 ml) and the combined extracts were dried over magnesium sulphate and evaporated under reduced pressure. The residue was purified by chromatography on silica gel using methanol and ammonium hydroxide in dichloromethane as eluant (7:1:93) to give the title compound as a glass (78 mg).

$^1$H-nmr (CDCl$_3$, 400 MHz) δ: 1.23 (m, 1H), 1.65 (m, 5H), 1.84 (m, 1H), 2.06 (s, 3H), 2.98 (m, 1H), 3.10 (t, 2H), 3.17 (m, 1H), 3.80 (s, 3H), 3.86 (t, 2H), 4.75 (s, 2H), 6.50 (d, 1H), 6.94 (s, 1H), 7.11 (m, 1H), 7.38 (d, 1H), 7.80 (s, 2H), 8.45 (d, 1H) LRMS: m/z ES$^+$ 426 [MH$^+$]

Preparations 287 to 288

The compounds of the following tabulated preparations of the general formula:

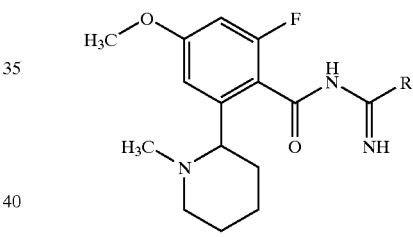

were prepared by a similar method to that of preparation 286 using the carboxylic acid from preparation 285 and the appropriate guanidine.

| Prep | R | Spectroscopic Data |
|---|---|---|
| 287 | ![structure with dimethoxy tetrahydroisoquinoline] | $^1$H-nmr(CDCl$_3$, 400 MHz) δ: 1.55(m, 5H), 2.08(m, 5H), 2.83(t, 2H), 3.00(m, 1H), 3.20(m, 1H), 3.85(t, 2H), 4.82(m, 9H), 4.61(s, 2H), 6.51(d, 1H), 6.61(s, 1H), 6.68(s, 1H), 6.97(s, 1H), 7.66(s, 2H)<br>LRMS: m/z ES$^-$ 483[M$^-$H] |
| 288 | ![structure with naphthyridine and methoxyethylamine] | $^1$H-nmr(CDCl$_3$, 400 MHz) δ: 1.26(m, 1H), 1.62(m, 4H), 2.00(m, 5H), 2.87(t, 2H), 2.95(m, 1H), 3.18(m, 1H), 3.38(s, 3H), 3.47(m, 2H), 3.55(t, 2H), 3.80(m, 5H), 4.53(s, 2H), 4.72(m, 1H), 6.28(d, 1H), 6.49(d, 1H), 6.93(s, 1H), 7.10(d, 1H), 7.70(s, 2H)<br>LRMS: m/z ES$^-$ 497[M$^-$H] |

Preparation 289

2-Amino-6-fluoro-4-methoxy-benzonitrile

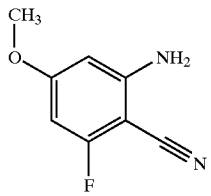

2,6-Difluoro-4-methoxy-benzonitrile (Mol. Cryst. Liq. Cryst. 1989, 172) (200 mg, 1.18 mmol) was dissolved in ethanolic ammonia (2M solution, 10 ml) and the mixture was heated at 140° C. in an autoclave for 16 hours. The reaction mixture was cooled to room temperature and the solvent was evaporated under reduced pressure. The residue was purified by chromatography on silica gel using ethyl acetate in pentane as eluant (20:80) to give the title compound as a white solid (165 mg). LRMS: m/z (ES$^+$) 189 [MNa$^+$]

Preparation 290

5-Chloromethyl-3,4-dihydro-1H-isoquinoline-2-carboxylic acid tert-butyl ester

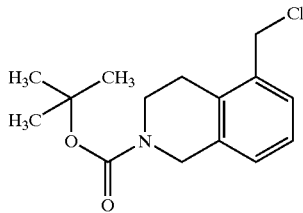

Triethylamine (160 μl, 1,16 mmol) and then methane sulphonyl chloride (72 μl, 0.92 mmol) were added to 5-hydroxymethyl-3,4-dihydro-1H-isoquinoline-2-carboxylic acid tert-butyl ester (202 mg, 0.77 mmol) (WO 02053558 p 59) in tetrahydrofuran (20 ml) and the mixture was stirred for 30 minutes. Tetrabutyl ammonium chloride (322 mg, 1.16 mmol) was added and the mixture was stirred for 2 hours at room temperature. The reaction mixture was diluted with ethyl acetate and the organic solution was washed with sodium hydrogen carbonate solution, dried over magnesium sulphate and evaporated under reduced pressure. The residue was purified by chromatography on silica gel using methanol in dichloromethane as eluant (2:98) to give the title compound (100 mg).

$^1$H-nmr (CDCl$_3$, 400 MHz) δ: 1.43 (s, 9H), 2.92 (m, 2H), 3.70 (m, 2H), 4.39 (s, 4H), 7.18 (m, 3H) LRMS: m/z (ES$^+$) 304 [MNa$^+$]

Preparation 291

5-(2-Methyl-imidazol-1-ylmethyl)-3,4-dihydro-1H-isoquinoline-2-carboxylic acid tert-butyl ester

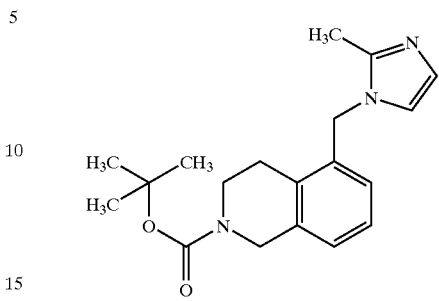

Sodium hydride (60% in mineral oil, 48 mg, 1.2 mmol) was added to 2-methylimidazole (103 mg, 1.25 mmol) in tetrahydrofuran (10 ml) under a nitrogen atmosphere. The mixture was stirred for 1.5 hours and then the chloromethyl compound from preparation 290 (325 mg, 1.15 mmol) was added in tetrahydrofuran (1 ml). The mixture was heated under reflux for 2 hours and then cooled to room temperature and stirred at room temperature for 16 hours. The reaction mixture was partitioned between ethyl acetate (75 ml) and water (75 ml). The phases were separated and the aqueous solution was extracted with ethyl acetate (2×35 ml). The combined ethyl acetate layers were dried over magnesium sulphate and evaporated under reduced pressure. The residue was purified by chromatography on silica gel using ammonium hydroxide and methanol in dichloromethane as eluant (gradient from 0:0:100 to 0.5:5:95) to give the title compound as a pale yellow oil (383 mg).

$^1$H-nmr (CDCl$_3$, 400 MHz) δ: 1.46, (s, 9H), 2.33 (s, 3H), 2.68 (t, 2H), 3.66 (t, 2H), 4.59 (s, 2H), 4.97 (s, 2H), 6.65 (m, 2H), 6.96 (s, 1H), 7.12 (m, 2H) LRMS: m/z (ES$^+$) 328 [MH$^+$]

Preparation 292

5-(2-Methyl-imidazol-1-ylmethyl)-1,2,3,4-tetrahydro-isoquinoline

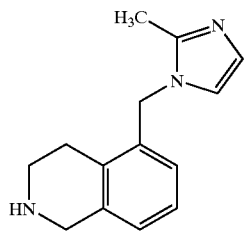

The protected amine from preparation 291 (290 mg, 0.88 mmol) was dissolved in dichloromethane (12 ml) and was cooled to 4° C. under a nitrogen atmosphere. Hydrogen chloride was bubbled into the solution for 10 minutes to give a saturated solution. The reaction mixture was stirred at 4° C. for 2.5 hours and then evaporated under reduced pressure. The residue was purified by chromatography on silica gel using ammonium hydroxide and methanol in dichloromethane as eluant (0.7:7:93). The material obtained was co evaporated with methanol to give the title compound as a pale yellow oil (180 mg).

$^1$H-nmr (CDCl$_3$, 400 MHz) δ: 2.33 (s, 3H), 2.60 (t, 2H), 3.18 (t, 2H), 4.02 (s, 2H), 4.96 (s, 2H), 6.58 (d, 1H), 6.71 (s, 1H), 6.96 (s, 1H), 6.99 (d, 1H), 7.10 (m, 1H) LRMS: m/z (ES⁺) 228 [MH⁺]

Preparation 293

[6-(5-Isopropyl-7-methoxy-4-oxo-3,4-dihydro-quinazolin-2-yl)-5,6,7,8-tetrahydro-[1,6]naphthyridin-2-ylmethyl]-carbamic acid tert-butyl ester

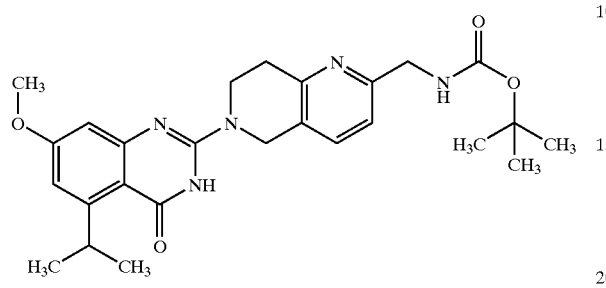

The chloro compound from preparation 269 (101 mg, 0.4 mmol) was added to the amine from preparation 182 (116 mg, 0.44 mmol) and triethylamine (168 μl, 1.2 mmol) in n-butanol (8 ml) and the mixture was heated under reflux for 2 hours. The reaction mixture was cooled to room temperature and was stirred for 16 hours. The solid formed was isolated by filtration and was washed with diethyl ether (20 ml), water (10 ml) and diethyl ether (40 ml). The residue was dried under vacuum at 90° C. for 4 hours to give the title compound (160 mg).

¹H-nmr (DMSOd₆ 400 MHz) δ: 1.15 (d, 6H), 1.38 (s, 9H), 2.92 (t, 2H), 3.80 (s, 3H), 3.92 (t, 2H), 4.15 (d, 2H), 4.53 (m, 1H), 4.78 (s, 2H), 6.80 (d, 1H), 7.10 (m, 2H), 7.18 (m, 1H), 7.58 (d, 1H) LRMS: m/z (ES⁺) 502 [MNa⁺]

Preparation 294

(6-Benzyl-5,6,7,8-tetrahydro-[2,6]naphthyridin-1-ylmethyl)-methyl-amine

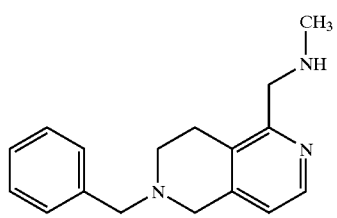

Methylamine (40% in water, 1 ml) and acetic acid (60 μl, 1 mmol) were added to the aldehyde from preparation 35 (115 mg, 0.46 mmol) in tetrahydrofuran (6 ml). The mixture was stirred at room temperature for 5 minutes and then sodium triacetoxyborohydride (636 mg, 3 mmol) was added. The mixture was stirred at room temperature for 1 hour and then was acidified with 2M hydrochloric acid. The mixture was stirred for 10 minutes and then basified with 1M sodium hydroxide. The reaction mixture was extracted with 5% methanol in dichloromethane (4×40 ml) and the combined organic solutions were dried over magnesium sulphate and evaporated under reduced pressure. The residue was purified by chromatography on silica gel using ammonium hydroxide and methanol in dichloromethane as eluant (1:7:93) to give the title compound as a yellow oil (57 mg). LRMS: m/z (ES⁺) 268 [MH⁺]

Preparation 295

(6-Benzyl-5 6,7,8-tetrahydro-[2,6]naphthyridin-1-ylmethyl)-methyl-carbamic acid tert-butyl ester

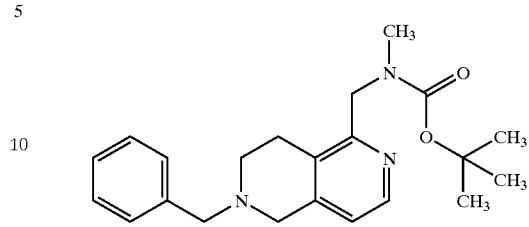

The amine from preparation 294 (57 mg, 0.21 mmol) was dissolved in dichloromethane and di-tert-butyl dicarbonate (55 mg, 0.25 mmol) was added. The mixture was stirred at room temperature for 2 hours then the reaction mixture was purified by chromatography on silica gel using methanol in dichloromethane as eluant (gradient 15 from 0:100 to 5:95) to give the title compound as an oil (61 mg).

LRMS: m/z (ES⁺) 390 [MNa⁺]

Preparation 296

Methyl-(5,6,7,8-tetrahydro-[2,6]naphthyridin-1-ylmethyl)-carbamic acid tert-butyl ester

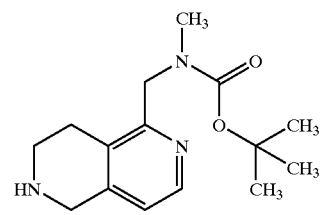

The title compound was obtained as a colourless oil from the benzyl compound from preparation 295 in 72% yield following the procedure described in preparation 109.

LRMS: m/z (ES⁺) 300 [MNa⁺]

Preparation 297

[2-(5-Isopropyl-7-methoxy-4-oxo-3,4-dihydro-quinazolin-2-yl)-1 2,3,4-tetrahydro-isoquinolin-5-ylmethyl]-methyl-carbamic acid tert-butyl ester

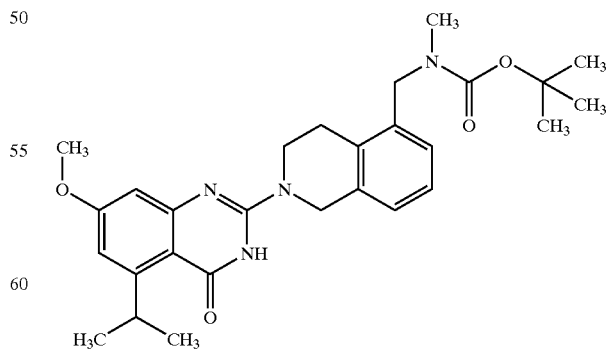

The chloro compound from preparation 269 (31 mg, 0.12 mmol) was added to the amine from preparation 296 (34 mg, 0.12 mmol) in n-butanol (2 ml) containing N,N- diisopropylethylamine (129 μl, 1 mmol) and the mixture was heated under reflux for 2.5 hours. The reaction mixture was cooled to room temperature and the solvent was evaporated under reduced pressure. The residue was purified by chromatography on silica gel using methanol in dichloromethane as eluant (gradient from 0:100 to 5:95) to give the title compound as an oil (59 mg).

LRMS: m/z (ES$^+$) 516 [MNa$^+$]

Preparation 298

(6-Benzyl-5,6,7,8-tetrahydro-[1,6]naphthyridin-2-yl)-(2-pyrrolidin-1-yl-ethyl)-amine

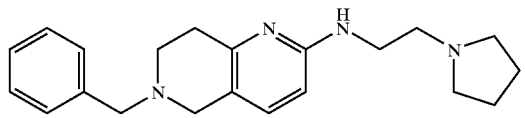

Copper (II) sulphate (70 mg) was added to a solution of 6-benzyl-2-chloro-5,6,7,8-tetrahydro-[1,6]naphthyridine (0.75 g, 2.9 mmol)(WO9830560 Example 33 b) in 2-pyrrolidin-1-yl-ethylamine (3 ml) and the mixture was heated in an autoclave to 150° C. for 24 hours. The reaction mixture was cooled to room temperature and was diluted with dichloromethane (50 ml). The solution was washed with 50% ammonium hydroxide solution (50 ml). The phases were separated and the aqueous phase was extracted with dichloromethane (2×50 ml). The combined organic solutions were dried over magnesium sulphate and evaporated under reduced pressure. The residue was purified by chromatography on silica gel using ammonium hydroxide and methanol in dichloromethane as eluant (gradient from 0.5:5:95 to 0.7:7:93) to give the title compound as a yellow oil (0.9 g). LRMS: m/z (ES$^+$) 337 [MH$^+$]

Preparation 299

(2-Pyrrolidin-1-yl-ethyl)-(5,6,7,8-tetrahydro-[1,6] naphthyridin-2-yl)-amine

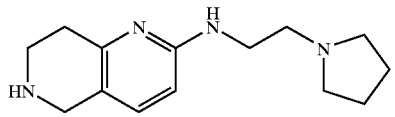

The title compound was obtained from the benzyl compound from preparation 298 (850 mg, 2.53 mmol) in 56% yield following the procedure described in preparation 109.

LRMS: m/z (ES$^+$) 247 [MH$^+$]

Preparation 300

5-Dimethylaminomethyl-3,4-dihydro-1H-isoquinoline-2-carboxylic acid tert-butyl ester

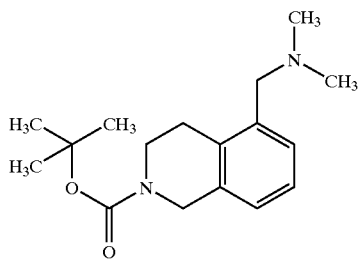

A solution of the aldehyde from preparation 25 (650 mg, 2.5 mmol), and dimethylamine (2M in tetrahydrofuran, 1.75 ml, 3.5 mmol)in tetrahydrofuran (5 ml) was stirred at room temperature for 3 hours. Sodium triacetoxyborohydride (1.47 g, 7 mmol) was added and the reaction stirred at room temperature for 18 hours. The mixture was partitioned between dichloromethane (50 ml) and sodium bicarbonate solution (30 ml), the layers separated, and the organic phase dried over magnesium sulphate and evaporated under reduced pressure. The residual oil was purified by chromatography on silica gel using dichloromethane:methanol:0.88 ammonia (98:2:0.2) as eluant to afford the title compound, 602 mg.

$^1$H-nmr (CDCl$_3$, 400 MHz) δ: 1.50 (s, 9H), 2.20 (s, 6H), 2.90 (t, 2H), 3.35 (s, 2H), 3.62 (t, 2H), 4.55 (s, 2H), 7.00 (m, 1H), 7.10 (d, 2H).

Preparation 301

Dimethyl-(1,2,3,4-tetrahydro-isoquinolin-5-ylmethyl)-amine hydrochloride

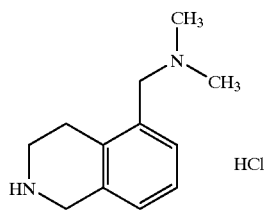

The title compound was obtained from the protected amine from preparation 300 (575 mg, 2 mmol) in quantitative yield following the procedure described in preparation 212.

LRMS: m/z (ES$^+$) 213 [MNa$^+$]

Preparation 302

(7-Benzyl-5,6,7,8-tetrahydro-pyrido[3,4-d]pyrimidin-4-yl)-ethyl-methylamine

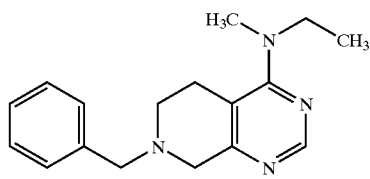

A mixture of the chloride from preparation 39 (1.20 g, 4.68 mmol) and N-methylethylamine (2 ml) in dichloromethane (10 ml) was stirred at room temperature for 18 hours, then under reflux for a further 8 hours. Acetonitrile (20 ml) was added, and the reaction stirred under reflux for an additional 24 hours. The cooled mixture was concentrated under reduced pressure and the residue partitioned between dichloromethane and 1% sodium bicarbonate solution. The organic layer was separated, dried over magnesium sulphate, and evaporated under reduced pressure. The crude product was purified by chromatography on silica gel using dichloromethane:methanol (100:0 to 94:6) to afford the title compound as a pale yellow oil, 1.26 g.

LRMS: m/z (ES$^+$) 283 [MH$^+$]

Preparation 303

Ethyl-methyl-5,6,7,8-tetrahydro-pyrido[3,4-d]pyrimidin-4-yl)amine

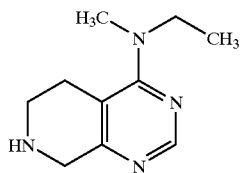

A mixture of the protected amine from preparation 302 (1.17 g, 4.15 mmol), ammonium formate (11.7 g) and 10% palladium on charcoal (1.11 g) in methanol (50 ml) was heated under reflux for 40 minutes. The cooled mixture was filtered through Arbocel®, and the filtrate poured into 1N sodium hydroxide solution. This mixture was continually extracted with dichloromethane for 4 hours, and the organic extract evaporated under reduced pressure. The crude product was purified by chromatography on silica gel using dichloromethane:methanol:0.88 ammonia (90:9:1) to give the title product as a clear oil, 600 mg.

LRMS: m/z (ES$^+$) 193 [MH$^+$]

Preparation 304 tert-Butyl[(tert-butoxycarbonyl)amino[](2-methoxyethyl)amino]methylenecarbamate

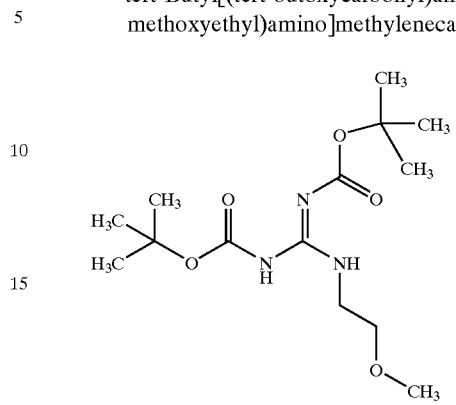

Mercury chloride (11.94 g, 44 mmol) was added to a rapidly stirring solution of 2-methoxyethylamine (3.0 g, 40 mmol), 1,3-bis(tert-butoxycarbonyl)-2-methyl-2-thiopseudourea (11.6 g, 40 mmol) and triethylamine (20.24 g, 200 mmol) in dichloromethane (100 ml), and the reaction stirred at room temperature for 17 hours. The mixture was filtered, the filtrate evaporated under reduced pressure and the residue triturated with hot ethyl acetate to remove further mercury salts. The filtrate was evaporated under reduced pressure and the crude product purified by chromatography on silica gel using cyclohexane:ethyl acetate (95:5 to 85:15) to give the title compound as a colourless oil, 8.2 g.

$^1$H-nmr (CDCl$_3$, 400 MHz) δ: 1.45 (s, 18H), 3.38 (s, 3H), 3.48 (m, 2H), 3.61 (m, 2H), 8.48 (bs, 1H). LRMS: m/z (ES$^+$) 340 [MNa$^+$]

Preparation 305

N-(2-Methoxyethyl)quanidine trifluoroacetate

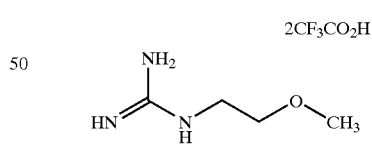

A solution of the compound from preparation 304 (8.1 g, 25.5 mmol) in trifluoroacetic acid (60 ml) was stirred at room temperature for 4 hours. The reaction was concentrated under reduced pressure and the residue azeotroped with toluene and then dichloromethane. The residue was dried in vacuo at 60° C. to afford the title compound as a colourless oil, 8.77 g.

$^1$H-nmr (DMSOd$_6$, 400 MHz) δ: 3.23 (m, 5H), 3.40 (m, 2H), 7.05 (bs, 4H), 7.55 (bs, 1H).

Preparation 306

6-Benzyl-N*2*-(2-methoxyethyl)-5,6,78-tetrahydro-pyrido[4,3-d]pyrimidine-2,4-diamine

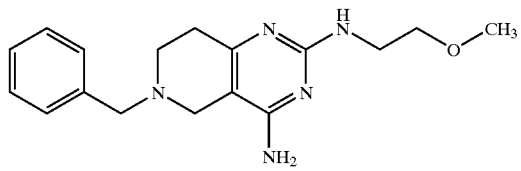

Sodium hydride (156 mg, 60% dispersion in mineral oil, 3.9 mmol) was added portionwise to dry ethanol (3.5 ml), and once addition was complete, the guanidine from preparation 305 (621 mg, 1.8 mmol) was added, and the solution heated under reflux for 30 minutes. 4-Amino-1-benzyl-1,2,5,6-tetrahydro-3-pyridinecarbonitrile (J. Med. Chem. 1991; 34 (9); 2899) (213 mg, 1 mmol) was added and the reaction heated under reflux for a further 17 hours. TLC analysis showed starting material remaining, so the cooled reaction was diluted with ethanol (3 ml), additional sodium hydride (10 mg, 60% dispersion in mineral oil, 0.4 mmol) added, and the reaction heated under reflux for a further 24 hours. The cooled mixture was partitioned between water (50 ml) and ethyl acetate (50 ml), the layers separated, the aqueous extracted with ethyl acetate (2×35 ml), and the combined organic solutions dried over magnesium sulphate and evaporated under reduced pressure. The residual oil was purified by column chromatography on silica gel using dichloromethane:methanol:0.88 ammonia (97:3:0.2 to 90:10:1) and the product azeotroped with ether to afford the title compound as a yellow solid, 58 mg.

$^1$H-nmr (CDCl$_3$, 400 MHz) δ: 2.68 (t, 2H), 2.78 (t, 2H), 3.22 (s, 2H), 3.37 (s, 3H), 3.52 (m, 4H), 3.70 (s, 2H), 4.32 (bs, 2H), 4.95 (s, 1H), 7.22–7.38 (m, 5H).

Preparation 307

N*2*-(2-methoxyethyl)-5,6,78-tetrahydro-pyrido[4,3-d]pyrimidine-2,4-diamine

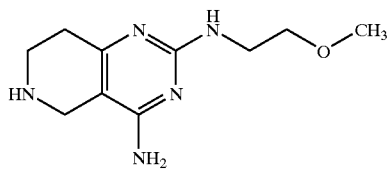

Ammonium formate (10 g, 158.5 mmol) was added to a mixture of the compound from preparation 306 (1.07 g, 3.41 mmol) and 10% palladium on charcoal (1.0 g) in methanol (75 ml), and the reaction heated under reflux for 35 minutes. The cooled mixture was filtered through Arbocel®, washing well with ethanol, and the combined filtrates evaporated under reduced pressure. The residue was purified by column chromatography on silica gel using dichloromethane:methanol:0.88 ammonia (95:5:0.5 to 85:12:2) and the product azeotroped with methanol and ether to afford the title compound as a white solid, 218 mg.

$^1$H-nmr (DMSOd$_6$, 400 MHz) δ: 2.37 (m, 2H), 2.82–3.50 (m, 12H), 5.63 (s, 1H0, 5.80 (bs, 2H). LRMS: m/z (ES$^+$) 224 [MH$^+$]

The invention is illustrated by the following examples:

EXAMPLE 1

5-Cyclopropyl-2-(5-[(cyclopropylamino)methyl]-3,4-dihydro-2(1H)-isoquinolinyl)-7-methoxy-4(3H)-quinazolinone

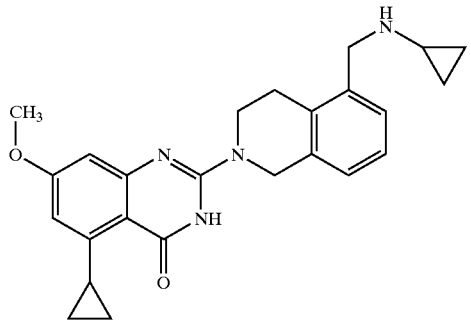

A mixture of the amine hydrochloride from preparation 95 (113 mg, 0.41 mmol), the chloride from preparation 18 (86 mg, 0.34 mmol) and diisopropylethylamine (0.36 mL, 1.7 mmol) in n-butanol (3 mL) was stirred under reflux for 2.5 hours. The cooled reaction mixture was concentrated under reduced pressure and the residue partitioned between dichloromethane (40 mL) and water. The layers were separated, the organic phase washed with brine, dried (MgSO$_4$) and concentrated under reduced pressure. The crude product was purified by column chromatography on silica gel using dichloromethane:methanol (97:3) as eluant to afford the title compound as a solid.

$^1$Hnmr (DMSOd6 400 MHz) δ: 0.13 (m, 2H), 0.35 (m, 2H), 0.63 (m, 2H), 0.90 (m, 2H), 2.07 (m, 2H), 2.90 (m, 2H), 3.49 (m,1H), 3.68 (s, 2H), 3.75 (m, 4H), 3.83 (m, 2H), 4.75 (s, 2H), 6.13 (m, 1H), 6.48 (m, 1H), 7.05 (m, 1H), 7.15 (m, 1H), 10.82 (bs, 1H). LRMS: m/z (ES$^+$) 417 [MH$^+$] Microanalysis found: C, 69.56; H, 6.54; N, 13.04. C$_{25}$H$_{28}$N$_4$O$_2$;0.8H$_2$O requires C, 69.69; H, 6.92; N, 13.00%.

EXAMPLES 2 TO 25

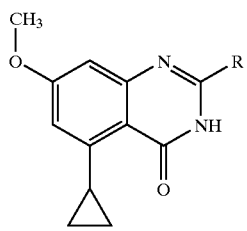

General Method

To a solution of the chloro-quinazolinone from preparation 18 (1 eq) in n-butanol (15 mL 5 per mmol) under nitrogen was added diisopropylethylamine (A) or triethylamine (B) (1.7–8.0 eq) and the appropriate secondary amine (1–2 eq). The resultant mixture was then heated at reflux for 1–6 hours, cooled and the product was isolated by filtration, washing with n-butanol and diethyl ether.

| Ex. no. | R | Base | Yield %/Form | Spectroscopic and Analytical Data |
|---|---|---|---|---|
| 2 (a) | [structure: 1,2,3,4-tetrahydroisoquinolin-5-yl-CH2-N(CH3)-cyclopropyl] | A | 29 white solid | ¹Hnmr(DMSOd₆, 400 MHz) δ: 0.30(m, 2H), 0.40(m, 2H), 0.63(m, 2H), 0.94(m, 2H), 1.73(m, 1H), 2.10(s, 3H), 2.90(m, 2H), 3.46(m, 1H), 3.60(s, 2H), 3.77(s, 3H), 3.80(m, 2H), 4.77(s, 2H), 6.13(s, 1H), 6.53(s, 1H), 7.10(m, 3H), 10.84(bs, 1H).<br>LRMS: m/z(ES⁺) 453[MNa⁺]<br>Microanalysis found: C, 72.07; H, 7.00; N, 12.94.<br>C₂₆H₃₀N₄O₂; 0.2H₂O requires<br>C, 71.93; H, 7.06; N, 12.90%. |
| 3 | [structure: 1,2,3,4-tetrahydroisoquinolin-5-yl-CH2-(3-azabicyclo[3.1.0]hexane)] | B | 76 white powder | ¹Hnmr(DMSOd₆, 400 MHz) δ: 0.27(m, 1H), 0.57(m, 1H), 0.63(m, 2H), 0.94(m, 2H), 1.35(m, 2H), 2.31(m, 2H), 2.77(d, 2H), 2.86(m, 2H), 3.50(m, 3H), 3.74(s, 3H), 3.80(m, 2H), 4.76(s, 2H), 6.13(s, 1H), 6.32(s, 1H), 7.10(m, 3H), 10.97(bs, 1H).<br>LRMS: m/z(ES⁺) 465[MNa⁺]<br>Microanalysis found: C, 72.83; H, 6.83; N, 12.52.<br>C₂₇H₃₀N₄O₂; 0.1C₄H₉OH requires<br>C, 73.14; H, 6.94; N, 12.45%. |
| 4 | [structure: 1,2,3,4-tetrahydroisoquinolin-5-yl-CH2-(4-methylpiperazin-1-yl)] | A | 88 white solid | ¹Hnmr(CDCl₃, 400 MHz) δ: 0.70(m, 2H), 0.97(m, 2H), 2.26(s, 3H), 2.44(m, 8H), 3.06(t, 2H), 3.41(m, 1H), 3.46(s, 2H), 3.85(s, 3H), 3.91(t, 2H), 4.87(s, 2H), 6.29(s, 1H), 6.67(d, 1H), 7.11(dd, 1H), 7.15(d, 2H), 10.01(bs, 1H).<br>LRMS: m/z(ES⁺) 482[MNa⁺] |
| 5 (a) | [structure: 1,2,3,4-tetrahydroisoquinolin-5-yloxy-(1-methylpiperidin-4-yl)] | A | 43 white solid | ¹Hnmr(DMSOd₆, 400 MHz) δ: 0.64(m, 2H), 0.90(m, 2H), 1.67(m, 2H), 1.87(m, 2H), 2.17(s, 3H), 2.25(m, 2H), 2.47(s, 3H), 2.65(m, 2H), 2.74(t, 2H), 3.49(m, 1H), 3.83(t, 2H), 4.37(m, 1H), 4.73(s, 2H), 6.13(s, 1H), 6.52(s, 1H), 6.75(d, 1H), 6.83(d, 1H), 7.11(dd, 1H), 11.00(bs, 1H).<br>LRMS: m/z(ES⁺) 461[MH⁺].<br>Microanalysis found: C, 69.55; H, 7.09; N, 11.78.<br>C₂₇H₃₂N₄O₃; 0.3H₂O requires<br>C, 69.59; H, 7.05; N, 12.02%. |
| 6 | [structure: 5,6,7,8-tetrahydro-1,6-naphthyridin-2-yl-NHCH3] | B | 86 white powder | ¹Hnmr(DMSOd₆, 400 MHz) δ: 0.62(m, 2H), 0.91(m, 2H), 2.75(m, 5H), 3.50(m, 1H), 3.77(s, 3H), 3.86(t, 2H), 4.58(s, 2H), 6.13(s, 1H), 6.25(m, 1H), 6.31(d, 1H), 6.53(s, 1H), 7.19(d, 1H), 10.99(bs, 1H).<br>LRMS: m/z(ES⁺) 400[MNa⁺].<br>Microanalysis found: C, 65.18; H, 6.03; N, 18.03.<br>C₂₁H₂₃N₅O₂; 0.5H₂O requires<br>C, 65.27; H, 6.26; N, 18.12%. |

| Ex. no. | R | Base | Yield %/Form | Spectroscopic and Analytical Data |
|---|---|---|---|---|
| 7 (a) | 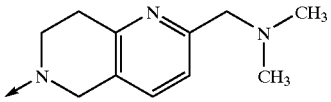 | A | 35 white solid | ¹H-nmr(DMSO-d₆, 400 MHz) δ: 0.64(m, 2H), 0.93(m, 2H), 2.16(s, 6H), 2.93(t, 2H), 3.47(m, 3H), 3.76(s, 3H), 3.93(t, 2H), 4.78(s, 2H), 6.15(s, 1H), 6.53(s, 1H), 7.24(d, 1H), 7.57(d, 1H), 11.08(bs, 1H). LRMS: m/z(ES⁻) 404[M − H⁻]. Microanalysis found: C, 67.08; H, 6.72; N, 16.98. $C_{23}H_{27}N_5O_2$; $0.3H_2O$ requires C, 67.23; H, 6.77; N, 17.04%. |
| 8 | 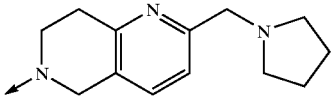 | A | 51 white solid | ¹H-nmr(DMSO-d₆, 400 MHz) δ: 0.64(m, 2H), 0.93(m, 2H), 1.70(m, 4H), 2.53(m, 4H), 2.94(t, 2H), 3.50(m, 1H), 3.69(s, 2H), 3.76(s, 3H), 3.93(t, 2H), 4.78(s, 2H), 6.15(s, 1H), 6.52(s, 1H), 7.25(d, 1H), 7.56(d, 1H), 11.08(bs, 1H). LRMS: m/z(ES⁺) 454[MNa⁺]. Microanalysis found: C, 66.72; H, 6.63; N, 15.41. $C_{25}H_{29}N_5O_2$; $0.9H_2O$ requires C, 67.06; H, 6.93; N, 15.64%. |
| 9 (a) | 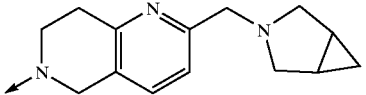 | B | 31 | ¹H-nmr(DMSO-d₆, 400 MHz) δ: 0.32(m, 1H), 0.63(m, 3H), 0.93(m, 2H), 1.35(m, 2H), 2.37(m, 2H), 2.90(m, 4H), 3.49(m, 1H), 3.63(s, 2H), 3.78(s, 3H), 3.92(t, 2H), 4.78(s, 2H), 6.15(s, 1H), 6.53(s, 1H), 7.18(d, 1H), 7.57(d, 1H), 11.05(bs, 1H). LRMS: m/z(ES⁺) 466[MNa⁺]. Microanalysis found: C, 69.91; H, 6.57; N, 15.67. $C_{26}H_{29}N_5O_2$; $0.2H_2O$ requires C, 69.84; H, 6.63; N, 15.66%. |
| 10 (b) | 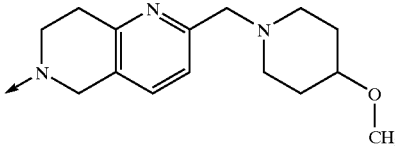 | A | 83 white solid | ¹H-nmr(DMSO-d₆, 400 MHz) δ: 0.62(m, 2H), 0.94(m, 2H), 1.40(m, 2H), 1.80(m, 2H), 2.16(m, 2H), 2.62(m, 2H), 2.96(m, 2H), 3.16(m, 1H), 3.20(s, 3H), 3.50(s, 2H), 3.78(s, 3H), 3.96(m, 2H), 4.22(m, 1H), 4.78(s, 2H), 6.18(m, 1H), 6.56(bs, 1H), 7.24(d, 1H), 7.58(d, 1H), 11.00(bs, 1H). LRMS: m/z(ES⁺) 477[MH⁺]. Microanalysis found: C, 67.22; H, 6.96; N, 14.40. $C_{27}H_{33}N_5O_3$; $0.5C_2H_5OH$ requires C, 67.45; H, 7.28; N, 14.05%. |
| 11 (a) | 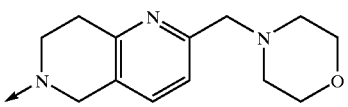 | A | 44 white solid | ¹H-nmr(DMSO-d₆, 400 MHz) δ: 0.65(m, 2H), 0.91(m, 2H), 2.38(m, 4H), 2.93(t, 2H), 3.51(m, 3H), 3.55(m, 4H), 3.76(s, 3H), 3.92(t, 2H), 4.77(s, 2H), 6.14(s, 1H), 6.52(s, 1H), 7.27(d, 1H), 7.56(d, 1H), 11.58(bs, 1H). LRMS: m/z(ES⁺) 470[MNa⁺]. Microanalysis found: C, 66.29; H, 6.50; N, 15.48. $C_{25}H_{29}N_5O_3$; $0.3H_2O$ requires C, 66.29; H, 6.59; N, 15.46%. |

(a) products were additionally purified by column chromatography on silica gel using dichloromethane:methanol or dichloromethane:methanol:0.88 ammonia as eluants.

(b) ethanol was used as a co-solvent in the reaction

EXAMPLE 11

5-Cyclopropyl-7-methoxy-2-(2-morpholin-4-ylmethyl-7,8-dihydro[1,6]-naphthyridin-6(5H)-yl)-4(3H)-quinazolinone

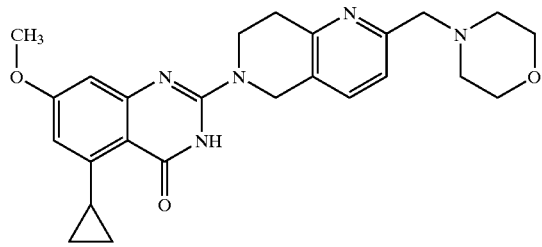

A mixture of the chloride from preparation 18 (351 mg, 1.4 mmol) in n-butanol (21 mL), the amine from preparation 106 (335 mg, 1.43 mmol) and N,N-diisopropylethylamine (633 mg, 4.9 mmol) was heated under reflux for 6 hours, then a further 7 hours at room temperature. The resulting precipitate was filtered off, washed with n-butanol, and dried in vacuo. The solid was purified by column chromatography on silica gel using an elution gradient of dichloromethane:methanol (97:3 to 93:7), and the product triturated with ether to afford the title compound as a white solid, 470 mg.

$^1$H-nmr (DMSO-d$_6$, 400 MHz) δ: 0.65 (m, 2H), 0.91 (m, 2H), 2.38 (m, 4H), 2.93 (t, 2H), 3.51 (m, 3H), 3.55 (m, 4H), 3.76 (s, 3H), 3.92 (t, 2H), 4.77 (s, 2H), 6.14 (s, 1H), 7.27 (d, 1H), 7.56 (d, 1H), 11.58 (bs, 1H). LRMS: m/z (ES$^+$) 470 [MNa$^+$]. Microanalysis found: C, 66.29; H, 6.50; N, 15.48. C$_{25}$H$_{29}$N$_5$O$_3$;0.3H$_2$O requires C, 66.29; H, 6.59; N, 15.46%.

EXAMPLES 12 TO 25

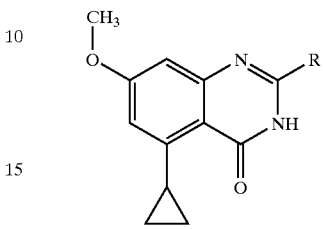

General Method

To a solution of the chloro-quinazolinone from preparation 18 (1 eq) in n-butanol (15 mL per mmol) under nitrogen was added diisopropylethylamine (A) or triethylamine (B) (1.7–8.0 eq) and the appropriate secondary amine (1–2 eq). The resultant mixture was then heated at reflux for 1–6 hours, cooled and the product was isolated by filtration, washing with n-butanol and diethyl ether.

| Ex. no. | R | Base | Yield %/Form | Spectroscopic and Analytical Data |
|---|---|---|---|---|
| 12 | | A | 66 solid | $^1$H-nmr(DMSO-d$_6$, 400 MHz) δ: 0.66(m, 2H), 0.93(m, 2H), 1.59(d, 1H), 1.80(d, 1H), 2.45(d, 1H), 2.76(d, 1H), 2.94(t, 2H), 3.47(s, 1H), 3.52(d, 2H), 3.77(m, 5H), 3.91(d, 1H), 3.95(t, 2H), 4.33(s, 1H), 4.78(s, 2H), 6.14(d, 1H), 6.53(d, 1H), 7.29(d, 1H), 7.56(d, 1H), 11.09(bs, 1H). LRMS: m/z(ES$^+$) 460[MH$^+$]. Microanalysis found: C, 67.96; H, 6.38; N, 15.12. C$_{26}$H$_{29}$N$_5$O$_3$ requires C, 67.67; H, 6.38; N, 15.12%. |
| 13 | | B | solid | $^1$H-nmr(CDCl$_3$, 400 MHz) δ: 0.70(m, 2H), 1.00(m, 2H), 2.96(t, 2H), 3.38(m, 1H), 3.48(m, 4H), 3.79(m, 4H), 3.83(s, 3H), 3.94(t, 2H), 4.69(s, 2H), 6.29(s, 1H), 6.51(d, 1H), 6.64(s, 1H), 7.30(d, 1H), 9.22(bs, 1H). LRMS: m/z(ES$^+$) 456[MNa$^+$] |
| 14 (a) | | A | 62 solid | $^1$H-nmr(CDCl$_3$, 400 MHz) δ: 0.71(m, 2H), 0.99(m, 2H), 2.34(s, 3H), 2.51(m, 4H), 2.97(t, 2H), 3.38(m, 1H), 3.43(m, 4H), 3.82(s, 3H), 3.98(t, 2H), 4.73(s, 2H), 6.27(s, 1H), 6.52(d, 1H), 6.64(s, 1H), 7.24(m, 1H), 9.60(bs, 1H). LRMS: m/z(ES$^+$) 469[MNa$^+$] |
| 15 | | A | 86 off-white solid | $^1$H-nmr(CDCl$_3$, 400 MHz) δ: 0.72(m, 2H), 1.00(m, 2H), 2.63(t, 2H), 3.37(m, 1H), 3.85(s, 3H), 3.97(t, 2H), 4.39(bs, 2H), 4.73(s, 2H), 6.31(d, 1H), 6.52(m, 3H), 6.66(d, 1H), 7.92(d, 1H). LRMS: m/z(ES$^+$) 364[MH$^+$] |

-continued

| Ex. no. | R | Base | Yield %/Form | Spectroscopic and Analytical Data |
|---|---|---|---|---|
| 16 | [structure: N,N-dimethylaminomethyl-tetrahydronaphthyridine] | A | 66 solid | ¹H-nmr(CDCl₃, 400 MHz) δ:<br>0.74(m, 2H), 0.98(m, 2H), 2.24(s, 6H),<br>3.09(m, 2H), 3.42(m, 1H), 3.54(s, 2H),<br>3.86(s, 3H), 4.01(t, 2H), 4.90(s, 2H),<br>6.31(d, 1H), 6.68(d, 1H), 7.01(d, 1H),<br>8.36(d, 1H), 10.96(bs, 1H).<br>LRMS: m/z(ES⁺) 406[MH⁺].<br>Microanalysis found: C, 67.92; H, 6.73; N, 17.23.<br>C₂₃H₂₇N₅O₂ requires C, 68.13; H, 6.71; N, 17.27%. |
| 17 | [structure: N-methyl-N-isopropylaminomethyl] | B | 50 white solid | ¹H-nmr(CDCl₃, 400 MHz) δ:<br>0.63(m, 2H), 0.91(m, 2H), 0.98(d, 6H),<br>1.97(s, 3H), 2.80(m, 1H), 3.00(m, 2H),<br>3.51(m, 1H), 3.61(s, 2H), 3.77(s, 3H),<br>3.85(t, 2H), 4.78(s, 2H), 6.15(s, 1H),<br>6.54(s, 1H), 7.13(d, 1H), 8.22(d, 1H),<br>11.12(bs, 1H).<br>LRMS: m/z(ES⁻) 432[M − H⁻].<br>Microanalysis found: C, 68.41; H, 7.23; N, 15.76.<br>C₂₅H₃₁N₅O₂; 0.25H₂O requires<br>C, 68.55; H, 7.25; N, 15.99%. |
| 18 | [structure: 2-azabicycloheptyl methyl] | B | 61 white solid | ¹H-nmr(CDCl₃, 400 MHz) δ:<br>0.74(m, 2H), 0.98(m, 2H), 1.26(d, 4H),<br>1.77(m, 4H), 3.19(m, 4H), 3.41(m, 1H),<br>3.65(s, 2H), 3.86(s, 3H), 3.97(t, 2H),<br>4.89(s, 2H), 6.31(d, 1H), 6.67(d, 1H),<br>7.01(d, 1H), 8.33(d, 1H), 10.44(bs, 1H).<br>LRMS: m/z(ES⁻) 456[M − H⁻]<br>Microanalysis found: C, 70.41; H, 6.80; N, 15.13.<br>C₂₇H₃₁N₅O₂; 0.25H₂O requires<br>C, 70.18; H, 6.87; N, 15.16%. |
| 19 | [structure: 4-methoxypiperidinylmethyl] | A | 38 white solid | ¹H-nmr(CDCl₃, 400 MHz) δ:<br>0.73(m, 2H), 0.99(m, 2H), 1.25(s, 1H),<br>1.85(m, 2H), 2.16(m, 3H), 2.70(m, 2H),<br>3.12(t, 2H), 3.20(m, 1H), 3.31(s, 3H),<br>3.40(m, 1H), 3.62(s, 2H), 3.85(s, 3H),<br>3.93(t, 2H), 4.87(s, 2H), 6.32(d, 1H),<br>6.88(d, 1H), 7.02(d, 1H), 8.36(d, 1H).<br>LRMS: m/z(ES⁺) 476[MH⁺]<br>Microanalysis found: C, 66.97; H, 7.00; N, 14.19.<br>C₂₇H₃₃N₅O₃; 0.50H₂O requires<br>C, 66.92; H, 7.07; N, 14.45%. |
| 20 (a) | [structure: morpholinylmethyl] | B | 91 white solid | ¹H-nmr(CDCl₃, 400 MHz) δ:<br>0.76(m, 2H), 0.99(m, 2H), 2.47(m, 4H),<br>3.11(t, 2H), 3.43(m, 1H), 3.64(s, 2H),<br>3.67(m, 4H), 3.87(s, 3H), 4.01(t, 2H),<br>4.92(s, 2H), 6.32(s, 1H), 6.68(s, 1H),<br>7.04(d, 1H), 8.37(d, 1H), 10.78(bs, 1H).<br>LRMS: m/z(ES⁺) 448[MH⁺]<br>Microanalysis found: C, 66.60; H, 6.51; N, 15.63.<br>C₂₅H₂₉N₅O₃; 0.20H₂O requires<br>C, 66.56; H, 6.59; N, 15.52%. |
| 21 (a) | [structure: oxa-azabicyclic methyl] | A | 25 yellow oil | ¹H-nmr(CDCl₃, 400 MHz) δ:<br>0.78(m, 2H), 1.00(m, 2H), 1.52–1.80(m, 4H),<br>1.98(m, 1H), 2.78(m, 1H), 2.98(m, 1H),<br>3.18(m, 2H), 3.42(m, 1H), 3.63(m, 1H),<br>3.90(s, 3H), 4.00(m, 2H), 4.17(m, 1H),<br>4.42(m, 1H), 4.90(s, 2H), 6.35(d, 1H),<br>6.67(d, 1H), 7.02(d, 1H), 8.37(d, 1H).<br>LRMS: m/z(ES⁻) 458[M − H-].<br>Microanalysis found: C, 67.48; H, 6.40; N, 15.10.<br>C₂₆H₂₉N₅O₃; requires C, 67.96; H, 6.36; N, 15.24%. |

-continued

| Ex. no. | R | Base | Yield %/Form | Spectroscopic and Analytical Data |
|---|---|---|---|---|
| 22 (a) | (pyrrolidinylmethyl-tetrahydropyrido[4,3-d]pyrimidine) | A | 54 off-white solid | $^1$H-nmr(CDCl$_3$, 400 MHz) δ: 0.73(m, 2H), 1.00(m, 2H), 1.78(m, 4H), 2.57(m, 4H), 3.04(t, 2H), 3.45(m, 1H), 3.72(s, 2H), 3.85(s, 3H), 4.08(t, 2H), 4.98(s, 2H), 6.34(d, 1H), 6.68(d, 1H), 8.95(s, 1H), 11.32(bs, 1H). LRMS: m/z(ES$^+$) 433[MH$^+$]. Microanalysis found: C, 66.23; H, 6.50; N, 19.21. C$_{24}$H$_{28}$N$_6$O$_2$ requires C, 66.65; H, 6.53; N, 19.43%. |
| 23 | (piperidinylmethyl-tetrahydropyrido[4,3-d]pyrimidine) | A | 38 white solid | $^1$H-nmr(CDCl$_3$, 400 MHz) δ: 0.73(m, 2H), 0.99(m, 2H), 1.42(m, 2H), 1.54(m, 4H), 2.40(m, 4H), 3.09(t, 2H), 3.43(m, 1H), 3.54(s, 2H), 3.85(s, 3H), 4.05(t, 2H), 4.96(s, 2H), 6.34(d, 1H), 6.67(d, 1H), 8.94(s, 1H), 10.85(bs, 1H). LRMS: m/z(ES$^+$) 447[MH$^+$]. Microanalysis found: C, 66.96; H, 6.82; N, 18.63. C$_{25}$H$_{30}$N$_6$O$_2$ requires C, 67.24; H, 6.77; N, 18.82%. |
| 24 | (4-methoxypiperidinylmethyl-tetrahydropyrido[4,3-d]pyrimidine) | A | 73 solid | $^1$H-nmr(CDCl$_3$, 400 MHz) δ: 0.73(m, 2H), 1.01(m, 2H), 1.55(m, 2H), 1.84(m, 2H), 2.23(m, 2H), 2.71(m, 2H), 3.07(t, 2H), 3.22(m, 1H), 3.31(s, 3H), 3.42(m, 1H), 3.57(s, 2H), 3.85(s, 3H), 4.06(t, 2H), 4.97(s, 2H), 6.34(d, 1H), 6.67(d, 1H), 8.94(s, 1H), 10.96(bs, 1H). LRMS: m/z(ES$^+$) 477[MH$^+$]. Microanalysis found: C, 63.66; H, 6.62; N, 17.13. C$_{26}$H$_{32}$N$_6$O$_3$; 0.75H$_2$O requires C, 63.72; H, 6.89; N, 17.15%. |
| 25 | (dimethylamino-imidazopyrazine) | A | 59 white solid | $^1$H-nmr(CDCl$_3$, 400 MHz) δ: 0.74(m, 2H), 1.00(m, 2H), 2.79(s, 6H), 3.36(m, 1H), 3.85(s, 3H), 3.95(t, 2H), 4.09(t, 2H), 4.89(s, 2H), 6.34(d, 1H), 6.56(s, 1H), 6.65(d, 1H), 10.81(bs, 1H). LRMS: m/z(ES$^+$) 381[MH$^+$]. Microanalysis found: C, 61.81; H, 6.25; N, 21.47. C$_{20}$H$_{24}$N$_6$O$_2$; 0.5H$_2$O requires C, 61.68; H, 6.47; N, 21.58%. |

(a) products were additionally purified by column chromatography on silica gel using dichloromethane:methanol or dichloromethane:methanol:0.88 ammonia as eluants.
(b) ethanol was used as a co-solvent in the reaction

EXAMPLE 26

5-Cyclopropyl-7-methoxy-2-(2-(1-piperidinylmethyl)-7,8-dihydropyrido[4,3-d]pyrimidin-6(5H)-yl)-4(3H)-quinazolinone

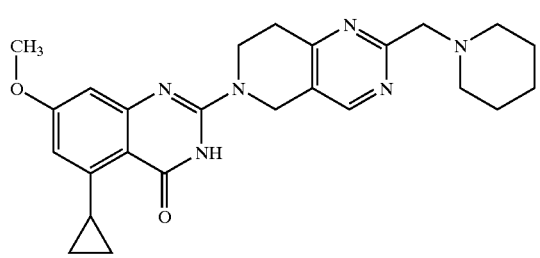

A mixture of the chloride from preparation 18 (302 mg, 1.2 mmol), the amine from preparation 124 (1.23 mmol) and diisopropylethylamine (646 mg, 5 mmol) in n-butanol (10 mL) was heated under reflux for 1.5 hours. The cooled mixture was diluted with water and extracted with dichloromethane (3×50 mL). The combined organic extracts were dried (MgSO$_4$) and evaporated under reduced pressure. The residue was purified by column chromatography on silica gel using an elution gradient of dichloromethane:methanol (100:0 to 90:10) to afford the title compound as an off-white solid, 307 mg.

$^1$H-nmr (CDCl$_3$, 400 MHz) δ: 0.72 (m, 2H), 0.96 (m, 2H), 1.48 (m, 2H), 1.71 (m, 4H), 2.70 (m, 4H), 3.07 (t, 2H), 3.53 (m, 1H), 3.84 (s, 3H), 3.88 (bs, 2H), 4.06 (t, 2H), 4.89 (s, 2H), 6.31 (s, 1H), 6.66 (s, 1H), 8.51 (s, 1H), 11.12 (bs, 1H). LRMS: m/z (ES$^+$) 447 [MH$^+$]Microanalysis found: C, 65.74; H, 6.83; N, 18.28. C$_{25}$H$_{30}$N$_6$O$_2$;0.5H$_2$O requires C, 65.91; H, 6.86; N, 18.45%.

EXAMPLE 27

2-(3-Amino-5,6-dihydroimidazo[1,5-a]pyrazin-7(8H)-yl)-5-cyclopropyl-7-methoxy-4(3H)-quinazolinone

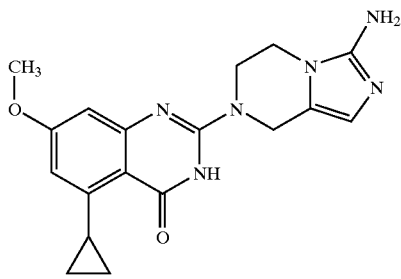

The title compound was obtained as a yellow solid in 23% yield, from the chloride from preparation 18 and the amine from preparation 136, following a similar procedure to that described in example 26, except dichloromethane:methanol:0.88 ammonia (90:10:1) was used as the column eluant.

$^1$H-nmr (DMSOd$_6$, 400 MHz) δ: 0.64 (m, 2H), 0.2 (m, 2H), 3.48 (m, 1H), 3.75 (m, 5H), 3.93 (t, 2H), 4.68 (s, 2H), 5.48 (s, 2H), 6.16 (s, 1H), 6.28 (s, 1H), 6.53 (s, 1H), 11.10 (bs, 1H). LRMS: m/z (ES$^+$) 353 [MH$^+$]

EXAMPLE 28

5-Cyclopropyl-7-methoxy-2-(3-[(2-methoxyethyl)(methyl)amino]-5,6-dihydroimidazo[1,5-a]pyrazin-7(8H)-yl)-4(3H)-quinazolinone

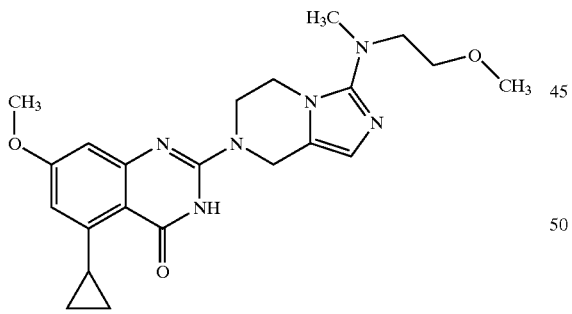

The title compound was obtained as a white solid in 45% yield, from the chloride from preparation 18 and the amine from preparation 133, following a similar procedure to that described in example 26.

$^1$H-nmr (CDCl$_3$, 400 MHz) δ: 0.73 (m, 2H), 0.96 (m, 2H), 2.82 (s, 3H), 3.21 (t, 2H), 3.49 (m, 1H), 3.50 (s, 3H), 3.51 (t, 2H), 3.84 (s, 3H), 3.96 (t, 2H), 4.09 (t, 2H), 4.91 (s, 2H), 6.33 (d, 1H), 6.55 (s, 1H), 6.65 (d, 1H), 11.38 (bs, 1H). LRMS: m/z (ES$^+$) 425 [MH$^+$]

EXAMPLE 29

5-Cyclopropyl-2-(3-ethyl-5,6-dihydroimidazo[1,2-a]pyrazin-7(8H)-yl)-7-methoxy-4(3H)-quinazolinone

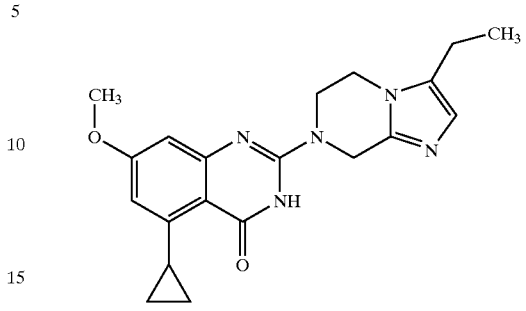

The title compound was obtained as a white solid in 43% yield, from the chloride from preparation 18 and the amine from preparation 131, following a similar procedure to that described in example 26, except dichloromethane:methanol:0.88 ammonia (95:50.5) was used as the column eluant.

$^1$H-nmr (DMSOd$_6$, 400 MHz) δ: 0.62 (m, 2H), 0.96 (m, 2H), 1.16 (t, 3H), 2.52 (m, 2H), 3.50 (m, 1H), 3.78 (s, 3H), 3.92 (m, 2H), 4.04 (m, 2H), 4.78 (s, 2H), 6.18 (s, 1H), 6.56 (s, 1H), 6.60 (s, 1H), 10.80, 11.25 (2×bs, 1H). LRMS: m/z (ES$^+$) 366 [MH$^+$]Microanalysis found: C, 64.26; H, 6.31; N, 18.10. $C_{20}H_{23}N_5O_2$;0.15CH$_2$Cl$_2$ requires C, 64.00; H, 6.21; N, 18.52%.

EXAMPLE 30

5-Cyclopropyl-7-methoxy-2-(5-(1-methyl-4-piperidinyl)-3,4-dihydro[2,6]naphthyridin-2(1H)-yl)-4(3H)-quinazolinone

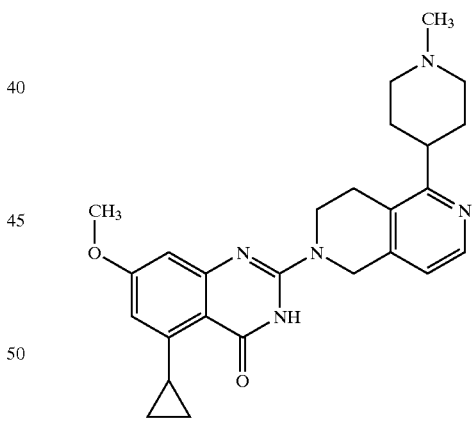

A mixture of the chloride from preparation 18 (0.40 mmol), the amine hydrochloride from preparation 120 (145.6 mg, 0.48 mmol) and triethylamine (223 μl, 1.60 mmol) in n-butanol (6 mL) was heated under reflux for 3 hours. The cooled mixture was concentrated under reduced pressure and the residue partitioned between water (4 mL) with saturated sodium bicarbonate solution (2 mL), and dichloromethane (30 mL), and the layers separated. The aqueous phase was extracted with further dichloromethane (2×20 mL), and the combined organic solutions dried (MgSO$_4$) and evaporated under reduced pressure. The residual solid was purified by column chromatography on silica gel using an elution gradient of dichloromethane:methanol:0.88 ammonia (95:5:0.2 to 90:10:0.6) to afford the title compound as a white solid, 110 mg.

$^1$H-nmr (DMSOd$_6$, 400 MHz) δ: 0.64 (m, 2H), 0.93 (m, 2H), 1.60 (m, 2H), 1.83 (m, 2H), 2.04 (m, 2H), 2.21 (s, 3H), 2.80 (m, 1H), 2.87 (m, 4H), 3.40 (m, 1H), 3.76 (s, 3H), 3.89 (t, 2H), 4.77 (s, 2H), 6.15 (s, 1H), 6.51 (d, 1H), 7.04 (d, 1H), 8.30 (d, 1H), 11.07 (bs, 1H). LRMS: m/z (ES$^+$) 446 [MH$^+$] Microanalysis found: C, 68.43; H, 7.11; N, 15.35. $C_{26}H_{31}N_5O_2;0.6H_2O$ requires C, 70.09; H, 7.11; N, 15.35%.

EXAMPLE 31

5-Cyclopropyl-2-(3-isopropyl-5,6-dihydroimidazo[1,5-a]pyrazin-7(8H)-yl)-7-methoxy-4(3H)-quinazolinone and

EXAMPLE 32

5-Cyclopropyl-2-(3-(1-hydroxy-1-methylethyl)-5,6-dihydroimidazo[1,5-a]pyrazin-7(8H)-yl)-7-methoxy-4(3H)-quinazolinone

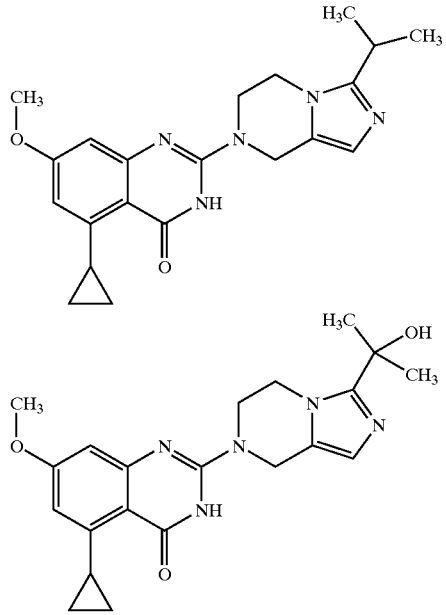

A mixture of the chloride from preparation 18 (80 mg, 0.32 mmol), the amines from preparations 120 and 121 (99 mg), and triethylamine (178μl, 1.28 mmol) in n-butanol (6 mL) was heated under reflux for 3.5 hours. The cooled mixture was concentrated under reduced pressure and the solid residue partitioned between dichloromethane (30 mL) and a solution of saturated sodium bicarbonate (1 mL) in water (5 mL), and the phases separated. The aqueous layer was extracted with dichloromethane (2×30 mL), and the combined organic extracts dried (MgSO$_4$) and evaporated under reduced pressure. The crude product was purified by column chromatography on silica gel using an elution gradient of dichloromethane:methanol (100:0 to 95:5) to afford the title compound of example 31, 42 mg.

$^1$H-nmr (CD$_3$OD, 400 MHz) δ: 0.65 (m, 2H), 0.97 (m, 2H), 1.28 (d, 6H), 3.10 (m, 1H), 3.33 (s, 1H), 3.82 (s, 3H), 4.07 (m, 2H), 4.13 (t, 2H), 4.84 (s, 2H), 6.34 (d, 1H), 6.75 (s, 1H); LRMS: m/z (ES$^+$) 380 [MH$^+$]; Microanalysis found: C, 65.77; H, 6.69; N, 18.46. $C_{21}H_{25}N_5O_2;0.2H_2O$ requires C, 65.84; H, 6.68; N, 18.28%.

Further elution gave the title compound of example 32, 40 mg.

$^1$H-nmr (CD$_3$OD, 400 MHz) δ: 0.62 (m, 2H), 0.97 (m, 2H), 1.56 (s, 6H), 3.29 (m, 1H), 3.82 (s, 3H), 4.00 (m, 2H), 4.53 (m, 2H), 4.84 (s, 2H), 6.34 (s, 1H), 6.70 (s, 1H), 6.75 (s, 1H); LRMS: m/z (ES$^+$) 396 [MH$^+$]; Microanalysis found: C, 63.12; H, 6.59; N, 17.21. $C_{21}H_{25}N_5O_3;0.07CH_2Cl_2$ requires C, 63.05; H, 6.31; N, 17.44%.

EXAMPLE 33

5-Cyclobutyl-7-methoxy-2-(2-(4-morpholinylmethyl)-7,8-dihydro[1,6]naphthyridin-6(5H)-yl)-4(3H)-quinazolinone

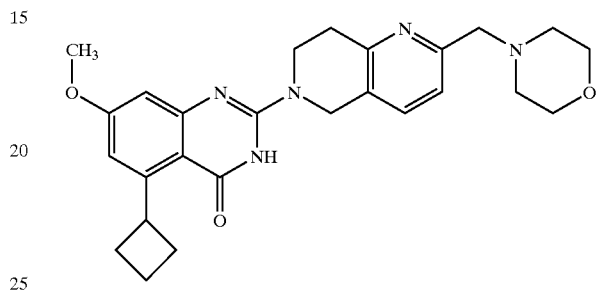

The title compound was obtained as a solid in 74% yield from the compounds from preparation 19 and 106, following the procedure described in example 4.

$^1$H-nmr (DMSOd$_6$, 400 MHz) D: 1.66–1.75 (m, 1H), 1.83–2.03 (m, 3H), 2.29 (m, 2H), 2.38 (m, 4H), 2.93 (t, 2H), 3.51 (s, 2H), 3.56 (m, 4H), 3.81 (s, 3H), 3.92 (t, 2H), 4.57 (m, 1H), 4.77 (s, 2H), 6.59 (s, 2H), 7.27 (d, 1H), 7.57 (d, 1H), 11.05 (bs, 1H). LRMS : m/z (ES$^+$) 462 [MH$^+$] Microanalysis found: C, 67.66; H, 6.78; N, 14.95. $C_{26}H_{31}N_5O_3$ requires C, 67.66; H, 6.77; N, 15.17%.

EXAMPLE 34

5-Cyclohexyl-7-methoxy-2-(2-(4-morpholinylmethyl)-7,8-dihydro[1,6]naphthyridin-6(5H)-yl)-4(3H)-quinazolinone

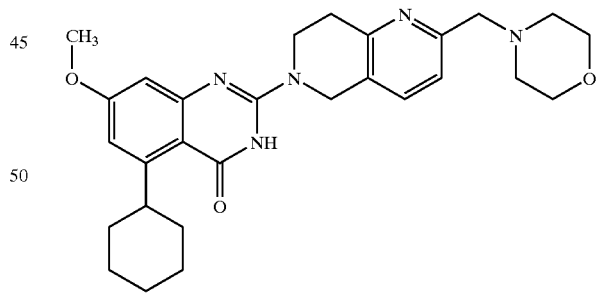

The title compound was obtained as a solid in 70% yield, after recrystallisation from diethyl ether, from the compounds from preparation 20 and 106, following a similar procedure to that described in example 26.

$^1$H-nmr (DMSOd$_6$, 400 MHz) δ: 1.15–1.46 (m, 5H), 1.66–1.84 (m, 5H), 2.38 (m, 4H), 2.94 (t, 2H), 3.52 (s, 2H), 3.57 (m, 4H), 3.79 (s, 3H), 3.93 (t, 2H), 4.14 (t, 1H), 4.77 (s, 2H), 6.57 (m, 2H), 7.27 (d, 1H), 7.57 (d, 1H), 11.03 (bs, 1H). LRMS: m/z (APCI$^+$) 490 [MH$^+$]Microanalysis found: C, 68.84; H, 7.33; N, 14.18. $C_{28}H_{35}N_5O_3$ requires C, 68.69; H, 7.21; N, 14.30%.

EXAMPLES 35 TO 39

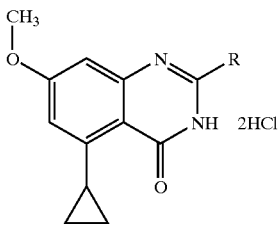

The following examples were prepared following the procedure described for examples 2 to 25. The compounds were then dissolved in a solution of dichloromethane with a minimum volume of methanol, then treated with 1N ethereal hydrochloric acid. The resultant mixture was evaporated under reduced pressure to afford the title compounds.

| Ex. no. | R | Base | Yield %/Form | Spectroscopic and Analytical Data |
|---|---|---|---|---|
| 35 | (morpholinylmethyl-tetrahydroisoquinoline) | A | 90 | $^1$H-nmr(DMSO-d$_6$, 400 MHz) δ: 0.76(m, 2H), 0.98(m, 2H), 3.18–3.35(m, 7H), 3.79(s, 3H), 3.88(s, 4H), 4.00(m, 2H), 4.16(s, 2H), 4.98(s, 2H), 6.38(s, 1H), 7.32(bs, 2H), 7.46(bs, 1H), 7.64(bs, 1H), 11.47(bs, 1H); LRMS(ES$^+$): m/z(MH$^+$) 447; Microanalysis: Found: C, 58.41; H, 6.57; N, 10.02. C$_{26}$H$_{30}$N$_4$O$_3$; 2HCl; H$_2$O requires C, 58.10; H, 6.38; N, 10.42% |
| 36 (a) | (3-methoxyazetidinylmethyl-tetrahydroisoquinoline) | A | 56 | $^1$H-nmr(DMSO-d$_6$, 400 MHz) δ: 0.74(m, 2H), 0.98(m, 2H), 3.10(m, 2H), 3.22(m, 3H), 3.32(m, 1H), 3.80(s, 3H), 3.92(m, 1H), 4.00–4.44(m, 9H), 5.02(s, 2H), 6.38(s, 1H), 7.33(d, 1H), 7.45(m, 2H), 11.50(bs, 1H); LRMS(ES$^+$): m/z(MH$^+$) 447; Microanalysis: Found: C, 59.36; H, 6.28; N, 10.53. C$_{26}$H$_{30}$N$_4$O$_3$; 2HCl; 0.4H$_2$O requires C, 59.29; H, 6.28; N, 10.64%. |
| 37 (b) | (tetrahydronaphthyridine) | B | 92 | $^1$H-nmr(DMSO-d$_6$, 400 MHz) δ: 0.71(m, 2H), 0.97(m, 2H), 3.26(t, 2H), 3.38(m, 1H), 3.74(s, 3H), 4.12(t, 2H), 5.08(s, 2H), 6.35(s, 1H), 7.07(bs, 1H), 7.75(dd, 1H), 8.20(m, 1H), 8.66(d, 1H). LRMS m/z: (ES$^-$) 347(M – H$^-$) |
| 38 (a) | (pyrrolidinylmethyl-tetrahydronaphthyridine) | A | 42 white solid | $^1$H-nmr(DMSO-d$_6$, 400 MHz) δ: 0.72(m, 2H), 0.99(m, 2H), 1.97(m, 4H), 3.00(m, 2H), 3.26–3.46(m, 5H), 3.80(s, 3H), 4.17 (m, 2H), 4.61(s, 2H), 5.12(s, 2H), 6.38(s, 1H), 7.28(bs, 1H), 7.57(bs, 1H), 8.46(d, 1H), 10.56(bs, 1H). LRMS m/z: (ES$^+$) 432(MH$^+$) |
| 39 | (piperidinylmethyl-tetrahydronaphthyridine) | A | 71 white solid | $^1$H-nmr(DMSO-d$_6$, 400 MHz) δ: 0.74(m, 2H), 0.97(m, 2H), 1.55(m, 2H), 1.82(m, 4H), 3.03(t, 2H), 3.16–3.38(m, 5H), 3.80(s, 3H), 4.16(t, 2H), 4.50(s, 2H), 5.17(s, 2H), 6.38(s, 1H), 7.32(d, 1H), 7.62(bs, 1H), 8.49(d, 1H), 10.04(bs, 1H). LRMS m/z: (ES$^+$) 446(MH$^+$) Microanalysis found: C, 58.21; H, 6.58; N, 13.05. C$_{26}$H$_{31}$N$_5$O$_2$; 2HCl; H$_2$O requires C, 58.32; H, 6.63; N, 12.79%. |

(b) 5,6,7,8-tetrahydro-1,6-naphthyridine(Chem. Pharm. Bull. 32, 2522, 1984) was used as the amine

EXAMPLE 40

5-Cyclopropyl-2-(2-[(dimethylamino)methyl]-7,8-dihydropyrido[4,3-d]pyrimidin-6(5H)-yl)-7-methoxy-4(3H)-quinazolinone dihydrochloride

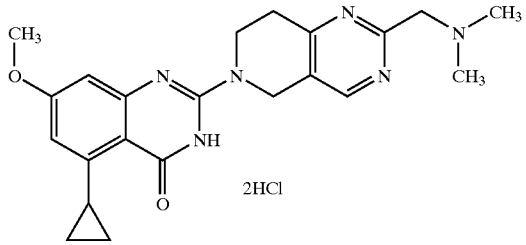

A mixture of the chloride from preparation 18 (60 mg, 0.24 mmol), the amine hydrochloride from preparation 121 (80 mg, 0.30 mmol) and diisopropylethylamine (258 mg, 2 mmol) in n-butanol (4 mL) was heated under reflux for 1.5 hours. The cooled mixture was poured into water and extracted with dichloromethane (3×50 mL). The combined organic extracts were dried ($MgSO_4$) and evaporated under reduced pressure. The residue was purified by column chromatography on silica gel using an elution gradient of dichloromethane:methanol (100:0 to 80:20). The product was re-dissolved in dichloromethane treated with 1 N ethereal hydrochloric acid (2 mL), and the solution evaporated under reduced pressure to afford the title compound as a light brown solid, 60 mg. $^1$H-nmr (DMSO-$d_6$ 400 MHz) δ: 0.72 (m, 2H), 0.97 (m, 2H), 2.87 (s, 6H), 3.14 (m, 2H), 3.36 (m, 1H), 3.79 (s, 3H), 4.18 (m, 2H), 4.56 (s, 2H), 5.13 (s, 2H), 6.38 (s, 1H), 7.42 (bs, 1H), 8.71 (s, 1H), 10.49 (bs, 1H). LRMS: m/z (ES$^+$) 407 [MH$^+$]Microanalysis: Found: C, 54.11; H, 5.94; N, 16.83. $C_{22}H_{26}N_6O_2$;2HCl;0.5$H_2$O requires C, 54.10; H, 5.98; N, 17.21%

EXAMPLES 41 TO 43

The following examples of general structure:

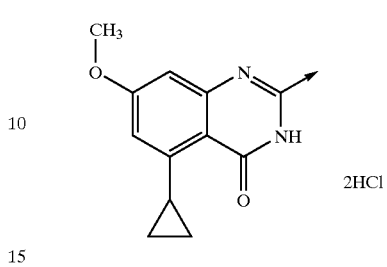

were prepared from the chloride from preparation 18, the appropriate amines and diisopropylethylamine, following a similar procedure to that described in example 40.

| Ex. no. | R | Yield %/Form | Spectroscopic and Analytical Data |
|---|---|---|---|
| 41 | (pyrido-pyrimidine-pyrrolidine) | 63 off-white solid | $^1$H-nmr(DMSOd$_6$, 400 MHz) δ: 0.68(m, 2H), 0.95(m, 2H), 1.85–2.05(m, 4H), 3.05(t, 2H), 3.15(m, 2H), 3.43(m, 1H), 3.60(m, 2H), 3.75(s, 3H), 4.05(m, 2H), 4.65(d, 2H), 4.95(s, 2H), 6.25(s, 1H), 6.85(bs, 1H), 8.73(s, 1H), 10.45(bs, 1H). LRMS: m/z(ES$^+$) 433[MH$^+$] |
| 42 (a) | (methylimidazopyrazine) | 86 white solid | $^1$H-nmr(CD$_3$OD, 400 MHz) δ: 0.77(m, 2H), 1.07(m, 2H), 2.66(s, 3H), 3.10(m, 1H), 3.91(s, 3H), 4.34(t, 2H), 4.43(t, 2H), 5.16(s, 2H), 6.64(d, 1H), 7.11(s, 1H), 7.46(s, 1H). LRMS: m/z(ES$^+$) 352[MH$^+$]. Microanalysis: Found: C, 54.19; H, 5.77; N, 16.28. $C_{19}H_{21}N_5O_2$; 2HCl requires C, 53.78; H, 5.46; N, 16.50% |
| 43 (a) | (ethylimidazopyrazine) | 78 yellow foam | $^1$H-nmr(CD$_3$OD, 400 MHz) δ: 0.78(m, 2H), 1.09(m, 2H), 1.41(t, 3H), 3.04(m, 3H), 3.92(s, 3H), 4.35(t, 2H), 4.46(t, 2H), 5.18(s, 2H), 6.65(s, 1H), 7.12(s, 1H), 7.49(s, 1H). LRMS: m/z(ES$^+$) 366[MH$^+$]. Microanalysis: Found: C, 53.58; H, 5.97; N, 15.27. $C_{20}H_{23}N_5O_2$; 2HCl requires C, 53.48; H, 5.88; N, 15.59% |

(a) triethylamine was used instead of diisopropylethylamine

EXAMPLE 44

5-Cyclopropyl-2-(5,6-dihydroimidazo[1,5-a]pyrazin-7(8H)-yl)-7-methoxy-4(3H)-quinazolinone dihydrochloride

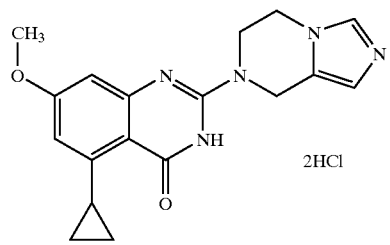

A mixture of the chloride from preparation 18 (70 mg, 0.28 mmol), the amine hydrochloride from preparation 129 (66 mg, 0.34 mmol) and triethylamine (113 μl, 1.1 2 mmol) in n-butanol (6 mL) was heated under reflux for 6 hours. The cooled mixture was concentrated under reduced pressure and the residual solid partitioned between water (5 mL) and dichloromethane:methanol (95:5, 50 mL) and the layers separated. The aqueous phase was extracted with dichloromethane:methanol (95:5, 2×30 mL), and the combined organic solutions dried (MgSO$_4$) and evaporated under reduced pressure. The product was purified by column chromatography on silica gel using an elution gradient of dichloromethane:methanol (98:2 to 90:10) to give a white solid. This was suspended in water, diluted with saturated sodium bicarbonate solution, and extracted with dichloromethane (3×50 mL). The combined organic extracts were dried (MgSO$_4$) and evaporated under reduced pressure. The solid was dissolved in dichloromethane:methanol (1:1, 8 mL), 1N ethereal hydrochloric acid added, and the mixture evaporated under reduced pressure to afford the title compound as a foam, 69 mg.

$^1$H-nmr (DMSOd$_6$, 400 MHz) δ: 0.74 (m, 2H), 0.99 (m, 2H), 3.25 (m, 1H), 3.81 (s, 3H), 4.20 (t, 2H), 4.46 (t, 2H), 5.10 (s, 2H), 6.42 (s, 1H), 7.01 (s, 1H), 7.64 (s, 1H), 9.15 (s, 1H). LRMS: m/z (ES$^+$) 338 [MH$^+$]Microanalysis found: C, 52.78; H, 5.46; N, 16.82. C$_{18}$H$_{19}$N$_5$O$_2$;2HCl requires C, 52.69; H, 5.16; N, 17.07%

EXAMPLE 45

5-Cyclopropyl-7-methoxy-2-(2-{[(2-methoxyethyl)(methyl)amino]methyl}-7,8-dihydropyrido[4,3-d]pyrimidin-6(5H)-yl)-4(3H)-guinazolinone hydrochloride

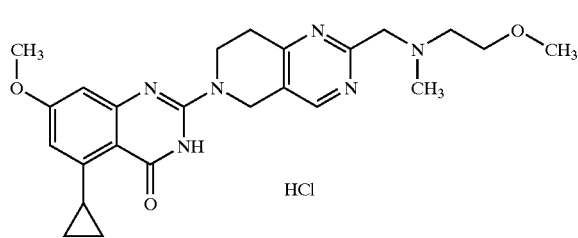

A mixture of the chloride from preparation 18 (140 mg, 0.5 mmol), the amine hydrochloride from preparation 122 (290 mg, 0.84 mmol) and triethylamine (390 μl, 2.8 mmol) in n-butanol (3mL) was heated under reflux for 1.5 hours. The cooled mixture was filtered, the resulting solid washed with n-butanol and diethyl ether, then dried at 60° C. in vacuo, to afford the title compound as a cream solid.

$^1$H-nmr (CDCl$_3$, 400 MHz) δ: 0.73 (m, 2H), 0.97 (m, 2H), 2.41 (s, 3H), 2.75 (t, 2H), 3.08 (t, 2H), 3.33 (s, 3H), 3.38 (m, 1H), 3.56 (t, 2H), 3.86 (m, 5H), 4.10 (t, 2H), 4.92 (s, 2H), 6.33 (s, 1H), 6.68 (s, 1H), 8.51 (s, 1H), 11.12 (bs, 1H). LRMS: m/z (ES$^-$) 449 [M-H$^-$]Microanalysis found: C, 58.44; H, 6.16; N, 16.97. C$_{24}$H$_{30}$N$_6$O$_3$;HCl;0.3H$_2$O requires C, 58.54; H, 6.47; N, 17.07%.

EXAMPLE 46

5-Cyclopropyl-7-methoxy-2-(2-{[2-(4-morpholinyl)ethoxy]methyl}-7,8-dihydropyrido[4,3-d]pyrimidin-6(5H)-yl)-4(3H)-guinazolinone hydrochloride

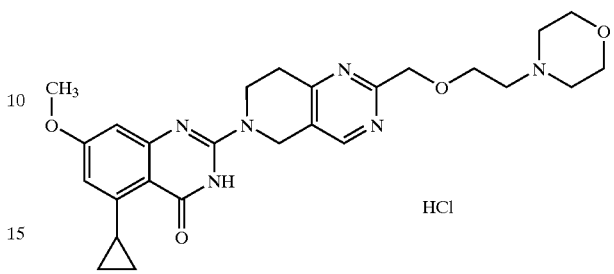

The title compound was obtained as a cream solid in 65% yield, from the chloride from preparation 18 and the amine hydrochloride from preparation 125, following a similar procedure to that described in example 45, except, diisopropylethylamine was used instead of triethylamine.

$^1$H-nmr (CDCl$_3$, 400 MHz) δ: 0.85 (m, 2H), 00.97 (m, 2H), 2.50 (m, 4H), 2.67 (m, 2H), 3.09 (m, 2H), 3.38 (m, 1H), 3.65 (m, 4H), 3.74 (t, 2H), 3.83 (s, 3H), 4.15 (m, 2H), 4.72 (s, 2H), 4.91 (s, 2H), 6.35 (s, 1H), 6.64 (s, 1H), 8.53 (s, 1H), 10.88 (bs, 1H), LRMS: m/z ES$^-$) 491 [M-H$^-$]Microanalysis found: C, 58.71; H, 6.15; N, 15.65. C$_{26}$H$_{32}$N$_6$O$_4$;HCl requires C, 59.03; H, 6.29; N, 15.89%.

EXAMPLE 47

5-Cyclopropyl-7-methoxy-2-(3-morpholin-4-ylmethyl-5,6-dihydro-8H-imidazo[1,5-a]pyrazin-7-yl)-3H-quinazolin-4-one

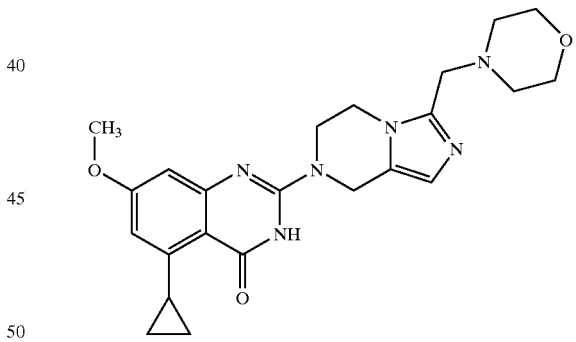

The chloro compound from preparation 18 (100 mg, 0.4 mmol) was mixed with the imidazopyrazine from preparation 173 (106 mg, 0.48 mmol) and triethylamine (167 μl, 1.2 mmol) in n-butanol (10 ml) under a nitrogen atmosphere and the mixture was heated under reflux for 6 hours. The reaction mixture was cooled to room temperature and the solid formed was isolated by filtration. The material obtained was washed with n-butanol (20 ml), diethyl ether (100 ml), water (20 ml) and diethyl ether (100 ml) and was then dried under vacuum at 80° C. for 4 hours to give the title compound (95 mg).

$^1$H-nmr (DMSOd$_6$ 400 MHz) δ: 1.65 (m, 2H), 1.94 (m, 2H), 2.34 (m, 4H), 3.53 (m, 7H), 3.78 (s, 3H), 3.98 (m, 2H), 4.12 (m, 2H), 4.80 (s, 2H), 6.19 (d, 1H), 6.57 (d, 1H), 6.59 (s, 1H), 11.20 (s, 1H) LRMS: m/z (ES$^+$) 459 [MNa$^+$]

Microanalysis found: C, 62.38; H, 6.39; H, 18.95; C$_{23}$H$_{28}$N$_6$O$_3$ 0.25 H$_2$O requires C, 62.29; H, 6.47; N, 19.25%

EXAMPLES 48 TO 86

The compounds of the following tabulated examples of the general formula:

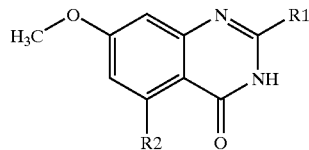

were prepared by the general method outlined below using the appropriate chloro compound and cyclic amine.

To a solution of the chloro-quinazolinone (1 eq) in n-butanol (15 ml per mmol) under nitrogen was added N,N-diisopropylethylamine or triethylamine (1.7–8 eq) and the appropriate secondary amine (1–2 eq). The resultant mixture was then heated under reflux for 1–6 hours, cooled and the product was isolated by filtration, washing with n-butanol and diethyl ether (Method a).

Some reaction mixtures were concentrated under reduced pressure, the residue partitioned between dichloromethane and water, the organic phase separated, dried (MgSO$_4$) and evaporated under reduced pressure (Method b).

Some products were additionally purified by column chromatography on silica gel using dichloromethane: methanol or dichloromethane: methanol: 0.88 ammonia as eluants (Method c).

| Ex No. (Method) | R1 | R2 | Yield % | Spectroscopic and analytical data |
|---|---|---|---|---|
| 48 (b) | [imidazopyrazine-CH$_2$OH] | [cyclopropyl] | 79 | $^1$H NMR(DMSOd$_6$, 400 MHz) δ: 0.66(m, 2H), 0.94(m, 2H), 0.35(m, 1H), 3.77(s, 3H), 3.99(m, 2H), 4.12(m, 2H), 4.42(d, 2H), 4.82(s, 2H), 5.16(t, 1H), 6.18(s, 1H), 6.56(s, 1H), 6.68(s, 1H). LRMS: m/z(ES$^+$) 390[MNa$^+$] Microanalysis found: C, 61.32; H, 5.76; N, 18.48; C$_{19}$H$_{21}$N$_5$O$_3$ 0.25H$_2$O requires; C, 61.36; H, 5.83; 18.83% |
| 49$^D$ (a) | [imidazopyrazine-piperidine-OCH$_3$] | [cyclopropyl] | 58 | $^1$H NMR(DMSOd$_6$, 400 MHz) δ: 0.66(m, 2H), 0.95(m, 2H), 1.56(m, 2H), 1.90(m, 2H), 2.79(m, 2H), 3.15(m, 2H), 3.25(s, 3H), 3.30(m, 1H), 3.50(m, 1H), 3.77(s, 3H), 3.86(m, 2H), 3.93(m, 2H), 4.76(s, 2H), 6.16(s, 1H), 6.47(s, 1H), 6.54(s, 1H), 11.10(s, 1H); LRMS: m/z(ES$^+$) 451[MH$^+$]; Microanalysis found: C, 63.65; 6.76; 18.40; C$_{24}$H$_{30}$N$_6$O$_3$ 0.1H$_2$O requires; C, 63.73; H, 6.73; N 18.58% |
| 50$^D$ (a) | [tetrahydronaphthyridine-CH$_2$-morpholine] | [cyclobutyl] | 74 | $^1$H NMR(DMSOd$_6$, 400 MHz) δ: 1.73(m, 1H), 1.96(m, 3H), 2.29(s, m, 2H), 2.38(m, 4H), 2.93(t, 2H), 3.51(s, 2H), 3.56(m, 4H), 3.80(s, 3H), 3.92(t, 2H), 4.51(m, 1H), 4.77(s, 2H), 6.59(s, 2H), 7.27(d, 1H), 7.57(d, 1H), 11.05(s, 1H); LRMS: m/z(ES$^+$) 485[MNa$^+$] |
| 51$^D$ (a) | [tetrahydronaphthyridine] | [isopropyl] | 41 | $^1$H NMR(DMSOd$_6$, 400 MHz) δ: 1.15(d, 6H), 2.98(t, 2H), 3.80(s, 3H), 3.94(t, 2H), 4.53(m, 1H), 4.80(s, 2H), 6.60(s, 2H), 7.20(m, 1H), 7.60(d, 1H), 8.38(d, 1H), 10.91(s, 1H); LRMS: m/z(ES$^+$) 451[MH$^+$]; Microanalysis: Found: C, 68.42; H, 6.50; N, 15.66; C$_{20}$H$_{22}$N$_4$O$_2$ requires; C, 68.55; H, 6.33; N, 15.99%. M.p. 227–229° C. |
| 52$^D$ (a) | [tetrahydroisoquinoline-CH$_2$-morpholine] | [isopropyl] | 58 | $^1$H NMR(DMSOd$_6$, 400 MHz) δ: 1.16(d, 6H), 2.33(m, 4H), 2.95(t, 2H), 3.42(s, 2H), 3.52(m, 4H), 3.79(s, 3H), 3.83(t, 2H), 4.55(m, 1H), 4.78(s, 2H), 6.58(s, 2H), 7.10(m, 3H). LRMS: m/z(ES$^+$) 449[MH$^+$]. Microanalysis: Found: C, 69.62; H, 7.31; N, 12.19; C$_{26}$H$_{32}$N$_4$O$_3$ requires; C, 69.62; H, 7.19; 12.49%. M.p. 231–233° C. |

| Ex No. (Method) | R1 | R2 | Yield % | Spectroscopic and analytical data |
|---|---|---|---|---|
| 53^D (a) | 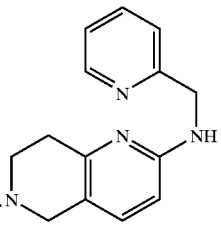 | 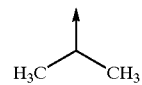 | 62 | ¹H NMR(DMSOd₆, 400 MHz) δ: 1.16(d, 6H), 2.71(t, 2H), 3.80(s, 3H), 3.86(t, 2H), 4.54(m, 5H), 6.40(d, 1H), 6.58(d, 2H), 6.81(s, 1H), 7.19(m, 2H), 7.30(d, 1H), 7.67(m, 1H), 8.48(d, 1H), 10.84(s, 1H). LRMS: m/z(ES⁺) 457[MH⁺]. Microanalysis: Found: C, 68.21; H, 6.21; 18.21; C₂₆H₂₈N₆O₂ requires C, 68.40; H, 6.18; N, 18.41% M.p. 227–229° C. |
| 54¹ (a) | 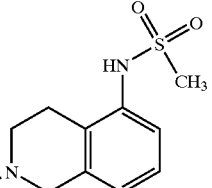 | 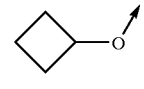 | 60 | ¹H-NMR(DMSOd₆, 400 MHz) δ: 1.62(m, 1H), 1.79(m, 1H), 2.08(m, 2H), 2.41(m, 2H), 2.90(t, 2H), 2.99(s, 3H), 3.79(m, 5H), 4.67(m, 1H), 4.76(s, 2H), 5.95(d, 1H), 6.30(s, 1H), 7.11(d, 1H), 7.20(m, 2H). LRMS: m/z(ES⁺) 471[MH⁺] |
| 55 (b) | 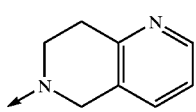 | 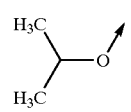 | 68 | ¹H-NMR(DMSOd₆, 400 MHz) δ: 1.27(d, 6H), 2.95(s, 2H), 3.80(s, 3H), 3.92(s, 2H), 4.54(m, 1H), 4.80(s, 2H), 6.20(s, 1H), 6.35(s, 1H), 7.20(m, 1H), 7.59(d, 1H), 8.39(s, 1H). LRMS: m/z(ES⁺) 367[MH⁺]. Microanalysis: Found; C, 64.63; H, 5.99; N, 15.01; C₂₀H₂₂N₄O₃ 0.25H₂O requires; C, 64.76; H, 6.11; N, 15.10% |
| 56 (a) | 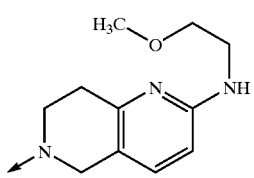 | 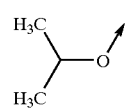 | 81 | ¹H-NMR(DMSOd₆, 400 MHz) δ: 1.27(d, 6H), 2.72(t, 2H), 3.27(m, 3H), 3.39(t, 2H), 3.44(m, 2H), 3.79(s, 3H), 3.85(t, 2H), 4.54(m, 3H), 6.18(s, 1H), 6.21(s, 1H), 6.32(s, 1H), 6.39(d, 1H), 7.18(d, 1H), 10.60(s, 1H). LRMS: m/z(ES⁺) 440[MH⁺]. Microanalysis: Found: C, 61.80; H, 6.62; N, 15.31; C₂₃H₂₉N₅O₄ 0.4H₂O requires C, 61.84; H, 6.72; N, 15.68% |
| 57² (a) | 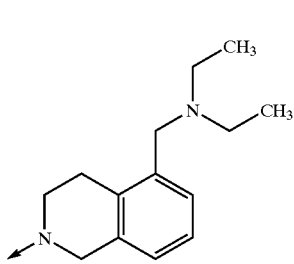 | 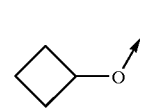 | 34 | ¹H-NMR(DMSOd₆, 400 MHz) δ: 0.95(t, 6H), 1.65(m, 1H), 1.79(m, 1H), 2.09(m, 2H), 2.44(m, 6H), 3.93(t, 2H), 3.48(s, 2H), 3.80(m, 2H), 4.69(t, 2H), 4.77(s, 2H), 5.92(d, 1H), 6.29(d, 1H), 7.10(m, 3H). LRMS: m/z(ES⁺) 463[MH⁺] |
| 58 (a) | 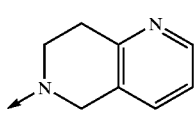 | 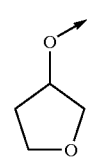 | 65 | ¹H-NMR(DMSOd₆, 400 MHz) δ: 2.01(m, 1H), 2.17(m, 1H), 2.96(t, 2H), 3.83(m, 9H), 4.79(s, 2H), 4.99(m, 1H), 6.14(s, 1H), 6.25(s, 1H), 7.20(m, 1H), 7.60(d, 1H), 8.38(d, 1H), 10.70(s, 1H) LRMS: m/z(ES⁺) 417[MNa⁺] Microanalysis: Found: C, 63.10; H, 5.72; N, 13.66; C₂₁H₂₂N₄O₄ 0.25H₂O requires; C, 63.23; H, 5.68; N, 14.04% |
| 59 (a) |  | 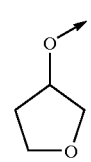 | 82 | ¹H-NMR(DMSOd₆, 400 MHz) δ: 2.02(m, 1H), 2.14(m, 1H), 2.72(t, 2H), 3.26(s, 3H), 3.38(m, 2H), 3.42(m, 2H), 3.85(m, 9H), 4.56(s, 2H), 4.99(m, 1H), 6.12(s, 1H), 6.21(s, 1H), 6.36(m, 2H), 7.18(d, 1H), 10.67(s, 1H). LRMS: m/z(ES⁺) 490[MNa⁺] Microanalysis: Found: C, 61.05; H, 6.21; N, 14.68; C₂₄H₂₉N₅O₅ 0.25H₂O requires; C, 61.07; H, 6.30; N, 14.84% |

-continued

| Ex No. (Method) | R1 | R2 | Yield % | Spectroscopic and analytical data |
|---|---|---|---|---|
| 60 (a) | 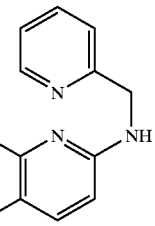 | 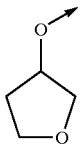 | 84 | $^1$H-NMR(DMSOd$_6$, 400 MHz) δ: 2.01(m, 1H), 2.15(m, 1H), 2.70(m, 2H), 3.82(m, 9H), 4.53(d, 2H), 4.59(s, 2H), 4.99(m, 1H), 6.12,(s, 1H), 6.23(s, 1H), 6.41(d, 1H), 6.83(s, 1H), 7.20(m, 2H), 7.32(d, 1H), 7.68(m, 1H), 8.47(d, 1H), 10.55(s, 1H). LRMS: m/z(ES$^+$) 501[MH$^+$]. Microanalysis: Found: C, 63.97; H, 5.68; N, 16.28; $C_{27}H_{28}N_6O_4$ 0.4H$_2$O requires; C 63.87; H, 5.68; N, 16.55% |
| 61$^D$ (a) | 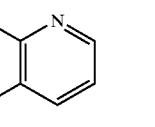 | 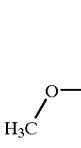 | 71 | $^1$H-NMR(DMSOd$_6$, 400 MHz) δ: 2.96(t, 2H), 3.36(s, 3H), 3.68(t, 2H), 3.79(s, 3H), 3.94(t, 2H), 4.09(t, 2H), 4.80(s, 2H), 6.20(d, 1H), 6.32(s, 1H), 7.20(m, 1H), 7.60(d, 1H), 8.38(d, 1H). LRMS: m/z(ES$^+$) 383[MH$^+$]. Microanalysis: Found: C, 61.94; H, 5.80; N, 14.16; $C_{20}H_{22}N_4O_4$ 0.3H$_2$O requires; C, 61.85; H, 5.88; N, 14.43% |
| 62$^D$ (a) | 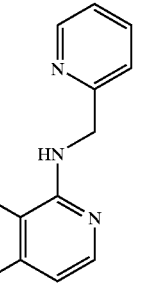 | 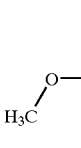 | 89 | $^1$H-NMR(DMSOd$_6$, 400 MHz) δ: 2.60(m, 2H), 3.37(s, 3H), 3.68(m, 2H), 3.80(s, 3H), 3.92(m, 2H), 4.09(m, 2H), 4.66(s, 4H), 6.20(s, 1H), 6.33(s, 1H), 6.40(d, 1H), 6.54(m, 1H), 7.15(m, 1H), 7.23(m, 1H), 7.63(m, 1H), 6.75(d, 1H), 8.46(d, 1H). LRMS: m/z(ES$^+$) 489[MH$^+$]. Microanalysis: Found: C, 63.41; H, 5.89; N, 16.67; $C_{26}H_{28}N_6O_4$ 0.25H$_2$O requires; C, 63.34; H, 5.83; N, 17.04% M.p. 216–218° C. |
| 63$^D$ (c) |  | 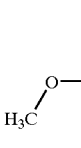 | 74 | $^1$H-NMR(DMSOd$_6$, 400 MHz) δ: 2.72(t, 2H), 3.26(s, 3H), 3.38(m, 5H), 3.41(m, 2H), 3.68(t, 2H), 3.80(s, 3H), 3.85(t, 2H), 4.09(t, 2H), 4.55(s, 2H), 6.19(s, 1H), 6.32(s, 1H), 6.36(d, 2H), 7.15(d, 1H) LRMS: m/z(ES$^+$) 456[MH$^+$] Microanalysis: Found: C, 60.44; H, 6.42; N, 15.27; $C_{23}H_{29}N_5O_5$ requires; C, 60.65; H, 6.42; N, 15.37% |
| 64$^D$ (a) | 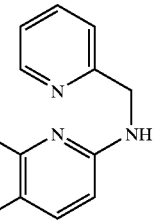 | 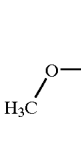 | 92 | $^1$H-NMR(DMSOd$_6$, 400 MHz) δ: 2.69(t, 2H), 3.35(s, 3H), 3.69(t, 2H), 3.80(s, 3H), 3.84(t, 2H), 4.09(t, 2H), 4.53(d, 2H), 4.58(s, 2H), 6.19(s, 1H), 6.32(s, 1H), 6.41(d, 1H), 6.83(t, 1H), 7.20(m, 2H), 7.31(d, 1H), 7.69(m, 1H), 8.48(d, 1H) LRMS: m/z(ES$^+$) 489[MH$^+$] Microanalysis: Found: C, 63.35; H, 5.83; N, 17.84; $C_{26}H_{28}N_6O_4$ 0.25H$_2$O requires; C, 63.34; H, 5.83; N, 17.04% |
| 65$^D$ (a) | 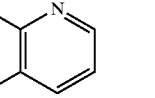 |  | 75 | $^1$H-NMR(DMSOd$_6$, 400 MHz) δ: 0.40(m, 2H), 0.52(m, 2H), 1.21(m, 1H), 2.95(t, 2H), 3.79(s, 3H), 3.88(d, 2H), 3.92(t, 2H), 4.79(s, 2H), 6.18(s, 1H), 6.31(s, 1H), 7.20(m, 1H), 7.60(d, 1H), 8.35(d, 1H), 10.75(s, 1H). LRMS: m/z(ES$^+$) 379[MH$^+$]. Microanalysis: Found: C, 66.34; H, 5.91; N, 14.60; $C_{21}H_{22}N_4O_3$ requires; C, 66.65; H, 5.86; N, 14.80%. M.p. 191–193° C. |

| Ex No. (Method) | R1 | R2 | Yield % | Spectroscopic and analytical data |
|---|---|---|---|---|
| 66<sup>D</sup> (a) | [2-(pyridin-2-ylmethylamino)-5,6,7,8-tetrahydro-2,7-naphthyridin-1-yl, attached via N7] | cyclopropylmethoxy | 76 | <sup>1</sup>H-NMR(DMSOd$_6$, 400 MHz) δ: 0.39(d, 2H), 0.52(d, 2H), 1.22(m, 1H), 2.60(m, 2H), 3.79(s, 3H), 3.89(d, 2H), 3.92(m, 2H), 4.66(s, 4H), 6.17(s, 1H), 6.32(s, 1H), 6.39(d, 1H), 6.52(m, 1H), 7.18(m, 1H), 7.22(m, 1H), 7.63(m, 1H), 7.74(d, 1H), 8.46(d, 1H). LRMS: m/z(ES<sup>+</sup>) 485[MH<sup>+</sup>]. Microanalysis: Found: C, 65.29; H, 5.96; N, 16.83; C$_{27}$H$_{28}$N$_6$O$_3$ 0.67H$_2$O requires; C, 65.30; H, 5.95; N, 16.92%. M.p. 160–162° C. |
| 67 (a) | [2-(pyridin-2-ylmethylamino)-5,6,7,8-tetrahydro-1,6-naphthyridine, attached via N6] | cyclopropylmethoxy | 86 | <sup>1</sup>H-NMR(DMSOd$_6$, 400 MHz) δ: 0.38(d, 2H), 0.32(d, 2H), 1.20(m, 1H), 2.69(t, 2H), 3.77(s, 3H), 3.83(m, 4H), 4.52(d, 2H), 4.56(s, 2H), 6.14(s, 1H), 6.29(s, 1H), 6.40(d, 1H), 6.79(t, 1H), 7.19(d, 2H), 7.30(d, 1H), 7.68(m, 1H), 7.47(d, 1H). LRMS: m/z(ES<sup>+</sup>) 485[MH<sup>+</sup>] Microanalysis: Found: C, 66.60; H, 5.99; N, 16.93; C$_{27}$H$_{28}$N$_6$O$_3$ requires; C, 66.93; H, 5.82; N, 17.34%. M.p. 204–206° C. |
| 68 (a) | [2-(pyridin-2-ylmethylamino)-5,6,7,8-tetrahydro-1,6-naphthyridine, attached via N6] | isopropoxy | 86 | <sup>1</sup>H-NMR(DMSOd$_6$, 400 MHz) δ: 1.28(d, 6H), 2.72(s, 2H), 3.79(s, 3H), 3.83(t, 2H), 4.54(m, 5H), 6.15(s, 1H), 6.33(s, 1H), 6.20(d, 1H), 6.85(s, 1H), 7.20(d, 2H), 7.32(d, 1H), 7.70(m, 1H), 8.49(s, 1H), 10.63(s, 1H). LRMS: m/z(ES<sup>+</sup>) 473[MH<sup>+</sup>]. Microanalysis: Found: C, 65.27; H, 6.07; N, 17.30; C$_{26}$H$_{28}$N$_6$O$_3$ 0.3H$_2$O requires; C, 65.34; H, 6.03; N, 17.58%. M.p. 234–236° C. |
| 69<sup>D</sup> (c) | [5-((3S)-1-methylpyrrolidin-3-yloxy)-1,2,3,4-tetrahydroisoquinolin-2-yl] | cyclopropyl | 39 | <sup>1</sup>Hnmr(DMSOd$_6$, 400 MHz) δ: 0.64(m, 2H), 0.92(m, 2H), 1.76(m, 1H), 2.28(m, 4H), 2.40(m, 1H), 2.62(m, 2H), 2.70(m, 2H), 2.80(m, 1H), 3.50(m, 1H), 3.76(s, 3H), 3.83(t, 2H), 4.73(s, 2H), 4.84(m, 1H), 6.13(s, 1H), 6.52(s, 1H), 6.74(m, 2H), 7.12(dd, 1H), 11.00(s, 1H). LRMS: m/z(ES<sup>+</sup>) 447[MH<sup>+</sup>] Microanalysis found: C, 68.72; H, 6.76; N, 12.22. C$_{26}$H$_{30}$N$_4$O$_3$; 0.4H$_2$O requires; C, 68.82; H, 6.84; N, 12.35%. |
| 70<sup>D</sup> (c) | [5-((3R)-1-methylpyrrolidin-3-yloxy)-1,2,3,4-tetrahydroisoquinolin-2-yl] | cyclopropyl | 8 | <sup>1</sup>Hnmr(DMSOd$_6$, 400 MHz) δ: 0.61(m, 2H), 0.88(m, 2H), 1.76(m, 1H), 2.24(m, 4H), 2.27(s, 3H), 2.40(m, 1H), 2.62(m, 2H), 2.67(m, 2H), 2.82(m, 1H), 3.46(m, 1H), 3.73(s, 3H), 3.79(t, 2H), 4.70(s, 2H), 4.82(m, 1H), 6.13(s, 1H), 6.52(s, 1H), 6.71(m, 2H), 7.09(dd, 1H), 11.00(s, 1H). LRMS: m/z(ES<sup>+</sup>) 447[MH<sup>+</sup>] Microanalysis found: C, 68.40; H, 6.85; N, 12.19. C$_{26}$H$_{30}$N$_4$O$_3$; 0.5H$_2$O requires; C, 68.55; H, 6.86; N, 12.30%. |

| Ex No. (Method) | R1 | R2 | Yield % | Spectroscopic and analytical data |
|---|---|---|---|---|
| 71<sup>D</sup> (a) | 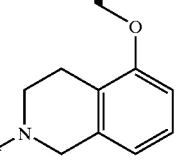 |  | 84 | ¹Hnmr(DMSOd₆, 400 MHz) δ: 0.65(m, 2H), 0.93(m, 2H), 1.60(m, 1H), 1.68(m, 2H), 1.95(m, 1H), 2.20(m, 1H), 2.38(s, 3H), 2.60(m, 1H), 2.73(m, 2H), 2.96(m, 1H), 3.49(m, 1H), 3.76(s, 3H), 3.83(m, 3H), 3.94(m, 1H), 4.75(s, 2H), 6.14(s, 1H), 6.52(s, 1H), 6.78(m, 2H), 7.14(dd, 1H), 11.00(s, 1H). LRMS: m/z(ES⁺) 461[MH⁺]. Microanalysis found: C, 70.30; H, 7.04; N, 12.09. $C_{27}H_{32}N_4O_3$ requires; C, 70.41; H, 7.00; N, 12.16%. |
| 72<sup>D</sup> (a) | 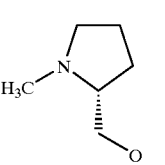 |  | 73 | ¹Hnmr(DMSOd₆, 400 MHz) δ: 0.63(m, 2H), 0.92(m, 2H), 1.60(m, 1H), 1.67(m, 2H), 1.95(m, 1H), 2.20(m, 1H), 2.37(s, 3H), 2.60(m, 1H), 2.72(t, 2H), 2.95(m, 1H), 3.49(m, 1H), 3.75(s, 3H), 3.82(m, 3H), 3.94(m, 1H), 4.73(s, 2H), 6.12(s, 1H), 6.51(s, 1H), 6.78(m, 2H), 7.12(dd, 1H), 10.97(s, 1H). LRMS: m/z(ES⁻) 459[M − H⁻]. Microanalysis found: C, 69.80; H, 7.07; N, 12.01. $C_{27}H_{32}N_4O_3$; $0.25H_2O$ requires; C, 69.73; H, 7.04; N, 12.05%. |
| 73<sup>D,3</sup> (b) | 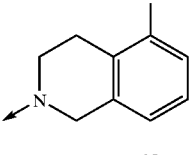 |  | 87 | ¹Hnmr(DMSOd₆, 400 MHz) δ: 0.64(m, 2H), 0.95(m, 2H), 2.40(s, 3H), 2.92(t, 2H), 3.50(m, 1H), 3.78(s, 3H), 3.95(t, 2H), 4.78(s, 2H), 6.17(s, 1H), 6.56(s, 1H), 7.07(d, 1H), 7.50(d, 1H), 11.12(s, 1H). LRMS: m/z(ES⁺) 363[MH⁺]. Microanalysis found: C, 66.98; H, 6.07; N, 14.70. $C_{21}H_{22}N_4O_2$; $0.70H_2O$ requires; C, 67.25; H, 6.29; N, 14.94%. |
| 74 (b) | 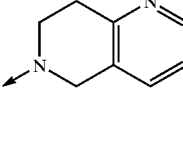 |  | 95 | ¹Hnmr(CDCl₃, 400 MHz) δ: 0.71(m, 2H), 0.97(m, 2H), 1.80–2.00(m, 4H), 2.07(m, 2H), 2.33(s, 3H), 3.00(m, 1H), 3.10(t, 2H), 3.39(m, 1H), 3.85(s, 3H), 4.02(t, 2H), 4.84(s, 2H), 6.29(s, 1H), 6.65(s, 1H), 7.07(d, 1H), 7.40(d, 1H), 10.03(m, 1H). LRMS: m/z(ES⁺) 447[MH⁺] Microanalysis found: C, 67.44; H, 6.96; N, 14.92. $C_{26}H_{31}N_5O_2$; $0.25CH_2Cl_2$ requires; C, 67.54; H, 6.80; N, 15.00%. |
| 75<sup>D</sup> (b) | 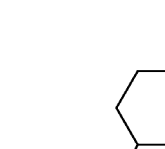 |  | 35 | ¹Hnmr(DMSOd₆, 400 MHz) δ: 0.65(m, 2H), 0.95(m, 2H), 2.61(t, 2H), 2.94(t, 2H), 3.50(m, 3H), 3.75(s, 2H), 3.78(s, 3H), 3.95(t, 2H), 4.48(m, 1H), 4.78(s, 2H), 6.15(s, 1H), 6.53(s, 1H), 7.25(d, 1H), 7.57(d, 1H). Microanalysis found: C, 64.10; H, 6.49; N, 16.10. $C_{23}H_{27}N_5O_3$; $0.5H_2O$ requires; C, 65.54; H, 6.46; N, 16.62%. |
| 76<sup>D</sup> (b) | 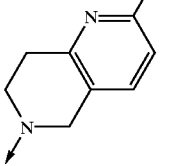 |  | 16 | ¹Hnmr(CDCl₃, 400 MHz) δ: 0.75(m, 2H), 0.99(m, 2H), 2.37(bs, 3H), 2.68(m, 2H), 3.14(t, 2H), 3.36(s, 3H), 3.39(m, 1H), 3.57(m, 2H), 3.73(m, 2H), 3.84(s, 3H), 4.03(t, 2H), 4.88(s, 2H), 6.30(s, 1H), 6.68(s, 1H), 7.38(m, 1H), 7.45(d, 1H), 10.37(bs, 1H). LRMS: m/z(ES⁺) 472[MNa⁺]. Microanalysis found: C, 65.82; H, 7.06; N, 15.01. $C_{25}H_{31}N_5O_3$; $0.3H_2O$ requires; C, 66.00; H, 7.00; N, 15.39%. |

-continued

| Ex No. (Method) | R1 | R2 | Yield % | Spectroscopic and analytical data |
|---|---|---|---|---|
| 77<sup>D</sup> (b) | *methoxy-azetidinyl-methyl-tetrahydronaphthyridine* | *cyclopropyl* | 30 | ¹Hnmr(CDCl₃, 400 MHz) δ: 0.75(m, 2H), 1.00(m, 2H), 3.05(m, 2H), 3.28(s, 3H), 3.40(m, 1H), 3.64(m, 1H), 3.83(s, 3H), 3.97(m, 2H), 4.14(m, 2H), 4.24(m, 2H), 4.83(s, 2H), 6.33(d, 1H), 6.65(s, 1H), 7.06(d, 1H), 8.38(d, 1H). LRMS: m/z(ES⁺) 448.8[MH⁺]. Microanalysis found: C, 65.15; H, 6.56; N, 14.92. C₂₅H₂₉N₅O₃; 0.75H₂O requires; C, 65.13; H, 6.67; N, 15.19%. |
| 78<sup>D</sup> (b) | *methoxy-pyrrolidinyl-methyl-tetrahydronaphthyridine* | *cyclopropyl* | 26 | ¹Hnmr(CDCl₃, 400 MHz) δ: 0.78(m, 2H), 1.01(m, 2H), 2.22(m, 2H), 3.18(m, 2H), 3.37(s, 3H), 3.40(m, 2H), 3.84(s, 3H), 4.02(m, 3H), 4.21(m, 1H), 4.90(s, 2H), 6.32(s, 1H), 6.65(s, 1H), 7.10(d, 1H), 8.38(d, 1H). LRMS: m/z(ES⁺) 462.9[MH⁺]. Microanalysis found: C, 63.38; H, 6.60; N, 14.15. C₂₆H₃₁N₅O₃; 0.45CH₂Cl₂ requires C, 63.56; H, 6.94; N, 14.01%. |
| 79 (a) | *oxabicyclic-amine-methyl-tetrahydronaphthyridine* | *cyclopropyl* | 51 | ¹Hnmr(DMSOd₆, 400 MHz) δ: 0.55(m, 2H), 0.93(m, 2H), 1.55(m, 1H), 1.75(m, 1H), 2.72(m, 1H), 3.00(m, 1H), 3.28–3.38(m, 4H), 3.50(m, 2H), 3.76(m, 5H), 3.90(m, 2H), 4.28(s, 2H), 4.80(s, 2H), 6.18(d, 1H), 6.56(d, 1H), 7.13(d, 1H), 8.24(d, 1H), 11.09(s, 1H). LRMS: m/z(ES⁺) 460[MH⁺] Microanalysis found: C, 67.26; H, 6.42; N, 15.02. C₂₆H₂₉N₅O₃; 0.25H₂O requires; C, 67.96; H, 6.36; N, 15.24%. |
| 80 (a) | *methoxy-methyl-N-methyl-aminomethyl-tetrahydropyridopyrimidine* | *cyclopropyl* |  | ¹Hnmr(CDCl₃, 400 MHz) δ: 0.68(m, 2H), 0.95(m, 2H), 1.03(d, 3H), 2.32(s, 3H), 2.98(m, 1H), 3.02(t, 2H), 3.26(m, 5H), 3.50(m, 1H), 3.80(s, 3H), 3.82(s, 2H), 2.99(t, 2H), 4.83(s, 2H), 6.27(d, 1H), 6.62(d, 1H), 8.48(s, 1H). LRMS: m/z(ES⁺) 487[MNa⁺] |
| 81 (a) | *methoxy-piperidinyl-methyl-tetrahydropyridopyrimidine* | *cyclopropyl* |  | ¹Hnmr(DMSOd₆ + TFAd, 400 MHz) δ: 0.78(m, 2H), 1.02(m, 2H), 1.18(m, 4H), 3.07(m, 4H), 3.17(t, 2H), 3.22(s, 3H), 3.30(m, 1H), 3.54(m, 1H), 3.82(s, 3H), 4.12(t, 2H), 4.60(m, 2H), 5.03(s, 2H), 6.44(s, 1H), 7.08(s, 1H), 8.76(s, 1H). LRMS: m/z(ES⁺) 477[MH⁺] |

| Ex No. (Method) | R1 | R2 | Yield % | Spectroscopic and analytical data |
|---|---|---|---|---|
| 82 (b) | *cyclopropylmethyl-substituted imidazo-tetrahydropyrazine* | *cyclopropyl* | 32 | ¹Hnmr(CDCl₃, 400 MHz) δ: 0.20(m, 2H), 0.57(m, 2H), 0.72(m, 2H), 1.00(m, 2H), 2.60(d, 2H), 3.32(m, 1H), 3.85(s, 3H), 4.03(t, 2H), 4.13(t, 2H), 4.91(s, 2H), 6.37(d, 1H), 6.65(s, 1H), 6.77(s, 1H). LRMS: m/z(ES⁺) 392[MH⁺] |
| 83ᴅ (a) | *morpholinyl-imidazo-tetrahydropyrazine* | *cyclopropyl* | 80 | ¹Hnmr(DMSOd₆, 400 MHz) δ: 0.65(m, 2H), 0.93(m, 2H), 2.95(m, 4H), 3.49(m, 1H), 3.69(m, 4H), 3.77(s, 3H), 3.90(t, 2H), 3.92(t, 2H), 4.76(s, 2H), 6.17(d, 1H), 6.50(s, 1H), 6.54(d, 1H), 11.12(s, 1H). LRMS: m/z(ES⁺) 445[MNa⁺] Microanalysis found: C, 62.44; H, 6.21; N, 19.60. $C_{22}H_{26}N_6O_3$ requires; C, 62.54; H, 6.20; N, 19.89%. |
| 84ᴅ (a) | *bridged morpholine-naphthyridine* | *cyclopropyl* | 66 | ¹H-NMR(DMSOd₆, 400 MHz) δ: 0.66(m, 2H), 0.93(m, 2H), 1.59(d, 1H), 1.80(d, 1H), 2.45(d, 1H), 2.76(d, 1H), 2.94(t, 2H), 3.47(s, 1H), 3.52(d, 2H), 3.77(m, 5H), 3.01(d, 1H), 3.95(t, 2H), 4.33(s, 1H), 4.78(s, 2H), 6.14(d, 1H), 6.53(d, 1H), 7.29(d, 1H), 7.56(d, 1H), 11.09(s, 1H). LRMS: m/z(ES⁺) 482[MNa⁺] Microanalysis: Found: C, 67.67; H, 6.38; N, 15.12; $C_{26}H_{29}N_5O_3$ requires; C, 67.96; H, 6.36; N, 15.24% |
| 85ᴅ (c) | *morpholinylmethyl-naphthyridine* | *cyclohexyl* | 70 | ¹H-NMR(DMSOd₆, 400 MHz) δ: 1.30(m, 5H), 1.79(m, 5H), 2.38(m, 4H), 2.94(t, 2H), 3.52(s, 2H), 3.57(m, 4H), 3.79(s, 3H), 3.93(t, 2H), 4.14(t, 1H), 4.77(s, 2H), 6.57(m, 2H), 7.27(d, 1H), 7.57(d, 1H), 11.03(s, 1H). LRMS: m/z(APCl⁺) 490[MH⁺]. Microanalysis: Found: C, 68.84; H, 7.33; N, 14.18; $C_{28}H_{35}N_5O_3$ requires; C, 68.69; H, 7.21; N, 14.30% M.p. 233–235° C. |
| 86ᴅ (a) | H₃C–O–CH₂CH₂–NH– *naphthyridine* | (CH₃)₂CH– (isopropyl) | 76 | ¹H NMR(DMSOd₆, 400 MHz) δ: 1.16(d, 6H), 2.72(t, 2H), 3.28(s, 3H), 3.39(m, 2H), 3.44(m, 2H), 3.80(s, 3H), 3.87(t, 2H), 4.54(m, 3H), 6.19(s, 1H), 6.38(d, 1H), 6.58(2xs, 2H), 7.15(d, 1H), 10.84(s, 1H) LRMS: m/z(ES⁺) 424[MH⁺] Microanalysis: Found: C, 65.18; H, 7.00; N, 16.41; $C_{23}H_{29}N_5O_3$ requires; C, 65.23; H, 6.90; N, 16.54% M.p. 160–162° C. |

ᴅN,N-Diisopropylethylamine was used as the base
¹N-(1,2,3,4-tetrahydro-5-isoquinolinyl)methanesulfonamide (WO 9830560) was used as the starting amine.
²N,N-diethyl-N-(1,2,3,4-tetrahydro-5-isoquinolinylmethyl)amine (WO 9830560) was used as the starting amine
³2-methyl-5,6,7,8-tetrahydro[1,6]naphthyridine (Chem. Pharm. Bull. 1984; 32(7); 2522) was used as the starting amine

EXAMPLE 87

5-Isopropyl-7-methoxy-2-(5-morpholin-4-ylmethyl-3,4-dihydro-1H-[2,6]naphthyridin-2-yl)-3H-quinazolin-4-one dihydrochloride

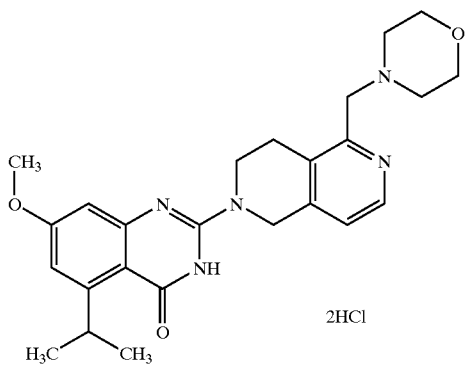

The chloro compound from preparation 269 (76 mg, 0.3 mmol) was mixed with the naphthyridine from preparation 117 (93 mg, 0.4 mmol) and N,N-diisopropylethylamine (129 µl, 1 mmol) in n-butanol (5 ml) and the mixture was heated under reflux for 2 hours. The reaction mixture was cooled to room temperature and ethyl acetate added. The solution was washed with water and brine then dried over magnesium sulphate. The residue was purified by chromatography on silica gel using methanol in dichloromethane as eluant (gradient from 0:100 to 7:93). The material obtained was dissolved in dichloromethane and ethereal hydrogen chloride (1M, 2 ml) was added. The solvent was evaporated under reduced pressure to give the title compound as on off white solid (73 mg).

$^1$H-NMR (DMSOd$_6$, 400 MHz) δ: 1.14 (d, 6H), 2.96 (t, 2H), 3.35 (m, 4H), 3.82 (s, 3H), 3.91 (m, 4H), 4.00 (t, 2H), 4.51 (m, 1H), 4.55 (s, 2H), 4.95 (s, 2H), 6.68 (s, 1H), 6.91 (s, 1H), 7.33 (d, 1H), 8.47 (d, 1H) LRMS: m/z (ES$^+$) 450 [MH$^+$]Microanalysis: Found: C, 57.77; H, 6.65; N, 13.25. C$_{25}$H$_{31}$N$_5$O$_3$ 2HCl requires; C, 57.47; H, 6.37; N, 13.40%

EXAMPLES 88 TO 122

The compounds of the following tabulated examples, (where n represents 1, 2 or 3 depending on the nature of R1), of the general formula:

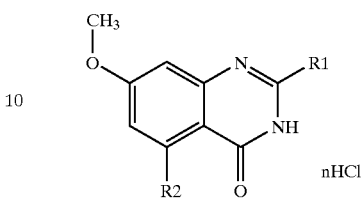

were prepared by the general method outlined below using the appropriate chloro compound and the cyclic amine.

General Procedure for Hydrochloride Salts.

To a solution of the chloro-quinazolinone (1 eq) in n-butanol (15 ml per mmol) under nitrogen was added N,N-diisopropylethylamine or triethylamine (1.7–8 eq) and the appropriate secondary amine (1–2 eq). The resultant mixture was then heated under reflux for 1–6 hours, cooled and the product was isolated by filtration, washing with n-butanol and diethyl ether (method a)

Some reaction mixtures were concentrated under reduced pressure, the residue partitioned between dichloromethane and water, the organic phase separated, dried (MgSO$_4$) and evaporated under reduced pressure, (method b).

Some products were additionally purified by column chromatography on silica gel using dichloromethane: methanol or dichloromethane: methanol: 0.88 ammonia as eluants, (method c).

The products that were obtained were dissolved in dichloromethane and ethereal hydrogen chloride solution was added. The solvents were evaporated under reduced pressure to give the product as the hydrochloride salt.

In the table following:

| Ex No. (method) | R1 | R2 | Yield % | Spectroscopic and analytical data |
|---|---|---|---|---|
| 88 (c) | H$_3$C-O-CH$_2$CH$_2$-N(CH$_3$)-CH$_2$-[tetrahydronaphthyridinyl] | (I) | 55 | $^1$H-NMR (DMSOd$_6$, 400 MHz) δ: 1.17 (d, 6H), 2.87 (s, 3H), 2.96 (t, 2H), 3.26 (s, 3H), 3.40 (t, 2H), 3.73 (t, 2H), 3.82 (s, 3H), 4.09 (t, 2H), 4.42 (m, 1H), 4.54 (s, 2H), 5.07 (s, 2H), 6.78 (s, 1H), 7.29 (d, 1H), 7.41 (s, 1H), 8.43 (d, 1H). LRMS: m/z (ES$^+$) 452 [MH$^+$] Microanalysis: Found: C, 55.84; H, 6.85; N, 12.82. C$_{25}$H$_{33}$N$_5$O$_3$ 2HCl 0.75 H$_2$O requires; C, 55.81; H, 6.84; N, 13.02% |
| 89 (c) | pyrrolidinyl-CH$_2$-[tetrahydropyridopyrimidinyl] | (I) | 41 | $^1$H-NMR (DMSOd$_6$, 400 MHz) δ: 1.25 (d, 6H), 1.88 (s, 4H), 2.85 (s, 4H), 3.14 (t, 2H), 3.88 (s, 3H), 4.06 (m, 4H), 4.57 (m, 1H), 4.91 (s, 2H), 6.72 (d, 1H), 6.76 (d, 1H), 6.55 (s, 1H). LRMS: m/z (ES$^+$) 435 [MH$^+$] |

-continued

| Ex No. (method) | R1 | R2 | Yield % | Spectroscopic and analytical data |
|---|---|---|---|---|
| 90<sup>D</sup> (a) | [structure: 1-amino-5,6,7,8-tetrahydro-2,7-naphthyridine] | (I) | 91 | $^1$H NMR (DMSOd$_6$, 400 MHz) δ: 1.16 (d, 6H), 2.66 (t, 2H), 3.80 (s, 3H), 3.98 (t, 2H), 4.50 (m, 1H), 4.88 (s, 2H), 6.70 (s, 1H), 6.77 (d, 1H), 6.88 (s, 1H), 7.83 (d, 1H), 7.93 (s, 2H). LRMS: m/z (ES$^+$) 444 [MH$^+$] |
| 91 (a) | [structure: methoxyethylamino pyrido-pyrimidine with NH$_2$] | (I) | 77 | $^1$H NMR (DMSOd$_6$, 400 MHz) δ: 1.18 (d, 6H), 2.82 (m, 2H), 3.27 (s, 3H), 3.46 (m, 2H), 3.51 (m, 2H), 3.80 (s, 3H), 4.00 (t, 2H), 4.48 (m, 1H), 4.60 (s, 2H), 6.79 (s, 1H), 7.30 (s, 1H), 7.68 (s, 2H), 8.45 (s, 1H). LRMS: m/z (ES$^+$) 440 [MH$^+$]. Microanalysis: Found: C, 51.50; H, 6.13; N, 18.97; C$_{22}$H$_{29}$N$_7$O$_3$ 2 HCl requires: C, 51.57; H, 6.10; N, 19.13% |
| 92 (a) | [structure: methylamino naphthyridine] | (I) | 78 | $^1$H NMR (DMSOd$_6$, 400 MHz) δ: 1.19 (d, 6H), 3.00 (s, 3H), 3.13 (m, 2H), 3.82 (s, 3H), 4.07 (m, 2H), 4.42 (m, 1H), 4.83 (s, 2H), 6.80 (d, 1H), 6.98 (d, 1H), 7.37 (s, 1H), 7.69 (d, 1H). LRMS: m/z (ES$^+$) 480 [MH$^+$] |
| 93 (a) | [structure: N-ethyl-N-methylamino pyrido-pyrimidine] | (I) | 73 | $^1$H NMR (DMSOd$_6$, 400 MHz) δ: 1.19 (m, 9H), 3.00 (m, 2H), 3.28 (s, 3H), 3.70 (q, 2H), 3.84 (s, 3H), 3.94 (m, 2H), 4.48 (m, 1H), 4.95 (s, 2H), 6.75 (s, 1H), 7.08 (s, 1H), 8.60 (s, 1H). LRMS: m/z (ES$^+$) 409 [MH$^+$]. Microanalysis: Found: C, 54.90; H, 6.49; N, 17.41 C$_{22}$H$_{28}$N$_6$O$_2$ 2HCl requires; C, 54.89; H, 6.28; N, 17.46% |
| 94 (a) | [structure: 3-methoxyazetidinyl-methyl tetrahydroisoquinoline] | (I) | 35 | $^1$H NMR (DMSOd$_6$, 400 MHz) δ: 1.17 (d, 6H), 3.03 (m, 2H), 3.25 (s, 2H), 3.40 (s, 2H), 3.82 (s, 3H), 3.97 (m, 4H), 4.26 (m, 3H), 4.43 (s, 1H), 4.52 (m, 1H), 4.90 (s, 2H), 6.90 (s, 1H), 7.30 (m, 3H). LRMS: m/z (ES$^+$) 449 [MH$^+$]. Microanalysis: Found: C, 58.97; H, 6.63; N, 10.60 C$_{26}$H$_{32}$N$_4$O$_3$ 2HCl 0.4 H$_2$O requires; C, 59.07; H, 6.63; N, 10.60% |
| 95 (c) | [structure: pyridin-2-ylmethylamino naphthyridine] | (I) | 61 | $^1$H NMR (DMSOd$_6$, 400 MHz) δ: 1.17 (d, 6H), 2.82 (m, 2H), 3.82 (s, 3H), 4.13 (m, 2H), 4.44 (m, 1H), 5.00 (s, 4H), 6.75 (d, 1H), 6.79 (s, 1H), 7.32 (s, 1H), 7.54 (m, 1H), 7.68 (d, 1H), 7.78 (d, 1H), 8.07 (m, 1H), 8.63 (d, 1H). LRMS: m/z (ES$^+$) 457 [MH$^+$]. Microanalysis: Found: C, 54.01; H, 5.75; N, 14.06; C$_{26}$H$_{28}$N$_6$O$_2$ 3HCl 0.6 H$_2$O requires; C, 54.15; H, 5.63; N, 14.57% |
| 96 (c) | [structure: methoxyethylamino-methyl tetrahydroisoquinoline] | (I) | 56 | $^1$H-NMR (CDCl$_3$, 400 MHz) δ: 1.23 (d, 6H), 2.82 (t, 2H), 3.06 (t, 2H), 3.34 (s, 3H), 3.50 (t, 2H), 3.80 (s, 3H), 3.86 (m, 4H), 4.76 (m, 1H), 4.80 (s, 2H), 6.70 (s, 2H), 7.10 (m, 1H), 7.20 (m, 2H). LRMS: m/z (ES$^+$) 437 [MH$^+$]. Microanalysis: Found: C, 55.36; H, 6.78; N, 10.14. C$_{25}$H$_{32}$N$_4$O$_3$ 2HCl 0.5 CH$_2$Cl$_2$ requires; C, 55.49; H, 6.39; N, 10.15% |

-continued

| Ex No. (method) | R1 | R2 | Yield % | Spectroscopic and analytical data |
|---|---|---|---|---|
| 97 (c) | *(structure: N,N-dimethylaminoethylamino-tetrahydronaphthyridine)* | (I) | 65 | ¹H-NMR (DMSOd₆, 400 MHz) δ: 1.16 (d, 6H), 2.82 (s, 6H), 2.89 (m, 2H), 3.38 (t, 2H), 3.84 (s, 3H), 4.04 (m, 2H), 4.09 (m, 2H), 4.43 (m, 1H), 4.90 (s, 1H), 5.02 (s, 2H), 6.78 (m, 2H), 7.30 (s, 1H), 7.80 (d, 1H), 8.41 (s, 1H), 10.80 (s, 1H). LRMS: m/z (ES⁺) 437 [MH⁺]. Microanalysis: Found: C, 52.19; H, 6.79; N, 14.92; C₂₄H₃₂N₆O₃ 3HCl 0.5 H₂O requires; C, 51.94; H, 6.54; N, 15.14% |
| 98 (c) | *(structure: N,N-dimethylaminomethyl-tetrahydroisoquinoline)* | (I) | 40 | ¹H-NMR (CDCl₃, 400 MHz) δ: 1.24 (d, 6H), 2.20 (s, 6H), 3.09 (t, 2H), 3.38 (s, 2H), 3.85 (m, 5H), 4.56 (m, 1H), 4.80 (s, 2H), 6.70 (s, 2H), 7.15 (m, 3H). LRMS: m/z (ES⁺) 407 [MH⁺] |
| 99 (a) | *(structure: 4-amino-2-dimethylamino-pyrido-pyrimidine)* | A | 66 | ¹H-NMR (DMSOd₆, 400 MHz) δ: 1.17 (d, 6H), 2.53 (m, 2H), 3.17 (s, 6H), 3.81 (s, 3H), 4.00 (m, 2H), 4.48 (m, 1H), 4.85 (s, 2H), 6.78 (s, 1H), 7.12 (s, 1H). LRMS: m/z (ES⁺) 410 [MH⁺]. Microanalysis: Found: C, 50.81; H, 6.16; N, 19.44; C₂₁H₂₇N₇O₂ 2HCl 0.75 H₂O requires; C, 50.86; H, 6.20; N, 19.77% |
| 100 (a) | *(structure: 4-(2-methoxyethylamino)-2-dimethylamino-pyrido-pyrimidine)* | (I) | 99 | ¹H-NMR (DMSOd₆, 400 MHz) δ: 1.16 (d, 6H), 3.16 (s, 6H), 3.24 (s, 3H), 3.50 (t, 2H), 3.59 (t, 3H), 3.80 (s, 3H), 3.90 (m, 2H), 4.50 (m, 1H), 4.73 (s, 2H), 6.72 (s, 1H), 6.80 (s, 1H), 8.38 (t, 1H). LRMS: m/z (ES⁺) 468 [MH⁺]. Microanalysis: Found: C, 53.27; H, 6.66; N, 17.99 C₂₄H₃₃N₇O₃ 2HCl requires; C, 53.33; H, 6.53; N, 18.14% |
| 101ᴰ (a) | *(structure: 4-methoxypiperidinylmethyl-tetrahydronaphthyridine)* | (I) | 55 | ¹H-nmr (CD₃OD, 400 MHz) δ: 1.23 (d, 6H), 2.04 (m, 2H), 2.13 (m, 2H), 3.03 (m, 2H), 3.39 (m, 5H), 3.50 (m, 2H), 3.62 (m, 1H), 3.93 (s, 3H), 4.07 (m, 2H), 4.49 (m, 1H), 4.55 (s, 2H), 4.98 (s, 2H), 6.91 (s, 1H), 6.99 (s, 1H), 7.35 (d, 1H), 8.53 (d, 1H). LRMS: m/z (ES⁺) 478 [MH⁺]. Microanalysis found: C, 58.97; H, 6.92; N, 12.71; C₂₇H₃₅N₅O₃ 2 HCl requires C, 58.91; H, 6.77; N, 12.72% |
| 102 (c) | *(structure: 3-methoxyazetidinylmethyl-tetrahydronaphthyridine)* | (I) | 45 | ¹H NMR (DMSOd₆, 400 MHz) δ: 1.18 (d, 6H), 1.26 (m, 2H), 2.91 (m, 2H), 3.25 (s, 3H), 3.82 (s, 3H), 4.08 (m, 4H), 4.32 (m, 1H), 4.41 (m, 1H), 4.64 (s, 2H), 5.04 (s, 2H), 6.78 (s, 1H), 7.23 (d, 1H), 7.10 (s, 1H), 8.38 (d, 1H), 10.78 (s, 1H). LRMS: m/z (ES⁺) 450 [MH⁺]. Microanalysis found: C, 55.62; H, 6.41; 12.78; C₂₅H₃₁N₅O₃ 2HCl H₂O requires; C, 55.56; H, 6.53; 12.96% |

-continued

| Ex No. (method) | R1 | R2 | Yield % | Spectroscopic and analytical data |
|---|---|---|---|---|
| 103 (b) | *(morpholinomethyl-tetrahydropyrido[3,4-d]pyrimidine)* | (I) | 63 | ¹H-NMR (CDCl₃, 400 MHz) δ: 1.25 (d, 6H), 2.59 (m, 4H), 3.14 (t, 2H), 3.76 (m, 6H), 3.88 (s, 3H), 4.00 (t, 2H), 4.54 (m, 1H), 4.89 (s, 2H), 6.71 (d, 1H), 6.76 (d, 1H), 8.57 (s, 1H), 9.75 (s, 1H). LRMS: m/z (ES⁺) 473 [MH⁺] Microanalysis: Found: C, 54.49; H, 6.41; N, 15.58. C₂₄H₃₀N₆O₃ 2 HCl 0.25 H₂O requires; C, 54.60; H, 6.20; N, 15.92% |
| 104 (c) | *(N,N-dimethylaminomethyl-tetrahydronaphthyridine)* | (I) | 40 | ¹H NMR (DMSOd₆, 400 MHz) δ: 1.18 (d, 6H), 2.87 (s, 6H), 2.95 (t, 2H), 3.83 (s, 3H), 4.08 (t, 2H), 4.46 (m, 1H), 4.52 (s, 2H), 5.04 (s, 2H), 6.72 (s, 1H), 7.31 (m, 2H), 8.46 (d, 1H). LRMS: m/z (ES⁺) 408 [MH⁺] Microanalysis: Found: C, 54.47; H, 6.62; N, 13.65. C₂₃H₂₉N₅O₂ 2HCl 1.5 H₂O requires C, 54.44; H, 6.75; N, 13.80% |
| 105 (c) | *(N,N-dimethylaminoethylamino-tetrahydronaphthyridine)* | (I) | 61 | ¹H NMR (DMSOd₆, 400 MHz) δ: 1.08 (d, 6H), 2.80 (s, 6H), 3.18 (s, 2H), 3.33 (t, 2H), 3.82 (s, 3H), 3.95 (m, 2H), 4.09 (m, 2H), 4.42 (m, 1H), 4.07 (s, 2H), 6.80 (s, 1H), 7.04 (d, 1H), 7.42 (s, 1H), 7.70 (d, 1H). LRMS: m/z (ES⁺) 437 [MH⁺] Microanalysis: Found: C, 51.75; H, 6.72; N, 14.93. C₂₄H₃₂N₆O₃ 3HCl 0.6 H₂O requires C, 51.78; H, 6.53; N, 15.09% |
| 106 (c) | *(2-methylimidazolylmethyl-tetrahydroisoquinoline)* | (I) | 88 | ¹H NMR (DMSOd₆, 400 MHz) δ: 1.20 (d, 6H), 2.60 (s, 3H), 2.96 (t, 2H), 3.86 (s, 3H), 4.08 (t, 2H), 4.42 (m, 1H), 5.05 (s, 2H), 5.42 (s, 2H), 6.80 (s, 1H), 6.84 (d, 1H), 7.26 (m, 2H), 7.41 (s, 1H), 7.58 (s, 2H). LRMS: m/z (ES⁺) 444 [MH⁺]. Microanalysis: Found: C, 59.19; H, 6.47; N, 13.28; C₂₆H₂₉N₅O₂ 2HCl 0.6 H₂O requires; C, 59.23; H, 6.16; 13.28% |
| 107 (c) | *(N-methyl-N-(2-methoxyethyl)aminomethyl-tetrahydropyrido[3,4-d]pyrimidine)* | (II) | 67 | ¹H NMR (DMSOd₆, 400 MHz) δ: 1.64 (m, 4H), 2.48 (s, 2H), 2.90 (s, 3H), 3.07 (t, 3H), 3.26 (s, 3H), 3.42 (t, 2H), 3.70 (t, 2H), 3.80 (s, 3H), 3.93 (m, 2H), 4.05 (t, 2H), 4.32 (m, 1H), 4.58 (s, 2H), 4.92 (s, 2H), 6.86 (s, 1H), 6.93 (s, 1H) 8.74 (s, 1H), 10.17 (s, 1H). LRMS: m/z (ES⁺) 495 [MH⁺]. Microanalysis found: C, 55.21; H, 6.59; N, 14.71; C₂₆H₃₄N₆O₄ 2HCl requires; C, 55.03; H, 6.39; N, 14.81% |
| 108 (a) | *(pyrrolidinylmethyl-tetrahydropyrido[3,4-d]pyrimidine)* | (II) | 57 | ¹H NMR (DMSOd₆, 400 MHz) δ: 1.64 (m, 4H), 1.98 (m, 4H), 3.12 (m, 4H), 3.42 (m, 2H), 3.61 (s, 2H), 3.81 (s, 3H), 3.97 (m, 2H), 4.18 (s, 2H), 4.22 (m, 1H), 4.62 (m, 2H), 5.08 (s, 2H), 6.78 (s, 1H), 7.39 (s, 1H), 8.76 (s, 1H), 10.73 (s, 1H) LRMS: m/z (ES⁺) 477 [MH⁺] |

| Ex No. (method) | R1 | R2 | Yield % | Spectroscopic and analytical data |
|---|---|---|---|---|
| 109 (c) | [structure: pyrido-pyrimidine with CH₂N(CH₃)₂] | (II) | 71 | ¹H NMR (DMSOd₆, 400 MHz) δ: 1.62 (m, 4H), 2.86 (s, 6H), 3.09 (t, 3H), 3.42 (m, 2H), 3.81 (s, 3H), 3.93 (m, 2H), 4.11 (m, 2H), 4.27 (m, 1H), 4.57 (s, 2H), 5.06 (s, 2H), 6.77 (s, 1H), 8.76 (s, 1H), 10.37 (s, 1H). LRMS: m/z (ES⁻) 449 [MH⁻] Microanalysis found: C, 56.66; H, 6.47; N, 16.33; $C_{24}H_{30}N_6O_3$ 1.6 HCl requires; C, 56.65; H, 6.26; N, 16.51% |
| 110 (c) | [structure: tetrahydronaphthyridine with CH₂-pyrrolidine] | (II) | 60 | ¹H NMR (DMSOd₆, 400 MHz) δ: 1.64 (m, 4H), 1.98 (m, 4H), 2.95 (m, 2H), 3.40 (m, 6H), 3.80 (s, 3H), 3.99 (m, 4H), 4.32 (m, 1H), 4.59 (s, 2H), 4.95 (s, 2H), 6.63 (s, 1H), 7.30 (d, 1H), 8.42 (d, 1H), 10.27 (s, 1H). LRMS: m/z (ES⁺) 467 [MH⁺] |
| 111 (a) | [structure: imidazo-piperazine] | (II) | 75 | ¹H NMR (DMSOd₆, 400 MHz) δ: 1.66 (m, 4H), 2.46 (s, 2H), 3.42 (t, 2H), 3.81 (s, 3H), 3.93 (d, 2H), 4.23 (m, 3H), 4.43 (s, 2H), 5.08 (s, 2H), 6.74 (s, 1H), 7.22 (s, 1H), 7.61 (s, 1H), 9.15 (s, 1H). LRMS: m/z (ES⁺) 482 [MH⁺]. Microanalysis found: C, 54.95; H, 5.86; N, 15.77; $C_{20}H_{23}N_5O_3$ HCl H₂O requires; C, 55.11; H, 6.01; N, 16.07% |
| 112 (c) | [structure: tetrahydronaphthyridine with CH₂-morpholine] | (II) | 18 | ¹H NMR (DMSOd₆, 400 MHz) δ: 1.66 (m, 4H), 3.03 (m, 2H), 3.35 (s, 4H), 3.43 (m, 2H), 3.84 (s, 3H), 3.90 (s, 6H), 4.13 (s, 2H), 4.24 (m, 1H), 4.57 (s, 2H), 5.13 (s, 2H), 6.78 (s, 1H), 7.32 (d, 1H), 7.58 (s, 1H), 8.47 (d, 1H), 11.0 (s, 1H). LRMS: m/z (ES⁺) 492 [MH⁺] |
| 113 (c) | [structure: tetrahydronaphthyridine with CH₂N(CH₃)₂] | (II) | 10 | ¹H-nmr (CD₃OD, 400 MHz) δ: 1.67 (m, 4H), 2.87 (s, 6H), 3.15 (s, 2H), 3.43 (m, 2H), 3.81 (s, 3H), 3.95 (m, 2H), 4.00 (s, 2H), 4.32 (m, 1H), 4.54 (s, 2H), 4.98 (s, 2H), 6.69 (s, 1H), 7.30 (d, 1H), 8.46 (d, 1H). LRMS: m/z (ES⁺) 450 [MH⁺] |
| 114 (c) | [structure: tetrahydroisoquinoline with CH₂-morpholine] | (II) | 77 | ¹H NMR (DMSOd₆, 400 MHz) δ: 1.63 (m, 4H), 3.15 (s, 4H), 3.22 (t, 2H), 3.42 (m, 3H), 3.88 (m, 11H), 4.28 (m, 1H), 4.38 (s, 2H), 4.92 (s, 2H), 6.73 (s, 1H), 7.27 (s, 1H), 7.33 (d, 1H), 7.61 (d, 1H), 11.17 (s, 1H). LRMS: m/z (ES⁺) 491 [MH⁺]; Microanalysis found: C, 58.45; H, 6.54; N, 9.58; $C_{28}H_{34}N_4O_4$ 2HCl 0.65 H₂O requires; C, 58.46; H, 6.54; N, 9.74% |

| Ex No. (method) | R1 | R2 | Yield % | Spectroscopic and analytical data |
|---|---|---|---|---|
| 115 (a) | 3-methoxyazetidin-1-ylmethyl attached to tetrahydroisoquinoline | (II) | 70 | ¹H NMR (DMSOd₆, 400 MHz) δ: 1.67 (m, 4H), 3.12 (s, 2H), 3.22 (s, 3H), 3.42 (m, 2H), 3.82 (s, 3H), 3.94 (m, 12H), 5.01 (s, 2H), 6.79 (s, 1H), 7.32 (m, 2H), 7.51 (m, 2H), 11.47 (s, 1H). LRMS: m/z (ES⁺) 491 [MH⁺]. Microanalysis found: C, 58.76; H, 6.53; N, 9.65; $C_{28}H_{34}N_4O_4$ 2HCl 0.5 $H_2O$ requires; C, 58.74; H, 6.51; N, 9.79% |
| 116 (c) | 2-(pyrrolidin-1-yl)ethylamino attached to tetrahydronaphthyridine | (III) | 83 | ¹H-NMR (DMSOd₆, 400 MHz) δ: 1.47 (m, 1H), 1.90 (m, 6H), 2.52 (m, 2H), 3.35 (m, 6H), 3.90 (m, 11H), 4.80 (s, 2H), 5.80 (t, 1H), 6.98 (s, 1H), 7.00 (d, 1H), 7.19 (s, 1H), 7.71 (d, 1H). LRMS: m/z (ES⁺) 491 [MH⁺]. Microanalysis: Found: C, 53.69; H, 6.54; N, 13.89; $C_{27}H_{34}N_6O_3$ 3HCl 0.25 $H_2O$ requires; C, 53.65; H, 6.25; N, 13.90% |
| 117 (a) | 2-methoxyethylamino attached to tetrahydronaphthyridine | (III) | 54 | ¹H-NMR (DMSOd₆, 400 MHz) δ: 1.49 (m, 1H), 1.82 (m, 2H), 2.50 (m, 2H), 3.08 (m, 2H), 3.28 (s, 3H), 3.53 (t, 2H), 3.61 (m, 2H), 3.80 (m, 4H), 4.02 (m, 3H), 4.78 (s, 2H), 5.80 (t, 1H), 6.94 (d, 1H), 7.02 (d, 1H), 7.12 (s, 1H), 7.72 (d, 1H). LRMS: m/z (ES⁺) 452 [MH⁺]. Microanalysis: Found: C, 53.37; H, 5.97; N, 12.66; $C_{24}H_{29}N_5O_4$ 2HCl 0.25 $CH_2Cl_2$ requires; C, 53.38; H, 5.82, 12.83% |
| 118 (c) | 2-(dimethylamino)ethylamino attached to tetrahydronaphthyridine | (III) | 87 | ¹H-NMR (DMSOd₆, 400 MHz) δ: 1.50 (m, 1H), 1.82 (m, 2H), 2.51 (m, 2H), 2.81 (s, 6H), 3.11 (m, 2H), 3.32 (t, 2H), 3.82 (m, 4H), 3.91 (m, 2H), 4.01 (m, 3H), 4.80 (s, 2H), 5.80 (t, 1H), 6.95 (s, 1H), 6.99 (d, 1H), 7.13 (s, 1H), 7.69 (d, 1H). LRMS: m/z (ES⁺) 465 [MH⁺]. Microanalysis: Found: C, 52.32; H, 6.45; N, 14.66; $C_{25}H_{32}N_6O_3$ 3HCl requires; C, 52.32; H, 6.15; N, 14.64% |
| 119 (a) | amino attached to tetrahydronaphthyridine | (III) | 89 | ¹H-NMR (DMSOd₆, 400 MHz) δ: 1.49 (m, 1H), 1.80 (m, 2H), 2.50 (m, 2H), 3.80 (m, 5H), 4.06 (m, 3H), 4.98 (s, 2H), 5.79 (m, 1H), 6.73 (d, 1H), 7.95 (d, 1H), 7.22 (s, 1H), 7.86 (d, 1H), 8.08 (s, 2H). LRMS: m/z (ES⁺) 394 [MH⁺]. Microanalysis: Found: C, 50.46; H, 5.22; N, 13.68; $C_{21}H_{23}N_5O_3$ 3HCl requires; C, 50.16; H, 5.21; N, 13.93% |

-continued

| Ex No. (method) | R1 | R2 | Yield % | Spectroscopic and analytical data |
|---|---|---|---|---|
| 120 (a) | 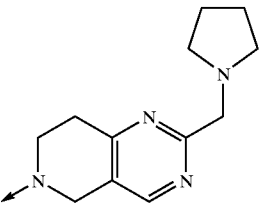 | —Cl | 17 | ¹H-NMR (DMSOd₆, 400 MHz) δ: 1.64 (s, 4H), 2.51 (s, 4H), 2.93 (m, 2H), 3.73 (s, 2H), 3.81 (s, 3H), 3.95 (t, 2H), 4.81 (s, 2H), 6.70 (s, 1H), 6.73 (s, 1H), 8.58 (s, 1H). LRMS: m/z (ES⁺) 427, 427 [MH⁺] M.p. 190–191° C. |
| 121 (a) | 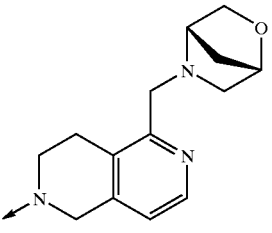 | —Cl | 45 | ¹H-NMR (DMSOd₆, 400 MHz) δ: 2.02 (d, 1H), 2.40 (d, 1H), 2.90 (s, 2H), 3.42 (m, 1H), 3.74 (d, 1H), 3.82 (s, 3H), 4.02 (m, 2H), 4.28 (d, 1H), 4.48 (s, 1H), 4.65 (m, 4H), 4.97 (s, 2H), 6.81 (s, 1H), 7.00 (s, 1H), 7.30 (d, 1H), 8.42 (d, 1H). LRMS: m/z (ES⁺) 454, 456 [MH⁺]. M.p. 314–315° C. |
| 122 (c) | 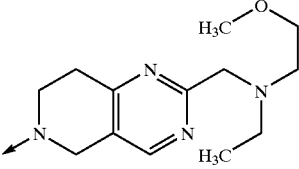 | (IV) | | ¹H-nmr (CDCl₃ + TFAd, 400 MHz) δ: 0.77 (m, 2H), 1.14 (m, 2H), 1.44 (t, 3H), 2.96 (m, 1H), 3.36 (t, 2H), 3.39 (s, 3H), 3.54 (q, 2H), 3.60 (m, 2H), 3.80 (m, 2H), 3.88 (s, 3H), 4.18 (m, 2H), 4.66 (m, 1H), 4.80 (m, 1H), 5.16 (s, 2H), 6.62 (s, 1H), 6.99 (s, 1H), 8.70 (s, 1H). LRMS: m/z (ES⁺) 487 [MNa⁺]. Microanalysis found: C, 59.08; H, 6.85; N, 16.08. C₂₅H₃₂N₆O₃; HCl; 0.5 H₂O requires C, 58.87; H, 6.72; N, 16.48%. |

ᴰTriethylamine was used as the base (I) represents  H₃C   CH₃;

(II) represents 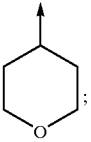 ;

(III) represents 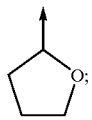 ;

(IV) represents 

EXAMPLE 123

2-(2-Aminomethyl-7,8-dihydro-5H-[1,6]naphthyridin-6-yl)-5-isopropyl-7-methoxy-3H-quinazolin-4-one dihydrochloride

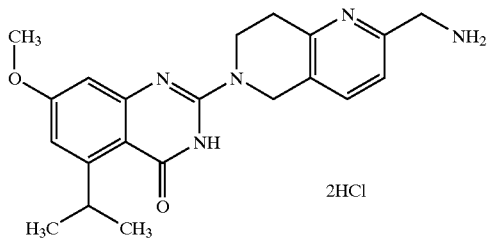

Hydrogen chloride gas was bubbled for 10 minutes into a solution of the protected amine from preparation 293 (155 mg, 0.32 mmol) in dichloromethane at 0° C. The solution was stirred at 0° C. for 1.5 hours and then the mixture was degassed by a stream of nitrogen being blown through the mixture. The solvent was evaporated under reduced pressure and the residue was dried under vacuum to give the title compound as a white solid (146 mg).

$^1$H-nmr (CD$_3$OD, 400 MHz) δ: 1.23 (d, 6H), 3.21 (t, 2H), 3.90 (s, 3H), 4.07 (t, 2H), 4.06 (s, 2H), 4.48 (m, 1H), 4.94 (s, 2H), 6.86 (s, 1H), 6.90 (s, 1H), 7.33 (d, 1H), 7.72 (d, 1H) LRMS: m/z (ES$^+$) 380 [MH$^+$]Microanalysis: Found: C, 55.61; H, 6.21; N, 15.12; C$_{21}$H$_{25}$N$_5$O$_2$ 2HCl requires; C, 55.76; H, 6.02; N, 15.48%

EXAMPLE 124

2-(7,8-Dihydro-5H-[1,6]naphthyridin-6-yl)-7-methoxy-5-(1-methyl-piperidin-2-yl)-3H-quinazolin-4-one trihydrochloride

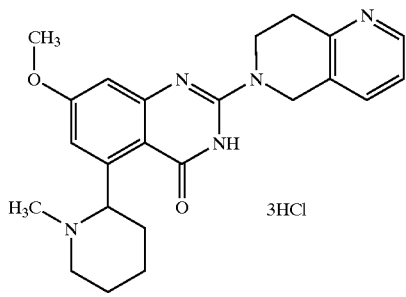

3-Methylpentan-3-ol (5 ml) was added to the guanidine from preparation 286 (86 mg, 0.2 mmol) and potassium t-butoxide (67 mg, 0.6 mmol) and the mixture was heated under reflux for 1 hour. A further quantity of potassium t-butoxide (45 mg, 0.4 mmol) was added and the mixture was heated under reflux for a further 1 hour. The reaction mixture was cooled to room temperature and 1M citric acid (3 ml) was added. The mixture was added to water and was basified with 0.5M sodium hydroxide solution. The solution was extracted with dichloromethane (3×50 ml) and the combined organic solutions were dried over magnesium sulphate and evaporated under reduced pressure. The residue was purified by chromatography on silica gel using methanol and ammonium hydroxide in dichloromethane as eluant (gradient from 0:0:100 to 10:1:90). The material isolated was dissolved in dichloromethane and 1M hydrogen chloride in dichloromethane was added. The mixture was evaporated under reduced pressure to give the title compound as a white solid (26 mg).

$^1$H-nmr (DMSOd$_6$ 400 MHz) δ: 1.80 (m, 10H), 2.40 (m, 2H), 3.08 (m, 1H), 3.49 (m, 2H), 3.97 (s, 3H), 4.12 (m, 2H), 5.07 (s, 2H), 7.77 (m, 1H), 8.00 (d, 1H), 8.60 (m, 1H), 8.63 (d, 1H) LRMS: m/z (ES$^+$) 406 [MH$^+$]

EXAMPLE 125

2-(6,7-Dimethoxy-3,4-dihydro-1H-isoquinolin-2-yl)-7-methoxy-5-(1-methyl-piperidin-2-yl)-3H-quinazolin-4-one dihydrochloride

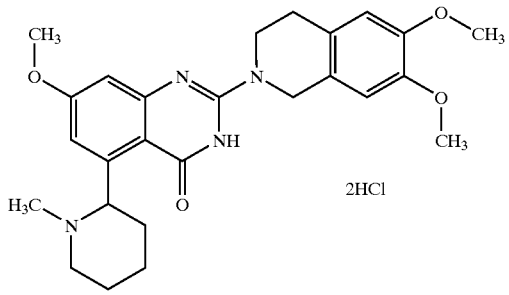

The title compound was obtained from the guanidine from preparation 287 in 27% yield following the procedure described in Example 124.

$^1$H-nmr (DMSOd$_6$ 400 MHz) δ: 1.80 (m, 10H), 2.85 (t, 2H), 3.80 (m, 13H), 4.80 (s, 2H), 6.78 (d, 2H), 6.89 (d, 1H), 7.20 (s, 1H) LRMS: m/z (ES$^+$) 465 [MH$^+$]

EXAMPLE 126

7-Methoxy-2-[2-(2-methoxy-ethylamino)-3,4-dihydro-1H-isoquinolin-2-yl]-5-(1-methyl-piperidin-2-yl)-3H-quinazolin-4-one trihydrochloride

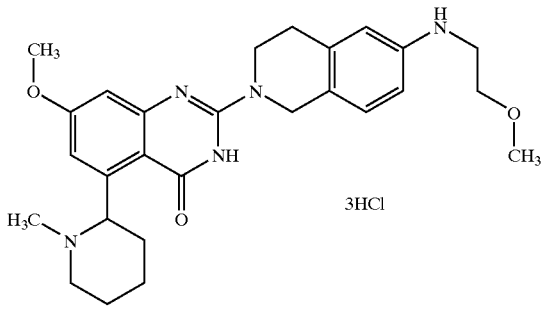

The title compound was obtained from the guanidine from preparation 288 in 27% yield following a similar procedure to that described in Example 124.

$^1$H-nmr (DMSOd$_6$ 400 MHz) δ: 1.60 (m, 11H), 3.50 (m, 16H), 4.72 (s, 2H), 6.89 (d, 1H), 7.00 (d, 1H), 7.70 (m, 2H) LRMS: m/z (ES$^+$) 479 [MH$^+$]Microanalysis: Found: C, 53.53; H, 6.73; N, 13.66; C$_{26}$H$_{34}$N$_6$O$_3$ 3HCl 0.25 (CH$_3$CH$_3$)$_2$O requires; C, 53.47; H, 6.56; N, 13.86%

EXAMPLE 127

5-(Butane-1-sulfonyl)-7-methoxy-2-[5-(2-methoxy-ethylamino)-3,4-dihydro-1H-[2,6]naphthyridin-2-yl]-3H-quinazolin-4-one

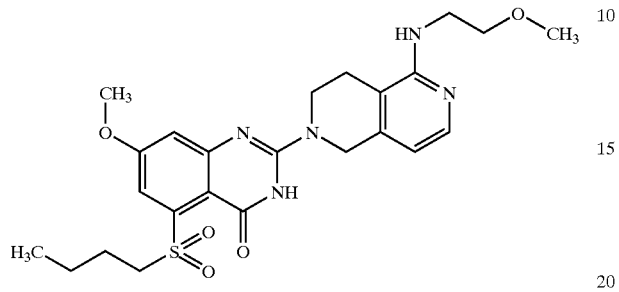

Caesium carbonate (450 mg, 1.38 mmol) was added to the guanidine from preparation 224 (177 mg, 0.55 mmol) in N,N-dimethylformamide (2 ml) and the suspension was stirred for 1 hour at room temperature. The imidazolide solution from preparation 280 (3 ml, 0.46 mmol) was added and the mixture was stirred at room temperature for 42 hours. The solvent was evaporated under reduced pressure and the residue was partitioned between ethyl acetate (25 ml) and pH7 buffer (40 ml). The phases were separated and the aqueous solution was extracted with ethyl acetate (2×25 ml). The combined organic solutions were washed with brine (3×15 ml), dried over magnesium sulphate and evaporated under reduced pressure.

The material obtained was dissolved in 1,2-dimethoxyethane (3 ml) and was added to potassium tert-butoxide (139 mg, 1.24 mmol) under a nitrogen atmosphere. The mixture was heated under reflux for 1.5 hours and then was cooled to room temperature and partitioned between dichloromethane (25 ml) and pH7 buffer. The phases were separated and the aqueous solution was extracted with dichloromethane (2×25 ml). The combined organic solutions were dried over magnesium sulphate and evaporated under reduced pressure. The residue was purified by chromatography on silica gel using methanol in dichloromethane as eluant (gradient from 2:98 to 4:96). The material obtained was dried under vacuum at 60° C. for 24 hours to give the title compound (29 mg).

$^1$H-nmr (CDCl$_3$, 400 MHz) δ: 0.89 (t, 3H), 1.42 (m, 2H), 1.72 (m, 2H), 2.63 (m, 2H), 3.38 (s, 3H), 3.59 (t, 2H), 3.68 (m, 2H), 3.79 (m, 2H), 3.93 (s, 3H), 3.98 (t, 2H), 4.55 (s, 1H), 4.72 (s, 2H), 6.44 (d, 1H), 7.00 (d, 1H), 7.72 (s, 1H), 7.99 (d, 1H) LRMS: m/z ES$^+$502 [MH$^+$]

EXAMPLE 128

5-(Butane-1-sulfonyl)-7-methoxy-2-{5-[(Pyridin-2-ylmethyl)-amino]-3,4-dihydro-1H-[2,6]naphthyridin-2-yl}-3H-quinazolin-4-one

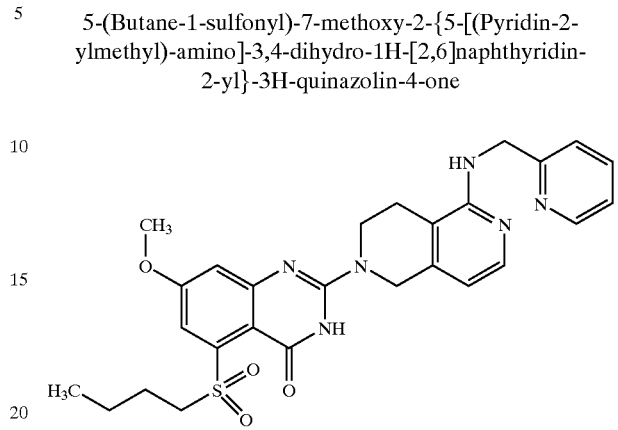

The title compound was obtained from the imidazolide solution from preparation 280 and the guanidine from preparation 223 in 7% yield following the procedure described in Example 127.

$^1$H-nmr (CDCl$_3$, 400 MHz) δ: 0.88 (t, 3H), 1.40 (m, 2H), 1.74 (m, 2H), 2.77 (t, 2H), 3.80 (m, 2H), 3.93 (s, 3H), 3.99 (t, 2H), 4.71 (s, 2H), 4.77 (d, 2H), 5.70 (m, 1H), 6.47 (d, 1H), 7.00 (m, 1H), 7.16 (m, 1H), 7.29 (m, 1H), 7.64 (m, 1H), 7.72 (s, 1H), 8.01 (d, 1H), 8.56 (d, 1H) LRMS: m/z (ES$^+$) 535 [MH$^+$]

EXAMPLE 129

5-Isopropyl-7-methoxy-2-[1-(2-pyrrolidin-1-yl-ethyl)-1,4,6,7-tetrahydro-pyrazolo[4,3-c]pyridin-5-yl]-3H-quinazolin-4-one

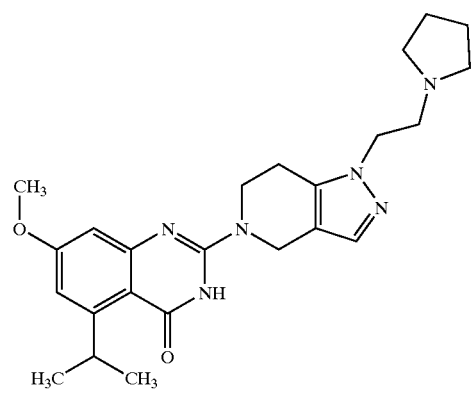

EXAMPLE 130

5-Isopropyl-7-methoxy-2-[2-(2-pyrrolidin-1-yl-ethyl)-2,4,6,7-tetrahydro-pyrazolo[4,3-c]pyridin-5-yl]-3H-quinazolin-4-one

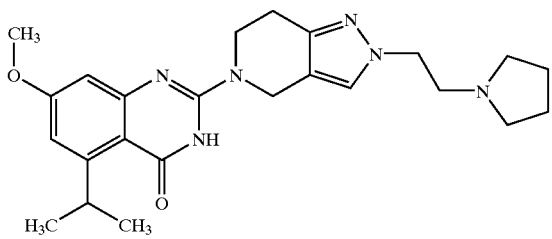

The chloro compound from preparation 269 (91 mg, 0.36 mmol) was added to a mixture of the amines from preparation 229-A and preparation 229-B (60:40 mixture, 206 mg, 0.45 mmol) in n-butanol (3 ml) containing N,N-diisopropylethylamine (350 μl, 2 mmol). The reaction mixture was heated under reflux for 2 hours and then was cooled to room temperature and diluted with ethyl acetate (350 ml). The organic mixture was washed with sodium hydrogen carbonate solution (2×15 ml), dried over magnesium sulphate and evaporated under reduced pressure.

The residue was purified by chromatography on a Chiralpak® AS 250 mm×20 mm column, using diethylamine and propan-2ol in n-hexane (0.05:9.95:90) as eluant at a flow rate of 10 ml/minute to give the title compound of Example 129 (31 mg).

$^1$H-nmr (CD$_3$OD, 400 MHz) δ: 1.20 (d, 6H), 1.72 (m, 4H), 2.52 (m, 4H), 2.90 (m, 4H), 3.84 (s, 3H), 3.99 (m, 2H), 4.16 (t, 2H), 2.53 (m, 1H), 4.65 (s, 2H), 6.71 (m, 2H), 7.35 (s, 1H) LRMS: m/z (ES$^+$) 437 [MH$^+$]

Also isolated was the title compound of Example 130 (16 mg):

$^1$H-NMR (CDCl$_3$, 400 MHz) δ: 1.25 (d, 6H), 1.80 (m, 4H), 2.63 (m, 4H), 2.90 (m, 2H), 3.02 (m, 2H), 3.86 (s, 3H), 4.02 (m, 2H), 4.25 (m, 2H), 4.59 (m, 1H), 4.75 (s, 2H), 6.68 (s, 1H), 6.71 (s, 1H), 7.29 (s, 1H) LRMS: m/z (ES$^-$) 435 [M-H$^-$]

EXAMPLE 131

5-Chloro-7-methoxy-2-(5-pyrrolidin-1-ylmethyl-3,4-dihydro-1H-[2,6]naphthyridin-2-yl)-3H-quinazolin-4-one dihydrochloride

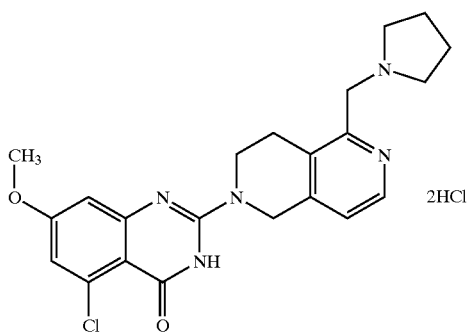

The title compound was obtained from the chloro compound from preparation 273 and the amine from preparation 113 in 74% yield following the procedure described in Example 86.

$^1$H-nmr (DMSOd$_6$ 400 MHz) δ: 1.63 (m, 4H), 2.41 (m, 4H), 3.00 (t, 2H), 4.69 (s, 2H), 3.80 (s, 3H), 3.88 (t, 2H), 4.81 (s, 2H), 6.68 (d, 1H), 6.71 (d, 1H), 7.12 (d, 1H), 8.24 (d, 1H), 11.20 (s, 1H) LRMS: m/z (ES$^+$) 426 [MH$^+$] Microanalysis: Found: C, 49.42; H, 5.63; N, 12.51; C$_{22}$H$_{24}$ClN$_5$O$_2$ 2HCl 2H$_2$O requires; C, 49.40; H, 5.65; N, 13.09%

EXAMPLE 132

5-Isopropyl-7-methoxy-2-[2-(4-methyl-piperazin-1-yl)-7,8-dihydro-5H-[1,6]naphthyridin-6-yl]-3H-quinazolin-4-one trihydrochloride

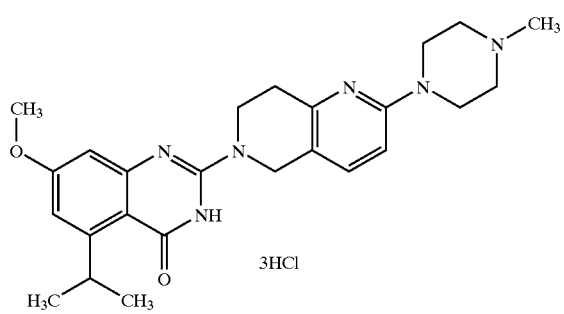

The chloro compound from preparation 269 (101 mg, 0.4 mmol) was added to the amine from preparation 110 (104 mg, 0.45 mmol) in n-butanol (5 ml) containing N,N-diisopropylethylamine (129 μl, 1 mmol) and the mixture was heated under reflux for 2 hours. The reaction mixture was cooled to room temperature and the solid formed was isolated by filtration. The material obtained was dissolved in 5% methanol in dichloromethane and ethereal hydrogen chloride (1M, 2 ml) was added. The solvent was evaporated under reduced pressure and the residue was dried under vacuum to give the title compound (176 mg).

$^1$H-nmr (DMSOd$_6$ 400 MHz) δ: 1.19 (d, 6H), 2.77 (s, 3H), 3.00 (m, 4H), 3.34 (t, 2H), 3.47 (m, 2H), 3.83 (s, 3H), 4.40 (m, 3H), 4.91 (s, 2H), 6.81 (s, 1H), 6.90 (d, 1H), 7.50 (m, 2H), 13.38 (s, 1H) LRMS: m/z (ES$^+$) 449 [MH$^+$] Microanalysis: Found: C, 53.26; H, 6.49; N, 14.90; C$_{25}$H$_{32}$N$_6$O 3HCl 0.25H$_2$O requires; C, 53.39; H, 6.36; N, 14.94%

EXAMPLE 133

5-Isopropyl-7-methoxy-2-(5-methylaminomethyl-3,4-dihydro-1H-[2,6]naphthyridin-2-yl)-3H-quinazolin-4-one dihydrochloride

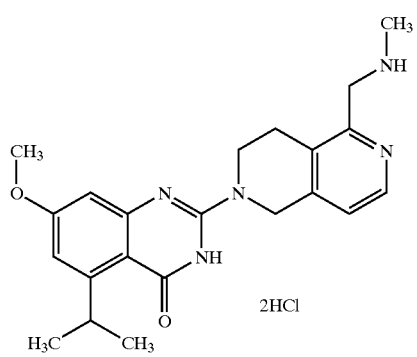

The protected amine from preparation 297 (59 mg, 0.12 mmol) was dissolved in dichloromethane (1 ml) and trifluoroacetic acid (1 ml) was added. The reaction mixture was stirred at room temperature for 30 minutes and then the solvent was evaporated under reduced pressure. The residue was purified by chromatography on silica gel using ammonium hydroxide and methanol in dichloromethane as eluant (1:7:93). The material obtained was dissolved in dichloromethane and ethereal hydrogen chloride (1M, 1 ml) was added. The solvent was evaporated under reduced pressure and the residue was dried under vacuum to give the title compound as an off white solid (26 mg).

$^1$H-nmr (DMSOd$_6$ 400 MHz) δ: 1.19 (d, 6H), 2.63 (s, 3H), 2.98 (t, 2H), 3.84 (s, 3H), 4.15 (t, 2H), 4.30 (s, 2H), 4.41 (m, 1H), 5.12 (s, 2H), 6.80 (s, 1H), 7.26 (d, 1H), 7.55 (s, 1H), 8.46 (d, 1H), 9.26 (s, 1H) LRMS: m/z (ES$^+$) 394 [MH$^+$]

All of the compounds illustrated in examples 1 to 133 display pA2 values versus α1L (in the method described above) of greater than 7.

Particular compounds of interest display the following pA2 values versus α1L (in the method described above):

| Example Number | pA2 v α1L |
|---|---|
| 7 | 9.5 |
| 8 | 9.6 |
| 10 | 9.7 |
| 11 | 10.0 |
| 12 | 9.7 |
| 16 | 9.5 |
| 20 | 9.8 |
| 21 | 10 |
| 38 | 9.5 |
| 39 | 9.6 |

We claim:
1. A compound of formula (I):

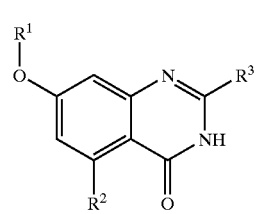

(I)

or a pharmaceutically acceptable salt or solvate thereof, wherein $R^1$ represents $C_{1-4}$ alkyl;

$R^2$ represents halo, $C_{1-4}$ alkyl, $C_{3-6}$ cycloalkyl, $C_{3-6}$ cycloalkyloxy, —SO$_2$(C$_{1-4}$ alkyl), C$_{1-4}$ alkyloxy (substituted by C$_1$–C$_4$ alkoxy), Het or —OHet;

$R^3$ represents a bicyclic group of the formula

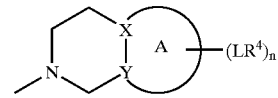

wherein X and Y are selected from C and N, provided that at least one is C;

Ring A together with X and Y represents a 5- or 6-membered aromatic ring containing 0, 1, 2 or 3 nitrogen atoms in the ring;

n is 0, 1 or 2

L independently represents a direct link, C$_{1-4}$ alkylene or C$_{1-4}$ alkoxyalkylene;

$R^4$ independently represents H, —NR$^5$R$^6$, C$_{3-6}$ cycloalkyl, —OR$^7$, Het$^1$ or Het$^4$;

$R^5$ and $R^6$ are independently selected from H, C$_{3-6}$ cycloalkyl, C$_{3-6}$ cycloalkyl-C$_{1-4}$ alkylene, —SO$_2$(C$_{1-4}$ alkyl) and C$_{1-4}$ alkyl (optionally substituted with —OR$^8$, —NR$^{10}$R$^{11}$, Het$^1$ or Het$^4$);

$R^7$ is selected from H, C$_{1-4}$ alkyl, C$_{1-4}$ alkoxyalkyl, C$_{3-6}$ cycloalkyl, Het$^2$ and C$_{1-4}$alkyl-Het$^3$;

$R^8$ is H or C$_{1-4}$alkyl;

Het, Het$^1$, Het$^2$ and Het$^3$ independently represent a 4 to 7 membered saturated heterocyclic group which may be mono- or bi-cyclic and which contains one or more heteroatoms selected from N, O or S, optionally substituted with OR$^9$ and/or C$_{1-4}$ alkyl optionally substituted by OR$^9$;

Het$^4$ represents a 5 or 6 membered unsaturated heterocyclic group containing one or more heteroatoms selected from N, O or S, optionally substituted with C$_{1-4}$ alkyl;

$R^9$ is H or C$_{1-4}$ alkyl;

$R^{10}$ and $R^{11}$ are independently selected from H and C$_{1-4}$ alkyl.

2. A compound of formula (I) according to claim 1, or a pharmaceutically acceptable salt or solvate thereof, wherein Het, Het$^1$, Het$^2$ and Het$^3$ contain at least one N atom and are linked to L through an N atom.

3. A compound of formula (I) according to claim 1, or a pharmaceutically acceptable salt or solvate thereof, wherein Het, Het$^1$, Het$^2$ and Het$^3$ include azetidine, pyrrolidine, piperidine, piperazine, azepane, morpholine, homomorpholine, or one of the following ring systems optionally substituted by OR⁹, C₁₋₄ alkyl optionally substituted by OR⁹.

4. A compound of formula (I) according to claim 1, or a pharmaceutically acceptable salt or solvate thereof, wherein $R^1$ is $CH_3$.

5. A compound of formula (I) according to claim 1, or a pharmaceutically acceptable salt or solvate thereof, wherein $R^2$ is cyclopropyl.

6. A compound of formula (I) according to claim 1, or a pharmaceutically acceptable salt or solvate thereof, wherein L represents methylene.

7. A compound of formula (I) according to claim 1, or a pharmaceutically acceptable salt or solvate thereof, wherein $R^3$ represents a group chosen from a or b where $LR^4$ is $CH_2Het^1$ or $CH_2NR^5R^6$ and $Het^1$, $R^5$ and $R^6$ are as defined in claim 1.

8. A compound of formula (I) according to claim 7, wherein $Het^1$ is N-linked morpholinyl.

9. A compound of formula (I) according to claim 1, or a pharmaceutically acceptable salt or solvate thereof, wherein $R^5$ and $R^6$ are independently selected from H or $C_{1-3}$ alkyl optionally substituted by $OCH_3$.

10. A compound of formula (I) according to any of the preceding claims, or a pharmaceutically acceptable salt or solvate thereof, wherein Het, $Het^1$, $Het^2$ and $Het^3$ are selected from the group comprising pyrrolidine, piperidine, morpholine and 11. A compound of formula (I) as defined in claim 1 selected from:
   5-cyclopropyl-7-methoxy-2-(2-([dimethylamino]methyl)-7,8-dihydro[1,6]naphthyridin-6(5H)-yl)-4(3H)-quinazolinone;
   5-cyclopropyl-7-methoxy-2-(2-(1-pyrrolidinylmethyl)-7,8-dihydro[1,6]naphthyridin-6(5H)-yl)-4(3H)-quinazolinone;
   5-cyclopropyl-7-methoxy-2-(2-(4-methoxypiperidin-1-ylmethyl)-7,8-dihydro[1,6]naphthyridin-6(5H)-yl)-4(3H)-quinazolinone;
   5-cyclopropyl-7-methoxy-2-(2-(4-morpholinylmethyl)-7,8-dihydro[1,6]naphthyridin-6(5H)-yl)-4(3H)-quinazolinone;
   5-cyclopropyl-7-methoxy-2-(2-[(1S,4S)-2-oxa-5-azabicyclo[2.2.1]hept-5-ylmethyl]-7,8-dihydro[1,6]naphthyridin-6(5H)-yl)-4(3H)-quinazolinone;
   5-cyclopropyl-7-methoxy-2-(5-([dimethylamino]methyl)-3,4-dihydro[2,6]naphthyridin-2(1H)-yl)-4(3H)-quinazolinone;
   5-cyclopropyl-7-methoxy-2-(5-(4-morpholinylmethyl)-3,4-dihydro[2,6]naphthyridin-2(1H)-yl)-4(3H)-quinazolinone;
   5-cyclopropyl-7-methoxy-2-(5-[(1S,4S)-2-oxa-5-azabicyclo[2.2.1]hept-5-ylmethyl]-3,4-dihydro[2,6]naphthyridin-2(1H)-yl)-4(3H)-quinazolinone;
   5-cyclopropyl-7-methoxy-2-(5-(1-pyrrolidinylmethyl)-3,4-dihydro[2,6]naphthyridin-2(1H)-yl)-4(3H)-quinazolinone;
   5-cyclopropyl-7-methoxy-2-(5-(1-piperidinylmethyl)-3,4-dihydro[2,6]naphthyridin-2(1H)-yl)-4(3H)-quinazolinone;
and pharmaceutically acceptable salts or solvates thereof.

12. 5-cyclopropyl-7-methoxy-2-(2-(4-morpholinylmethyl)-7,8-dihydro[1,6]naphthryidin-6(5H)-yl)-4(3H)-quinazolinone, or a pharmaceutically acceptable salt or solvate thereof.

13. A process for the preparation of a compound of formula (I) as defined in claim 1, or a pharmaceutically acceptable salt or solvate thereof, comprising reacting a quinazolinone (II) with an amine (III):

wherein $R^1$, $R^2$, X, Y, $LR^4$ and n are as defined in claim 1 and LG represents a leaving group, and where desired or necessary converting the resulting compound of formula (I) into a pharmaceutically acceptable salt or solvate.

14. A pharmaceutical composition including a compound of the formula (I) as defined in claim 1, or a pharmaceutically acceptable salt or solvate thereof, together with a pharmaceutically acceptable excipient, diluent or carrier.

15. A method of treating hypertension, myocardial infarction, male erectile dysfunction, hyperlipidaemia, cardiac arrhythmia and benign prostatic hyperplasia in a mammal, which comprises administering a therapeutically effective amount of a compound of the formula (I) as defined in claim 1, or with a pharmaceutically acceptable salt, solvate or composition thereof, to a mammal in need of such treatment.

16. A method according to claim 15, for treating benign prostatic hyperplasia.

* * * * *